US007122644B2

(12) United States Patent
Yen-Potin et al.

(10) Patent No.: US 7,122,644 B2
(45) Date of Patent: Oct. 17, 2006

(54) METHODS AND COMPOSITIONS FOR INHIBITING NEOPLASTIC CELL GROWTH

(75) Inventors: Frances Yen-Potin, Vandoeuvre-les-Nancy (FR); Blake Denison, Dublin, CA (US); Aymeric Duclert, Saint-Maur (FR); Lydie Bougueleret, Petit-Lancy (CH); Catherine Clusel, Vincennes (FR); Jean-Baptiste Dumas Milne Edwards, Paris (FR); Bernard Bihain, Cancale (FR); Barbara Bour, San Diego, CA (US); Dana Ebbets-Reed, Encinitas, CA (US); Luisa Salter-Cid, San Diego, CA (US)

(73) Assignee: Serono Genetics Institute S.A., Evry (FR)

( * ) Notice: Subject to any disclaimer, the term of this patent is extended or adjusted under 35 U.S.C. 154(b) by 739 days.

(21) Appl. No.: 10/121,034

(22) Filed: Apr. 10, 2002

(65) Prior Publication Data

Related U.S. Application Data

(60) Division of application No. 09/750,580, filed on Dec. 28, 2000, now Pat. No. 6,455,280, which is a continuation-in-part of application No. 09/599,362, filed on Jun. 21, 2000, now abandoned, and a continuation-in-part of application No. PCT/IB00/01011, filed on Jun. 21, 2000, which is a continuation-in-part of application No. PCT/IB99/02058, filed on Dec. 20, 1999, and a continuation-in-part of application No. 09/469,099, filed on Dec. 21, 1999, now abandoned, and a continuation-in-part of application No. PCT/IB01/01111, filed on May 23, 2001, which is a continuation-in-part of application No. 09/751,877, filed on Dec. 28, 2000, now abandoned, said application No. 09/750,580 is a continuation-in-part of application No. 09/599,362, filed on Jun. 21, 2000, now abandoned, and a continuation-in-part of application No. PCT/IB00/01011, filed on Jun. 21, 2000, which is a continuation-in-part of application No. PCT/IB99/02058, filed on Dec. 20, 1999, and a continuation-in-part of application No. 09/469,099, filed on Dec. 21, 1999, now abandoned.

(60) Provisional application No. 60/113,686, filed on Dec. 22, 1998, provisional application No. 60/141,032, filed on Jun. 25, 1999.

(51) Int. Cl.
*C07H 21/04* (2006.01)
(52) U.S. Cl. ..................... 536/23.1; 536/23.5
(58) Field of Classification Search .............. 536/23.1, 536/23.5
See application file for complete search history.

(56) References Cited

U.S. PATENT DOCUMENTS

| 5,877,011 A | 3/1999 | Armentano et al. |
| 6,548,633 B1 * | 4/2003 | Edwards et al. ............ 530/300 |

FOREIGN PATENT DOCUMENTS

| DE | 198 16 395 A1 | 10/1999 |
| EP | EP 0 625 572 B1 | 11/1994 |
| EP | 0 976 824 A1 | 2/2000 |
| EP | 0 978 824 B1 | 2/2000 |
| WO | WO 93/15196 A1 | 8/1993 |
| WO | WO 96/34981 A3 | 7/1996 |
| WO | WO 98/31818 A3 | 7/1998 |
| WO | WO 98/45437 A3 | 10/1998 |
| WO | WO 00/03013 A3 | 1/2000 |
| WO | WO 01/21658 A1 | 3/2001 |

OTHER PUBLICATIONS

Yaginuma et al. Proc. Natl. Acad. Sci. USA, 1987, 84:2678-2682.*
DATABASE EMBL Online!; Acc No. Q9UBJ3; XP002207832.
Hendrik, N. et al. "Apolipoprotein A-V"; The Journal of Biological Chemistry, vol. 276, No. 48: 44512-20, Nov. 2001.
Van Der Vliet, H.N., et al.; "Apolipoprotein A-V: a novel apolipoprotein associated with an early phase of liver regeneration"; JBC Papers In Press, Publ. Sep. 27, 2001 as Manuscript M106888200; The American Society for Biochemistry and Molecular Biology, Inc.
Pennacchio, L.A., et al.; "An Apolipoprotein Influencing Triglycerides in Humans and Mice Revealed by Comparative Sequencing"; SCIENCE, vol. 294, Oct. 5, 2001, pp. 169-173.
Hattori, et al., Database GENBANK, Accession No. AP001480, May 2000.

(Continued)

*Primary Examiner*—Gary Nickol
*Assistant Examiner*—Sean Aeder
(74) *Attorney, Agent, or Firm*—Saliwanchik, Lloyd & Saliwanchik

(57) ABSTRACT

The invention provides the genomic sequence of GSSP-2, GSSP-2 cDNAs and GSSP-2 polypeptides. Further the invention provides polynucleotides including biallelic markers derived from the GSSP-2 gene and from genomic regions flanking the gene. This invention also provides polynucleotides and methods suitable for genotyping a nucleic acid molecule containing sample for one or more biallelic markers of the invention. Further, the invention provides methods to detect a statistical correlation between a biallelic marker allele and a phenotype and/or between a biallelic marker haplotype and a phenotype. The invention also concerns methods and compositions for killing neoplastic cells or inhibiting neoplastic cell growth. In particular, the present invention concerns cell proliferation arresting/inhibiting and apoptosis/necrosis inducing compositions and methods for the treatment of tumors. The present invention is directed to novel polypeptides and to nucleic acid molecules encoding those polypeptides.

4 Claims, 11 Drawing Sheets

OTHER PUBLICATIONS

Marra, et al., Database GENBANK, Accession No. AI528320, Mar. 1999.

Waters, et al., Database GENBANK, Accession No. AF086808, Oct. 1998.

NCBI Single Nucleotide Polymorphism, "A database of single nucleotide polymorphisms", www.ncbi.nlm.nih.gov/SNP, Mar. 2001.

Lee, et al., "Irresitable force meets immovable object SNP mapping of complex diseases", Trens. in Genet., http://news.bmn.com/hmsbeagle/118/notes/feature12, Jan. 2002.

Shelkh, T.H. et al. (1999) EMBL database XP002162303; ac:AC007707; *Homo sapiens* chromosomes 11 clone 442a11 from RPCI11 Library map 11q23, complete sequence (Abstract).

Lohee, P. et al., "Genetic Polymorphism of human plasma apolipoprotein A-IV is due to nucleotide substitutions in the apolipoprotein A-IV gene", *J. Biol. Chem.*, Jun. 15, 1990, pp. 10061-10064, vol. 265, No. 17.

Lohee, P. et al. "Three genetic variants of human plasma apolipoprotein A-IV", *J. Biol. Chem.*, 1991, p. 13513-13518, vol. 268.

Norman, R.A. et al. "Empirically determined power calculations for single locus allelic association studies", *Am.J. Hum.Gen.*, 2000, p. 320. vol. 67, No. 4, abstract.

Oseda, J. et al. (1996) EMBL database XP002162305, ac: AC048409; Apolipoprotein A-IV precursor (APO-AIV) (Abstract).

Tenkanon. J. et al. "A novel polymorphism of apolipoprotein A-IV is the result of an asparagine to serine substitution at residue 127", *Biochim. Biophys. Acts*, 1992, pp. 27-33, vol. 1138.

Jacobs, K.A. et al. "A genetic selection for isolating cDNAs encoding secreted proteins", *Gene*, NL Elsevier Biomedical Press, Amsterdam, Oct. 1, 1997, pp. 289-296, vol. 198, ISSN:0378-1119.

Jacobs, K.A. et al. "A novel method for isolating eukaryotic cDNA clones encoding secreted proteins", *Journal of Cellular Biochemistry Supplement*, Mar. 10, 1995, p. 19, XP002027248.

Shirozu, M. et al. "Characterization of novel secreted and membrane proteins isolated by the signal sequence 'Trap Method'", *Genomics*, U.S. Academic Press, San Diego, Nov. 1, 1996, pp. 273-280, vol. 37, No. 3, XP002054773; ISSN: 0688-7543.

Van Der Vliet, H.N. et al. "Identification of the human analog of rat RAP 3" (unpublished) "Direct Submission"; *Experimental Hepatology*, Nov. 9, 1999, Locus AF202889.

Van Der Vliet, H.N. et al. "Identification of the human analog of rat RAP 3" (unpublished) "Direct Submission"; *Experimental Hepatology*, Nov. 9, 1999, Locus AF202890.

Adams, et al., "Initial assessment of human gene diversity and expression patterns based upon 83 million nucleotides of cDNA sequence", *Nature*, Sep. 28, 1995, pp. 1-174, vol. 377 Supp.

Carninci, et al., "High-efficiency full-length cDNA cloning and biotinylated CAP trapper", *Genomics*, 1996, pp. 327-336.

Hillier, et al., "Generation and analysis of 280,000 human expressed sequence tags", *Genome Research*, 1996, pp. 807-828.

Kato, et al., "Construction of a human full-length cDNA bank", *Gene*, 1994, pp. 243-250.

Nomura, et al. "Prediction of the coding sequence of unidentified human genes. I. The coding sequences of 40 new genes (KIAA0001-KIAA0040) deduced by analysis of randomly sampled cDNA clones from human immature myeloid cell line KG-1", *DNA Research*, 1994, pp. 27-35, vol. 1.

Gunner Von Heijne, "A new method for predicting signal sequence cleavage sites", *Nucleic Acids Research*, 1986, vol. 14, No. 11.

* cited by examiner

| SEQ ID NO. | BIALLELIC MARKER ID | ORIGINAL ALLELE | ALTERNATIVE ALLELE |
|---|---|---|---|
| 1 | 20-828-311 | C | T |
| 1, 4 | 17-42-319 | C | T |
| 1, 2, 4 | 17-41-250 | C | T |
| 1 | 20-841-149 | A | G |
| 1 | 20-842-115 | G | A |
| 1 | 20-853-415 | C | T |

FIG. 1

| SEQ ID NO. | Biallelic Marker ID | Original Allele | Alternative Allele | Position Range of Preferred Sequences |
|---|---|---|---|---|
| 1 | 20-828-311 | C | T | 739-1739 |
| 1 | 17-42-319 | C | T | 10946-12958; 13470-13526; 13641-13752 |
| 1 | 17-41-250 | C | T | 14271-17969 |
| 1 | 20-841-149 | A | G | 41718-42718 |
| 1 | 20-842-115 | G | A | 44942-45942 |
| 1 | 20-853-415 | C | T | 76558-77558 |
| 2 | 17-41-250 | C | T | 1-1879 |
| 4 | 17-42-319 | C | T | 1-1498; 1613-1724 |
| 4 | 17-41-250 | C | T | 2243-3940; 3941-5381 |

FIG. 2

| SEQ ID NO. | POSITION OF CONFLICT | NUCLEOTIDE |
|---|---|---|
| 1 | 13269 (SEQ ID NO: 1) | T (original) |
| 4 | 1241 (SEQ ID NO: 4) | C (alternative) |

FIG. 3A

| SEQ ID NO. | POSITION OF CONFLICT | NUCLEOTIDE |
|---|---|---|
| 1 | 13475 (SEQ ID No 1) | G (original) |
| 4 | 1447 (SEQ ID No 4) | A (alternative) |

FIG. 3B

| SEQ. ID. NO | POSITION RANGE OF MICROSEQUENCING PRIMERS | COMPLEMENTARY POSITIN RANGE OF MICROSEQUENCING PRIMERS |
|---|---|---|
| 1 | 1220-1238 | 1240-1258 |
| 1 | 12328-12346 | 12348-12366 |
| 1 | 15222-15240 | 15242-15260 |
| 1 | 42199-42217 | 42219-42237 |
| 1 | 45423-45441 | 45443-45461 |
| 1 | 77039-77057 | 77059-77077 |
| 4 | 300-318 | 320-338 |
| 4 | 3194-3212 | 3214-3232 |

FIG. 4

| SEQ. ID NO. | POSITION RANGE OF AMPLIFICATION PRIMERS | COMPLEMENTARY POSITION RANGE OF AMPLIFICATION PRIMERS |
|---|---|---|
| 1 | 929-949 | 1357-1377 |
| 1 | 12029-12050 | 12581-12603 |
| 1 | 14992-15012 | 15460-15482 |
| 1 | 42070-42090 | 42572-42591 |
| 1 | 45328-45347 | 45863-45883 |
| 1 | 76644-76664 | 77166-77185 |
| 4 | 1-11022 | 553-11575 |
| 4 | 899-11920 | 1441-12461 |
| 4 | 1246-12267 | 1632-12651 |
| 4 | 2964-13984 | 3432-14454 |

FIG. 5

| SEQ. ID NO | POSITION RANGE OF PROBES |
|---|---|
| 1 | 1227-1251 |
| 1 | 12335-12359 |
| 1 | 15229-15253 |
| 1 | 42206-42230 |
| 1 | 45430-45454 |
| 1 | 77046-77070 |
| 4 | 307-331 |
| 4 | 3201-3225 |

FIG. 6

METHODS AND COMPOSITIONS FOR INHIBITING NEOPLASTIC CELL GROWTH

RELATED APPLICATIONS

This application is a divisional of U.S. application Ser. No. 09/750,580, filed Dec. 28, 2000(now U.S. Pat. No. 6,455,280, which is a continuation-in-part of U.S. patent application Ser. No. 09/599,362, filed Jun. 21, 2000 (now abandoned) and PCT International Patent Application No. PCT/IB00/01011, filed Jun. 21, 2000, (which claims the benefit of U.S. Provisional Patent Application Ser. No. 60/141,032, filed Jun. 25, 1999), each of which are a continuation-in-part of PCT International Patent Application No. PCT/IB99/02058, filed Dec. 20, 1999 and U.S. patent application Ser. No. 09/469,099, filed Dec. 21, 1999. This application is also a continuation-in-part of PCT International Patent Application No. PCT/IB01/01111, filed May 23, 2001, which is a continuation-in-part of U.S. patent application Ser. No. 09/751,877, filed Dec. 28, 2000, which is a divisional of U.S. patent application Ser. No. 09/750,580, filed Dec. 28, 2000(now U.S. Pat. No. 6,455,280) which is a continuation-in-part of U.S. patent application Ser. No. 09/599,362, filed Jun. 21, 2000 (which claims the benefit of U.S. Provisional Patent Application Ser. No. 60/141,032, filed Jun. 25, 1999), both of which are a continuation-in-part of PCT International Patent Application No. PCT/IB99/02058, filed Dec. 20, 1999 and U.S. patent application Ser. No. 09/469,099, filed Dec. 21, 1999 (now abandoned). PCT International Patent Application No. PCT/IB99/02058 and U.S. patent application Ser. No. 09/469,099 both claim benefit of U.S. Provisional Patent Application Ser. No. 60/113,686, filed Dec. 22, 1998, and U.S. Provisional Patent Application Ser. No. 60/141,032, filed Jun. 25, 1999. The disclosures of U.S. application Ser. No. 09/750,580, filed Dec. 28, 2000; U.S. patent application Ser. No. 09/599,362, filed Jun. 21, 2000; PCT International Patent Application No. IB00/01011, filed Jun. 21, 2000; PCT International Patent Application No. IB99/02058, filed Dec. 20, 1999; U.S. patent application Ser. No. 09/469,099, filed Dec. 21, 1999; U.S. Provisional Patent Application No. 60/113,686, filed Dec. 22, 1998; and U.S. Provisional Patent Application No. 60/141,032, filed Jun. 5, 1999; are incorporated herein by reference in their entireties.

FIELD OF THE INVENTION

The present invention concerns methods and compositions for inhibiting neoplastic cell growth. In particular, the present invention concerns antitumor compositions and methods for the treatment of tumors.

BACKGROUND OF THE INVENTION

Apoptosis is a form of programmed cell death which occurs through the activation of cell-intrinsic suicide machinery. The biochemical machinery responsible for apoptosis is expressed in most, if not all, cells. Apoptosis is primarily a physiologic process necessary to remove individual cells that are no longer needed or that function abnormally. Apoptosis is a regulated event dependent upon active metabolism and protein synthesis by the dying cell.

The morphological and biochemical characteristics of cells dying by apoptosis differ markedly from those of cells dying by necrosis. During apoptosis, cells decrease in size and round up. The nuclear chromatin undergoes condensation and fragmentation. Cell death is preceded by DNA fragmentation. The DNA of apoptotic cells is nonrandomly degraded by endogenous calcium and magnesium-dependent endonuclease(s) inhibited by zinc ions. This enzyme(s) gives fragments of approx. 200 base pairs (bp) or multiples of 200 bp by cutting the linker DNA running between nucleosomes. Thus DNA appears to be one of the most important targets of the process that leads to cell suicide. The apoptotic cell then breaks apart into many plasma membrane-bound vesicles called "apoptotic bodies," which contain fragments of condensed chromatin and morphologically intact organelles such as mitochondria. Apoptotic cells and bodies are rapidly phagocytosed, thereby protecting surrounding tissues from injury. The rapid and efficient clearance of apoptotic cells makes apoptosis extremely difficult to detect in tissue sections.

In contrast, necrosis is associated with rapid metabolic collapse that leads to cell swelling, early loss of plasma membrane integrity, and ultimate cell rupture. Cytosolic contents leach from the necrotic cell causing injury and inflammation to surrounding tissue.

In contrast to the cell death caused by cell injury, apoptosis is an active process of gene-directed, cellular self-destruction and that it serves a biologically meaningful function. (Kerr, J. F. R and J. Searle. *J. Pathol.* 107:41, 1971). Apoptosis plays a key role in the human body from the early stages of embryonic development through to the inevitable decline associated with old age. (Wyllie, A. H. *Int. Rev. Cytol.* 68:251, 1980). The normal function of the immune, gastrointestinal and hematopoietic system relies on the normal function of apoptosis. When the normal function of apoptosis goes awry, the cause or the result can be one of a number of diseases, including: cancer, viral infections, auto-immune disease/allergies, neurodegeneration or cardiovascular diseases. Because of the versatility of apoptosis involved in human diseases, apoptosis is becoming a prominent buzzword in the pharmaceutical research field.

The idea of modulating apoptosis as a means of treating and/or preventing cancer is a relatively new idea (Cope, F. O and Wille, J. *Apoptosis: The Molecular Basis of Cell Death*. Cold Spring Harbor Laboratory Press, p. 61, 1991). Apoptosis modulation is a potential mechanism for controlling the growth of tumor cells without the side effects of many current cancer treatment regimes. In addition to cancer, recent studies show that multiple cytotoxic stimuli well known to cause necrosis can lead to apoptosis instead when cells are exposed to the same noxious agents at lower concentrations.

Malignant tumors (cancers) are the second leading cause of death in the United States, after heart disease (Boring et al., *CA Cancel J. Clin.*, 43:7 (1993)).

Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state a cell proliferates under conditions in which the normal cells would not grow. Cancer manifests itself in a wide variety of forms, characterized by different degrees of invasiveness and aggressiveness.

Despite recent advances in cancer therapy, there is a great need for new therapeutic agents capable of inhibiting neoplastic cell growth. Accordingly, an objective of the present invention is methods and compositions capable of inhibiting the growth of neoplastic cells, such as cancer cells, by inducing apoptosis and necrosis.

SUMMARY OF THE INVENTION

The present invention is relates to embodiments including, but not limited to, GSSP-2 polypeptides, polynucleotides encoding GSSP-2 polypeptides, vectors comprising GSSP-2 polynucleotides, and cells comprising GSSP-2 polynucleotides, as well as to pharmaceutically and physiologically acceptable compositions comprising GSSP-2 polypeptides and methods of contacting neoplastic cells with GSSP-2 polypeptides to suppress tumor growth.

In particular, the present invention relates to methods and compositions for inhibiting neoplastic cell growth, killing neoplastic cells and treating cancer. More particularly, the invention concerns methods and compositions to inhibit cellular proliferation of neoplastic cells, induce cytotoxicity in neoplastic cells and kill neoplastic cells. These properties thus make GSSP-2 useful in the treatment neoplastic disease, including cancers, such as breast, prostate, colon, ovarian, renal, liver and CNS cancers, leukemia, lymphoma, sarcoma, melanoma, etc., preferably liver cancers, in mammalian patients, preferably humans.

A first embodiment of the invention is a recombinant, purified or isolated polynucleotide comprising, or consisting of a mammalian genomic sequence, gene, or fragments thereof. In one aspect the sequence is derived from a human, mouse or other mammal. In a preferred aspect, the genomic sequence includes isolated, purified, or recombinant polynucleotides comprising a contiguous span of at least 12, 15, 18, 20, 22, 25, 30, 35, 40, 50, 60, 70, 80, 90, 100, 150, 200, 500, 1000, 2000, 5000, 10000 or 50000 nucleotides of SEQ ID NO: 1, or the complements thereof, wherein said contiguous span comprises at least 1, 2, 3, 5, 6, 7 or 8 of the following nucleotide positions of SEQ ID NO: 1: 739–1739; 10946–12958; 13470–13526; 13641–13752; 14271–17969; 41718–42718; 44942–45942; and 76558–77558. Further preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1, or the complements thereof, wherein said contiguous span contains one or more of the nucleotides at positions 1239, 12347, 15241, 42218, 45442, or 77058. Optionally, the polynucleotide consists of, consists essentially of, or comprises a contiguous span of nucleotides of a human genomic sequence, preferably a sequence selected from SEQ ID NO: 1, wherein said contiguous span is at least 6, 8, 10, 12, 15, 20, 25, 30, 50, 100, 200, 500 or 1000 nucleotides in length and contains one or more of the nucleotides at positions 13269 or 13475.

Another embodiment of the invention is a recombinant, purified or isolated polynucleotide comprising, or consisting of a mammalian genomic sequence, gene, or fragments thereof. In one aspect the sequence is derived from a human, mouse or other mammal. In a preferred aspect, the genomic sequence is selected from the human genomic sequence of SEQ ID NO: 4. Optionally, the polynucleotide consists of, consists essentially of, or comprises a contiguous span of nucleotides of a human genomic sequence, preferably a sequence selected from SEQ ID NO: 4, wherein said contiguous span is at least 6, 8, 10, 12, 15, 20, 25, 30, 50, 100, 200, 500, 1000, 2000, 3000, 4000 or 5000 nucleotides in length and contains one or more of the nucleotides at positions 1241 or 1447. Optionally, the polynucleotide consists of, consists essentially of, or comprises a contiguous span of nucleotides of a human genomic sequence, preferably SEQ ID NO: 4, wherein said contiguous span comprises at least 6, 8, 10, 12, 15, 20, 25, 30, 50, 100, 200, 500 or 1000 nucleotides of the following nucleotide positions of SEQ ID NO: 4: 1–1498, 1613–1724, 2243–3940, and 3941–5381.

Another embodiment of the present invention is a recombinant, purified or isolated polynucleotide comprising, or consisting of a mammalian cDNA sequence, or fragments thereof. In one aspect the sequence is derived from a human, mouse or other mammal. In a preferred aspect, the cDNA sequence is selected from the human cDNA sequence of SEQ ID NO: 2 or the complement thereto. Optionally, said polynucleotide consists of, consists essentially of, or comprises a contiguous span of nucleotides of a mammalian cDNA sequence, preferably SEQ ID NO: 2. Preferred fragments of said cDNA include the fragments delineated by the exons of SEQ ID NO:4 (1–1498, 1613–1724, 2243–3940 and 3941–5381).

A further embodiment of the present invention is a recombinant, purified or isolated polynucleotide, or the complement thereof, encoding a mammalian GSSP-2 protein, fragment thereof or other polypeptide of the present invention. In one aspect the GSSP-2 protein sequence is from a human, mouse or other mammal. In a preferred aspect, the GSSP-2 protein sequence is selected from the human GSSP-2 protein sequence of SEQ ID NO: 3. Optionally, said fragment of GSSP-2 polynucleotide consists of, consists essentially of, or comprises a nucleic acid sequence encoding a contiguous stretch of at least 8, 10, 12, 15, 20, 25, 30, 50, 100, 200, 300 or 350 amino acids from SEQ ID NO: 3, as well as any other human, mouse or mammalian GSSP-2 polypeptide of the present invention. The invention further includes polypeptides and isolated nucleic acid molecules encoding such polypeptides, including mRNAs, DNAs, cDNAs, genomic DNA as well as biologically active and diagnostically or therapeutically useful fragments, analogs and derivatives thereof.

A further embodiment of the invention is a purified or isolated mammalian GSSP-2 gene or cDNA sequence, or polynucleotide encoding a mammalian GSSP-2 polypeptide or fragment thereof.

An embodiment of the invention is the polynucleotide primers and probes disclosed herein.

An embodiment of the present invention is a recombinant, purified or isolated polypeptide comprising or consisting of a mammalian GSSP-2 protein, or a fragment thereof. In one aspect the GSSP-2 protein sequence is from a human, mouse or other mammal. In a preferred aspect, the GSSP-2 protein sequence is selected from the human GSSP-2 protein sequence of SEQ ID NO: 3. Optionally, said fragment of GSSP-2 polypeptide consists of, consists essentially of, or comprises a contiguous stretch of at least 8, 10, 12, 15, 20, 25, 30, 50, 100, 200, 300 or 350 amino acids from SEQ ID NO: 3, as well as any other human, mouse or mammalian GSSP-2 polypeptide. The invention further includes polypeptides and isolated nucleic acid molecules encoding such polypeptides, including mRNAs, DNAs, cDNAs, genomic DNA as well as biologically active and diagnostically or therapeutically useful fragments, analogs and derivatives thereof. The invention also includes a chimeric molecule comprising a polypeptide fused to a heterologous amino acid sequence.

Another embodiment of the invention encompasses any polynucleotide or polypeptide of the invention attached to a solid support. In addition, the polynucleotides or polypeptides of the invention which are attached to a solid support encompass polynucleotides or polypeptides with any further limitation described in this disclosure. Optionally, said polynucleotides or polypeptides are specified as attached individually or in groups of at least 2, 5, 8, 10, 12, 15, 20, or 25 distinct polynucleotides of the inventions to a single solid support. Optionally, when multiple polynucleotides or polypeptides are attached to a solid support they are attached at random locations, or in an ordered array. Optionally, said ordered array is addressable.

Another embodiment of the present invention is an antibody composition capable of specifically binding to a polypeptide of the invention. Optionally, said antibody is polyclonal or monoclonal. Optionally, said polypeptide is an epitope-containing fragment of at least 8, 10, 12, 15, 20, 25, or 30 amino acids of a human, mouse, or mammalian GSSP-2 protein, preferably a sequence selected from SEQ ID NO: 3.

A further embodiment of the present invention is a vector comprising any polynucleotide of the invention. Optionally, said vector is a cloning vector, an expression vector, gene therapy vector, amplification vector, gene targeting vector, or knock-out vector.

A further embodiment of the present invention is a host cell recombinant for any vector or polynucleotide of the invention.

A further embodiment of the present invention is a mammalian host cell comprising a GSSP-2 regulatory region (e.g., 5' promoter) or exonic or intronic or any combination thereof altered or disrupted by homologous recombination with a knock out or knock in vector.

A further embodiment of the present invention is a nonhuman host mammal or animal comprising a polynucleotide of the invention.

In another related aspect, the invention features a cell that is recombinant for a polynucleotide encoding a GSSP-2 polypeptide of the invention. In a preferred embodiment of this aspect, the polynucleotide is expressed in the cell. In various preferred embodiments, the cell is present in a patient having a disease that is caused by excessive cell growth or insufficient cell death and the cell is selected from the group that includes bladder carcinoma, hepatocarcinoma, hepatoblastoma, rhabdomyosarcoma, ovarian carcinoma, cervical carcinoma, lung carcinoma, breast carcinoma, squamous cell carcinoma in head and neck, esophageal carcinoma, thyroid carcinoma, astrocytoma, ganglioblastoma, neuroblastoma, lymphoma, myeloma, sarcoma and neuroepithelioma.

An embodiment of the present invention is a transgenic animal generated from a cell genetically engineered to lack nucleic acid molecule encoding a GSSP-2 polypeptide, where the transgenic animal lacks expression of the GSSP-2 polypeptide.

In a related aspect, the invention features a transgenic animal generated from a cell that contains a substantially pure nucleic acid molecule that replaces DNA encoding a GSSP-2 polypeptide, where the nucleic acid molecule is expressed in the transgenic animal.

An embodiment of the present invention includes the nucleic acid and amino acid sequences of mutant or low frequency GSSP-2 alleles derived from neoplastic patients, tissues or cell lines. The present invention also encompasses methods which utilize detection of these mutant GSSP-2 sequences in an individual or tissue sample to diagnosis a neoplastic disease, assess the risk of developing a neoplastic disease or assess the likely severity of said disorder. An embodiment of the present invention is a method of obtaining an allele of the GSSP-2 gene which is associated with a detectable phenotype comprising obtaining a nucleic acid sample from an individual expressing the detectable phenotype, contacting the nucleic acid sample with an agent capable of specifically detecting a nucleic acid molecule encoding the GSSP-2 protein, and isolating the nucleic acid molecule encoding the GSSP-2 protein. In one aspect of this method, the contacting step comprises contacting the nucleic acid sample with at least one nucleic acid probe capable of specifically hybridizing to said nucleic acid molecule encoding the GSSP-2 protein. In another aspect of this embodiment, the contacting step comprises contacting the nucleic acid sample with an antibody capable of specifically binding to the GSSP-2 protein. In another aspect of this embodiment, the step of obtaining a nucleic acid sample from an individual expressing a detectable phenotype comprises obtaining a nucleic acid sample from an individual suffering from a neoplastic disease.

Another embodiment of the present invention is a method of obtaining an allele of the GSSP-2 gene which is associated with a detectable phenotype comprising obtaining a nucleic acid sample from an individual expressing the detectable phenotype, contacting the nucleic acid sample with an agent capable of specifically detecting a sequence within the 11 q23 region of the human genome, identifying a nucleic acid molecule encoding the GSSP-2 protein in the nucleic acid sample, and isolating the nucleic acid molecule encoding the GSSP-2 protein. In one aspect of this embodiment, the nucleic acid sample is obtained from an individual suffering from a neoplastic disease (e.g., cancer).

A further embodiment of the invention encompasses methods of genotyping a biological sample comprising determining the identity of an allele at an GSSP-2-related biallelic marker. In addition, the genotyping methods of the invention encompass methods with any further limitation described in this disclosure, or those following: Optionally, said GSSP-2-related biallelic marker is a GSSP-2-related biallelic marker positioned in SEQ ID NOs: 1, 2 or 4; one or more GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250. Optionally, said method further comprises determining the identity of a second allele at said biallelic marker, wherein said first allele and second allele are not base paired (by Watson & Crick base pairing) to one another. Optionally, said biological sample is derived from a single individual or subject. Optionally, said method is performed in vitro. Optionally, said biallelic marker is determined for both copies of said biallelic marker present in said individual's genome. Optionally, said biological sample is derived from multiple subjects or individuals. Optionally, said method further comprises amplifying a portion of said sequence comprising the biallelic marker prior to said determining step. Optionally, wherein said amplifying is performed by PCR, LCR, or replication of a recombinant vector comprising an origin of replication and said portion in a host cell. Optionally, wherein said determining is performed by a hybridization assay, sequencing assay, microsequencing assay, or allele-specific amplification assay.

An additional embodiment of the invention comprises methods of estimating the frequency of an allele in a population comprising determining the proportional representation of an allele at a GSSP-2-related biallelic marker in said population. In addition, the methods of estimating the frequency of an allele in a population of the invention encompass methods with any further limitation described in this disclosure, or those following: Optionally, said GSSP-2-related biallelic marker is a GSSP-2-related biallelic marker positioned in SEQ ID NOs: 1, 2 or 4; one or more GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250. Optionally, determining the proportional representation of an allele at a GSSP-2-related biallelic marker is accomplished by determining the identity of the alleles for both copies of said biallelic marker present in the genome of each individual in said population and calculating the proportional representation of said allele at said GSSP-2-related biallelic marker for the population. Optionally, determining the proportional representation is accomplished by performing a genotyping method of the invention on a pooled biological sample derived from a representative number of individuals, or each individual, in said population, and calculating the proportional amount of said nucleotide compared with the total.

A further embodiment of the invention comprises methods of detecting an association between a genotype and a phenotype, comprising the steps of a) genotyping at least one GSSP-2-related biallelic marker in a trait positive population according to a genotyping method of the invention; b) genotyping said GSSP-2-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following: SEQ ID NOs: 1, 2 or 4; one or more GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250. Optionally, said control population is a trait negative population, or a random population. Optionally, each of said genotyping steps a) and b) is performed on a single pooled biological sample derived from each of said populations. Optionally, each of said genotyping of steps a) and b) is performed separately on biological samples derived from each individual in said population or a subsample thereof. Optionally, said phenotype is a neoplastic disease; a response to an agent acting on lipid metabolism and/or liver related disorders; or a side effect to an agent acting on lipid metabolism. Optionally, said method comprises the additional steps of determining the phenotype in said trait positive and said control populations prior to step c).

An additional embodiment of the present invention encompasses methods of estimating the frequency of a haplotype for a set of biallelic markers in a population, comprising the steps of: a) genotyping at least one GSSP-2-related biallelic marker for both copies of said set of biallelic marker present in the genome of each individual in said population or a subsample thereof, according to a genotyping method of the invention; b) genotyping a second biallelic marker by determining the identity of the allele at said second biallelic marker for both copies of said second biallelic marker present in the genome of each individual in said population or said subsample, according to a genotyping method of the invention; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, or those following: Optionally, said GSSP-2-related biallelic marker is a GSSP-2-related biallelic marker positioned in SEQ ID NOs: 1, 2 or 4; one or more GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250. Optionally, said haplotype determination method is an expectation-maximization algorithm.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following: Optionally, said GSSP-2-related biallelic is a GSSP-2-related biallelic marker positioned in SEQ ID NOs: 1, 2 or 4; one or more GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250. Optionally, said haplotype exhibits a p-value of less than $1 \times 10^{-3}$ in an association with a trait positive population with a disorder, preferably a neoplastic disease. Optionally, said control population is a trait negative population, or a random population. Optionally, said phenotype is a neoplastic disease; a response to an agent acting on a neoplastic disease; or a side effect to an agent acting on a neoplastic disease. Optionally, said method comprises the additional steps of determining the phenotype in said trait positive and said control populations prior to step c).

Another embodiment of the present invention comprises a method of identifying molecules which specifically bind to a GSSP-2 protein, preferably the protein of SEQ ID NO: 3 or a portion thereof: comprising the steps of introducing a nucleic a nucleic acid molecule encoding the protein of SEQ ID NO: 3 or a portion thereof into a cell such that the protein of SEQ ID NO: 3 or a portion thereof contacts proteins expressed in the cell and identifying those proteins expressed in the cell which specifically interact with the protein of SEQ ID NO: 3 or a portion thereof.

Another embodiment of the present invention is a method of identifying molecules which specifically bind to the protein of SEQ ID NO: 3 or a portion thereof. One step of the method comprises linking a first nucleic acid molecule encoding the protein of SEQ ID NO: 3 or a portion thereof to a first indicator nucleic acid molecule encoding a first indicator polypeptide to generate a first chimeric nucleic acid molecule encoding a first fusion protein. The first fusion protein comprises the protein of SEQ ID NO: 3 or a portion thereof and the first indicator polypeptide. Another step of the method comprises linking a second nucleic acid molecule encoding a test polypeptide to a second indicator nucleic acid molecule encoding a second indicator polypeptide to generate a second chimeric nucleic acid molecule encoding a second fusion protein. The second fusion protein comprises the test polypeptide and the second indicator polypeptide. Association between the first indicator protein and the second indicator protein produces a detectable result.

Another step of the method comprises introducing the first chimeric nucleic acid molecule and the second chimeric nucleic acid molecule into a cell. Another step comprises detecting the detectable result.

An embodiment of the present invention is a method of identifying a compound that modulates apoptosis and/or necrosis. The method includes: (a) providing a cell that has a GSSP-2 gene; (b) contacting the cell with a candidate compound; and (c) monitoring expression of the GSSP-2 gene, where an alteration in the level of expression of the GSSP-2 gene indicates the presence of a compound which modulates apoptosis and/or necrosis. In one preferred embodiment of this aspect, the alteration that is an increase of GSSP-2 mRNA or protein indicates the compound is increasing apoptosis or necrosis, and the alteration that is a decrease indicates the compound is decreasing apoptosis and/or necrosis. In various embodiments of this aspect, the cell is transformed and the cell is not able to induce apoptosis and/or necrosis.

In a related aspect, the invention features another method of identifying a compound that is able to modulate apoptosis and/or necrosis that includes: (a) providing a cell including a reporter gene operably linked to a promoter from a GSSP-2 gene; (b) contacting the cell with a candidate compound; and (c) measuring expression of the reporter gene, where a change in the expression in response to the candidate compound identifies a compound that is able to modulate apoptosis and/or necrosis. In one preferred embodiment of this aspect, the alteration that is an increase in reporter gene activity indicates the compound is increasing apoptosis and/or necrosis, and the alteration that is a decrease indicates the compound is decreasing apoptosis and/or necrosis.

An embodiment of the present invention is a method of identifying a compound that is able to inhibit GSSP-2-mediated apoptosis and/or necrosis that includes: (a) providing a cell expressing or contacted with an apoptosis and/or necrosis-inducing amount of GSSP-2; (b) contacting the cell with a candidate compound; and (c) measuring the level of apoptosis and/or necrosis in the cell, where a decrease in the level of apoptosis and/or necrosis relative to a level of apoptosis and/or necrosis in a cell not contacted with the candidate compound indicates a compound that is able to inhibit GSSP-2-mediated apoptosis and/or necrosis. In various embodiments of this aspect, the cell is transformed and the cell is not able to induce apoptosis and/or necrosis.

An embodiment of the present invention is a method of identifying a compound that is able to induce GSSP-2-mediated apoptosis and/or necrosis that includes: (a) providing a cell expressing or contacting with an apoptosis and/or necrosis-inducing amount of GSSP-2; (b) contacting the cell with a candidate compound; and (c) measuring level of apoptosis and/or necrosis in the cell, where an increase in the level relative to a level in a cell not contacted with the candidate compound indicates a compound that able to induce GSSP-2-mediated apoptosis and/or necrosis. In various embodiments of this aspect, the cell is transformed and the cell is not able to induce apoptosis and/or necrosis.

A further embodiment of the present invention is a method of inducing apoptosis and/or necrosis in a cell by contacting the cell with an apoptosis and/or necrosis inducing amount of GSSP-2 polypeptide or fragment thereof.

In related aspects, the invention includes methods of inducing apoptosis and/or necrosis by either providing a transgene encoding a GSSP-2 polypeptide or fragment thereof to a cell of an animal such that the transgene is positioned for expression in the cell; or by administering to the cell a compound which increases GSSP-2 biological activity in a cell.

An embodiment of the invention is a method of inhibiting the cellular proliferation of a neoplastic cell comprising: (a) contacting said cell with an effective amount of a polypeptide of SEQ ID NO: 3 or a polypeptide encoded by the human cDNA of clone 117-005-2-0-E10-FLC, or an apoptosis or cytotoxicity inducing polypeptide fragment of SEQ ID NO: 3 or clone 117-005-2-0-E10-FLC. In another aspect of the invention, said neoplastic cell is selected from the group consisting of a hepatocellular carcinoma cell and a lymphoma cell. In another aspect of the invention, said neoplastic cell is a transformed cell. In yet another aspect of the invention, said neoplastic cells are from a malignant tumor or benign tumor.

Another embodiment of the invention is a method of preferentially inhibiting the cellular proliferation of a neoplastic cell compared to a normal cell comprising: (a) contacting said cell with an effective amount of a polypeptide of the present invention or a polypeptide encoded by the human cDNA of clone 117-005-2-0-E10-FLC, or an apoptosis or cytotoxicity inducing polypeptide fragment of SEQ ID NO: 3 or clone 117-005-2-0-E10-FLC. In a preferred aspect of the invention, said neoplastic cell is selected from the group consisting of hepatocellular carcinoma cell and a lymphoma cell. In another aspect of the invention, said neoplastic cell is a transformed cell. In yet another aspect of the invention, said neoplastic cell is a cell of a malignant or benign tumor.

Another embodiment of the invention is a method of inducing cytotoxicity in a neoplastic cell comprising: (a) contacting said cell with an effective amount of a polypeptide of SEQ ID NO: or a polypeptide encoded by the human cDNA of clone 117-005-2-0-E10-FLC, or a cytotoxicity-inducing polypeptide fragment of SEQ ID NO: 3 or clone 117-005-2-0-E10-FLC. In one aspect of the invention, inducing cytotoxicity refers to inducing apoptosis. In another aspect, inducing cytotoxicity refers to inducing necrosis. In another aspect of the invention, said neoplastic cell is selected from the group consisting of hepatocellular carcinoma cell and a lymphoma cell. In another aspect of the invention, said neoplastic cell is a transformed cell. In yet another aspect of the invention, said neoplastic cell is a cell of a malignant or benign tumor.

Another embodiment of the invention is a method of preferentially inducing cytotoxicity in a neoplastic cell compared to a normal cell comprising: (a) contacting said cell with an effective amount of a polypeptide of SEQ ID NO: 3 or a polypeptide encoded by the human cDNA of clone 117-005-2-0-E10-FLC, or an cytotoxicity inducing polypeptide fragment of SEQ ID NO: 3 or clone 117-005-2-0-E10-FLC. In one aspect of the invention, inducing cytotoxicity refers to inducing apoptosis. In another aspect, inducing cytotoxicity refers to inducing necrosis. In another aspect of the invention, said neoplastic cell is selected from the group consisting of hepatocellular carcinoma cell and a lymphoma cell. In another aspect of the invention, said neoplastic cell is a transformed cell. In yet another aspect of the invention, said neoplastic cell is a cell of a malignant or benign tumor.

In preferred embodiment, the GSSP-2 is from a mammal (e.g., a human or rodent); the cell is in a mammal (e.g., a human or rodent); the cell is in a mammal diagnosed or suspected as having a condition involving neoplastic cell growth, (e.g., a cancer such as prostate cancer, skin cancer, pancreatic carcinoma, colon cancer, melanoma, ovarian cancer, liver cancer, small cell lung carcinoma, non-small cell lung carcinoma, cervical cancer, breast cancer, bladder cancer, brain cancer, neuroblastoma/glioblastoma, leukemia, head and neck cancer, kidney cancer, lymphoma, myeloma and ovarian cancer).

Another embodiment of the invention is a method of suppressing tumor growth comprising: (a) contacting said tumor with an effective amount of a polypeptide of SEQ ID NO: 3 or a polypeptide encoded by the human cDNA of clone 117-005-2-0-E10-FLC, or an apoptosis and/or necrosis inducing polypeptide fragment of SEQ ID NO: 3 or clone 117-005-2-0-E10-FLC. The method of suppressing tumor growth comprises the effects selected from the group consisting of: (a) inhibiting cell growth or proliferation in said tumor; (b) killing cells in said tumor; (c) inducing apoptosis in said tumor; (d) inducing necrosis in said tumor; (e) preventing or inhibiting tumor cell invasion; and (f) preventing or inhibiting tumor cell metastasis. In another aspect of the invention, said tumor is selected from the group consisting of bladder carcinoma, hepatocarcinoma, hepatoblastoma, rhabdomyosarcoma, ovarian carcinoma, cervical carcinoma, lung carcinoma, breast carcinoma, squamous cell carcinoma in head and neck, esophageal carcinoma, thyroid carcinoma, astrocytoma, ganglioblastoma, neuroblastoma, lymphoma, myeloma, sarcoma and neuroepithelioma. In yet another aspect of the invention, said tumor is malignant or benign.

An embodiment of the present invention is a method of treating a patient having a neoplastic disease (e.g., cancer) characterized by proliferation of neoplastic cells which comprises administering to the patient an amount of a polypeptide of the invention, effective to: (a) selectively induce apoptosis and/or necrosis in such neoplastic cells and thereby inhibit their proliferation; (b) inhibit cell growth and proliferation of the neoplastic cells; (c) inhibit invasion of the neoplastic cells; (d) inhibit metastasis of the neoplastic cells; (e) kill neoplastic cells; (g) preferentially inhibit cell growth and proliferation of the neoplastic cells; and (h) preferentially kill neoplastic cells.

Another embodiment of the present invention features a method of treating a neoplastic disease in an individual comprising administering to an individual in need of such treatment an GSSP-2 polypeptide of the invention in a pharmaceutically or physiologically acceptable composition such as a composition comprising a carrier. Alternatively, antagonists or agonists of GSSP-2 activity can be provided, or compounds that enhance or inhibit the expression of GSSP-2.

The present invention further relates to methods of preferentially killing neoplastic cells and treating diseases/disorders such as cancer, (e.g., prostate cancer, skin cancer, pancreatic carcinoma, colon cancer, melanoma, ovarian cancer, liver cancer, small cell lung carcinoma, non-small cell lung carcinoma, cervical cancer, breast cancer, bladder cancer, brain cancer, neuroblastoma/glioblastoma, leukemia, head and neck cancer, kidney cancer, lymphoma, myeloma and ovarian cancer).

The present invention also relates to pharmaceutical or physiologically acceptable compositions comprising, an active agent, the polypeptides, polynucleotide or antibodies of the present invention. A preferred composition further comprises a carrier.

The present invention relates to an article of manufacture comprising: (a) a container; and (b) a composition comprising an active agent contained within the container; wherein said active agent in the composition is a GSSP-2 polypeptide, or an agonist thereof. A preferred composition comprises a further growth inhibitory agent, cytotoxic agent or chemotherapeutic agent.

Another embodiment of the present invention is a method of administering a drug or a treatment comprising the steps of: a) obtaining a nucleic acid sample from an individual; b) determining the identity of the polymorphic base of at least one GSSP-2-related biallelic marker which is associated with a positive response to the treatment or the drug; or at least one biallelic GSSP-2-related biallelic marker which is associated with a negative response to the treatment or the drug; and c) administering the treatment or the drug to the individual if the nucleic acid sample contains said biallelic marker associated with a positive response to the treatment or the drug or if the nucleic acid sample lacks said biallelic marker associated with a negative response to the treatment or the drug. In addition, the methods of the present invention for administering a drug or a treatment encompass methods with any further limitation described in this disclosure, or those following, specified alone or in any combination: optionally, said GSSP-2-related biallelic marker may be in a sequence selected individually or in any combination from the group consisting of SEQ ID NOs: 1, 2 and 4; and the complements thereof; or optionally, the administering step comprises administering the drug or the treatment to the individual if the nucleic acid sample contains said biallelic marker associated with a positive response to the treatment or the drug and the nucleic acid sample lacks said biallelic marker associated with a negative response to the treatment or the drug.

Another embodiment of the present invention is a method of selecting an individual for inclusion in a clinical trial of a treatment or drug comprising the steps of: a) obtaining a nucleic acid sample from an individual; b) determining the identity of the polymorphic base of at least one GSSP-2-related biallelic marker which is associated with a positive response to the treatment or the drug, or at least one GSSP-2-related biallelic marker which is associated with a negative response to the treatment or the drug in the nucleic acid sample, and c) including the individual in the clinical trial if the nucleic acid sample contains said GSSP-2-related biallelic marker associated with a positive response to the treatment or the drug or if the nucleic acid sample lacks said biallelic marker associated with a negative response to the treatment or the drug. In addition, the methods of the present invention for selecting an individual for inclusion in a clinical trial of a treatment or drug encompass methods with any further limitation described in this disclosure, or those following, specified alone or in any combination: Optionally, said GSSP-2-related biallelic marker may be in a sequence selected individually or in any combination from the group consisting of SEQ ID NOs: 1, 2 and 4; and the complements thereof; optionally, the including step comprises administering the drug or the treatment to the individual if the nucleic acid sample contains said biallelic marker associated with a positive response to the treatment or the drug and the nucleic acid sample lacks said biallelic marker associated with a negative response to the treatment or the drug.

Another embodiment of the present invention is a method of determining whether an individual is at risk of developing a neoplastic disease (e.g., cancer); and determining whether the nucleotides present at one or more of the GSSP-2-related biallelic markers of the invention are indicative of a risk of developing a neoplastic disease. Optionally, said GSSP-2-related biallelic marker is a GSSP-2-related biallelic marker positioned in SEQ ID NOs: 1, 2 or 4; one or more GSSP- 2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250.

Another embodiment of the present invention is a method of determining whether an individual is at risk of developing a neoplastic disease comprising obtaining a nucleic acid sample from the individual and determining whether the nucleotides present at one or more of the polymorphic bases in a GSSP-2-related biallelic marker. Optionally, said GSSP-2-related biallelic is a GSSP-2-related biallelic marker positioned in SEQ ID NOs: 1, 2 or 4; one or more of the GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250.

Another embodiment of the present invention is a method of categorizing the risk of an individual developing a neoplastic disease comprising the step of assaying a sample taken from the individual to determine whether the individual carries an allelic variant of GSSP-2 associated with an increased risk of a neoplastic disease. In one aspect of this embodiment, the sample is a nucleic acid sample. In another aspect a nucleic acid sample is assayed by determining the frequency of the GSSP-2 transcripts present. In another aspect of this embodiment, the sample is a protein sample. In another aspect of this embodiment, the method further comprises determining whether the GSSP-2 protein in the sample binds an antibody specific for a GSSP-2 isoform associated with a neoplastic disease.

Another embodiment of the present invention is a method of categorizing the risk of an individual developing a neoplastic disease comprising the step of determining whether the identities of the polymorphic bases of one or more biallelic markers which are in linkage disequilibrium with the GSSP-2 gene are indicative of an increased risk of a neoplastic disease. Another embodiment of the invention encompasses the use of any polynucleotide for, or any polynucleotide for use in, determining the identity of an allele at a GSSP-2-related biallelic marker. In addition, the polynucleotides of the invention for use in determining the identity of an allele at a GSSP-2-related biallelic marker encompass polynucleotides with any further limitation described in this disclosure, or those following: Optionally, said GSSP-2-related biallelic marker is a GSSP-2-related biallelic marker positioned in SEQ ID NOs: 1, 2 or 4; one or more GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250. Optionally, said polynucleotide may comprise a sequence disclosed in the present specification. Optionally, said polynucleotide may consist of, or consist essentially of any polynucleotide described in the present specification. Optionally, said determining is performed in a hybridization assay, sequencing assay, microsequencing assay, or allele-specific amplification assay. Optionally, said polynucleotide is attached to a solid support, array, or addressable array. Optionally, said polynucleotide is labeled.

Another embodiment of the invention encompasses the use of any polynucleotide for, or any polynucleotide for use in, amplifying a segment of nucleotides comprising an GSSP-2-related biallelic marker. In addition, the polynucleotides of the invention for use in amplifying a segment of nucleotides comprising a GSSP-2-related biallelic marker encompass polynucleotides with any further limitation described in this disclosure, or those following: Optionally, said GSSP-2-related biallelic marker is a GSSP-2-related biallelic marker positioned in SEQ ID NOs: 1, 2 or 4; one or more GSSP-2-related biallelic marker selected from the group consisting of 20-828-311, 17-42-319, 17-41-250, 20-841-149, 20-842-115, and 20-853-415; or more preferably a GSSP-2-related biallelic marker selected from the group consisting of 17-42-319 and 17-41-250. Optionally, said polynucleotide may comprise a sequence disclosed in the present specification. Optionally, said polynucleotide may consist of, or consist essentially of any polynucleotide described in the present specification. Optionally, said amplifying is performed by a PCR or LCR. Optionally, said polynucleotide is attached to a solid support, array, or addressable array. Optionally, said polynucleotide is labeled.

An additional embodiment of the present invention is a GSSP-2 nucleic acid molecule for use in modulating apoptosis, a GSSP-2 polypeptide for use in modulating apoptosis and/or necrosis, the use of a GSSP-2 polypeptide for the manufacture of a medicament for the modulation of apoptosis and/or necrosis, and the use of a GSSP-2 nucleic acid molecule for the manufacture of a medicament for the modulation of apoptosis and/or necrosis.

Additional embodiments and aspects of the present invention are set forth in the Detailed Description of the Invention and the Examples.

BRIEF DESCRIPTION OF THE DRAWINGS

FIG. 1 is a chart containing a list of the GSSP-2-related biallelic markers. Each marker is described by indicating its SEQ ID NO., the biallelic marker ID, and the "ORIGINAL" allele and the "ALTERNATIVE" allele.

FIG. 2 is a chart containing a list of biallelic markers surrounded by preferred sequences. In the column labeled, "POSITION RANGE OF PREFERRED SEQUENCE" of FIG. 2, regions of particularly preferred sequences are listed for each SEQ ID which contain a GSSP-2-related biallelic marker, as well as particularly preferred regions of sequences that may not contain a GSSP-2-related biallelic marker but, which are in sufficiently close proximity to a GSSP-2-related biallelic marker to be useful as amplification or sequencing primers.

FIGS. 3A and 3B are charts containing two nucleotide changes that conflict with existing genomic sequence. The SEQ ID NO., the position of conflict in SEQ ID No 1 and the corresponding position of conflict in SEQ ID No 4 as well as the "original" nucleotide present at the position of conflict in SEQ ID No 1 and the "alternative" nucleotide present at the position of conflict in SEQ ID No 4 are provided.

FIG. 4 is a chart listing microsequencing primers which may be used to genotype GSSP-2-related biallelic markers and other preferred microsequencing primers for use in genotyping GSSP-2-related biallelic markers. Each of the primers which falls within the strand of nucleotides included in the Sequence Listing are described by indicating their Sequence ID number and the positions of the first and last nucleotides (position range) of the primers in the Sequence ID. Since the sequences in the Sequence Listing are single stranded and half the possible microsequencing primers are composed of nucleotide sequences from the complementary strand, the primers that are composed of nucleotides in the complementary strand are described by indicating their SEQ ID numbers and the positions of the first and last nucleotides to which they are complementary (complementary position range) in the Sequence ID.

FIG. 5 is a chart listing amplification primers which may be used to amplify polynucleotides containing one or more GSSP-2-related biallelic markers. Each of the primers which falls within the strand of nucleotides included in the Sequence Listing are described by indicating their Sequence ID number and the positions of the first and last nucleotides (position range) of the primers in the Sequence ID. Since the sequences in the Sequence Listing are single stranded and half the possible amplification primers are composed of nucleotide sequences from the complementary strand, the primers that are composed of nucleotides in the complementary strand are defined by the SEQ ID numbers and the positions of the first and last nucleotides to which they are complementary (complementary position range) in the Sequence ID.

FIG. 6 is a chart listing preferred probes useful in genotyping GSSP-2-related biallelic markers by hybridization assays. The probes are generally 25-mers with a GSSP-2-related biallelic marker in the center position, and described by indicating their Sequence ID number and the positions of the first and last nucleotides (position range) of the probes in the Sequence ID. The probes complementary to the sequences in each position range in each Sequence ID are also understood to be a part of this preferred list even though they are not specified separately.

BRIEF DESCRIPTION OF THE SEQUENCE LISTING

Figure 7:
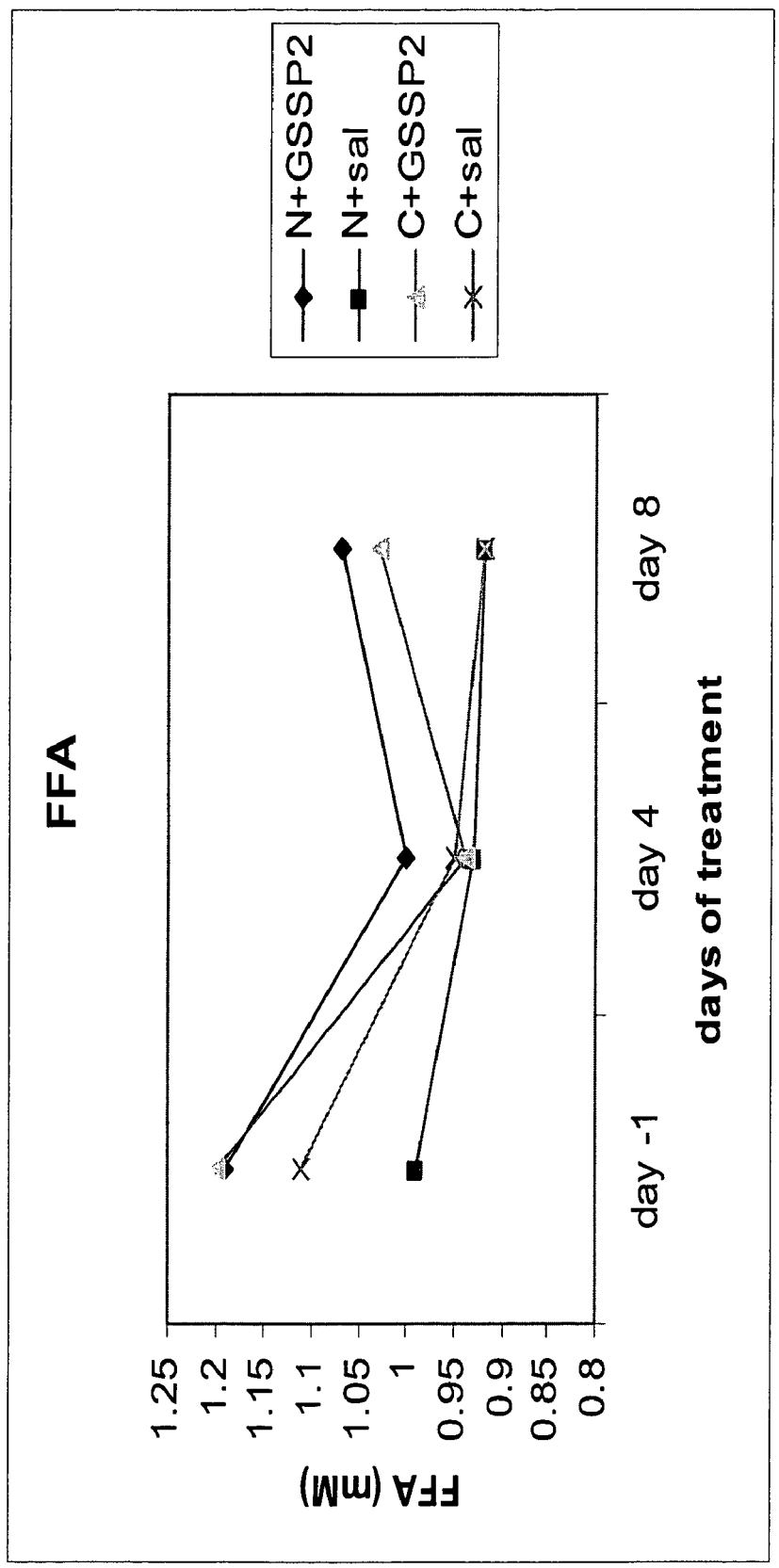
FIGS. 7, 8, 9, are graphs indicating the plasma levels of free fatty acids, glucose, triglycerides, respectively, after injecting GSSP2 in vivo.

SEQ ID NO: 1, Genbank Accession No. 007707, contains a partial genomic sequence from chromosome 11. The sequence comprises the 5' regulatory region (upstream untranscribed region), the exons and introns, and the 3' regulatory region (downstream untranscribed region) of GSSP-2.

SEQ ID NO: 2 contains a cDNA sequence of GSSP-2.

SEQ ID NO: 3 contains the amino acid sequence encoded by the cDNA of SEQ ID NO: 2.

SEQ ID NO: 4 contains an alternative genomic sequence of GSSP-2 comprising the 5' regulatory region (upstream untranscribed region), the exons and introns, and the 3' regulatory region (downstream untranscribed region).

SEQ ID NO: 5 contains a primer containing the additional PU 5' sequence described further in Example 1.

SEQ ID NO: 6 contains a primer containing the additional RP 5' sequence described further in Example 1.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine. The nucleotide code of the original allele for each biallelic marker is the following:

| Biallelic marker | Original allele |
|---|---|
| 5-124-273 | A (for example) |

In some instances, the polymorphic bases of the biallelic markers alter the identity of an amino acids in the encoded polypeptide. This is indicated in the accompanying Sequence Listing by use of the feature VARIANT, placement of an Xaa at the position of the polymorphic amino acid, and definition of Xaa as the two alternative amino acids. For example if one allele of a biallelic marker is the codon CAC, which encodes histidine, while the other allele of the biallelic marker is CAA, which encodes glutamine, the Sequence Listing for the encoded polypeptide will contain an Xaa at the location of the polymorphic amino acid. In this instance, Xaa would be defined as being histidine or glutamine. In addition, all of the possible combinations of possible sequences comprising a variant are included in, or may be excluded from, the present invention as individual species.

In other instances, Xaa may indicate an amino acid whose identity is unknown because of nucleotide sequence ambiguity. In this instance, the feature UNSURE is used, placement of an Xaa at the position of the unknown amino acid and definition of Xaa as being any of the 20 amino acids or a limited number of amino acids suggested by the genetic code.

DETAILED DESCRIPTION OF THE INVENTION

The invention includes a method of killing or inhibiting proliferation of neoplastic cells or reducing the metastasis and/or invasiveness of neoplastic cells. The cytotoxicity of GSSP-2 can be exploited preferably against neoplastic cells (e.g., hepatocarcinoma), as compared to normal cells. For example, the invention can be used to kill neoplastic cells. The mechanism by which this cytotoxicity occurs is not completely understood, but the selective killing of the cancer cells is believed to occur through apoptosis and necrosis.

GSSP-2-induced cell proliferation arrest and apoptotic activity can occur with less cytotoxicity to normal cells or tissues than is found with conventional cytotoxic therapeutics, preferably without substantial cytotoxicity to normal cells or tissues. For example, it has been unexpectedly observed that GSSP-2 can induce cytotoxicity in cancer cells while producing little or substantially no cytotoxicity in normal cells. Thus, unlike conventional cytotoxic anticancer therapeutics, which typically kill all growing cells, GSSP-2 can produce differential cytotoxicity: tumor cells are selectively killed whereas normal cells are spared.

Initially, analysis of GSSP-2 mRNA expression revealed that the gene is expressed selectively in the fetal liver and in the liver. Further, the expression of the mouse homologs is decreased in 2 animal models of obesity (namely, cafeteria-fed mice and NZO); therefore, the function of GSSP-2 was investigated. Recombinant GSSP-2 was produced in bacterial cells and purified. The human GSSP-2 cDNA was cloned and given the internal designation 117-005-2-0-E10-FLC. Clone 117-005-2-0-E10-FLC was deposited as part of a pool of clones with the European Collection of Cell Cultures (ECACC), CAMR, Porton Down, Salisbury, Wiltshire SP4 0JG, United Kingdom on Jun. 17, 1999 and given the accession No. 99061735. SEQ ID NO: 2 represents the nucleotide sequence of the GSSP-2 cDNA. SEQ ID NO: 3 represents the protein encoded by SEQ ID NO: 2.

The GSSP-2 gene is located on chromosome 11q23, and the genomic sequence extends over 4 kb. The GSSP-2 gene is present in a chimeric cosmid that corresponds to a translocation between chromosome 11q23 and 22q11. This is a frequent translocation that occurs as the result of meiotic malsegregation, and is found in families with acute myeloid leukemia, Ewing sarcoma and peripheral neuroepithelioma.

GSSP-2 was tested for biological effect in cultured cells. These assays included a standardized FACS-based analysis test for detection of apoptosis and necrosis in Jurkat cells, and evaluation of cell proliferation by conventional cell counting and Trypan blue exclusion. The results of this first screen were quite striking. Cell numbers were reduced by as much as 75% after 72 hours of treatment. The effect was determined to be dose dependent and can be detected with protein concentrations as low as 2.5 µg/ml. Further, the effect is saturable with maximum activity at concentrations greater than 50 µg/ml. Time course experiments suggested that the reduction in cell number was the result of an initial arrest in cell proliferation followed by the triggering of cell death (apoptosis and necrosis) which became evident as early as 48 hours after exposing the cells to GSSP2. Interestingly, incubation of Jurkat cells with GSSP-2 for only six hours was sufficient to trigger irreversible cell proliferation arrest and cell death (apoptosis and necrosis), which still occur 24–48 hours after removal of the protein from the cell culture.

In order to verify that the effects observed were due to GSSP-2 and not bacterial contaminant, the inventors carried out endotoxin removal from the protein preparation. Furthermore, in all experiments the inventors used a negative control that consisted of an irrelevant protein that had been prepared in the same exact fashion and which had no activity in their assays. Next, the inventors screened GSSP-2 effect on a series of transformed cell lines. In addition to Jurkat cells (a T lymphoma cell line), GSSP-2 also arrested cell proliferation and induced cytotoxicity in K562 cells (ATCC No. CCL-243). GSSP-2-induced cell proliferation arrest and cytotoxic activity was also observed in three hepatocarcinoma cell lines: Hep G2, Hep 3B and PLC. HELA cells, a human uterine cervical cancer carcinoma cell line, appear to exhibit an arrest of cellular proliferation when treated with GSSP-2; whereas, EL4 cells, a murine lymphoma cell line, appear to be the only transformed cells to be resistant to the GSSP-2-mediated effect. In contrast, GSSP-2 did not have any effect in any of the primary and untransformed cells tested thus far. These include primary rat hepatocytes, human fibroblasts, human peripheral blood mononuclear cells, and both mouse and human untransformed muscle cell lines. In conclusion, in vitro GSSP-2 has the potential for arresting or at least inhibiting cell proliferation and triggering cell death by way of apoptosis and necrosis in hepatocarcinoma and lymphoma cells without affecting normal hepatocytes and lymphocytes.

Further experiments were conducted to ascertain that the GSSP-2 protein is not toxic, or at least does not have a significant effect on the health of mice when administered in vivo. Twenty-five micrograms of GSSP-2 were administered to mice twice a day for a period of 8 days. No significant heath effects were observed, e.g. no significant differences in food intake or hepatic enzyme levels. Also, the protein of SEQ ID NO: 3 encoded by the cDNA of SEQ ID NO: 2 exhibits homology to apolipoprotein A-IV. Lipoproteins such as HDL and LDL contain characteristic apolipoproteins that are responsible for targeting them to certain tissues and for activating enzymes required for the trafficking of the lipid fraction of the lipoprotein, including cholesterol. GSSP-2 is 52% similar (29% identical) to apolipoprotein A-IV (apo A-IV) and therefore is likely to have a similar function, in addition to the embodiments described herein.

I. Definitions

Before describing the invention in greater detail, the following definitions are set forth to illustrate and define the meaning and scope of the terms used to describe the invention herein.

The terms "GSSP-2 gene," when used herein, encompasses genomic, mRNA and cDNA sequences encoding the GSSP-2 protein, including the untranslated regulatory regions of the genomic DNA. The "GSSP-2 gene" further refers to a sequence comprising or consisting of SEQ ID NOs: 1 or 4.

The term "heterologous protein" or "heterologous polynucleotide", when used herein, is intended to designate any polypeptide or polynucleotide other than a GSSP-2 protein of the invention.

The term "GSSP-2 biological activity" is intended for polypeptides exhibiting a biological or functional activity described herein which is at least similar, but not necessarily identical, to an activity of the full length or mature GSSP-2 polypeptide of the invention. The biological activity of a given polypeptide may be assessed using a suitable biological assay well known to those skilled in the art As used interchangeably herein, the terms "nucleic acid molecule", "oligonucleotide", and "polynucleotide", unless specifically stated otherwise, include RNA or, DNA (either single or double stranded, coding, complementary or antisense), or RNA/DNA hybrid sequences of more than one nucleotide in either single chain or duplex form (although each of the above species may be particularly specified). The term "nucleotide" as used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The polynucleotide sequences of the invention may be prepared by any known method, including synthetic, recombinant, ex vivo generation, or a combination thereof, as well as utilizing any purification methods known in the art. Methylenemethylimino linked oligonucleosides as well as mixed backbone compounds having, may be prepared as described in U.S. Pat. Nos. 5,378,825; 5,386,023; 5,489,677; 5,602,240; and 5,610,289. Formacetal and thioformacetal linked oligonucleosides may be prepared as described in U.S. Pat. Nos. 5,264,562 and 5,264,564. Ethylene oxide linked oligonucleosides may be prepared as described in U.S. Pat. No. 5,223,618. Phosphinate oligonucleotides may be prepared as described in U.S. Pat. No. 5,508,270. Alkyl phosphonate oligonucleotides may be prepared as described in U.S. Pat. No. 4,469,863. 3'-Deoxy-3'-methylene phosphonate oligonucleotides may be prepared as described in U.S. Pat. Nos. 5,610,289 or 5,625,050. Phosphoramidite oligonucleotides may be prepared as described in U.S. Pat. No. 5,256,775 or U.S. Pat. No. 5,366,878. Alkylphosphonothioate oligonucleotides may be prepared as described in published PCT applications WO 94/17093 and WO 94/02499. 3'-Deoxy-3'-amino phosphoramidate oligonucleotides may be prepared as described in U.S. Pat. No. 5,476,925. Phosphotriester oligonucleotides may be prepared as described in U.S. Pat. No. 5,023,243. Borano phosphate oligonucleotides may be prepared as described in U.S. Pat. Nos. 5,130,302 and 5,177,198. The polynucleotide sequences of the invention may be prepared by any known method, including synthetic, recombinant, ex vivo generation, or a combination thereof, as well as utilizing any purification methods known in the art.

The term "isolated" further requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. Specifically excluded from the definition of "isolated" are: naturally-occurring chromosomes (such as chromosome spreads), artificial chromosome libraries, genomic libraries, and cDNA libraries that exist either as an in vitro nucleic acid molecule preparation or as a transfected/transformed host cell preparation, wherein the host cells are either an in vitro heterogeneous preparation or plated as a heterogeneous population of single colonies. Also specifically excluded are the above libraries wherein a specified polynucleotide of the present invention makes up less than 5% of the number of nucleic acid molecule inserts in the vector molecules. Further specifically excluded are whole cell genomic DNA or whole cell RNA or mRNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

As used herein, the term "purified" does not require absolute purity; rather, it is intended as a relative definition. Individual 5' EST clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4-10^6$ fold purification of the native message. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both). As a preferred embodiment, the polynucleotides of the present invention are at least; 10%, 20%, 30%, 40%, 50%, 60%, 70%, 80%, 90%, 95%, 96%, 96%, 98%, 99%, or 100% pure relative to heterologous polynucleotides. As a further preferred embodiment the polynucleotides have an "at least" purity ranging from any number, to the thousandth position, between 90% and 100% (e.g., 5' EST at least 99.995% pure) relative to heterologous polynucleotides. Additionally, purity of the polynucleotides may be expressed as a percentage (as described above) relative to all materials and compounds other than the carrier solution. Each number, to the thousandth position, may be claimed as individual species of purity.

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

The terms "polypeptide", "peptides", "oligopeptide" and "protein" refer to a polymer of amino acids without regard to the length of the polymer; thus, the terms are used interchangeably. This term also does not specify or exclude chemical or post-expression modifications of the polypeptides of the invention, although chemical or post-expression modifications of these polypeptides may be included excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1–12 (1983); Seifter et al, Meth Enzymol 182: 626–646 (1990); Rattan et al., Ann NY Acad Sci 663:48–62 (1992).). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring. The term "polypeptide" may also be used interchangeably with the term "protein".

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the terms "recombinant polynucleotide" and "polynucleotide construct" are used interchangeably herein to refer to linear or circular, purified or isolated polynucleotides that have been artificially designed and which comprise at least two nucleotide sequences that are not found as contiguous nucleotide sequences in their initial natural environment. In particular, this terms mean that the polynucleotide or cDNA is adjacent to "backbone" nucleic acid molecules to which it is not adjacent in its natural environment. Additionally, to be "enriched" the cDNAs will represent 5% or more of the number of nucleic acid molecule inserts in a population of nucleic acid backbone molecules. Backbone molecules according to the present invention include nucleic acid molecules such as expression vectors, self-replicating nucleic acid, viruses, integrating nucleic acids, and other vectors or nucleic acid molecules used to maintain or manipulate a nucleic acid molecule insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousandth position, e.g., 99.5%) # of the number of nucleic acid inserts in the population of recombinant backbone molecules.

The term "purified polypeptide" is used herein to describe a polypeptide of the invention which has been separated from other compounds including, but not limited to nucleic acid molecules, lipids, carbohydrates and other proteins. A polypeptide is substantially pure when at least about 50%, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as polyacrylamide gel electrophoresis of a sample, followed by visualizing a single polypeptide band upon staining the gel. For certain purposes higher resolution can be provided by using HPLC or other means well known in the art.

As used herein, the term "non-human animal" refers to any non-human animal, including insects, birds, rodents and more usually mammals. Preferred non-human animals include: primates; farm animals such as swine, goats, sheep, donkeys, cattle, horses, chickens, rabbits; and rodents, preferably rats or mice. As used herein, the term "animal" is used to refer to any species in the animal kingdom, preferably vertebrates, including birds and fish, and more preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule, in this case a GSSP-2 polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope comprises at least 6 such amino acids, and more usually at least 8–10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506.

The term "domain" refers to an amino acid fragment with specific biological properties. This term encompasses all known structural and linear biological motifs. Examples of such motifs include but are not limited to leucine zippers, helix-turn-helix motifs, glycosylation sites, ubiquitination sites, alpha helices, and beta sheets, signal peptides which direct the secretion of the encoded proteins, sites for post-translational modification, enzymatic active sites, substrate binding sites, and enzymatic cleavage sites.

A "promoter" refers to a DNA sequence recognized by the synthetic machinery of the cell required to initiate the specific transcription of a gene.

A sequence which is "operably linked" to a regulatory sequence such as a promoter means that said regulatory element is in the correct location and orientation in relation to the nucleic acid molecule to control RNA polymerase initiation and expression of the nucleic acid molecule of interest.

As used herein, the term "operably linked" refers to a linkage of polynucleotide elements in a functional relationship. A sequence which is "operably linked" to a regulatory sequence such as a promoter means that said regulatory element is in the correct location and orientation in relation to the nucleic acid molecule to control RNA polymerase initiation and expression of the nucleic acid molecule of interest. For instance, a promoter or enhancer is operably linked to a coding sequence if it affects the transcription of the coding sequence.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease, a beneficial response to or side effects related to a treatment. Preferably, said trait can be, but not limited to, lipid metabolism related disorders and/or liver related disorders.

The term "allele" is used herein to refer to variants of a nucleotide sequence. A biallelic polymorphism has two forms. Diploid organisms may be homozygous or heterozygous for an allelic form.

The term "heterozygosity rate" is used herein to refer to the incidence of individuals in a population which are heterozygous at a particular allele. In a biallelic system, the heterozygosity rate is on average equal to $2 P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

The term "genotype" as used herein refers the identity of the alleles present in an individual or a sample. In the context of the present invention, a genotype preferably refers to the description of the biallelic marker alleles present in an individual or a sample. The term "genotyping" a sample or an individual for a biallelic marker involves determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention, a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. In the context of the present invention, "single nucleotide polymorphism" preferably refers to a single nucleotide substitution. Typically, between different individuals, the polymorphic site may be occupied by two different nucleotides.

The term "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

The invention also concerns GSSP-2-related biallelic markers. The term "GSSP-2-related biallelic marker" is used interchangeably herein to relate to all biallelic markers in linkage disequilibrium with the biallelic markers of the GSSP-2 gene. The term GSSP-2-related biallelic marker includes both the genic and non-genic biallelic markers described in Table 1.

The term "non-genic" is used herein to describe GSSP-2-related biallelic markers, as well as polynucleotides and primers which occur outside the nucleotide positions shown in the human GSSP-2 genomic sequence of SEQ ID No 1. The term "genic" is used herein to describe GSSP-2-related biallelic markers as well as polynucleotides and primers which do occur in the nucleotide positions shown in the human GSSP-2 genomic sequence of SEQ ID NOs: 1 and 4.

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, 4$^{th}$ edition, 1995).

The term "original nucleotide" refers to the nucleotides present at the conflict positions 1241 and 1447 of SEQ ID No 4 as previously identified in Genbank. They were previously identified as a T at position 13269 of SEQ ID No 1 and a G at position 13475 of SEQ ID No 1.

The term "alternative nucleotide" refers to the nucleotides present at the conflict positions 1241 and 1447 of SEQ ID No 4 as determined by the inventors. They are a C at position 1241 and an A at position 1447.

The term "neoplastic cells" as used herein refers to cells that result from abnormal new growth. A neoplastic cell further includes transformed cells, cancer cells including blood cancers and solid tumors (benign and malignant).

As used herein, the term "tumor" refers to an abnormal mass or population of cells that result from excessive cell division, whether malignant or benign, and all pre-cancerous and cancerous cells and tissues. A "tumor" is further defined as two or more neoplastic cells.

"Malignant tumors" are distinguished from benign growths or tumors in that, in addition to uncontrolled cellular proliferation, they will invade surrounding tissues and may additionally metastasize.

The term "transformed cells," "malignant cells" or "cancer" are interchangeable and refer to cells that have undergone malignant transformation, but may also include lymphocyte cells that have undergone blast transformation. Malignant transformation is a conversion of normal cells to malignant cells. Transformed cells have a greater ability to cause tumors when injected into animals. Transformation can be recognized by changes in growth characteristics, particularly in requirements for macromolecular growth factors, and often also by changes in morphology. Transformed cells usually proliferate without requiring adhesion to a substratum and usually lack cell to cell inhibition and pile up after forming a monolayer in cell culture.

The term "neoplastic disease" as used herein refers to a condition characterized by uncontrolled, abnormal growth of cells. Neoplastic diseases include cancer. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, kidney cancer, vulval cancer, thyroid cancer, hepatic carcinoma, skin cancer, melanoma, brain cancer, ovarian cancer, neuroblastoma, myeloma, various types of head and neck cancer, acute lymphoblastic leukemia, acute myeloid leukemia, Ewing sarcoma and peripheral neuroepithelioma. Preferred cancers include liver cancer, lymphoma, acute lymphoblastic leukemia, acute myeloid leukemia, Ewing sarcoma and peripheral neuroepithelioma. All of the possible cancers listed herein are included in, or may be excluded from, the present invention as individual species.

As used herein, the term "carcinoma" refers to a new growth that arises from epithelium, found in skin or, more commonly, the lining of body organs (adenocarcinoma), for example: breast, prostate, lung, stomach or bowel. Carcinomas include bladder carcinoma, hepatocarcinoma, hepatoblastoma, rhabdomyosarcoma, ovarian carcinoma, cervical carcinoma, lung carcinoma, breast carcinoma, colorectal carcinoma, uterine cervical cancer carcinoma, endometrioid carcinoma, paraganglioma, squamous cell carcinoma in head and neck, esophageal carcinoma, thyroid carcinoma, astrocytoma, neuroblastoma and neuroepithelioma. All of the possible carcinomas listed herein are included in, or may be excluded from, the present invention as individual species.

The term "immortalized cells" as used herein refers to cells reproduce indefinitely. The cells escape from the normal limitation on growth of a finite number of division cycles. The term does not include malignant cells.

The term "normal cells" as used herein refers to cells that have a limitation on growth, i.e. a finite number of division cycles (the Hayflick limit); therefore, is a non tumorigenic cell. Normal cell include primary cells, which is a cell or cell line taken directly from a living organism which is not immortalized.

The term "cell cycle" as used herein refers to the cyclic biochemical and structural events occurring during growth and division of cells. The stages of the cell cycle include $G_0$ (Gap 0; rest phase), G1 (Gap 1), S phase (DNA synthesis), G2 (Gap 2) and M phase (mitosis).

The term "cell growth" as used herein refers to an increase in the size of a population of cells.

The term "cell division" as used herein refers to mitosis, i.e., the process of cell reproduction.

The term "proliferation" as used herein means growth and division of cells. "Actively proliferating" means cells that are actively growing and dividing.

The term "inhibiting cellular proliferation" as used herein refers to slowing and/or preventing the growth and division of cells. Cells may further be specified as being arrested in a particular cell cycle stage: G1 (Gap 1), S phase (DNA synthesis), G2 (Gap 2) or M phase (mitosis).

The term "preferentially inhibiting cellular proliferation" as used herein refers to slowing and/or preventing the growth and division of cells as compared to normal cells.

The term "metastasis" refers to the transfer of disease (e.g., cancer) from one organ and/or tissue to another not directly connected with it. As used herein, metastasis refers to neoplastic cell growth in an unregulated fashion and spread to distal tissues and organs of the body.

The term "inhibiting metastasis" refers to slowing and/or preventing metastasis or the spread of neoplastic cells to a site remote from the primary growth area.

The term "invasion" as used herein refers to the spread of cancerous cells to surrounding tissues.

The term "inhibiting invasion" to slowing and/or preventing the spread of cancerous cells to surrounding tissues.

The term "apoptosis" as used herein refers to programmed cell death as signaled by the nuclei in normally functioning human and animal cells when age or state of cell health and condition dictates. "Apoptosis" is an active process requiring metabolic activity by the dying cell, often characterized by cleavage of the DNA into fragments that give a so called laddering pattern on gels. Cells that die by apoptosis do not usually elicit the inflammatory responses that are associated with necrosis, though the reasons are not clear. Cancerous cells, however, are unable to experience, or have a reduction in, the normal cell transduction or apoptosis-driven natural cell death process. Morphologically, apoptosis is characterized by loss of contact with neighboring cells, concentration of cytoplasm, endonuclease activity-associated chromatin condensation and pyknosis, and segmentation of the nucleus, among others.

The term "necrosis" as used herein refers to the sum of the morphological changes indicative of cell death and caused by the progressive degradative action of enzymes, it may affect groups of cells or part of a structure or an organ. Morphologically, necrosis is characterized by marked swelling of mitochondria, swelling of cytoplasm and nuclear alteration, followed by cell destruction and autolysis. It occurs passively or incidentally.

The term "inducing apoptosis" refers to increasing the number of cells that undergo apoptosis, or the rate by which cells undergo apoptosis, in a given cell population. Preferably, the cell population is selected from a group including hepatocellular carcinoma cells and lymphoma and leukemia (B and T) cells. It will be appreciated that the increase in apoptosis provided by a GSSP-2 polypeptide in a given assay or physiological environment will vary, but that one skilled in the art can determine the statistically significant change or a therapeutically effective change in the level of apoptosis which identifies a GSSP-2 polypeptide or a compound which modulates GSSP-2 or is a GSSP-2 therapeutic. Preferably the increase is at least 1.25, 1.5, 2, 5, 10, 50, 100, 500 or 1000 fold increase as compared to normal, untreated or negative control cells.

The term "inhibiting apoptosis" refers to any decrease in the number of cells which undergo apoptosis relative to an untreated control. Preferably, the decrease is at least 1.25, 1.5, 2, 5, 10, 50, 100, 500 or 1000 fold decrease as compared to normal, untreated or negative control cells.

The term "transgene" refers to any polynucleotide which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

The term "transgenic" refers to any cell which includes a DNA sequence which is inserted by artifice into a cell and becomes part of the genome of the organism which develops from that cell. As used herein, the transgenic organisms are generally transgenic mammals (e.g., rodents such as rats or mice) and the DNA (transgene) is inserted by artifice into the nuclear genome.

The term "knockout mutation" refers to an alteration in the nucleic acid sequence that reduces the biological activity of the polypeptide normally encoded therefrom by at least 80% relative to the unmutated gene. The mutation may, without limitation, be an insertion, deletion, frameshift mutation, or a missense mutation. Preferably, the mutation is an insertion or deletion, or is a frameshift mutation that creates a stop codon.

The term "knockin mutation" refers to an alteration in the nucleic acid sequence that increases the biological activity of the polypeptide normally encoded therefrom by at least 25% relative to the unmutated gene. The alternative is generally an insertion of a coding or regulatory sequence.

The term "positioned for expression" refers to a DNA molecule that is positioned adjacent to a DNA sequence which directs transcription and translation of the sequence (i.e., facilitates the production of, e.g., a GSSP-2 polypeptide, a recombinant protein or a RNA molecule).

The term "reporter gene" refers to any gene which encodes a product whose expression is detectable. A reporter gene product may have one of the following attributes, without restriction: fluorescence (e.g., green fluorescent protein), enzymatic activity (e.g., luciferase or chloramphenicol acetyl transferase), toxicity (e.g., ricin), or an ability to be specifically bound by a second molecule (e.g., biotin or a detectably labeled antibody).

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

The term "patient" as used herein refers to a mammal, including animals, preferably mice, rats, dogs, cats, cattle, sheep, or primates, most preferably humans that are in need of treatment.

The term "in need of such treatment" as used herein refers to a judgment made by a care giver such as a physician, nurse, or nurse practitioner in the case of humans that a patient requires or would benefit from treatment. This judgment is made based on a variety of factors that are in the realm of a care giver's expertise, but that include the knowledge that the patient is ill, or will be ill, as the result of a condition that is treatable by the compounds of the invention.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

"Carriers" as used herein include pharmaceutically or physiologically acceptable carriers, excipients, or stabilizers which are nontoxic to the cell or mammal being exposed thereto at the dosages and concentrations employed. Often the pharmaceutically or physiologically acceptable carrier is an aqueous pH buffered solution. Examples of pharmaceutically or physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The terms "pharmaceutically acceptable carrier" or "physiologically acceptable carrier" refer to a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in Remington's Pharmaceutical Sciences, (18.sup.th edition), ed. A. Gennaro, 1990, Mack Publishing Company, Easton, Pa.

An "effective amount" of a composition disclosed herein or an agonist thereof, in reference to "inhibiting the cellular proliferation" of a neoplastic cell, is an amount capable of inhibiting, to some extent, the growth of target cells. The term further includes an amount capable of invoking a growth inhibitory, cytostatic and/or cytotoxic effect and/or apoptosis and/or necrosis of the target cells. An "effective amount" of a GSSP-2 polypeptide or an agonist thereof for purposes of inhibiting neoplastic cell growth may be determined empirically and in a routine manner using methods well known in the art.

A "therapeutically effective amount", in reference to the treatment of neoplastic disease or neoplastic cells, refers to an amount capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder. A "therapeutically effective amount" of a GSSP-2 polypeptide or an agonist thereof for purposes of treatment of tumor may be determined empirically and in a routine manner.

A "growth inhibitory amount" of a GSSP-2 polypeptide or an agonist thereof is an amount capable of inhibiting the growth of a cell, especially a malignant tumor cell, e.g., cancer cell, either in vitro or in vivo. A "growth inhibitory amount" of a GSSP-2 polypeptide or an agonist thereof for purposes of inhibiting neoplastic cell growth may be determined empirically and in a routine manner using methods well known in the art.

A "cytotoxic amount" of a GSSP-2 polypeptide or an agonist thereof is an amount capable of causing the destruction of a cell, especially tumor, e.g., cancer cell, either in vitro or in vivo. A "cytotoxic amount" of a GSSP-2 polypeptide or an agonist thereof for purposes of inhibiting neoplastic cell growth may be determined empirically and in a routine manner using methods well known in the art.

The terms "killing" or "inducing cytotoxicity" as used herein refer to inducing cell death by either apoptosis and/or necrosis, whereby embodiments of the invention include only apoptosis, only necrosis and both apoptosis and necrosis.

The term "cytotoxic agent" as used herein refers to a substance that inhibits or prevents the function of cells, for example by inhibiting progression of the cell cycle, and/or causes cell death. The term is intended to include radioactive isotopes, chemotherapeutic agents, and toxins such as enzymatically active toxins of bacterial, fungal, plant or animal origin, or fragments thereof.

A "chemotherapeutic agent" is a chemical compound useful in the treatment of cancer, e.g., blood or solid tumor. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rh6ne-PoulencRorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see, U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits cell growth, especially neoplastic cell, e.g., cancer cells, either in vitro or in vivo. Thus, the growth inhibitory agent is one which significantly reduces the percentage of the target cells in anyone or all of the cell cycle phases, including $G_0$, G1, S phase, G2 and mitosis. Examples of growth inhibitory agents include agents that block cell cycle progression (at a place other than S phase), such as agents that induce G 1 arrest and M-3 phase arrest. Classical M-phase blockers include the vincas (vincristine and vinblastine), taxol, and topo 11 inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al., (W B Saunders: Philadelphia, 199), especially p. 13.

The term "agonist" is used in the broadest sense and includes any molecule that mimics a biological activity of a native GSSP-2 polypeptide disclosed herein. Suitable agonist molecules specifically include agonist antibodies or antibody fragments, fragments or amino acid sequence variants of native GSSP-2 polypeptides, peptides, small organic molecules, etc. Methods for identifying agonists of a GSSP-2 polypeptide may comprise contacting a tumor cell with a candidate agonist and measuring the inhibition of tumor cell growth.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

The terms "comprising", "consisting of" and "consisting essentially of" are defined according to their standard meaning. A defined meaning set forth in the M.P.E.P. controls over a defined meaning in the art and a defined meaning set forth in controlling Federal Circuit case law controls over a meaning set forth in the M.P.E.P. With this in mind, the terms may be substituted for one another throughout the instant application in order to attach a specific meaning associated with each term.

The term "host cell recombinant for" a particular polynucleotide of the present invention, means a host cell that has been altered by the hands of man to contain said polynucleotide in a way not naturally found in said cell. For example, said host cell may be transiently or stably transfected or transduced with said polynucleotide of the present invention.

SEQ ID NO: 3 and the corresponding polypeptide encoded by the human cDNA of the clone 117-005-2-0-E10-FLC may be substituted for one another, as may SEQ ID NO: 2 and the human cDNA of clone 117-005-2-0-E10-FLC.

Unless otherwise specified in the application, nucleotides and amino acids of polynucleotides and polypeptides respectively of the present invention are contiguous and not interrupted by heterologous sequences.

II. Polynucleotides of the Present Invention

A. Genomic Sequences of the GSSP-2 Gene

The present invention concerns the genomic sequence of GSSP-2. The present invention encompasses the GSSP-2 gene, or GSSP-2 genomic sequences consisting of, consisting essentially of, or comprising the sequence of SEQ ID NOs: 1 and 4, a sequence complementary thereto, as well as fragments and variants thereof. These polynucleotides may be purified, isolated, or recombinant.

The invention also encompasses a purified, isolated, or recombinant polynucleotide comprising a nucleotide sequence having at least 70, 75, 80, 85, 90, 95, 99, 99.8% nucleotide identity with a nucleotide sequence of SEQ ID NOs: 1 and 4 or a complementary sequence thereto or a fragment thereof. The nucleotide differences in regards to the nucleotide sequence of SEQ ID NOs: 1 and 4 may be randomly distributed throughout the entire nucleic acid molecule. Nevertheless, preferred nucleic acid molecules are those wherein the nucleotide differences as regards to the nucleotide sequence of SEQ ID NOs: 1 and 4 are predominantly located outside the coding sequences contained in the exons. These nucleic acid molecules, as well as their fragments and variants, may be used as oligonucleotide primers or probes in order to detect the presence of a copy of the GSSP-2 gene in a test sample, or alternatively in order to amplify a target nucleotide sequence within the GSSP-2 sequences.

Another object of the invention consists of a purified, isolated, or recombinant nucleic acid molecule that hybridizes with the nucleotide sequence of SEQ ID NOs: 1 and 4 or a complementary sequence thereto or a variant thereof, under the stringent hybridization conditions as defined above.

Particularly preferred nucleic acid molecules of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1, or the complements thereof, wherein said contiguous span comprises at least 1, 2, 3, 5, or 10 of the following nucleotide positions of SEQ ID No 1: 739–1739; 10946–12958; 13470–13526; 13641–13752; 14271–17969; 41718–42718; 44942–45942; and 76558–77558. Further preferred nucleic acid molecules of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1, or the complements thereof, wherein said contiguous span comprises a T at position 1239, a T at position 12347, a T at position 15241, a G at position 42218, an A at 45442, or a T at 77058. See Table 1 below. It should be noted that nucleic acid fragments of any size and sequence may also be comprised by the polynucleotides described in this section.

Particularly preferred nucleic acid molecules of the invention also include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4, or the complements thereof, wherein said contiguous span comprises at least 1, 2, 3, 5, or 10 of the following nucleotide positions of SEQ ID No 4: 1–1498; 1613–1724; 2243–3940; and 3941–5381. Additional preferred nucleic acid molecules of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4, or the complements thereof, wherein said contiguous span comprises one or more of the nucleotides at positions 1241 and 1447. Further preferred nucleic acid molecules of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4, or the complements thereof, wherein said contiguous span comprises a T at position 319 or a T at position 3213. See Table 1 below. It should be noted that nucleic acid fragments of any size and sequence may also be comprised by the polynucleotides described in this section.

TABLE 1

| BIALLELIC MARKER ID | ALLELES | POSITION OF BIALLELIC MARKER IN SEQ ID |
|---|---|---|
| Genic Biallelic Markers (SEQ ID NO: 1) | | |
| 17-42-319 | C/T | SEQ ID No 1, position 12347 |
| 17-41-250 | C/T | SEQ ID No 1, position 15241 |
| NON-GENIC BIALLELIC MARKERS (SEQ ID NO: 1) | | |
| 20-828-311 | C/T | SEQ ID NO 1, POSITION 1239 |
| 20-841-149 | A/G | SEQ ID No 1, position 42218 |
| 20-842-115 | A/G | SEQ ID No 1, position 45442 |
| 20-853-415 | C/T | SEQ ID No 1, position 77058 |
| Genic Biallelic markers (SEQ ID NO: 2) | | |
| 17-41-250 | C/T | SEQ ID NO 2, POSITION 1153 |
| GENIC BIALLELIC MARKERS (SEQ ID NO: 4) | | |
| 17-42-319 | C/T | SEQ ID NO 4, POSITION 319 |
| 17-41-250 | C/T | SEQ ID NO 4, POSITION 3213 |

The GSSP-2 genomic nucleic acid comprises 4 exons. The exon positions in SEQ ID NOs: 1 and 4 are detailed below in Table 2.

TABLE 2

| | Position in SEQ ID NO: 1 | | | Position in SEQ ID NO: 1 | |
|---|---|---|---|---|---|
| Exon | Beginning | End | Intron | Beginning | End |
| 1 | 12947 | 12958 | 1 | 12959 | 13469 |
| 2 | 13470 | 13526 | 2 | 13527 | 13640 |
| 3 | 13641 | 13752 | 3 | 13753 | 14270 |
| | 14271 | 15968 | | | |

TABLE 2-continued

| Exon | Position in SEQ ID No 4 Beginning | Position in SEQ ID No 4 End | Intron | Position in SEQ ID No 4 Beginning | Position in SEQ ID No 4 End |
|---|---|---|---|---|---|
| 1 | 919 | 930 | 1 | 931 | 1441 |
| 2 | 1442 | 1498 | 2 | 1499 | 1612 |
| 3 | 1613 | 1724 | 3 | 1725 | 2242 |
| 4 | 2243 | 3940 | | | |

Thus, the invention embodies purified, isolated, or recombinant polynucleotides comprising a nucleotide sequence selected from the group consisting of the 4 exons of the GSSP-2 gene, or a sequence complementary thereto. The invention also deals with purified, isolated, or recombinant nucleic acid molecules comprising a combination of at least two exons of the GSSP-2 gene, wherein the polynucleotides are arranged within the nucleic acid molecule, from the 5'-end to the 3'-end of said nucleic acid molecule, in the same order as in SEQ ID NOs: 1 and 4.

Intron 1 refers to the nucleotide sequence located between Exon 1 and Exon 2, and so on. The position of the introns is detailed in Table 2. Thus, the invention embodies purified, isolated, or recombinant polynucleotides comprising a nucleotide sequence selected from the group consisting of the 3 introns of the GSSP-2 gene, or a sequence complementary thereto.

While this section is entitled "Genomic Sequences of GSSP-2," it should be noted that nucleic acid fragments of any size and sequence may also be comprised by the polynucleotides described in this section, flanking the genomic sequences of GSSP-2 on either side or between two or more such genomic sequences.

B. cDNA Sequences

The expression of the GSSP-2 gene has been shown to lead to the production of at least one mRNA species, the nucleic acid sequence of which is set forth in SEQ ID No 2.

Another object of the invention is a purified, isolated, or recombinant nucleic acid molecule comprising the nucleotide sequence of SEQ ID No 2, complementary sequences thereto, as well as allelic variants, and fragments thereof. Moreover, preferred polynucleotides of the invention include purified, isolated, or recombinant GSSP-2 cDNAs consisting of, consisting essentially of, or comprising the sequence of SEQ ID No 2. Particularly preferred nucleic acid molecules of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2, or the complements thereof, wherein said contiguous span comprises at least 1, 2, 3, 5, or 10 of the following nucleotide positions of SEQ ID No 2: 1–1879. Further preferred nucleic acid molecules of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2, or the complements thereof, wherein said contiguous span comprises a T at position 1153. See Table 1 above.

The invention also pertains to a purified or isolated nucleic acid molecules comprising a polynucleotide having at least 95% nucleotide identity with a polynucleotide of SEQ ID No 2, advantageously 99% nucleotide identity, preferably 99.5% nucleotide identity and most preferably 99.8% nucleotide identity with a polynucleotide of SEQ ID No 2, or a sequence complementary thereto or a biologically active fragment thereof.

Another object of the invention relates to purified, isolated or recombinant nucleic acid molecules comprising a polynucleotide that hybridizes, under the stringent hybridization conditions defined herein, with a polynucleotide of SEQ ID No 2, or a sequence complementary thereto or a variant thereof or a biologically active fragment thereof.

TABLE 3

| | Position range of 5'UTR | Position range of ORF | Position range of 3'UTR |
|---|---|---|---|
| SEQ ID No 2 | 1–20 | 21  1121 | 1122–1879 |

The cDNA of SEQ ID No 2 includes a 5'-UTR region starting from the nucleotide at position 1 and ending at the nucleotide in position 20 of SEQ ID No 2. The cDNA of SEQ ID No 2 includes a 3'-UTR region starting from the nucleotide at position 1122 and ending at the nucleotide at position 1879 of SEQ ID No 2.

Consequently, the invention concerns a purified, isolated, and recombinant nucleic acid molecule comprising a nucleotide sequence of the 5' UTR of the GSSP-2 cDNA, a sequence complementary thereto, or an allelic variant thereof. The invention also concerns a purified, isolated, and recombinant nucleic acid molecule comprising a nucleotide sequence of the 3'UTR of the GSSP-2 cDNA, a sequence complementary thereto, or an allelic variant thereof.

While this section is entitled "GSSP-2 cDNA Sequences," it should be noted that nucleic acid fragments of any size and sequence may also be comprised by the polynucleotides described in this section, flanking the genomic sequences of GSSP-2 on either side or between two or more such genomic sequences.

i. Coding Regions

The GSSP-2 open reading frame is contained in the corresponding mRNA of SEQ ID No 2. More precisely, the effective GSSP-2 coding sequence (CDS) includes the region between nucleotide position 21 (first nucleotide of the ATG codon) and nucleotide position 1121 (end nucleotide of the TGA codon) of SEQ ID No 2.

The above disclosed polynucleotide that contains the coding sequence of the GSSP-2 gene may be expressed in a desired host cell or a desired host organism, when this polynucleotide is placed under the control of suitable expression signals. The expression signals may be either the expression signals contained in the regulatory regions in the GSSP-2 gene of the invention or in contrast the signals may be exogenous regulatory nucleic sequences. Such a polynucleotide, when placed under the suitable expression signals, may also be inserted in a vector for its expression and/or amplification.

C. Regulatory Sequences of GSSP-2

As mentioned, the genomic sequence of the GSSP-2 gene contains regulatory sequences both in the non-coding 5'-flanking region and in the non-coding 3'-flanking region that border the GSSP-2 coding region containing the three exons of this gene.

The 5'-regulatory sequence of the GSSP-2 gene is localized between the nucleotide in position 10946 and the nucleotide in position 12946 of the nucleotide sequence of SEQ ID No 1. The 3'-regulatory sequence of the GSSP-2 gene is localized between nucleotide position 15969 and nucleotide position 17969 of SEQ ID No 1.

The 5'-regulatory sequence of the GSSP-2 gene is localized between the nucleotide in position 1 and the nucleotide in position 918 of the nucleotide sequence of SEQ ID No 4. The 3'-regulatory sequence of the GSSP-2 gene is localized between nucleotide position 3941 and nucleotide position 5381 of SEQ ID No 4.

Polynucleotides derived from the 5' and 3' regulatory regions are useful in order to detect the presence of at least a copy of a nucleotide sequence of SEQ ID NOs: 1 and 4 or a fragment thereof in a test sample.

The promoter activity of the 5' regulatory regions contained in GSSP-2 can be assessed as described below.

In order to identify the relevant biologically active polynucleotide fragments or variants of SEQ ID NOs: 1 and 4, one of skill in the art will refer to the book of Sambrook et al. (Sambrook, 1989) which describes the use of a recombinant vector carrying a marker gene (i.e. beta galactosidase, chloramphenicol acetyl transferase, etc.) the expression of which will be detected when placed under the control of a biologically active polynucleotide fragments or variants of SEQ ID NOs: 1 and 4. Genomic sequences located upstream of the first exon of the GSSP-2 gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, β galactosidase, or green fluorescent protein. The sequences upstream the GSSP-2 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequence within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has reduced or obliterated promoter activity, such as described, for example, by Coles et al. (1998), the disclosure of which is incorporated herein by reference in its entirety. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well-known to those skilled in the art and is described in WO 97/17359, U.S. Pat. No. 5,374,544; EP 582 796; U.S. Pat. No. 5,698,389; U.S. Pat. No. 5,643,746; U.S. Pat. No. 5,502,176; and U.S. Pat. No. 5,266,488; the disclosures of which are incorporated by reference herein in their entirety.

The strength and the specificity of the promoter of the GSSP-2 gene can be assessed through the expression levels of a detectable polynucleotide operably linked to the GSSP-2 promoter in different types of cells and tissues. The detectable polynucleotide may be either a polynucleotide that specifically hybridizes with a predefined oligonucleotide probe, or a polynucleotide encoding a detectable protein, including a GSSP-2 polypeptide or a fragment or a variant thereof. This type of assay is well-known to those skilled in the art and is described in U.S. Pat. No. 5,502,176; and U.S. Pat. No. 5,266,488; the disclosures of which are incorporated by reference herein in their entirety. Some of the methods are discussed in more detail below.

Polynucleotides carrying the regulatory elements located at the 5' end and at the 3' end of the GSSP-2 coding region may be advantageously used to control the transcriptional and translational activity of an heterologous polynucleotide of interest.

Thus, the present invention also concerns a purified or isolated nucleic acid comprising a polynucleotide which is selected from the group consisting of the 5' and 3' regulatory regions, or a sequence complementary thereto or a biologically active fragment or variant thereof. "5' regulatory region" refers to the nucleotide sequence located between positions 10946 and 12946 of SEQ ID No 1. "3' regulatory region" refers to the nucleotide sequence located between positions 15969 and 17969 of SEQ ID No 1.

Thus, the present invention further concerns a purified or isolated nucleic acid molecule comprising a polynucleotide which is selected from the group consisting of the 5' and 3' regulatory regions, or a sequence complementary thereto or a biologically active fragment or variant thereof. "5' regulatory region" refers to the nucleotide sequence located between positions 1 and 918 of SEQ ID No 4. "3' regulatory region" refers to the nucleotide sequence located between positions 3941 and 5381 of SEQ ID No 4.

The invention also pertains to a purified or isolated nucleic acid molecule comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, or a sequence complementary thereto or a variant thereof or a biologically active fragment thereof.

Another object of the invention consists of purified, isolated or recombinant nucleic acid molecules comprising a polynucleotide that hybridizes, under the stringent hybridization conditions defined herein, with a polynucleotide selected from the group consisting of the nucleotide sequences of the 5'- and 3' regulatory regions, or a sequence complementary thereto or a variant thereof or a biologically active fragment thereof.

Preferred fragments of the 5' regulatory region have a length of about 1500 or 1000 nucleotides, preferably of about 500 nucleotides, more preferably about 400 nucleotides, even more preferably 300 nucleotides and most preferably about 200 nucleotides.

Preferred fragments of the 3' regulatory region are at least 50, 100, 150, 200, 300 or 400 bases in length.

For the purpose of the invention, a nucleic acid molecule or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The regulatory polynucleotides of the invention may be prepared from the nucleotide sequence of SEQ ID NOs: 1 and 4 by cleavage using suitable restriction enzymes, as described for example in the book of Sambrook et al. (1989). The regulatory polynucleotides may also be prepared by digestion of SEQ ID NOs: 1 and 4 by an exonuclease enzyme, such as Bal31 (Wabiko et al., 1986). These regulatory polynucleotides can also be prepared by nucleic acid chemical synthesis, as described elsewhere in the specification.

The regulatory polynucleotides according to the invention may be part of a recombinant expression vector that may be used to express a coding sequence in a desired host cell or host organism. The recombinant expression vectors according to the invention are described elsewhere in the specification.

A preferred 5'-regulatory polynucleotide of the invention includes the 5'-untranslated region (5'-UTR) of the GSSP-2 cDNA, or a biologically active fragment or variant thereof.

A preferred 3'-regulatory polynucleotide of the invention includes the 3'-untranslated region (3'-UTR) of the GSSP-2 cDNA, or a biologically active fragment or variant thereof.

A further object of the invention consists of a purified or isolated nucleic acid molecule comprising:

a) a nucleic acid molecule comprising a regulatory nucleotide sequence selected from the group consisting of:

(i) a nucleotide sequence comprising a polynucleotide of the 5' regulatory region or a complementary sequence thereto;

(ii) a nucleotide sequence comprising a polynucleotide having at least 95% of nucleotide identity with the nucleotide sequence of the 5' regulatory region or a complementary sequence thereto;

(iii) a nucleotide sequence comprising a polynucleotide that hybridizes under stringent hybridization conditions with the nucleotide sequence of the 5' regulatory region or a complementary sequence thereto; and (iv) a biologically active fragment or variant of the polynucleotides in (i), (ii) and (iii);

b) a polynucleotide encoding a desired polypeptide or a nucleic acid molecule of interest, operably linked to the nucleic acid molecule defined in (a) above;

c) Optionally, a nucleic acid molecule comprising a 3'-regulatory polynucleotide, preferably a 3'-regulatory polynucleotide of the GSSP-2 gene.

In a specific embodiment of the nucleic acid molecule defined above, said nucleic acid molecule includes the 5'-untranslated region (5'-UTR) of the GSSP-2 cDNA, or a biologically active fragment or variant thereof.

In a second specific embodiment of the nucleic acid molecule defined above, said nucleic acid molecule includes the 3'-untranslated region (3'-UTR) of the GSSP-2 cDNA, or a biologically active fragment or variant thereof.

The regulatory polynucleotide of the 5' regulatory region, or its biologically active fragments or variants, is operably linked at the 5'-end of the polynucleotide encoding the desired polypeptide or polynucleotide.

The regulatory polynucleotide of the 3' regulatory region, or its biologically active fragments or variants, is advantageously operably linked at the 3'-end of the polynucleotide encoding the desired polypeptide or polynucleotide.

The desired polypeptide encoded by the above-described nucleic acid molecule may be of various nature or origin, encompassing proteins of prokaryotic or eukaryotic origin. Among the polypeptides expressed under the control of a GSSP-2 regulatory region include bacterial, fungal or viral antigens. Also encompassed are eukaryotic proteins such as intracellular proteins, like "house keeping" proteins, membrane-bound proteins, like receptors, and secreted proteins like endogenous mediators such as cytokines. The desired polypeptide may be the GSSP-2 protein, especially the protein of the amino acid sequence of SEQ ID No 3, or a fragment or a variant thereof.

The desired nucleic acid molecules encoded by the above-described polynucleotide, usually an RNA molecule, may be complementary to a desired coding polynucleotide, for example to the GSSP-2 coding sequence, and thus useful as an antisense polynucleotide.

Such a polynucleotide may be included in a recombinant expression vector in order to express the desired polypeptide or the desired nucleic acid molecule in host cell or in a host organism. Suitable recombinant vectors that contain a polynucleotide such as described herein are disclosed elsewhere in the specification.

D. Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

i. DNA Construct that Enables Directing Temporal and Spatial GSSP-2 Gene Expression in Recombinant Cell Hosts and in Transgenic Animals In order to study the physiological and phenotypic consequences of a lack of synthesis of the GSSP-2 protein, both at the cell level and at the multi cellular organism level, the invention also encompasses DNA constructs and recombinant vectors enabling a conditional expression of a specific allele of the GSSP-2 genomic sequence or cDNA and also of a copy of this genomic sequence or cDNA harboring substitutions, deletions, or additions of one or more bases as regards to the GSSP-2 nucleotide sequence of SEQ ID NOs: 1, 2 or 4, or a fragment thereof, these base substitutions, deletions or additions being located either in an exon, an intron or a regulatory sequence, but preferably in the 5'-regulatory sequence or in an exon of the GSSP-2 genomic sequence or within the GSSP-2 cDNA of SEQ ID No 2. In a preferred embodiment, the GSSP-2 sequence comprises a biallelic marker of the present invention. In a preferred embodiment, the GSSP-2 sequence comprises a biallelic marker of the present invention, preferably one of the biallelic markers 20-828-311, 17-42-319, 17-41-250, 20-841-149, 20-842-115, and 20-853-415. In a more preferred embodiment, the GSSP-2 sequence comprises a biallelic marker of the present invention, preferably one of the biallelic markers 17-42-319 or 17-41-250.

The present invention embodies recombinant vectors comprising any one of the polynucleotides described in the present invention. More particularly, the polynucleotide constructs according to the present invention can comprise any of the polynucleotides described in the "Genomic Sequences of the GSSP-2 Gene" section, the "GSSP-2 cDNA Sequences" section, the "Coding Regions" section, and the "Oligonucleotide Probes and Primers" section.

A first preferred DNA construct is based on the tetracycline resistance operon tet from *E. coli* transposon Tn10 for controlling the GSSP-2 gene expression, such as described by Gossen et al. (1992, 1995) and Furth et al. (1994). Such a DNA construct contains seven tet operator sequences from Tn10 (tetop) that are fused to either a minimal promoter or a 5'-regulatory sequence of the GSSP-2 gene, said minimal promoter or said GSSP-2 regulatory sequence being operably linked to a polynucleotide of interest that codes either for a sense or an antisense oligonucleotide or for a polypeptide, including a GSSP-2 polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprise both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, the expression of the polynucleotide of interest is silent in the absence of tetracycline and induced in its presence.

ii. DNA Constructs Allowing Homologous Recombination: Replacement Vectors

A second preferred DNA construct will comprise, from 5'-end to 3'-end: (a) a first nucleotide sequence that is comprised in the GSSP-2 genomic sequence; (b) a nucleotide sequence comprising a positive selection marker, such as the marker for neomycine resistance (neo); and (c) a second nucleotide sequence that is comprised in the GSSP-2 genomic sequence, and is located on the genome downstream the first GSSP-2 nucleotide sequence (a).

In a preferred embodiment, this DNA construct also comprises a negative selection marker located upstream the nucleotide sequence (a) or downstream the nucleotide sequence (c). Preferably, the negative selection marker comprises the thymidine kinase (tk) gene (Thomas et al., 1986), the hygromycine beta gene (Te Riele et al., 1990), the hprt gene (Van der Lugt et al., 1991; Reid et al., 1990) or the Diphteria toxin A fragment (Dt-A) gene (Nada et al., 1993; Yagi et al. 1990). Preferably, the positive selection marker is located within a GSSP-2 exon sequence so as to interrupt the sequence encoding a GSSP-2 protein. These replacement vectors are described, for example, by Thomas et al. (1986; 1987), Mansour et al. (1988) and Koller et al. (1992).

The first and second nucleotide sequences (a) and (c) may be indifferently located within a GSSP-2 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

iii. DNA Constructs Allowing Homologous Recombination: Cre-LoxP System

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986). The recombination by the Cre enzyme between two loxP sites having an identical orientation leads to the deletion of the DNA fragment.

The Cre-loxP system used in combination with a homologous recombination technique has been first described by Gu et al. (1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al. (1995), or by lipofection of the enzyme into the cells, such as described by Baubonis et al. (1993); (b) transfecting the cell host with a vector comprising the Cre coding sequence operably linked to a promoter functional in the recombinant cell host, which promoter being optionally inducible, said vector being introduced in the recombinant cell host, such as described by Gu et al. (1993) and Sauer et al. (1988); (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994).

In a specific embodiment, the vector containing the sequence to be inserted in the GSSP-2 gene by homologous recombination is constructed in such a way that selectable markers are flanked by loxP sites of the same orientation, it is possible, by treatment by the Cre enzyme, to eliminate the selectable markers while leaving the GSSP-2 sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al. (1994).

Thus, a third preferred DNA construct of the invention comprises, from 5'-end to 3'-end: (a) a first nucleotide sequence that is comprised in the GSSP-2 genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the GSSP-2 genomic sequence, and is located on the genome downstream of the first GSSP-2 nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may result from the breeding of two transgenic animals, the first transgenic animal bearing the GSSP-2-derived sequence of interest containing the loxP sites as described above and the second transgenic animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995).

The DNA constructs described above may be used to introduce a desired nucleotide sequence of the invention, preferably a GSSP-2 genomic sequence or a GSSP-2 cDNA sequence, and most preferably an altered copy of a GSSP-2 genomic or cDNA sequence, within a predetermined location of the targeted genome, leading either to the generation of an altered copy of a targeted gene knock-out homologous recombination) or to the replacement of a copy of the targeted gene by another copy sufficiently homologous to allow an homologous recombination event to occur (knock-in homologous recombination). In a specific embodiment, the DNA constructs described above may be used to introduce a GSSP-2 genomic sequence or a GSSP-2 cDNA sequence comprising at least one biallelic marker of the present invention, preferably at least one biallelic marker selected from the group consisting of 20-828-311, 17-42-319, 17-41-250, 20-841-149, 20-842-115, and 20-853-415.

iv. Nuclear Antisense DNA Constructs

Other compositions containing a vector of the invention comprising an oligonucleotide fragment of the nucleic sequence SEQ ID No 2, preferably a fragment including the start codon of the GSSP-2 gene, as an antisense tool that inhibits the expression of the corresponding GSSP-2 gene. Preferred methods using antisense polynucleotide according to the present invention are the procedures described by Sczakiel et al. (1995) or those described in PCT Application No WO 95/24223, the disclosures of which are incorporated by reference herein in their entirety.

Preferably, the antisense tools are chosen among the polynucleotides (15–200 bp long) that are complementary to the 5' end of the GSSP-2 mRNA. In one embodiment, a combination of different antisense polynucleotides complementary to different parts of the desired targeted gene are used.

Preferred antisense polynucleotides according to the present invention are complementary to a sequence of the mRNAs of GSSP-2 that contains either the translation initiation codon ATG or a splicing site. Further preferred antisense polynucleotides according to the invention are complementary of the splicing site of the GSSP-2 mRNA.

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al. (1994). In a preferred embodiment, these GSSP-2 antisense polynucleotides also comprise, within the ribozyme cassette, a histone stem-loop structure to stabilize cleaved transcripts against 3'-5' exonucleolytic degradation, such as the structure described by Eckner et al. (1991).

E. Oligonucleotide Primers and Probes

Polynucleotides derived from the GSSP-2 gene are useful in order to detect the presence of at least a copy of a nucleotide sequence of SEQ ID NOs: 1 and 4, or a fragment, complement, or variant thereof in a test sample.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1, or the complements thereof, wherein said contiguous span comprises at least 1, 2, 3, 5, or 10 of the following nucleotide positions of SEQ ID No 1: 739–1739; 10946–12958; 13470–13526; 13641–13752; 14271–17969; 41718–42718; 44942–45942; and 76558–77558. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1, or the complements thereof, wherein said contiguous span comprises a T at position 1239, a T at position 12347, a T at position 15241, a G at position 42218, an A at 45442, or a T at 77058.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4, or the complements thereof, wherein said contiguous span comprises at least 1, 2, 3, 5, or 10 of the following nucleotide positions of SEQ ID No 4: 1–1498; 1613–1724; 2243–3940; and 3941–5381. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4, or the complements thereof, wherein said contiguous span comprises one or more of the nucleotides at positions 1241 or 1447. Further preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4, or the complements thereof, wherein said contiguous span comprises a T at position 319 or a T at position 3213.

Another object of the invention is a purified, isolated, or recombinant nucleic acid molecule comprising the nucleotide sequence of SEQ ID No 2, complementary sequences thereto, as well as allelic variants, and fragments thereof. Moreover, preferred probes and primers of the invention include purified, isolated, or recombinant GSSP-2 cDNAs consisting of, consisting essentially of, or comprising the sequence of SEQ ID No 2. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2, or the complements thereof, wherein said contiguous span comprises at least 1, 2, 3, 5, or 10 of the following nucleotide positions of SEQ ID No 2: 1–1879. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2, or the complements thereof, wherein said contiguous span comprises a T at position 1153.

Thus, the invention also relates to nucleic acid probes characterized in that they hybridize specifically, under the stringent hybridization conditions defined above, with a nucleic acid molecule selected from the group consisting of the nucleotide sequences 739–1739; 10946–12958; 13470–13526; 13641–13752; 14271–17969; 41718–42718; 44942–45942; and 76558–77558 of SEQ ID No 1 or a variant thereof or a sequence complementary thereto.

Thus, the invention also relates to nucleic acid probes characterized in that they hybridize specifically, under the stringent hybridization conditions defined above, with a nucleic acid molecule selected from the group consisting of the nucleotide sequences 1–1498; 1613–1724; 2243–3940; and 3941–5381 of SEQ ID No 4 or a variant thereof or a sequence complementary thereto.

In one embodiment the invention encompasses isolated, purified, and recombinant polynucleotides consisting of, or consisting essentially of a contiguous span of 8 to 50 nucleotides of any one of SEQ ID NOs: 1, 2 or 4 and the complement thereof, wherein said span includes a GSSP-2-related biallelic marker in said sequence; optionally, wherein said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; more preferably said GSSP-2-related biallelic marker is selected from the group consisting of 17-42-319 and 17-41-250, and the complements thereof; optionally, wherein said contiguous span is 18 to 35 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide. In a preferred embodiment, said probes comprises, consists of, or consists essentially of a sequence selected from the following sequences of SEQ ID No 1: 1227–1251, 12335–12359, 15229–15253, 42206–42230, 45430–45454 and 77046–77070 and the complementary sequences thereto; and from the following sequences of SEQ ID No 4: 307–331 and 3201–3225 and the complementary sequences thereto.

In another embodiment the invention encompasses isolated, purified and recombinant polynucleotides comprising, consisting of, or consisting essentially of a contiguous span of 8 to 50 nucleotides of SEQ ID NOs: 1, 2 or 4, or the complements thereof, wherein the 3' end of said contiguous span is located at the 3' end of said polynucleotide, and wherein the 3' end of said polynucleotide is located within 20 nucleotides upstream of a GSSP-2-related biallelic marker in said sequence; optionally, wherein said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, wherein said GSSP-2-related biallelic marker is selected from the group consisting of 17-42-319 and 17-41-250, and the complements thereof, or optionally the biallelic markers in linkage disequilibrium therewith; optionally, wherein the 3' end of said polynucleotide is located 1 nucleotide upstream of said GSSP-2-related biallelic marker in said sequence; and optionally, wherein said polynucleotide consists essentially of a sequence selected from the following sequences of SEQ ID No 1: 1220–1238, 12328–12346, 15222–15240, 42199–42217, 45423–45441, 77039–77057, 1240–1258, 12348–12366, 15242–15260, 42219–42237, 45443–45461 and 77059–77077; and from the following sequences of SEQ ID No 4: 300–318, 3194–3212, 320–338 and 3214–3232.

In a further embodiment, the invention encompasses isolated, purified, or recombinant polynucleotides comprising, consisting of, or consisting essentially of a sequence selected from the following sequences of SEQ ID No 1: 929–949, 12029–12050, 14992–15012, 42070–42090, 45328–45347, 76644–76664, 1357–1377, 12581–12603, 15460–15482, 42572–42591, 45863–45883, and 77166–77185; and from the following sequences of SEQ ID No 4: 1–11022, 899–11920, 1246–12267, 2964–13984, 553–11575, 1441–12461, 1632–12651, and 3432–14454.

In an additional embodiment, the invention encompasses polynucleotides for use in hybridization assays, sequencing assays, and enzyme-based mismatch detection assays for determining the identity of the nucleotide at a GSSP-2-related biallelic marker in SEQ ID NOs: 1, 2 or 4, or the complements thereof, as well as polynucleotides for use in amplifying segments of nucleotides comprising a GSSP-2-related biallelic marker in SEQ ID NOs: 1, 2 or 4, or the complements thereof; optionally, wherein said GSSP-2-related biallelic marker is selected from the group consisting of 20-828-311, 17-42-319, 17-41-250, 20-841-149, 20-842-115, and 20-853-415, and the complements thereof, or more preferably the biallelic markers in linkage disequilibrium therewith; optionally, wherein said GSSP-2-related biallelic marker is selected from the group consisting of 17-42-319 and 17-41-250, and the complements thereof.

A probe or a primer according to the invention has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes and primers can range from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art. A preferred probe or primer consists of a nucleic acid molecule comprising a polynucleotide selected from the group of the nucleotide sequences of 1227–1251, 12335–12359, 15229–15253, 42206–42230, 45430–45454, 77046–77070, 929–949, 12029–12050, 14992–15012, 42070–42090, 45328–45347, 76644–76664, 1357–1377, 12581–12603, 15460–15482, 42572–42591, 45863–45883, 77166–77185, 1220–1238, 12328–12346, 15222–15240, 42199–42217, 45423–45441, 77039–77057, 1240–1258, 12348–12366, 15242–15260, 42219–42237, 45443–45461 and 77059–77077 of SEQ ID No 1 and the complementary sequence thereto; and 307–331, 3201–3225, 1–11022, 899–11920, 1246–12267, 2964–13984, 553–11575, 1441–12461, 1632–12651, 3432–14454, 300–318, 3194–3212, 320–338 and 3214–3232 of SEQ ID No 4 and the complementary sequence thereto; for which the respective locations in the sequence listing are provided in FIGS. 4, 5 and 6.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

The primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592.

Detection probes are generally nucleic acid sequences or uncharged nucleic acid analogs such as, for example peptide nucleic acids which are disclosed in International Patent Application WO 92/20702, morpholino analogs which are described in U.S. patents Numbered U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, $^{32}$P, $^{35}$S, $^{3}$H, $^{125}$I), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No. FR-7810975 or by Urdea et al (1988) or Sanchez-Pescador et al (1988). In addition, the probes according to the present invention may have structural characteristics such that they allow the signal amplification, such structural characteristics being, for example, branched DNA probes as those described by Urdea et al. in 1991 or in the European patent No. EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid molecule on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the GSSP-2 gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acid molecules on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also comprises a method for detecting the presence of a nucleic acid molecule comprising a nucleotide sequence selected from a group consisting of SEQ ID NOs: 1, 2 or 4, a fragment or a variant thereof and a complementary sequence thereto in a sample, said method comprising the following steps of:

a) bringing into contact a nucleic acid probe or a plurality of nucleic acid probes which can hybridize with a nucleotide sequence included in a nucleic acid molecule selected form the group consisting of the nucleotide sequences of SEQ ID NOs: 1, 2 or 4, a fragment or a variant thereof and a complementary sequence thereto and the sample to be assayed; and b) detecting the hybrid complex formed between the probe and a nucleic acid molecule in the sample.

The invention further concerns a kit for detecting the presence of a nucleic acid molecule comprising a nucleotide sequence selected from a group consisting of SEQ ID NOs: 1, 2 or 4, a fragment or a variant thereof and a complementary sequence thereto in a sample, said kit comprising:

a) a nucleic acid probe or a plurality of nucleic acid probes which can hybridize with a nucleotide sequence included in a nucleic acid molecule selected form the group consisting of the nucleotide sequences of SEQ ID NOs: 1, 2 or 4, a fragment or a variant thereof and a complementary sequence thereto; and b) optionally, the reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate. In a third preferred embodiment, the nucleic acid probe or the plurality of nucleic acid probes comprise either a sequence which is selected from the group consisting of the nucleotide sequences of 1227–1251, 12335–12359, 15229–15253, 42206–42230, 45430–45454, 77046–77070, 929–949, 12029–12050, 14992–15012, 42070–42090, 45328–45347, 76644–76664, 1357–1377, 12581–12603, 15460–15482, 42572–42591, 45863–45883, 77166–77185, 1220–1238, 12328–12346, 15222–15240, 42199–42217, 45423–45441, 77039–77057, 1240–1258, 12348–12366, 15242–15260, 42219–42237, 45443–45461 and 77059–77077 of SEQ ID No 1 or the complementary sequence thereto; and 307–331, 3201–3225, 1–11022, 899–11920, 1246–12267, 2964–13984, 553–11575, 1441–12461, 1632–12651, 3432–14454, 300–318, 3194–3212, 320–338 and 3214–3232 of SEQ ID No 4 or the complementary sequence thereto.

F. Oligonucleotide Arrays

A substrate comprising a plurality of oligonucleotide primers or probes of the invention may be used either for detecting or amplifying targeted sequences in the GSSP-2 gene and may also be used for detecting mutations in the coding or in the non-coding sequences of the GSSP-2 gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092.

These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

In another embodiment of the oligonucleotide arrays of the invention, an oligonucleotide probe matrix may advantageously be used to detect mutations occurring in the GSSP-2 gene and preferably in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the GSSP-2 gene that have been identified according, for example to the technique used by Huang et al. (1996) or Samson et al. (1996).

Another technique that is used to detect mutations in the GSSP-2 gene is the use of a high-density DNA array. Each oligonucleotide probe constituting a unit element of the high density DNA array is designed to match a specific subsequence of the GSSP-2 genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the GSSP-2 gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996.

Consequently, the invention concerns an array of nucleic acid molecules comprising at least one polynucleotide described above as probes and primers. Preferably, the invention concerns an array of nucleic acid molecules comprising at least two polynucleotides described above as probes and primers.

A further object of the invention consists of an array of nucleic acid sequences comprising either at least one of the sequences selected from the group consisting of 1227–1251, 12335–12359, 15229–15253, 42206–42230, 45430–45454, 77046–77070, 929–949, 12029–12050, 14992–15012, 42070–42090, 45328–45347, 76644–76664, 1357–1377, 12581–12603, 15460–15482, 42572–42591, 45863–45883, 77166–77185, 1220–1238, 12328–12346, 15222–15240, 42199–42217, 45423–45441, 77039–77057, 1240–1258, 12348–12366, 15242–15260, 42219–42237, 45443–45461 and 77059–77077 of SEQ ID No 1, and the complementary sequence thereto; and 307–331, 3201–3225, 1–11022, 899–11920, 1246–12267, 2964–13984, 553–11575, 1441–12461, 1632–12651, 3432–14454, 300–318, 3194–3212, 320–338 and 3214–3232 of SEQ ID No 4, and the complementary sequence thereto; a fragment thereof of at least 8, 10, 12, 15, 18, 20, 25, 30, or 40 consecutive nucleotides thereof, and at least one sequence comprising a biallelic marker selected from the group consisting of 20-828-311, 17-42-319, 17-41-250, 20-841-149, 20-842-115, and 20-853-415, and the complements thereto.

The invention also pertains to an array of nucleic acid sequences comprising either at least two of the sequences selected from the group consisting of 1227–1251, 12335–12359, 15229–15253, 42206–42230, 45430–45454, 77046–77070, 929–949, 12029–12050, 14992–15012, 42070–42090, 45328–45347, 76644–76664, 1357–1377, 12581–12603, 15460–15482, 42572–42591, 45863–45883, 77166–77185, 1220–1238, 12328–12346, 15222–15240, 42199–42217, 45423–45441, 77039–77057, 1240–1258, 12348–12366, 15242–15260, 42219–42237, 45443–45461 and 77059–77077 of SEQ ID No 1, and the complementary sequence thereto; and 307–331, 3201–3225, 1–11022, 899–11920, 1246–12267, 2964–13984, 553–11575, 1441–12461, 1632–12651, 3432–14454, 300–318, 3194–3212, 320–338 and 3214–3232 of SEQ ID No 4, and the complementary sequence thereto, a fragment thereof of at least 8 consecutive nucleotides thereof, and at least two sequences comprising a biallelic marker selected from the group consisting of 20-828-311, 17-42-319, 17-41-250, 20-841-149, 20-842-115, and 20-853-415, and the complements thereof.

G. Variants and Fragments of the Polynucleotides of the Invention

The invention relates to variants and fragments of the polynucleotides described herein, particularly of a GSSP-2 gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function, as described herein, or activity as the mature GSSP-2 protein, or those in which the polynucleotides encode polypeptides which maintain or increase a particular biological activity, while reducing a second biological activity. Preferred polynucleotide fragments are polynucleotides that encode polypeptide fragments of the invention that induce apoptosis in neoplastic cells, kill neoplastic cells or inhibit cellular proliferation.

A polynucleotide fragment is a polynucleotide having a sequence that is entirely the same as part but not all of a given nucleotide sequence, preferably the nucleotide sequence of a GSSP-2 gene, and variants thereof. The fragment can be a portion of an intron or an exon of a GSSP-2 gene. It can also be a portion of the regulatory regions of GSSP-2. Preferably, such fragments comprise at least one of the biallelic markers 20-828-311, 17-42-319, 17-41-250, 20-841-149, 20-842-115, and 20-853-415, or the complements thereto, or a biallelic marker in linkage disequilibrium with one or more of the biallelic markers 20-828-311, 17-42-319, 17-41-250, 20-841-149, 20-842-115, and 20-853-415.

Such fragments may be "free-standing", i.e. not part of or fused to other polynucleotides, or they may be comprised within a single larger polynucleotide of which they form a part or region. Indeed, several of these fragments may be present within a single larger polynucleotide.

Optionally, such fragments may consist of, or consist essentially of a contiguous span of at least 8, 10, 12, 15, 18, 20, 25, 35, 40, 50, 70, 80, 100, 250, 500 or 1000 nucleotides in length. A set of preferred fragments contain at least one of the biallelic markers 20-828-311, 17-42-319, 17-41-250, 20-841-149, 20-842-115, and 20-853-415 of the GSSP-2 gene which are described herein or the complements thereto.

In addition to the above preferred nucleic acid sizes, further preferred sub-genuses of nucleic acids comprise at least 8 nucleotides, wherein "at least 8" is defined as any integer between 8 and the integer representing the 3' most nucleotide position as set forth in the sequence listing or elsewhere herein. Further included as preferred polynucleotides of the present invention are nucleic acid fragments at least 8 nucleotides in length, as described above, that are further specified in terms of their 5' and 3' position. The 5' and 3' positions are represented by the position numbers set forth in the sequence listing below. For allelic, degenerate and other variants, position 1 is defined as the 5' most nucleotide of the ORF, i.e., the nucleotide "A" of the start codon with the remaining nucleotides numbered consecutively. Therefore, every combination of a 5' and 3' nucleotide position that a polynucleotide fragment of the present invention, at least 8 contiguous nucleotides in length, could occupy is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the polynucleotide sequence of the present invention minus 8, and where "y" equals an integer between 9 and the number of nucleotides of the polynucleotide sequence of the present invention; and where "x" is an integer smaller then "y" by at least 8.

The present invention also provides for the exclusion of any species of polynucleotide fragments of the present invention specified by 5' and 3' positions or sub-genuses of polynucleotides specified by size in nucleotides as described above. Any number of fragments specified by 5' and 3' positions or by size in nucleotides, as described above, may be excluded.

III. GSSP-2 Proteins and Polypeptide Fragments

The term "GSSP-2 polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies GSSP-2 proteins from humans, including isolated or purified GSSP-2 proteins consisting of, consisting essentially of, or comprising the sequence of SEQ ID No 3.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, 100, 200 or 300 amino acids of SEQ ID No 3. The present invention also embodies isolated, purified, and recombinant polypeptides comprising a contiguous span of at least 6 amino acids, preferably at least 8 to 10 amino acids, more preferably at least 12, 15, 20, 25, 30, 40, 50, 100, 200 or 300 amino acids of SEQ ID No 3. In other preferred embodiments the contiguous stretch of amino acids comprises the site of a mutation or functional mutation, including a deletion, addition, swap or truncation of the amino acids in the GSSP-2 protein sequence.

The invention also encompasses a purified, isolated, or recombinant polypeptides comprising an amino acid sequence having at least 70, 75, 80, 85, 90, 95, 98 or 99% amino acid identity with the amino acid sequence of SEQ ID No 3 or a fragment thereof.

GSSP-2 proteins are preferably isolated from human or mammalian tissue samples or expressed from human or mammalian genes. The GSSP-2 polypeptides of the invention can be made using routine expression methods known in the art or as described herein in Example 4. The polynucleotide encoding the desired polypeptide, is ligated into an expression vector suitable for any convenient host. Both eukaryotic and prokaryotic host systems are used in forming recombinant polypeptides, and a summary of some of the more common systems are provided herein. The polypeptide is then isolated from lysed cells or from the culture medium and purified to the extent needed for its intended use. Purification is by any technique known in the art, for example, differential extraction, salt fractionation, chromatography, centrifugation, and the like.

The invention also relates to variants, fragments, analogs and derivatives of the polypeptides described herein, including mutated GSSP-2 proteins.

The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the mutated GSSP-2 is fused with another compound, such as a compound to increase the half-life of the polypeptide (for example, polyethylene glycol, antibody or receptor), or 4) one in which the additional amino acids are fused to the mutated GSSP-2, such as a leader or secretory sequence or a sequence which is employed for purification of the mutated GSSP-2 or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a GSSP-2 gene and variants thereof.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged.

In particular embodiments, conservative substitutions of interest are shown in Table 4 under the heading of preferred substitutions. If such substitutions result in a change in biological activity, then more substantial changes, denominated exemplary substitutions in Table 4, or as further described below in reference to amino acid classes, are introduced and the products screened.

TABLE 4

| Original Residue | Exemplary Substitutions | Preferred Substitutions |
| --- | --- | --- |
| Ala (A) | val; leu; ile | val |
| Arg (R) | lys; gin; asn | lys |
| Asn (N) | gin; his; lys; arg | gin |
| Asp (D) | glu | glu |
| Cys (C) | ser | ser |
| Gin (Q) | asn | asn |
| Glu (E) | asp | asp |
| Gly (G) | pro; ala | ala |
| His (H) | asn; gin; lys; arg | arg |
| Ile (I) | leu; val; met; ala; phe; norleucine | leu |
| Leu (L) | norleucine; ile; val; met; ala; phe | ile |
| Lys (K) | arg; gin; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the GSSP-2 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the GSSP-2 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main chain conformation of the variant [Cunningham and Wells, Science, 244: 1081–1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

i. Modifications of GSSP-2

Covalent modifications of GSSP-2 are included within the scope of this invention. One type of covalent modification includes reacting targeted amino acid residues of a GSSP-2 polypeptide with an organic derivatizing agent that is capable of reacting with selected side chains or the N- or C-terminal residues of the GSSP-2. Derivatization with bifunctional agents is useful, for instance, for crosslinking GSSP-2 to a water-insoluble support matrix or surface for use in the method for purifying anti-GSSP-2 or anti-GSSP-2 antibodies, and vice-versa. Commonly used crosslinking agents include, e.g., 1,1-bis(diazoacetyl)-2-phenylethane, glutaraldehyde, N-hydroxysuccinim ide esters, for example, esters with 4-azidosalicylic acid, homobifunctional imidoesters, including disuccinimidyl esters such as 3,3'-dithio-bis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the GSSP-2 polypeptide included within the scope of this invention comprises altering the native glycosylation pattern of the polypeptide. "Altering the native glycosylation pattern" is intended for purposes herein to mean deleting one or more carbohydrate moieties found in native sequence GSSP-2 (either by removing the underlying glycosylation site or by deleting the glycosylation by chemical and/or enzymatic means), and/or adding one or more glycosylation sites that are not present in the native sequence GSSP-2. In addition, the phrase includes qualitative changes in the glycosylation of the native proteins, involving a change in the nature and proportions of the various carbohydrate moieties present.

Addition of glycosylation sites to the GSSP-2 polypeptide may be accomplished by altering the amino acid sequence. The alteration may be made, for example, by the addition of, or substitution by, one or more serine or threonine residues to the native sequence GSSP-2 (for O-linked glycosylation sites). The GSSP-2 amino acid sequence may optionally be altered through changes at the DNA level, particularly by mutating the DNA encoding the GSSP-2 polypeptide at preselected bases such that codons are generated that will translate into the desired amino acids.

Another means of increasing the number of carbohydrate moieties on the GSSP-2 polypeptide is by chemical or enzymatic coupling of glycosides to the polypeptide. Such methods are described in the art, e.g., in WO 87/05330 published I 1 Sep. 1987, and in Aplin and Wriston, CRC Crit. Rev. Biochem. pp. 259–306 (1981).

Removal of carbohydrate moieties present on the GSSP-2 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al, Anal. Biochem., 118:131 (1981). Enzymatic cleavage of carbohydrate moieties on polypeptides can be achieved by the use of a variety of endo- and exo-glycosidases as described by Thotakura et al, Meth. Enzvmol., 138:350 (1987). Another type of covalent modification of GSSP-2 comprises linking the GSSP-2 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670, 417; 4,791,192 or 4,179,337.

In addition to the above polypeptide fragments, further preferred sub-genuses of polypeptides comprise at least 8 amino acids, wherein "at least 8" is defined as any integer between 8 and the integer representing the C-terminal amino acid of the polypeptide of the present invention including the polypeptide sequences of the sequence listing below. Further included are species of polypeptide fragments at least 8 amino acids in length, as described above, that are further specified in terms of their N-terminal and C-terminal positions. Preferred species of polypeptide fragments specified by their N-terminal and C-terminal positions include the signal peptides delineated in the sequence listing below. However, included in the present invention as individual species are all polypeptide fragments, at least 8 amino acids in length, as described above, and may be particularly specified by a N-terminal and C-terminal position. That is, every combination of a N-terminal and C-terminal position that a fragment at least 8 contiguous amino acid residues in length could occupy, on any given amino acid sequence of the sequence listing or of the present invention is included in the present invention The present invention also provides for the exclusion of any fragment species specified by N-terminal and C-terminal positions or of any fragment sub-genus specified by size in amino acid residues as described above. Any number of fragments specified by N-terminal and C-terminal positions or by size in amino acid residues as described above may be excluded as individual species.

It is noted that the species of polypeptide fragments of the present invention may alternatively be described by the formula "n to c"; where "n" equals the N-terminal most amino acid position and "c" equals the C-terminal most amino acid position of the polynucleotide; and further where "n" equals an integer between 1 and the number of amino acids of the polypeptide sequence of the present invention minus 6, and where "c" equals an integer between 7 and the number of amino acids of the polypeptide sequence of the present invention; and where "n" is an integer smaller then "c" by at least 6.

The above polypeptide fragments of the present invention can be immediately envisaged using the above description and are therefore not individually listed solely for the purpose of not unnecessarily lengthening the specification. Moreover, the above fragments need not be active since they would be useful, for example, in immunoassays, in epitope mapping, epitope tagging, as vaccines, and as molecular weight markers. The above fragments may also be used to generate antibodies to a particular portion of the polypeptide. These antibodies can then be used in immunoassays well known in the art to distinguish between human and non-human cells and tissues or to determine whether cells or tissues in a biological sample are or are not of the same type which express the polypeptide of the present invention. Preferred polypeptide fragments of the present invention comprising a signal peptide may be used to facilitate secretion of either the polypeptide of the same gene or a heterologous polypeptide using methods well known in the art. Another embodiment of the present invention is an isolated or purified polypeptide comprising a signal peptide of one of the polypeptides of SEQ ID No 3.

A specific embodiment of a modified GSSP-2 peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH— bond. The invention also encompasses a human GSSP-2 polypeptide or a fragment or a variant thereof in which at least one peptide bond has been modified as described above.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have from about 5, 6, 7, 8, 9 or 10 to 15, 10 to 20, 15 to 40, or 30 to 55 amino acids long. Preferred are those fragments containing at least one amino acid mutation in the GSSP-2 protein.

In addition, shorter protein fragments is produced by chemical synthesis. Alternatively the proteins of the invention is extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any GSSP-2 cDNA, including SEQ ID No 2, is used to express GSSP-2 proteins and polypeptides. The nucleic acid molecule encoding the GSSP-2 protein or polypeptide to be expressed is operably linked to a promoter in an expression vector using conventional cloning technology. The GSSP-2 insert in the expression vector may comprise the full coding sequence for the GSSP-2 protein or a portion thereof. For example, the GSSP-2 derived insert may encode a polypeptide comprising at least 10 consecutive amino acids of the GSSP-2 protein of SEQ ID No 3.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al, U.S. Pat. No. 5,082,767, the disclosures of which are incorporated by reference herein in their entirety.

In one embodiment, the entire coding sequence of the GSSP-2 cDNA through the poly A signal of the cDNA are operably linked to a promoter in the expression vector. Alternatively, if the nucleic acid molecule encoding a portion of the GSSP-2 protein lacks a methionine to serve as the initiation site, an initiating methionine can be introduced next to the first codon of the nucleic acid molecule using conventional techniques. Similarly, if the insert from the GSSP-2 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid molecule encoding the GSSP-2 protein or a portion thereof is obtained by PCR from a bacterial vector containing the GSSP-2 cDNA of SEQ ID No 2 using oligonucleotide primers complementary to the GSSP-2 cDNA or portion thereof and containing restriction endonuclease sequences for Pst I incorporated into the 5' primer and BglII at the 5' end of the corresponding cDNA 3' primer, taking care to ensure that the sequence encoding the GSSP-2 protein or a portion thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

The above procedures may also be used to express a mutant GSSP-2 protein responsible for a detectable phenotype or a portion thereof.

The expressed protein is purified using conventional purification techniques such as ammonium sulfate precipitation or chromatographic separation based on size or charge. The protein encoded by the nucleic acid insert may also be purified using standard immunochromatography techniques. In such procedures, a solution containing the expressed GSSP-2 protein or portion thereof, such as a cell extract, is applied to a column having antibodies against the GSSP-2 protein or portion thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of the GSSP-2 protein or a portion thereof, the proteins expressed from host cells containing an expression vector containing an insert encoding the GSSP-2 protein or a portion thereof can be compared to the proteins expressed in host cells containing the expression vector without an insert. The presence of a band in samples from cells containing the expression vector with an insert which is absent in samples from cells containing the expression vector without an insert indicates that the GSSP-2 protein or a portion thereof is being expressed. Generally, the band will have the mobility expected for the GSSP-2 protein or portion thereof. However, the band may have a mobility different than that expected as a result of modifications such as glycosylation, ubiquitination, or enzymatic cleavage.

Antibodies capable of specifically recognizing the expressed GSSP-2 protein or a portion thereof are described below.

If antibody production is not possible, the nucleic acids encoding the GSSP-2 protein or a portion thereof is incorporated into expression vectors designed for use in purification schemes employing chimeric polypeptides. In such strategies the nucleic acid molecule encoding the GSSP-2 protein or a portion thereof is inserted in frame with the gene encoding the other half of the chimera. The other half of the chimera is β-globin or a nickel binding polypeptide encoding sequence. A chromatography matrix having antibody to β-globin or nickel attached thereto is then used to purify the chimeric protein. Protease cleavage sites is engineered between the β-globin gene or the nickel binding polypeptide and the GSSP-2 protein or portion thereof. Thus, the two polypeptides of the chimera is separated from one another by protease digestion.

One useful expression vector for generating β-globin chimeric proteins is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (1986) and many of the methods are available from Stratagene, Life Technologies, Inc., or Promega. Polypeptide may additionally be produced from the construct using in vitro translation systems such as the In vitro Express™ Translation Kit (Stratagene).

A. Antibodies that Bind GSSP-2 Polypeptides of the Invention

Any GSSP-2 polypeptide or whole protein may be used to generate antibodies capable of specifically binding to an expressed GSSP-2 protein or fragments thereof as described.

One antibody composition of the invention is capable of specifically binding or specifically bind to the GSSP-2 protein of SEQ ID No 3. For an antibody composition to specifically bind to a first variant of GSSP-2, it must demonstrate at least a 5%, 10%, 15%, 20%, 25%, 50%, or 100% greater binding affinity for a full length first variant of the GSSP-2 protein than for a full length second variant of the GSSP-2 protein in an ELISA, RIA, or other antibody-based binding assay.

In a preferred embodiment, the invention concerns antibody compositions, either polyclonal or monoclonal, capable of selectively binding, or selectively bind to an epitope-containing a polypeptide comprising a contiguous span of at least 6 amino acids, preferably at least 8 to 10 amino acids, more preferably at least 12, 15, 20, 25, 30, 40, 50, or 100 amino acids of SEQ ID No 3.

The invention also concerns a purified or isolated antibody capable of specifically binding to a mutated GSSP-2 protein or to a fragment or variant thereof comprising an epitope of the mutated GSSP-2 protein. In another preferred embodiment, the present invention concerns an antibody capable of binding to a polypeptide comprising at least 10 consecutive amino acids of a GSSP-2 protein and including at least one of the amino acids which can be encoded by the trait causing mutations.

In a preferred embodiment, the invention concerns the use in the manufacture of antibodies of a polypeptide comprising a contiguous span of at least 6 amino acids, preferably at least 8 to 10 amino acids, more preferably at least 12, 15, 20, 25, 30, 40, 50, or 100 amino acids of SEQ ID No 3.

Non-human animals or mammals, whether wild-type or transgenic, which express a different species of GSSP-2 than the one to which antibody binding is desired, and animals which do not express GSSP-2 (i.e. a GSSP-2 knock out animal as described herein) are particularly useful for preparing antibodies. GSSP-2 knock out animals will recognize all or most of the exposed regions of a GSSP-2 protein as foreign antigens, and therefore produce antibodies with a wider array of GSSP-2 epitopes. Moreover, smaller polypeptides with only 10 to 30 amino acids may be useful in obtaining specific binding to GSSP-2 proteins. In addition, the humoral immune system of animals which produce a species of GSSP-2 that resembles the antigenic sequence will preferentially recognize the differences between the animal's native GSSP-2 species and the antigen sequence, and produce antibodies to these unique sites in the antigen sequence. Such a technique will be particularly useful in obtaining antibodies that specifically bind to the GSSP-2 protein.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method for detecting specifically the presence of a GSSP-2 polypeptide according to the invention in a biological sample, said method comprising the following steps:

a) bringing into contact the biological sample with a polyclonal or monoclonal antibody that specifically binds a GSSP-2 polypeptide comprising an amino acid sequence of SEQ ID No 3, or to a peptide fragment or variant thereof; and b) detecting the antigen-antibody complex formed.

The invention also concerns a diagnostic kit for detecting in vitro the presence of a GSSP-2 polypeptide according to the present invention in a biological sample, wherein said kit comprises:

a) a polyclonal or monoclonal antibody that specifically binds a GSSP-2 polypeptide comprising an amino acid sequence of SEQ ID No 3, or to a peptide fragment or variant thereof, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991); U.S. Pat. Nos. 5,573,920, 4,474,893, 5,601,819, 4,714,681, 4,925,648; Kostelny, S. A. et al. (1992).

In some embodiments, the antibodies may be capable of specifically binding to a protein or polypeptide encoded by GSSP-2-related nucleic acid molecules, fragments of GSSP-2-related nucleic acids, positional segments of GSSP-2-related nucleic acids or fragments of positional segments of GSSP-2-related nucleic acids. In some embodiments, the antibody may be capable of binding an antigenic determinant or an epitope in a protein or polypeptide encoded by GSSP-2-related nucleic acids, fragments of GSSP-2-related nucleic acids, positional segments of GSSP-2-related nucleic acids or fragments of positional segments of GSSP-2-related nucleic acids.

In other embodiments, the antibodies may be capable of specifically binding to an GSSP-2-related polypeptide, fragment of an GSSP-2-related polypeptide, positional segment of an GSSP-2-related polypeptide or fragment of a positional segment of an GSSP-2-related polypeptide. In some embodiments, the antibody may be capable of binding an antigenic determinant or an epitope in an GSSP-2-related polypeptide, fragment of an GSSP-2-related polypeptide, positional segment of an GSSP-2-related polypeptide or fragment of a positional segment of an GSSP-2-related polypeptide.

Antibodies of the present invention may be described or specified in terms of the epitope(s) or portion(s) of a polypeptide of the present invention which are recognized or specifically bound by the antibody. In the case of secreted proteins, the antibodies may specifically bind a full-length protein encoded by a nucleic acid molecule of the present invention, a mature protein (i.e. the protein generated by cleavage of the signal peptide) encoded by a nucleic acid molecule of the present invention, or a signal peptide encoded by a nucleic acid molecule of the present invention. Moreover, the epitope(s) or polypeptide portion(s) may be specified as described herein, e.g., by N-terminal and C-terminal positions, by size in contiguous amino acid residues, or listed in the figures and sequence listing. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., 1988 (incorporated by reference in the entirety).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effecter molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al., 1988; Hammerling, et al., 1981; (said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484,5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992); and Sawai, H. et al. (1995); and Better, M. et al. (1988) (said references incorporated by reference in their entireties).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988). For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986); Gillies, S. D. et al. (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., (1991); Studnicka G. M. et al. (1994); Roguska M. A. et al. (1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Preferred cell types are transformed cells or cancer cells. Preferred targets are cell surface receptors expressed on transformed cells or cancer cells. Methods of making recombinantly fused or chemically conjugated antibodies are well known in the art as are suitable cell types and target receptors. See e.g., U.S. Pat. Nos. 6,074,644; 6,071,519; 6,028,174; 5,980,896; 5,980, 895; 5,869,045; 5,792,458; 5,024,834; 4,902,495; 4,545,985 (said references incorporated by reference in their entireties). Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994); U.S. Pat. No. 5,474,981; Gillies, S. O. et al. (1992); Fell, H. P. et al. (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603; 5,622,929, 5,359,046, 5,349,053, 5,447,851, 5,112,946; EP 0 307 434, EP 0 367 166; WO 96/04388, WO 91/06570;

Ashkenazi, A. et al. (1991); Zheng, X. X. et al (1995); and Vil, H. et al. (1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al (1998); Pitard, V. et al. (1997); Liautard, J. et al. (1997); Carlson, N. G. et al. (1997); Taryman, R. E. et al. (1995); Muller, Y. A. et al. (1998); Bartunek, P. et al. (1996) (said references incorporated by reference in their entireties).

As discussed above, antibodies of the polypeptides of the invention can, in turn, be utilized to generate anti-idiotypic antibodies that "mimic" polypeptides of the invention using techniques well known to those skilled in the art. See, e.g. Greenspan and Bona, (1989); Nissinoff, (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and =thereby block its biological activity.

B. Epitopes and Antibody Fusions

A preferred embodiment of the present inventions directed to epitope-bearing polypeptides and epitope-bearing polypeptide fragments. These epitopes may be "antigenic epitopes" or both an "antigenic epitope" and an "immunogenic epitope." An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes (See, e.g., Geysen, et al., 1983). It is particularly noted that although a particular epitope may not be immunogenic, it is nonetheless useful since antibodies can be made to both immunogenic and antigenic epitopes.

An epitope can comprise as few as 3 amino acids in a spatial conformation, which is unique to the epitope. Generally an epitope consists of at least 6 such amino acids, and more often at least 8–10 such amino acids. In preferred embodiment, antigenic epitopes comprise a number of amino acids that is any integer between 3 and 50. Fragments which function as epitopes may be produced by any conventional means (See, e.g. Houghten, R. A., 1985), also, further described in U.S. Pat. No. 4,631,211. Methods for determining the amino acids which make up an epitope include x-ray crystallography, 2-dimensional nuclear magnetic resonance, and epitope mapping, e.g., the Pepscan method described by Mario H. Geysen et al. (1984); PCT Publication No. WO 84/03564; and PCT Publication No. WO 84/03506. Another example is the algorithm of Jameson and Wolf, (1988) (said references incorporated by reference in their entireties). The Jameson-Wolf antigenic analysis, for example, may be performed using the computer program PROTEAN, using default parameters (Version 4.0 Windows, DNASTAR, Inc., 1228 South Park Street Madison, Wis.

Predicted antigenic epitopes are shown below. It is pointed out that the immunogenic epitope list describe only amino acid residues comprising epitopes predicted to have the highest degree of immunogenicity by a particular algorithm. Polypeptides of the present invention that are not specifically described as immunogenic are not considered non-antigenic. This is because they may still be antigenic in vivo but merely not recognized as such by the particular algorithm used. Alternatively, the polypeptides are probably antigenic in vitro using methods such a phage display. Thus, listed below are the amino acid residues comprising only preferred epitopes, not a complete list. In fact, all fragments of the polypeptides of the present invention, at least 6 amino acids residues in length, are included in the present invention as being useful as antigenic epitope. Moreover, listed below are only the critical residues of the epitopes determined by the Jameson-Wolf analysis. Thus, additional flanking residues on either the N-terminal, C-terminal, or both N- and C-terminal ends may be added to the sequences listed to generate an epitope-bearing portion at least 6 residues in length. Amino acid residues comprising other immunogenic epitopes may be determined by algorithms similar to the Jameson-Wolf analysis or by in vivo testing for an antigenic response using the methods described herein or those known in the art.

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length GSSP-2 sequence of the sequence listing. All combinations of sequences between the integers of 6 and the full-length sequence of a GSSP-2 polypeptide are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See, Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.;

(1985) and Bittle, F. J. et al., (1985). A preferred immunogenic epitope includes the nature GSSP-2 protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acid molecules encoding the above epitopes can also be recombined with a gene of interest as an epitope tag to aid in detection and purification of the expressed polypeptide.

Additional fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos. 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). (Each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

TABLE 5

| Preferred GSSP-2 immunogenic epitopes |
|---|
| Gln22 to Phe27 |
| Gln33 to Arg40 |
| Ser78 to Met92 |
| Gln128 to Thr133 |
| Gly265 to Pro274 |
| Phe288 to Thr292 |
| Leu355 to His360 |

III. Identity Between Nucleic Acids or Polypeptides

The terms "percentage of sequence identity" and "percentage identity" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul (1990)).

The BLAST programs may be used with the default parameters or with modified parameters provided by the user.

IV. Stringent Hybridization Conditions

By way of example and not limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in prehybridization mixture containing 100 µg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989; and Ausubel et al., 1989, are incorporated herein in their entirety. These hybridization conditions are suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985) or in Sambrook et al. (1989).

V. GSSP-2-Related Biallelic Markers

A. Advantages of the Biallelic Markers of the Present Invention

The GSSP-2-related biallelic markers of the present invention offer a number of important advantages over other genetic markers such as RFLP (Restriction fragment length polymorphism) and VNTR (Variable Number of Tandem Repeats) markers.

The first generation of markers, were RFLPs, which are variations that modify the length of a restriction fragment. But methods used to identify and to type RFLPs are relatively wasteful of materials, effort, and time. The second generation of genetic markers were VNTRs, which can be categorized as either minisatellites or microsatellites. Minisatellites are tandemly repeated DNA sequences present in units of 5–50 repeats which are distributed along regions of the human chromosomes ranging from 0.1 to 20 kilobases in length. Since they present many possible alleles, their informative content is very high. Minisatellites are scored by performing Southern blots to identify the number of tandem repeats present in a nucleic acid sample from the individual being tested. However, there are only 10$^4$ potential VNTRs that can be typed by Southern blotting. Moreover, both RFLP and VNTR markers are costly and time-consuming to develop and assay in large numbers.

Single nucleotide polymorphism or biallelic markers can be used in the same manner as RFLPs and VNTRs but offer several advantages. SNP are densely spaced in the human genome and represent the most frequent type of variation. An estimated number of more than 10$^7$ sites are scattered along the 3×10$^9$ base pairs of the human genome. Therefore, SNP occur at a greater frequency and with greater uniformity than RFLP or VNTR markers which means that there is a greater probability that such a marker will be found in close proximity to a genetic locus of interest. SNP are less variable than VNTR markers but are mutationally more stable.

Also, the different forms of a characterized single nucleotide polymorphism, such as the biallelic markers of the present invention, are often easier to distinguish and can therefore be typed easily on a routine basis. Biallelic markers have single nucleotide based alleles and they have only two common alleles, which allows highly parallel detection and automated scoring. The biallelic markers of the present invention offer the possibility of rapid, high throughput genotyping of a large number of individuals.

Biallelic markers are densely spaced in the genome, sufficiently informative and can be assayed in large numbers. The combined effects of these advantages make biallelic markers extremely valuable in genetic studies. Biallelic markers can be used in linkage studies in families, in allele sharing methods, in linkage disequilibrium studies in populations, in association studies of case-control populations or of trait positive and trait negative populations. An important aspect of the present invention is that biallelic markers allow association studies to be performed to identify genes involved in complex traits. Association studies examine the frequency of marker alleles in unrelated case- and control-populations and are generally employed in the detection of polygenic or sporadic traits. Association studies may be conducted within the general population and are not limited to studies performed on related individuals in affected families (linkage studies). Biallelic markers in different genes can be screened in parallel for direct association with disease or response to a treatment. This multiple gene approach is a powerful tool for a variety of human genetic studies as it provides the necessary statistical power to examine the synergistic effect of multiple genetic factors on a particular phenotype, drug response, sporadic trait, or disease state with a complex genetic etiology.

B. Candidate Gene of the Present Invention

Different approaches can be employed to perform association studies: genome-wide association studies, candidate region association studies and candidate gene association studies. Genome-wide association studies rely on the screening of genetic markers evenly spaced and covering the entire genome. The candidate gene approach is based on the study of genetic markers specifically located in genes potentially involved in a biological pathway related to the trait of interest. In the present invention, GSSP-2 is the candidate gene. The candidate gene analysis clearly provides a shortcut approach to the identification of genes and gene polymorphisms related to a particular trait when some information concerning the biology of the trait is available. However, it should be noted that all of the biallelic markers disclosed in the instant application can be employed as part of genome-wide association studies or as part of candidate region association studies and such uses are specifically contemplated in the present invention and claims.

C. GSSP-2-Related Biallelic Markers and Polynucleotides Related Thereto

The invention also concerns GSSP-2-related biallelic markers. As used herein the term "GSSP-2-related biallelic marker" relates to a set of biallelic markers in linkage disequilibrium with the GSSP-2 gene. The term GSSP-2-related biallelic marker includes the biallelic markers designated 20-828-311, 17-42-319, 17-41-250, 20-841-149, 20-842-115, and 20-853-415.

The biallelic markers of the present invention are disclosed in Table 1. Their location on the GSSP-2 gene is indicated in Table 1 and also as a single base polymorphism in the features of SEQ ID NOs: 1, 2 and 4. The pairs of primers allowing the amplification of a nucleic acid molecule containing the polymorphic base of one GSSP-2 biallelic marker are listed in FIG. 5.

Two GSSP-2-related biallelic markers, 17-42-319 and 17-41-250, are located in the genomic sequence of GSSP-2. Both markers are located in SEQ ID NOs: 1 and 4. Biallelic marker 17-42-319 is located in the 5' Regulatory region (position 12347 of SEQ ID NO: 1 and position 319 of SEQ ID NO: 4), and therefore may alter enhancer regions or regulatory regions. 17-41-250 is located in exon 4 (position 15241 of SEQ ID NO: 1 and 3213 of SEQ ID NO: 4), and therefore may alter transcription in the gene.

The invention also relates to a purified and/or isolated nucleotide sequence comprising a polymorphic base of a GSSP-2-related biallelic marker, preferably of a biallelic marker selected from the group consisting of 20-828-311, 17-42-319, 17-41-250, 20-841-149, 20-842-115, and 20-853-415, and the complements thereof. The sequence has between 8 and 1000 nucleotides in length, and preferably comprises at least 8, 10, 12, 15, 18, 20, 25, 35, 40, 50, 60, 70, 80, 100, 250, 500 or 1000 contiguous nucleotides of a nucleotide sequence selected from the group consisting of SEQ ID NOs: 1, 2 and 4 or a variant thereof or a complementary sequence thereto. These nucleotide sequences comprise the polymorphic base of either allele 1 or allele 2 of the considered biallelic marker. Optionally, said biallelic marker may be within 6, 5, 4, 3, 2, or 1 nucleotides of the center of said polynucleotide or at the center of said polynucleotide. Optionally, the 3' end of said contiguous span may be present at the 3' end of said polynucleotide. Optionally, biallelic marker may be present at the 3' end of said polynucleotide. Optionally, said polynucleotide may further comprise a label. Optionally, said polynucleotide can be attached to solid support. In a further embodiment, the polynucleotides defined above can be used alone or in any combination.

The invention also relates to a purified and/or isolated nucleotide sequence comprising a between 8 and 1000 nucleotides in length, and preferably at least 8, 10, 12, 15, 18, 20, 25, 35, 40, 50, 60, 70, 80, 100, 250, 500 or 1000 contiguous nucleotides of a nucleotide sequence selected from the group consisting of SEQ ID NOs: 1, 2 and 4 or a variant thereof or a complementary sequence thereto. Optionally, the 3' end of said polynucleotide may be located within or at least 2, 4, 6, 8, 10, 12, 15, 18, 20, 25, 50, 100, 250, 500, or 1000 nucleotides upstream of a GSSP-2-related biallelic marker in said sequence. Optionally, said GSSP-2-related biallelic marker is selected from the group consisting of 20-828-311, 17-42-319, 17-41-250, 20-841-149, 20-842-115, and 20-853-415; Optionally, the 3' end of said polynucleotide may be located within or at least 2, 4, 6, 8, 10, 12, 15, 18, 20, 25, 50, 100, 250, 500, or 1000 nucleotides upstream of a GSSP-2-related biallelic marker in said sequence. Optionally, the 3' end of said polynucleotide may be located 1 nucleotide upstream of a GSSP-2-related biallelic marker in said sequence. Optionally, said polynucleotide may further comprise a label. Optionally, said polynucleotide can be attached to solid support. In a further embodiment, the polynucleotides defined above can be used alone or in any combination.

In a preferred embodiment, the sequences comprising a polymorphic base of one of the biallelic markers listed in FIG. 1 are selected from the group consisting of the nucleotide sequences that have a contiguous span of, that consist of, that are comprised in, or that comprises a polynucleotide selected from the group consisting of the nucleic acids of the sequences set forth as the amplicons listed in FIG. 5 or a variant thereof or a complementary sequence thereto.

The invention further concerns a nucleic acid molecule encoding the GSSP-2 protein, wherein said nucleic acid molecule comprises a polymorphic base of a biallelic marker selected from the group consisting of 20-828-311, 17-42-319, 17-41-250, 20-841-149, 20-842-115, and 20-853-415, and the complements thereof.

The invention also encompasses the use of any polynucleotide for, or any polynucleotide for use in, determining the identity of one or more nucleotides at a GSSP-2-related biallelic marker. In addition, the polynucleotides of the invention for use in determining the identity of one or more nucleotides at a GSSP-2-related biallelic marker encompass polynucleotides with any further limitation described in this disclosure, or those following, specified alone or in any combination. Optionally, said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, said GSSP-2-related biallelic marker is selected from the group consisting of 17-42-319 and 17-41-250, and the complements thereof, or optionally the biallelic markers in linkage disequilibrium therewith; Optionally, said polynucleotide may comprise a sequence disclosed in the present specification; Optionally, said polynucleotide may consist of, or consist essentially of any polynucleotide described in the present specification; Optionally, said determining may be performed in a hybridization assay, sequencing assay, microsequencing assay, or an enzyme-based mismatch detection assay; Optionally, said polynucleotide may be attached to a solid support, array, or addressable array; Optionally, said polynucleotide may be labeled. A preferred polynucleotide may be used in a hybridization assay for determining the identity of the nucleotide at a GSSP-2-related biallelic marker. Another preferred polynucleotide may be used in a sequencing or microsequencing assay for determining the identity of the nucleotide at a GSSP-2-related biallelic marker. A third preferred polynucleotide may be used in an enzyme-based mismatch detection assay for determining the identity of the nucleotide at a GSSP-2-related biallelic marker. A fourth preferred polynucleotide may be used in amplifying a segment of polynucleotides comprising a GSSP-2-related biallelic marker. Optionally, any of the polynucleotides described above may be attached to a solid support, array, or addressable array; Optionally, said polynucleotide may be labeled.

Additionally, the invention encompasses the use of any polynucleotide for, or any polynucleotide for use in, amplifying a segment of nucleotides comprising a GSSP-2-related biallelic marker. In addition, the polynucleotides of the invention for use in amplifying a segment of nucleotides comprising a GSSP-2-related biallelic marker encompass polynucleotides with any further limitation described in this disclosure, or those following, specified alone or in any combination: Optionally, said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, said GSSP-2-related biallelic marker is selected from the group consisting of 17-42-319 and 17-41-250, and the complements thereof. Optionally, said polynucleotide may comprise a sequence disclosed in the present specification; Optionally, said polynucleotide may consist of, or consist essentially of any polynucleotide described in the present specification; Optionally, said amplifying may be performed by a PCR or LCR. Optionally, said polynucleotide may be attached to a solid support, array, or addressable array. Optionally, said polynucleotide may be labeled.

The primers for amplification or sequencing reaction of a polynucleotide comprising a biallelic marker of the invention may be designed from the disclosed sequences for any method known in the art. A preferred set of primers are fashioned such that the 3' end of the contiguous span of identity with a sequence selected from the group consisting of SEQ ID NOs: 1, 2 and 4 or a sequence complementary thereto or a variant thereof is present at the 3' end of the primer. Such a configuration allows the 3' end of the primer to hybridize to a selected nucleic acid sequence and dramatically increases the efficiency of the primer for amplification or sequencing reactions. Allele specific primers may be designed such that a polymorphic base of a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of the primer of the invention may be located within or at least 2, 4, 6, 8, 10, 12, 15, 18, 20, 25, 50, 100, 250, 500, or 1000 nucleotides upstream of a GSSP-2-related biallelic marker in said sequence or at any other location which is appropriate for their intended use in sequencing, amplification or the location of novel sequences or markers. Thus, another set of preferred amplification primers comprise an isolated polynucleotide consisting essentially of a contiguous span of 8 to 50 nucleotides in a sequence selected from the group consisting of SEQ ID NOs: 1, 2 and 4 or a sequence complementary thereto or a variant thereof, wherein the 3' end of said contiguous span is located at the 3' end of said polynucleotide, and wherein the 3' end of said polynucleotide is located upstream of a GSSP-2-related biallelic marker in said sequence. Preferably, those amplification primers comprise a sequence selected from the group consisting of the sequences 929–949, 12029–12050, 14992–15012, 42070–42090, 45328–45347, 76644–76664, 1357–1377, 12581–12603, 15460–15482, 42572–42591, 45863–45883, and 77166–77185 of SEQ ID NO: 1; and 1–11022, 899–11920, 1246–12267, 2964–13984, 553–11575, 1441–12461, 1632–12651, and 3432–14454 of SEQ ID NO: 4. Primers with their 3' ends located 1 nucleotide upstream of a biallelic marker of GSSP-2 have a special utility as microsequencing assays. Preferred microsequencing primers are described in FIG. 4. Optionally, said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, said GSSP-2-related biallelic marker is selected from the group consisting of 17-42-319 and 17-41-250, and the complements thereof, or optionally the biallelic markers in linkage disequilibrium therewith.

The probes of the present invention may be designed from the disclosed sequences for any method known in the art, particularly methods which allow for testing if a marker disclosed herein is present. A preferred set of probes may be designed for use in the hybridization assays of the invention in any manner known in the art such that they selectively bind to one allele of a biallelic marker, but not the other under any particular set of assay conditions. Preferred hybridization probes comprise the polymorphic base of either allele 1 or allele 2 of the considered biallelic marker. Optionally, said biallelic marker may be within 6, 5, 4, 3, 2, or 1 nucleotides of the center of the hybridization probe or at the center of said probe. In a preferred embodiment, the probes are selected in the group consisting of the sequences 1227–1251, 12335–12359, 15229–15253, 42206–42230, 45430–45454, and 77046–77070 of SEQ ID NO: 1, and the complementary sequence thereto; and 307–331 and 3201–3225 of SEQ ID NO: 4, and the complementary sequence thereto.

It should be noted that the polynucleotides of the present invention are not limited to having the exact flanking sequences surrounding the polymorphic bases which are enumerated in Sequence Listing. Rather, it will be appreciated that the flanking sequences surrounding the biallelic markers may be lengthened or shortened to any extent compatible with their intended use and the present invention specifically contemplates such sequences. The flanking regions outside of the contiguous span need not be homologous to native flanking sequences which actually occur in human subjects. The addition of any nucleotide sequence which is compatible with the nucleotides intended use is specifically contemplated.

Primers and probes may be labeled or immobilized on a solid support as described in "Oligonucleotide Probes and Primers".

The polynucleotides of the invention which are attached to a solid support encompass polynucleotides with any further limitation described in this disclosure, or those following, specified alone or in any combination: Optionally, said polynucleotides may be specified as attached individually or in groups of at least 2, 5, 8, 10, 12, 15, 20, or 25 distinct polynucleotides of the invention to a single solid support. Optionally, polynucleotides other than those of the invention may attached to the same solid support as polynucleotides of the invention. Optionally, when multiple polynucleotides are attached to a solid support they may be attached at random locations, or in an ordered array. Optionally, said ordered array may be addressable.

The present invention also encompasses diagnostic kits comprising one or more polynucleotides of the invention with a portion or all of the necessary reagents and instructions for genotyping a test subject by determining the identity of a nucleotide at a GSSP-2-related biallelic marker. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an enzyme-based mismatch detection assay method.

VI. Methods for De Novo Identification of Biallelic Markers

Any of a variety of methods can be used to screen a genomic fragment for single nucleotide polymorphisms such as differential hybridization with oligonucleotide probes, detection of changes in the mobility measured by gel electrophoresis or direct sequencing of the amplified nucleic acid. A preferred method for identifying biallelic markers involves comparative sequencing of genomic DNA fragments from an appropriate number of unrelated individuals.

In a first embodiment, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the pooling of the DNA samples substantially reduces the number of DNA amplification reactions and sequencing reactions, which must be carried out. Moreover, this method is sufficiently sensitive so that a biallelic marker obtained thereby usually demonstrates a sufficient frequency of its less common allele to be useful in conducting association studies.

In a second embodiment, the DNA samples are not pooled and are therefore amplified and sequenced individually. This method is usually preferred when biallelic markers need to be identified in order to perform association studies within candidate genes. Preferably, highly relevant gene regions such as promoter regions or exon regions may be screened for biallelic markers. A biallelic marker obtained using this method may show a lower degree of informativeness for conducting association studies, e.g. if the frequency of its less frequent allele may be less than about 10%. Such a biallelic marker will, however, be sufficiently informative to conduct association studies and it will further be appreciated that including less informative biallelic markers in the genetic analysis studies of the present invention, may allow in some cases the direct identification of causal mutations, which may, depending on their penetrance, be rare mutations.

The following is a description of the various parameters of a preferred method used by the inventors for the identification of the biallelic markers of the present invention.

A. Genomic DNA Samples

The genomic DNA samples from which the biallelic markers of the present invention are generated are preferably obtained from unrelated individuals corresponding to a heterogeneous population of known ethnic background. The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician. Details of a preferred embodiment are provided in Example 1. The person skilled in the art can choose to amplify pooled or unpooled DNA samples.

B. DNA Amplification

The identification of biallelic markers in a sample of genomic DNA may be facilitated through the use of DNA amplification methods. DNA samples can be pooled or unpooled for the amplification step. DNA amplification techniques are well known to those skilled in the art.

Amplification techniques that can be used in the context of the present invention include, but are not limited to, the ligase chain reaction (LCR) described in EP-A-320 308, WO 9320227 and EP-A-439 182, the polymerase chain reaction (PCR, RT-PCR) and techniques such as the nucleic acid sequence based amplification (NASBA) described in Guatelli J. C., et al. (1990) and in Compton J. (1991), Q-beta amplification as described in European Patent Application No 4544610, strand displacement amplification as described in Walker et al. (1996) and EP A 684 315 and, target mediated amplification as described in PCT Publication WO 9322461.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall et al. (1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid molecule in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195; 4,683,202; and 4,965,188, the disclosures of which are incorporated herein by reference in their entireties.

The PCR technology is the preferred amplification technique used to identify new biallelic markers. A typical example of a PCR reaction suitable for the purposes of the present invention is provided in Example 2.

One of the aspects of the present invention is a method for the amplification of the human GSSP-2 gene, particularly of a fragment of the genomic sequence of SEQ ID NOs: 1 or 4 or of the cDNA sequence of SEQ ID NO: 2, or a fragment or a variant thereof in a test sample, preferably using the PCR technology. This method comprises the steps of:

a) contacting a test sample with amplification reaction reagents comprising a pair of amplification primers as described above and located on either side of the polynucleotide region to be amplified, and b) optionally, detecting the amplification products.

The invention also concerns a kit for the amplification of a GSSP-2 gene sequence, particularly of a portion of the genomic sequence of SEQ ID NOs: 1 or 4 or of the cDNA sequence of SEQ ID NO: 2, or a variant thereof in a test sample, wherein said kit comprises:

a) a pair of oligonucleotide primers located on either side of the GSSP-2 region to be amplified;

b) optionally, the reagents necessary for performing the amplification reaction.

In one embodiment of the above amplification method and kit, the amplification product is detected by hybridization with a labeled probe having a sequence which is complementary to the amplified region. In another embodiment of the above amplification method and kit, primers comprise a sequence which is selected from the group consisting of the nucleotide sequences of 929–949, 12029–12050, 14992–15012, 42070–42090, 45328–45347, 76644–76664, 1357–1377, 12581–12603, 15460–15482, 42572–42591, 45863–45883, 77166–77185, 1220–1238, 12328–12346, 15222–15240, 42199–42217, 45423–45441, 77039–77057, 1240–1258, 12348–12366, 15242–15260, 42219–42237, 45443–45461 and 77059–77077 of SEQ ID NO: 1; and 1–11022, 899–11920, 1246–12267, 2964–13984, 553–11575, 1441–12461, 1632–12651, 3432–14454, 300–318, 3194–3212, 320–338 and 3214–3232 of SEQ ID NO: 4.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier L. and Green P., 1991). All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequences encoding the candidate genes, focus on promoters, exons and splice sites of the genes. A biallelic marker presents a higher probability to be an eventual causal mutation if it is located in these functional regions of the gene. Preferred amplification primers of the invention include the nucleotide sequences 929–949, 12029–12050, 14992–15012, 42070–42090, 45328–45347, 76644–76664, 1357–1377, 12581–12603, 15460–15482, 42572–42591, 45863–45883, and 77166–77185 of SEQ ID NO: 1; and 1–11022, 899–11920, 1246–12267, 2964–13984, 553–11575, 1441–12461, 1632–12651, and 3432–14454 of SEQ ID NO: 4; detailed further in Example 2.

C. Sequencing of Amplified Genomic DNA and Identification of Single Nucleotide Polymorphisms The amplification products generated as described above, are then sequenced using any method known and available to the skilled technician. Methods for sequencing DNA using either the dideoxy-mediated method (Sanger method) or the Maxam-Gilbert method are widely known to those of ordinary skill in the art. Such methods are for example disclosed in Sambrook et al. (1989). Alternative approaches include hybridization to high-density DNA probe arrays as described in Chee et al. (1996).

Preferably, the amplified DNA is subjected to automated dideoxy terminator sequencing reactions using a dye-primer cycle sequencing protocol. The products of the sequencing reactions are run on sequencing gels and the sequences are determined using gel image analysis. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products, which contain biallelic markers to be identified. The detection limit for the frequency of biallelic polymorphisms detected by sequencing pools of 100 individuals is approximately 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele. Preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples, the frequency of the minor allele of such a biallelic marker may be less than 0.1.

D. Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bona fide biallelic marker at a particular position in a sequence. All of the genotyping, haplotyping, association, and interaction study methods of the invention may optionally be performed solely with validated biallelic markers.

E. Evaluation of the Frequency of the Biallelic Markers of the Present Invention The validated biallelic markers are further evaluated for their usefulness as genetic markers by determining the frequency of the least common allele at the biallelic marker site. The higher the frequency of the less common allele the greater the usefulness of the biallelic marker is association and interaction studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. A biallelic marker wherein the frequency of the less common allele is 30% or more is termed a "high quality biallelic marker." All of the genotyping, haplotyping, association, and interaction study methods of the invention may optionally be performed solely with high quality biallelic markers.

VII. Methods for Genotyping an Individual for Biallelic Markers

Methods are provided to genotype a biological sample for one or more biallelic markers of the present invention, all of which may be performed in vitro. Such methods of genotyping comprise determining the identity of a nucleotide at a GSSP-2 biallelic marker site by any method known in the art. These methods find use in genotyping case-control populations in association studies as well as individuals in the context of detection of alleles of biallelic markers which are known to be associated with a given trait, in which case both copies of the biallelic marker present in individual's genome are determined so that an individual may be classified as homozygous or heterozygous for a particular allele.

These genotyping methods can be performed on nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

In one embodiment the invention encompasses methods of genotyping comprising determining the identity of a nucleotide at a GSSP-2-related biallelic marker or the complement thereof in a biological sample; optionally, wherein said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, wherein said GSSP-2-related biallelic marker is selected from the group consisting of 17-42-319 and 17-41-250, and the complements thereof, or optionally the biallelic markers in linkage disequilibrium therewith; optionally, wherein said biological sample is derived from a single subject; optionally, wherein the identity of the nucleotides at said biallelic marker is determined for both copies of said biallelic marker present in said individual's genome; optionally, wherein said biological sample is derived from multiple subjects; Optionally, the genotyping methods of the invention encompass methods with any further limitation described in this disclosure, or those following, specified alone or in any combination; Optionally, said method is performed in vitro; optionally, further comprising amplifying a portion of said sequence comprising the biallelic marker prior to said determining step; Optionally, wherein said amplifying is performed by PCR, LCR, or replication of a recombinant vector comprising an origin of replication and said fragment in a host cell; optionally, wherein said determining is performed by a hybridization assay, a sequencing assay, a microsequencing assay, or an enzyme-based mismatch detection assay.

A. Source of Nucleic Acids for Genotyping

Any source of nucleic acid molecules, in purified or non-purified form, can be utilized as the starting nucleic acid molecule, provided it contains or is suspected of containing the specific nucleic acid sequence desired. DNA or RNA may be extracted from cells, tissues, body fluids and the like as described above. While nucleic acid molecules for use in the genotyping methods of the invention can be derived from any mammalian source, the test subjects and individuals from which nucleic acid samples are taken are generally understood to be human.

B. Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention. Amplification of DNA may be achieved by any method known in the art. Amplification techniques are described above in the section entitled, "DNA Amplification."

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention.

In some embodiments the present invention provides primers for amplifying a DNA fragment containing one or more biallelic markers of the present invention. Preferred amplification primers are listed in FIG. 5. It will be appreciated that the primers listed are merely exemplary and that any other set of primers which produce amplification products containing one or more biallelic markers of the present invention are also of use.

The spacing of the primers determines the length of the segment to be amplified. In the context of the present invention, amplified segments carrying biallelic markers can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for the biallelic markers may be any sequence which allow the specific amplification of any DNA fragment carrying the markers. Amplification primers may be labeled or immobilized on a solid support as described in "Oligonucleotide Probes and Primers."

C. Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al. (1989), denaturing gradient gel electrophoresis (DGGE), heteroduplex analysis, mismatch cleavage detection, and other conventional techniques as described in Sheffield et al. (1991), White et al. (1992), Grompe et al. (1989 and 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, enzyme-based mismatch detection assay, or hybridization assay. The following is a description of some preferred methods. A highly preferred method is the microsequencing technique. The term "sequencing" is generally used herein to refer to polymerase extension of duplex primer/template complexes and includes both traditional sequencing and microsequencing.

i. Sequencing Assays

The nucleotide present at a polymorphic site can be determined by sequencing methods. In a preferred embodiment, DNA samples are subjected to PCR amplification before sequencing as described above. DNA sequencing methods are described in "Sequencing Of Amplified Genomic DNA And Identification Of Single Nucleotide Polymorphisms".

Preferably, the amplified DNA is subjected to automated dideoxy terminator sequencing reactions using a dye-primer cycle sequencing protocol. Sequence analysis allows the identification of the base present at the biallelic marker site.

ii. Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid molecule. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883, the disclosure of which is incorporated herein by reference in its entirety. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al. (1997). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Harju et al., 1993) or biotinylated ddNTP and horseradish peroxidase-conjugated streptavidin with o-phenylenediamine as a substrate (WO 92/15712, the disclosure of which is incorporated herein by reference in its entirety). As yet another alternative solid-phase microsequencing procedure, Nyren et al. (1993) described a method relying on the detection of DNA polymerase activity by an enzymatic luminometric inorganic pyrophosphate detection assay (ELIDA).

Pastinen et al. (1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences 1220–1238, 12328–12346, 15222–15240, 42199–42217, 45423–45441, 77039–77057, 1240–1258, 12348–12366, 15242–15260, 42219–42237, 45443–45461 and 77059–77077 of SEQ ID NO: 1; and 300–318, 3194–3212, 320–338 and 3214–3232 of SEQ ID NO: 4. It will be appreciated that the microsequencing primers listed in FIG. 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in FIG. 4, or fragments comprising at least 8, 12, 15, 20, 25, 30, 40, or 50 consecutive nucleotides thereof, to the extent that such lengths are consistent with the primer described, and having a 3' terminus immediately upstream of the corresponding biallelic marker, for determining the identity of a nucleotide at a biallelic marker site.

iii. Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end. Methods, primers and various parameters to amplify DNA fragments comprising biallelic markers of the present invention are further described above in "Amplification Of DNA Fragments Comprising Biallelic Markers."

Allele Specific Amplification Primers

Discrimination between the two alleles of a biallelic marker can also be achieved by allele specific amplification, a selective strategy, whereby one of the alleles is amplified without amplification of the other allele. For allele specific amplification, at least one member of the pair of primers is sufficiently complementary with a region of a GSSP-2 gene comprising the polymorphic base of a biallelic marker of the present invention to hybridize therewith and to initiate the amplification. Such primers are able to discriminate between the two alleles of a biallelic marker.

This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well within the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. (1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "DNA Amplification". LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069, the disclosure of which is incorporated herein by reference in its entirety. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

iv. Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acid molecules due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridization can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acid molecules and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acid molecules in homogeneous solutions. When they bind to their targets they undergo a conformational reorganization that restores the fluorescence of an internally quenched fluorophore (Tyagi et al., 1998).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. Preferred probes comprise a nucleotide sequence selected from the group consisting of amplicons listed in FIG. 6 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. Preferred probes comprise a nucleotide sequence selected from the group consisting of 1227–1251, 12335–12359, 15229–15253, 42206–42230, 45430–45454, and 77046–77070 of SEQ ID NO: 1; and 307–331 and 3201–3225 of SEQ ID NO: 4 and the sequences complementary thereto. In preferred embodiments the polymorphic base(s) are within 5, 4, 3, 2, 1, nucleotides of the center of the said polynucleotide, more preferably at the center of said polynucleotide.

Preferably the probes of the present invention are labeled or immobilized on a solid support. Labels and solid supports are further described in "Oligonucleotide Probes and Primers." The probes can be non-extendable as described in "Oligonucleotide Probes and Primers."

By assaying the hybridization to an allele specific probe, one can detect the presence or absence of a biallelic marker allele in a given sample. High-Throughput parallel hybridization in array format is specifically encompassed within "Hybridization Assays" and are described below.

v. Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual, which target sequences including a polymorphic marker. EP 785280, the disclosure of which is incorporated herein by reference in its entirety, describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of nucleotides. Tiling strategies are further described in PCT application No. WO 95/11995. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length. In further embodiments, the chip may comprise an array including at least one of the sequences selected from the group consisting of amplicons listed in FIG. 5 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides of the invention. Solid supports and polynucleotides of the present invention attached to solid supports are further described in "Oligonucleotide Probes and Primers."

vi. Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is incorporated herein by reference in its entirety, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts.

For genotyping biallelic markers, the microfluidic system may integrate nucleic acid amplification, microsequencing, capillary electrophoresis and a detection method such as laser-induced fluorescence detection.

VI. Methods of Genetic Analysis Using the Biallelic Markers of the Present Invention Different methods are available for the genetic analysis of complex traits (see Lander and Schork, 1994). The search for disease-susceptibility genes is conducted using two main methods: the linkage approach in which evidence is sought for cosegregation between a locus and a putative trait locus using family studies, and the association approach in which evidence is sought for a statistically significant association between an allele and a trait or a trait causing allele (Khoury et al., 1993). In general, the biallelic markers of the present invention find use in any method known in the art to demonstrate a statistically significant correlation between a genotype and a phenotype. The biallelic markers may be used in parametric and non-parametric linkage analysis methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention may be conducted on any scale. The whole set of biallelic markers of the present invention or any subset of biallelic markers of the present invention corresponding to the candidate gene may be used. Further, any set of genetic markers including a biallelic marker of the present invention may be used. A set of biallelic polymorphisms that could be used as genetic markers in combination with the biallelic markers of the present invention has been described in WO 98/20165. As mentioned above, it should be noted that the biallelic markers of the present invention may be included in any complete or partial genetic map of the human genome. These different uses are specifically contemplated in the present invention and claims.

A. Linkage Analysis

Linkage analysis is based upon establishing a correlation between the transmission of genetic markers and that of a specific trait throughout generations within a family. Thus, the aim of linkage analysis is to detect marker loci that show cosegregation with a trait of interest in pedigrees.

i. Parametric Methods

When data are available from successive generations there is the opportunity to study the degree of linkage between pairs of loci. Estimates of the recombination fraction enable loci to be ordered and placed onto a genetic map. With loci that are genetic markers, a genetic map can be established, and then the strength of linkage between markers and traits can be calculated and used to indicate the relative positions of markers and genes affecting those traits (Weir, 1996). The classical method for linkage analysis is the logarithm of odds (lod) score method (see Morton, 1955; Ott, 1991). Calculation of lod scores requires specification of the mode of inheritance for the disease (parametric method). Generally, the length of the candidate region identified using linkage analysis is between 2 and 20 Mb. Once a candidate region is identified as described above, analysis of recombinant individuals using additional markers allows further delineation of the candidate region. Linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population). However, parametric linkage analysis suffers from a variety of drawbacks. First, it is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, parametric linkage analysis approaches have proven difficult when applied to complex genetic traits, such as those due to the combined action of multiple genes and/or environmental factors. It is very difficult to model these factors adequately in a lod score analysis. In such cases, too large an effort and cost are needed to recruit the adequate number of affected families required for applying linkage analysis to these situations, as recently discussed by Risch, N. and Merikangas, K. (1996).

ii. Non-Parametric Methods

The advantage of the so-called non-parametric methods for linkage analysis is that they do not require specification of the mode of inheritance for the disease, they tend to be more useful for the analysis of complex traits. In non-parametric methods, one tries to prove that the inheritance pattern of a chromosomal region is not consistent with random Mendelian segregation by showing that affected relatives inherit identical copies of the region more often than expected by chance. Affected relatives should show excess "allele sharing" even in the presence of incomplete penetrance and polygenic inheritance. In non-parametric linkage analysis the degree of agreement at a marker locus in two individuals can be measured either by the number of alleles identical by state (IBS) or by the number of alleles identical by descent (IBD). Affected sib pair analysis is a well-known special case and is the simplest form of these methods.

The biallelic markers of the present invention may be used in both parametric and non-parametric linkage analysis. Preferably biallelic markers may be used in non-parametric methods which allow the mapping of genes involved in complex traits. The biallelic markers of the present invention may be used in both IBD- and IBS-methods to map genes affecting a complex trait. In such studies, taking advantage of the high density of biallelic markers, several adjacent biallelic marker loci may be pooled to achieve the efficiency attained by multi-allelic markers (Zhao et al., 1998).

B. Population Association Studies

The present invention comprises methods for identifying if the GSSP-2 gene is associated with a detectable trait using the biallelic markers of the present invention. In one embodiment the present invention comprises methods to detect an association between a biallelic marker allele or a biallelic marker haplotype and a trait. The trait may include, but is not limited to, the following: body mass; plasma levels of leptin, insulin, free fatty acids (FFA), triglycerides (TG), glucose and GSSP-2 expression. Further, the invention comprises methods to identify a trait causing allele in linkage disequilibrium with any biallelic marker allele of the present invention.

As described above, alternative approaches can be employed to perform association studies: genome-wide association studies, candidate region association studies and candidate gene association studies. In a preferred embodiment, the biallelic markers of the present invention are used to perform candidate gene association studies. The candidate gene analysis clearly provides a short-cut approach to the identification of genes and gene polymorphisms related to a particular trait when some information concerning the biology of the trait is available. Further, the biallelic markers of the present invention may be incorporated in any map of genetic markers of the human genome in order to perform genome-wide association studies. Methods to generate a high-density map of biallelic markers has been described in U.S. Provisional Patent application Ser. No. 60/082,614. The biallelic markers of the present invention may further be incorporated in any map of a specific candidate region of the genome (a specific chromosome or a specific chromosomal segment for example).

As mentioned above, association studies may be conducted within the general population and are not limited to studies performed on related individuals in affected families. Association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies using the biallelic markers of the present invention can therefore be used to refine the location of a trait causing allele in a candidate region identified by Linkage Analysis methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention.

C. Determining the Frequency of a Biallelic Marker Allele or of a Biallelic Marker Haplotype in a Population Association studies explore the relationships among frequencies for sets of alleles between loci.

i. Determining the Frequency of an Allele in a Population

Allelic frequencies of the biallelic markers in a populations can be determined using one of the methods described above under the heading "Methods for genotyping an individual for biallelic markers", or any genotyping procedure suitable for this intended purpose. Genotyping pooled samples or individual samples can determine the frequency of a biallelic marker allele in a population. One way to reduce the number of genotypings required is to use pooled samples. A major obstacle in using pooled samples is in terms of accuracy and reproducibility for determining accurate DNA concentrations in setting up the pools. Genotyping individual samples provides higher sensitivity, reproducibility and accuracy and; is the preferred method used in the present invention. Preferably, each individual is genotyped separately and simple gene counting is applied to determine the frequency of an allele of a biallelic marker or of a genotype in a given population.

The invention also relates to methods of estimating the frequency of an allele in a population comprising: a) genotyping individuals from said population for said biallelic marker according to the method of the present invention; b) determining the proportional representation of said biallelic marker in said population. In addition, the methods of estimating the frequency of an allele in a population of the invention encompass methods with any further limitation described in this disclosure, or those following, specified alone or in any combination; optionally, wherein said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, wherein said GSSP-2-related biallelic marker is selected from the group consisting of 17-42-319 and 17-41-250, and the complements thereof. Optionally, determining the frequency of a biallelic marker allele in a population may be accomplished by determining the identity of the nucleotides for both copies of said biallelic marker present in the genome of each individual in said population and calculating the proportional representation of said nucleotide at said GSSP-2-related biallelic marker for the population; Optionally, determining the proportional representation may be accomplished by performing a genotyping method of the invention on a pooled biological sample derived from a representative number of individuals, or each individual, in said population, and calculating the proportional amount of said nucleotide compared with the total.

ii. Determining the Frequency of a Haplotype in a Population

The gametic phase of haplotypes is unknown when diploid individuals are heterozygous at more than one locus. Using genealogical information in families gametic phase can sometimes be inferred (Perlin et al., 1994). When no genealogical information is available different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al, 1989; Wu et al., 1989) or by isolation of single chromosome by limit dilution followed by PCR amplification (see Ruano et al., 1990). Further, a sample may be haplotyped for sufficiently close biallelic markers by double PCR amplification of specific alleles (Sarkar, G. and Sommer S. S., 1991). These approaches are not entirely satisfying either because of their technical complexity, the additional cost they entail, their lack of generalization at a large scale, or the possible biases they introduce. To overcome these difficulties, an algorithm to infer the phase of PCR-amplified DNA genotypes introduced by Clark, A. G. (1990) may be used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., 1977) leading to maximum-likelihood estimates of haplotype frequencies under the assumption of Hardy-Weinberg proportions (random mating) is used (see Excoffier L. and Slatkin M., 1995). The EM algorithm is a generalized iterative maximum-likelihood approach to estimation that is useful when data are ambiguous and/or incomplete. The EM algorithm is used to resolve heterozygotes into haplotypes. Haplotype estimations are further described below under the heading "Statistical Methods." Any other method known in the art to determine or to estimate the frequency of a haplotype in a population may be used.

The invention also encompasses methods of estimating the frequency of a haplotype for a set of biallelic markers in a population, comprising the steps of: a) genotyping at least one GSSP-2-related biallelic marker according to a method of the invention for each individual in said population; b) genotyping a second biallelic marker by determining the identity of the nucleotides at said second biallelic marker for both copies of said second biallelic marker present in the genome of each individual in said population; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, or those following, specified alone or in any combination: optionally, wherein said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, wherein said GSSP-2-related biallelic marker is selected from the group consisting of 17-42-319 and 17-41-

250, and the complements thereof, or optionally the biallelic markers in linkage disequilibrium therewith; Optionally, said haplotype determination method is performed by asymmetric PCR amplification, double PCR amplification of specific alleles, the Clark algorithm, or an expectation-maximization algorithm.

D. Linkage Disequilibrium Analysis

Linkage disequilibrium is the non-random association of alleles at two or more loci and represents a powerful tool for mapping genes involved in disease traits (see Ajioka R. S. et al., 1997). Biallelic markers, because they are densely spaced in the human genome and can be genotyped in greater numbers than other types of genetic markers (such as RFLP or VNTR markers), are particularly useful in genetic analysis based on linkage disequilibrium.

When a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombination events occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above, the mapping resolution achieved through the analysis of linkage disequilibrium is much higher than that of linkage studies. The high density of biallelic markers combined with linkage disequilibrium analysis provides powerful tools for fine-scale mapping. Different methods to calculate linkage disequilibrium are described below under the heading "Statistical Methods."

E. Population-Based Case-Control Studies of Trait-Marker Associations

As mentioned above, the occurrence of pairs of specific alleles at different loci on the same chromosome is not random and the deviation from random is called linkage disequilibrium. Association studies focus on population frequencies and rely on the phenomenon of linkage disequilibrium. If a specific allele in a given gene is directly involved in causing a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region. Case-control populations can be genotyped for biallelic markers to identify associations that narrowly locate a trait causing allele. As any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

i. Case-Control Populations (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected, trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. The terms "trait positive population", "case population" and "affected population" are used interchangeably herein.

An important step in the dissection of complex traits using association studies is the choice of case-control populations (see Lander and Schork, 1994). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity. The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations comprise phenotypically homogeneous populations. Trait positive and trait negative populations comprise phenotypically uniform populations of individuals representing each between 1 and 98%, preferably between 1 and 80%, more preferably between 1 and 50%, and more preferably between 1 and 30%, most preferably between 1 and 20% of the total population under study, and preferably selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of control individuals are included in such studies.

ii. Association Analysis

The invention also comprises methods of detecting an association between a genotype and a phenotype, comprising the steps of: a) determining the frequency of at least one GSSP-2-related biallelic marker in a trait positive population according to a genotyping method of the invention; b) determining the frequency of said GSSP-2-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following, specified alone or in any combination: optionally, wherein said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, wherein said GSSP-2-related biallelic marker is selected from the group consisting of 17-42-319 and 17-41-250, and the complements thereof, or optionally the biallelic markers in linkage disequilibrium therewith; Optionally, said control population may be a trait negative population, or a random population; Optionally, each of said genotyping steps a) and b) may be performed on a pooled biological sample derived from each of said populations; Optionally, each of said genotyping of steps a) and b) is performed separately on biological samples derived from each individual in said population or a subsample thereof.

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (i.e. the associated allele is the trait causing allele), or more likely the associated allele is in linkage disequilibrium with the trait causing allele. The specific characteristics of the associated allele with respect to the candidate gene function usually give further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker, and performing further association studies with the polymorphisms that are revealed in an iterative manner.

Association studies are usually run in two successive steps. In a first phase, the frequencies of a reduced number of biallelic markers from the candidate gene are determined in the trait positive and control populations. In a second phase of the analysis, the position of the genetic loci responsible for the given trait is further refined using a higher density of markers from the relevant region. However, if the candidate gene under study is relatively small in length, as is the case for GSSP-2, a single phase may be sufficient to establish significant associations.

iii. Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odd ratio are calculated. If a statistically significant association is found the relative risk for an individual carrying the given haplotype of being affected with the trait under study can be approximated.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following: optionally, wherein said GSSP-2-related biallelic marker is selected from the group consisting of 20-828-311, 17-42-319, 17-41-250, 20-841-149, 20-842-115, and 20-853-415, and the complements thereof, or optionally the biallelic markers in linkage disequilibrium therewith; optionally, wherein said GSSP-2-related biallelic marker is selected from the group consisting of 17-42-319 and 17-41-250, and the complements thereof, or optionally the biallelic markers in linkage disequilibrium therewith; Optionally, said control population is a trait negative population, or a random population. Optionally, said method comprises the additional steps of determining the phenotype in said trait positive and said control populations prior to step c).

iv. Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis comprises stratifying the case-control populations with respect to a given haplotype for the first loci and performing a haplotype analysis with the second loci with each subpopulation.

Statistical methods used in association studies are further described below.

F. Testing for Linkage in the Presence of Association

The biallelic markers of the present invention may further be used in TDT (transmission/disequilibrium test). TDT tests for both linkage and association and is not affected by population stratification. TDT requires data for affected individuals and their parents or data from unaffected sibs instead of from parents (see Spielmann S. et al., 1993; Schaid D. J. et al., 1996, Spielmann S. and Ewens W. J., 1998). Such combined tests generally reduce the false-positive errors produced by separate analyses.

VII. Statistical Methods

In general, any method known in the art to test whether a trait and a genotype show a statistically significant correlation may be used.

A. Methods in Linkage Analysis

Statistical methods and computer programs useful for linkage analysis are well-known to those skilled in the art (see Terwilliger J. D. and Ott J., 1994; Ott J., 1991).

B. Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to person skilled in the art can be used to estimate haplotype frequencies (see Lange K., 1997; Weir, B. S., 1996) Preferably, maximum-likelihood haplotype frequencies are computed using an Expectation-Maximization (EM) algorithm (see Dempster et al., 1977; Excoffier L. and Slatkin M., 1995). This procedure is an iterative process aiming at obtaining maximum-likelihood estimates of haplotype frequencies from multi-locus genotype data when the gametic phase is unknown. Haplotype estimations are usually performed by applying the EM algorithm using for example the EM-HAPLO program (Hawley M. E. et al., 1994) or the Arlequin program (Schneider et al., 1997). The EM algorithm is a generalized iterative maximum likelihood approach to estimation and is briefly described below.

In what follows, phenotypes will refer to multi-locus genotypes with unknown haplotypic phase. Genotypes will refer to mutli-locus genotypes with known haplotypic phase.

Suppose one has a sample of N unrelated individuals typed for K markers. The data observed are the unknown-phase K-locus phenotypes that can be categorized with F different phenotypes. Further, suppose that we have H possible haplotypes (in the case of K biallelic markers, we have for the maximum number of possible haplotypes $H=2^K$). For phenotype j with $c_j$ possible genotypes, we have:

$$P_j = \sum_{i=1}^{c_j} P(\text{genotype}(i)) = \sum_{i=1}^{c_j} P(h_k, h_l). \qquad \text{Equation 1}$$

Here, $P_J$ is the probability of the $j^{th}$ phenotype, and $P(h_k,h_l)$ is the probability of the $i^{th}$ genotype composed of haplotypes $h_k$ and $h_l$. Under random mating (i.e. Hardy-Weinberg Equilibrium), $P(h_k h_l)$ is expressed as:

$P(h_k, h_l) = P(h_k)^2$ for $h_k = h_l$, and $P(h_k, h_l) = 2P(h_k)P(h_l)$ for $h_k \neq h_l$. \qquad Equation 2

The E-M algorithm is composed of the following steps: First, the genotype frequencies are estimated from a set of initial values of haplotype frequencies. These haplotype frequencies are denoted $P_1^{(0)}, P_2^{(0)}, P_3^{(0)}, \ldots, P_H^{(0)}$. The initial values for the haplotype frequencies may be obtained from a random number generator or in some other way well known in the art. This step is referred to the Expectation step. The next step in the method, called the Maximization step, consists of using the estimates for the genotype frequencies to re-calculate the haplotype frequencies. The first iteration haplotype frequency estimates are denoted by $P_1^{(1)}, P_2^{(1)}, P_3^{(1)}, \ldots, P_H^{(1)}$. In general, the Expectation step at the $s^{th}$ iteration consists of calculating the probability of placing each phenotype into the different possible genotypes based on the haplotype frequencies of the previous iteration:

$$P(h_k, h_l)^{(s)} = \frac{n_j}{N}\left[\frac{P_j(h_k, h_l)^{(s)}}{P_j}\right], \qquad \text{Equation 3}$$

where $n_j$ is the number of individuals with the $j^{th}$ phenotype and $P_j(h_k,h_l)^{(s)}$ is the probability of genotype $h_k,h_l$ in phenotype j. In the Maximization step, which is equivalent to the gene-counting method (Smith, *Ann. Hum. Genet.*, 21:254–276, 1957), the haplotype frequencies are re-estimated based on the genotype estimates:

$$P_t^{(s+1)} = \frac{1}{2}\sum_{j=1}^{F}\sum_{i=1}^{c_j}\delta_{it}P_j(h_k, h_l)^{(s)}. \qquad \text{Equation 4}$$

Here, $\delta_{it}$ is an indicator variable which counts the number of occurrences that haplotype t is present in $i^{th}$ genotype; it takes on values 0, 1, and 2.

The E-M iterations cease when the following criterion has been reached. Using Maximum Likelihood Estimation (MLE) theory, one assumes that the phenotypes j are distributed multinomially. At each iteration s, one can compute the likelihood function L. Convergence is achieved when the difference of the log-likehood between two consecutive iterations is less than some small number, preferably $10^{-7}$.

Methods to Calculate Linkage Disequilibrium Between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention ($M_i$, $M_j$) having alleles ($a_i/b_i$) at marker $M_i$ and alleles ($a_j/b_j$) at marker $M_j$ can be calculated for every allele combination ($a_i,a_j$; $a_i,b_j$; $b_i,a_j$ and $b_i,b_j$), according to the Piazza formula:

$\Delta_{a_ia_j} = \sqrt{\theta 4} - \sqrt{(\theta 4 + \theta 3)(\theta 4 + \theta 2)}$, where:

$\theta 4 = - - - =$ frequency of genotypes not having allele $a_i$ at $M_i$ and not having allele $a_j$ at $M_j$ θ3=−+=frequency of genotypes not having allele $a_i$ at $M_i$ and having allele $a_j$ at θ2=+−=frequency of genotypes having allele $a_i$ at $M_i$ and not having allele $a_j$ at $M_j$ Linkage disequilibrium (LD) between pairs of biallelic markers ($M_i$, $M_j$) can also be calculated for every allele combination ($a_i,a_j$; $a_i,b_j$; $b_i,a_j$ and $b_i,b_j$), according to the maximum-likelihood estimate (MLE) for delta (the composite genotypic disequilibrium coefficient), as described by Weir (Weir B. S., 1996). The MLE for the composite linkage disequilibrium is:

$$D_{aiaj}=(2n_1+n_2+n_3+n_4/2)/N-2(pr(a_i)\cdot pr(a_j))$$

Where $n_1=\Sigma$ phenotype ($a_1/a_i$, $a_j/a_j$), $n_2=\Sigma$ phenotype ($a_i/a_i$, $a_j/b_j$), $n_3=\Sigma$ phenotype ($a_i/b_i$, $a_j/a_j$), $n_4=\Sigma$ phenotype ($a_1/b_1$, $a_j/b_j$) and N is the number of individuals in the sample.

This formula allows linkage disequilibrium between alleles to be estimated when only genotype, and not haplotype, data are available.

Another means of calculating the linkage disequilibrium between markers is as follows. For a couple of biallelic markers, $M_1$ ($a_1/b_1$) and $M_J$ ($a_J/b_J$), fitting the Hardy-Weinberg equilibrium, one can estimate the four possible haplotype frequencies in a given population according to the approach described above.

The estimation of gametic disequilibrium between ai and aj is simply:

$$D_{aiaj}=pr(\text{haplotype}(a_i,a_j))-pr(a_i).pr(a_j).$$

Where $pr(a_1)$ is the probability of allele $a_i$ and $pr(a_i)$ is the probability of allele $a_j$ and where $pr(\text{haplotype } (a_1, a_j))$ is estimated as in Equation 3 above.

For a couple of biallelic marker only one measure of disequilibrium is necessary to describe the association between $M_1$ and $M_j$.

Then a normalized value of the above is calculated as follows:

$$D'_{aiaj}=D_{aiaj}/\max(-pr(a_i).pr(a_j), -pr(b_i).pr(b_j)) \text{ with } D_{aiaj}<0$$

$$D'_{aiaj}=D_{aiaj}/\max(pr(b_i).pr(a_j), pr(a_i).pr(b_j)) \text{ with } D_{aiaj}>0$$

The skilled person will readily appreciate that other linkage disequilibrium calculation methods can be used.

Linkage disequilibrium among a set of biallelic markers having an adequate heterozygosity rate can be determined by genotyping between 50 and 1000 unrelated individuals, preferably between 75 and 200, more preferably around 100.

C. Testing for Association

Methods for determining the statistical significance of a correlation between a phenotype and a genotype, in this case an allele at a biallelic marker or a haplotype made up of such alleles, may be determined by any statistical test known in the art and with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if their is a statistically significant correlation between the haplotype and the phenotype (trait) under study. Any statistical tool useful to test for a statistically significant association between a genotype and a phenotype may be used. Preferably the statistical test employed is a chi-square test with one degree of freedom. A P-value is calculated (the P-value is the probability that a statistic as large or larger than the observed one would occur by chance).

i. Statistical Significance

In preferred embodiments, significance for diagnosis purposes, either as a positive basis for further diagnostic tests or as a preliminary starting point for early preventive therapy, the p value related to a biallelic marker association is preferably about $1\times10^{-2}$ or less, more preferably about $1\times10^{-4}$ or less, for a single biallelic marker analysis and about $1\times10^{-3}$ or less, still more preferably $1\times10^{-6}$ or less and most preferably of about $1\times10^{-8}$ or less, for a haplotype analysis involving two or more markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and a trait can be revealed and used for diagnosis and drug screening purposes.

ii. Phenotypic Permutation

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 1000 times. The repeated iterations allow the determination of the probability to obtain the tested haplotype by chance.

iii. Assessment of Statistical Association

To address the problem of false positives similar analysis may be performed with the same case-control populations in random genomic regions. Results in random regions and the candidate region are compared as described in a co-pending US Provisional patent application entitled "Methods, Software And Apparati For Identifying Genomic Regions Harboring A Gene Associated With A Detectable Trait," U.S. Ser. No. 60/107,986, filed Nov. 10, 1998, the contents of which are incorporated herein by reference.

D. Evaluation of Risk Factors

The association between a risk factor (in genetic epidemiology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities, that is:

$$RR=P(R^+)/P(R^-)$$

$$OR = \left[\frac{F^+}{1-F^+}\right] / \left[\frac{F^-}{(1-F^-)}\right]$$

In case-control studies, direct measures of the relative risk cannot be obtained because of the sampling design. However, the odds ratio allows a good approximation of the relative risk for low-incidence diseases and can be calculated:

$$OR=(F^+/(1-F^+))/(F^-/(1-F^-))$$

$F^+$ is the frequency of the exposure to the risk factor in cases and F is the frequency of the exposure to the risk factor in controls. $F^+$ and $F^-$ are calculated using the allelic or haplotype frequencies of the study and further depend on the underlying genetic model (dominant, recessive, additive . . . ).

One can further estimate the attributable risk (AR) which describes the proportion of individuals in a population exhibiting a trait due to a given risk factor. This measure is important in quantifying the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR=P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which, is approximated with the odds ratio when the trait under study has a relatively low incidence in the general population.

VIII. Identification of Biallelic Markers in Linkage Disequilibrium with the Biallelic Markers of the Invention Once a first biallelic marker has been identified in a genomic region of interest, the practitioner of ordinary skill in the art, using the teachings of the present invention, can easily identify additional biallelic markers in linkage disequilibrium with this first marker. As mentioned before any marker in linkage disequilibrium with a first marker associated with a trait will be associated with the trait. Therefore, once an association has been demonstrated between a given biallelic marker and a trait, the discovery of additional biallelic markers associated with this trait is of great interest in order to increase the density of biallelic markers in this particular region. The causal gene or mutation will be found in the vicinity of the marker or set of markers showing the highest correlation with the trait.

Identification of additional markers in linkage disequilibrium with a given marker involves: (a) amplifying a genomic fragment comprising a first biallelic marker from a plurality of individuals; (b) identifying of second biallelic markers in the genomic region harboring said first biallelic marker; (c) conducting a linkage disequilibrium analysis between said first biallelic marker and second biallelic markers; and (d) selecting said second biallelic markers as being in linkage disequilibrium with said first marker. Sub combinations comprising steps (b) and (c) are also contemplated.

Methods to identify biallelic markers and to conduct linkage disequilibrium analysis are described herein and can be carried out by the skilled person without undue experimentation. The present invention then also concerns biallelic markers which are in linkage disequilibrium with the biallelic markers 20-828-311, 17-42-319, 17-41-250, 20-841-149, 20-842-115, and 20-853-415 and which are expected to present similar characteristics in terms of their respective association with a given trait.

IX. Identification of Functional Mutations

Mutations in the GSSP-2 gene which are responsible for a detectable phenotype or trait may be identified by comparing the sequences of the GSSP-2 gene from trait positive and control individuals. Once a positive association is confirmed with a biallelic marker of the present invention, the identified locus can be scanned for mutations. In a preferred embodiment, functional regions such as exons and splice sites, promoters and other regulatory regions of the GSSP-2 gene are scanned for mutations. In a preferred embodiment the sequence of the GSSP-2 gene is compared in trait positive and control individuals. Preferably, trait positive individuals carry the haplotype shown to be associated with the trait and trait negative individuals do not carry the haplotype or allele associated with the trait. The detectable trait or phenotype may comprise a variety of manifestations of altered GSSP-2 function.

The mutation detection procedure is essentially similar to that used for biallelic marker identification. The method used to detect such mutations generally comprises the following steps:

(a) amplification of a region of the GSSP-2 gene comprising a biallelic marker or a group of biallelic markers associated with the trait from DNA samples of trait positive patients and trait-negative controls;

(b) sequencing of the amplified region;

(c) comparison of DNA sequences from trait positive and control individuals;

(d) determination of mutations specific to trait-positive patients.

In one embodiment, said biallelic marker is selected from the group consisting of 20-828-311, 17-42-319, 17-41-250, 20-841-149, 20-842-115, and 20-853-415, and the complements thereof. It is preferred that candidate polymorphisms be then verified by screening a larger population of cases and controls by means of any genotyping procedure such as those described herein, preferably using a microsequencing technique in an individual test format. Polymorphisms are considered as candidate mutations when present in cases and controls at frequencies compatible with the expected association results. Polymorphisms are considered as candidate "trait-causing" mutations when they exhibit a statistically significant correlation with the detectable phenotype.

X. Biallelic Markers of the Invention in Methods of Genetic Diagnostics

The biallelic markers of the present invention can also be used to develop diagnostics tests capable of identifying individuals who express a detectable trait as the result of a specific genotype or individuals whose genotype places them at risk of developing a detectable trait at a subsequent time. The trait analyzed using the present diagnostics may be any detectable trait, including body mass index (BMI), food intake, GSSP-2 expression, GSSP-2 concentration, liver regeneration, plasma levels of leptin, insulin, free fatty acids (FFA), triglycerides (TG) and glucose. Most preferably the trait analyzed is FFA. Such a diagnosis can be useful in the staging, monitoring, prognosis and/or prophylactic or curative therapy of diseases involving lipid metabolism and/or liver related disorders.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids.

The present invention provides diagnostic methods to determine whether an individual is at risk of developing a disease or suffers from a disease resulting from a mutation or a polymorphism in the GSSP-2 gene. The present invention also provides methods to determine whether an individual has a susceptibility to diseases involving lipid metabolism and/or liver related disorders.

These methods involve obtaining a nucleic acid sample from the individual and, determining, whether the nucleic acid sample contains at least one allele or at least one biallelic marker haplotype, indicative of a risk of developing the trait or indicative that the individual expresses the trait as a result of possessing a particular GSSP-2 polymorphism or mutation (trait-causing allele).

Preferably, in such diagnostic methods, a nucleic acid sample is obtained from the individual and this sample is genotyped using methods described above in "Methods of Genotyping DNA Samples for Biallelic Markers." The diagnostics may be based on a single biallelic marker or a on group of biallelic markers.

In each of these methods, a nucleic acid sample is obtained from the test subject and the biallelic marker pattern of one or more of the biallelic markers 20-828-311, 17-42-319, 17-41-250, 20-841-149, 20-842-115, and 20-853-415 is determined.

In one embodiment, a PCR amplification is conducted on the nucleic acid sample to amplify regions in which polymorphisms associated with a detectable phenotype have been identified. The amplification products are sequenced to determine whether the individual possesses one or more GSSP-2 polymorphisms associated with a detectable phenotype. The primers used to generate amplification products may comprise the primers listed in FIG. 5. Alternatively, the nucleic acid sample is subjected to microsequencing reactions as described above to determine whether the individual possesses one or more GSSP-2 polymorphisms associated with a detectable phenotype resulting from a mutation or a polymorphism in the GSSP-2 gene. The primers used in the microsequencing reactions may include the primers listed in FIG. 4. In another embodiment, the nucleic acid sample is contacted with one or more allele specific oligonucleotide probes which, specifically hybridize to one or more GSSP-2 alleles associated with a detectable phenotype. The probes used in the hybridization assay may include the probes listed in FIG. 6. In another embodiment, the nucleic acid sample is contacted with a second GSSP-2 oligonucleotide capable of producing an amplification product when used with the allele specific oligonucleotide in an amplification reaction. The presence of an amplification product in the amplification reaction indicates that the individual possesses one or more GSSP-2 alleles associated with a detectable phenotype.

In a preferred embodiment the identity of the nucleotide present at, at least one, biallelic marker selected from the group consisting of 20-828-311, 17-42-319, 17-41-250, 20-841-149, 20-842-115, and 20-853-415, and the complements thereof, is determined and the detectable trait is a disease involving lipid metabolism and/or liver related disorders. Diagnostic kits comprise any of the polynucleotides of the present invention.

These diagnostic methods are extremely valuable as they can, in certain circumstances, be used to initiate preventive treatments or to allow an individual carrying a significant haplotype to foresee warning signs such as minor symptoms.

Diagnostics, which analyze and predict response to a drug or side effects to a drug, may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects.

Clinical drug trials represent another application for the markers of the present invention. One or more markers indicative of response to an agent acting on lipid metabolism and/or liver related disorders or to side effects to an agent acting on lipid metabolism and/or a liver related disorder may be identified using the methods described above. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

XI. Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

The present invention encompasses a family of recombinant vectors that comprise a regulatory polynucleotide derived from the GSSP-2 genomic sequence, and/or a coding polynucleotide from either the GSSP-2 genomic sequence or the cDNA sequence.

Generally, a recombinant vector of the invention may comprise any of the polynucleotides described herein, including regulatory sequences, coding sequences and polynucleotide constructs, as well as any GSSP-2 primer or probe as defined above. More particularly, the recombinant vectors of the present invention can comprise any of the polynucleotides described in the "Genomic Sequences Of the GSSP-2 Gene" section, the "GSSP-2 cDNA Sequences" section, the "Coding Regions" section, the "Polynucleotide constructs" section, and the "Oligonucleotide Probes And Primers" section.

In a first preferred embodiment, a recombinant vector of the invention is used to amplify the inserted polynucleotide derived from a GSSP-2 genomic sequence of SEQ ID NOs: 1 and 4 or a GSSP-2 cDNA, for example the cDNA of SEQ ID NO: 2 in a suitable cell host, this polynucleotide being amplified at every time that the recombinant vector replicates.

A second preferred embodiment of the recombinant vectors according to the invention comprises expression vectors comprising either a regulatory polynucleotide or a coding nucleic acid molecule of the invention, or both. Within certain embodiments, expression vectors are employed to express the GSSP-2 polypeptide which can be then purified and, for example be used in ligand screening assays or as an immunogen in order to raise specific antibodies directed against the GSSP-2 protein. In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acid molecules encoding a GSSP-2 protein, preferably the GSSP-2 protein of the amino acid sequence of SEQ ID NO: 3 or variants or fragments thereof.

The invention also pertains to a recombinant expression vector useful for the expression of the GSSP-2 coding sequence, wherein said vector comprises a nucleic acid molecule of SEQ ID NO: 2.

Recombinant vectors comprising a nucleic acid molecule containing a GSSP-2-related biallelic marker is also part of the invention. In a preferred embodiment, said biallelic marker is selected from the group consisting of 20-828-311, 17-42-319, 17-41-250, 20-841-149, 20-842-115, and 20-853-415, and the complements thereof.

Some of the elements which can be found in the vectors of the present invention are described in further detail in the following sections.

A. General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may comprise a chromosomal, non-chromosomal, semi-synthetic and synthetic DNA. Such a recombinant vector can comprise a transcriptional unit comprising an assembly of:

(a) a genetic element or elements having a regulatory role in gene expression, for example promoters or enhancers. Enhancers are cis-acting elements of DNA, usually from about 10 to 300 bp in length that act on the promoter to increase the transcription.

(b) a structural or coding sequence which is transcribed into mRNA and eventually translated into a polypeptide, said structural or coding sequence being operably linked to the regulatory elements described in (a); and (c) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation signal, splice donor and acceptor sites, transcriptional termination sequences, and 5'-flanking non-transcribed sequences. DNA sequences derived from the SV40 viral genome, for example SV40 origin, early promoter, enhancer, splice and polyadenylation signals may be used to provide the required non-transcribed genetic elements.

The in vivo expression of a GSSP-2 polypeptide of SEQ ID NO: 3 or fragments or variants thereof may be useful in order to correct a genetic defect related to the expression of the native gene in a host organism or to the production of a biologically inactive GSSP-2 protein.

Consequently, the present invention also comprises recombinant expression vectors mainly designed for the in vivo production of the GSSP-2 polypeptide of SEQ ID NO: 3 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

B. Regulatory Elements i. Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid molecule in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid molecule for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic engineering. For example, one may refer to the book of Sambrook et al. (1989) or also to the procedures described by Fuller et al. (1996).

ii. Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

C. Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

D. Preferred Vectors i. Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

ii. Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994). Recombinant P1 clones comprising GSSP-2 nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, *E. coli* (preferably strain NS3529) harboring the P1 plasmid are grown overnight in a suitable broth medium containing 25 µg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising GSSP-2 nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA —30,000 molecular weight limit) and then dialyzed against microinjection buffer (10 mM Tris-HCl, pH 7.4; 250 µM EDTA) containing 100 mM NaCl, 30 µM spermine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

iii. Baculovirus Vectors

A suitable vector for the expression of the GSSP-2 polypeptide of SEQ ID NO: 3 or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC No CRL 1711) which is derived from *Spodoptera frugiperda*. See Example 4 for further details.

Other suitable vectors for the expression of the GSSP-2 polypeptide of SEQ ID NO: 3 or fragments or variants thereof in a baculovirus expression system include those described by Chai et al. (1993), Vlasak et al. (1983) and Lenhard et al. (1996).

iv. Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application No FR-93.05954). Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acid molecules are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., 1989, Julan et al., 1992 and Neda et al, 1991.

Yet another viral vector system that is contemplated by the invention comprises the adeno-associated virus (AAV).

The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al, 1989; McLaughlin et al., 1989). One advantageous feature of AAV derives from its reduced efficacy for transducing primary cells relative to transformed cells.

v. BAC Vectors

The bacterial artificial chromosome (BAC) cloning system (Shizuya et al., 1992) has been developed to stably maintain large fragments of genomic DNA (100–300 kb) in *E. coli*. A preferred BAC vector comprises a pBeloBAC11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

E. Delivery of the Recombinant Vectors

In order to effect expression of the polynucleotides and polynucleotide constructs of the invention, these constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987;), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediated transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid molecule may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No WO 90/11092 (Vical Inc.) and also in PCT application No. WO 95/11307 (Institut Pasteur, INSERM, Université d'Ottawa) as well as in the articles of Tacson et al. (1996) and of Huygen et al. (1996).

In still another embodiment of the invention, the transfer of a naked polynucleotide of the invention, including a polynucleotide construct of the invention, into cells may be proceeded with a particle bombarGSSP-2 nt (biolistic), said particles being DNA-coated microprojectiles accelerated to a high velocity allowing them to pierce cell membranes and enter cells without killing them, such as described by Klein et al. (1987).

In a further embodiment, the polynucleotide of the invention may be entrapped in a liposome (Ghosh and Bacchawat, 1991; Wong et al., 1980; Nicolau et al., 1987)

In a specific embodiment, the invention provides a composition for the in vivo production of the GSSP-2 protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0, 1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired GSSP-2 polypeptide or the desired fragment thereof is reintroduced into the animal body in order to deliver the recombinant protein within the body either locally or systemically.

XII. Cell Hosts

Another object of the invention comprises a host cell that is recombinant for a polynucleotide of the invention (e.g. a cell that has been transformed or transfected with one of the polynucleotides described herein, and in particular a polynucleotide either comprising a GSSP-2 regulatory polynucleotide or the coding sequence of the GSSP-2 polypeptide selected from the group consisting of SEQ ID NOs: 1, 2 and 4 or a fragment or a variant thereof. Also included are host cells that are transformed (prokaryotic cells) or that are transfected (eukaryotic cells) with a recombinant vector such as one of those described above. More particularly, the cell hosts of the present invention can comprise any of the polynucleotides described in the "Genomic Sequences of The GSSP-2 Gene" section, the "GSSP-2 cDNA Sequences" section, the "Coding Regions" section, the "Polynucleotide Constructs" section, and the "Oligonucleotide Probes and Primers" section.

A further recombinant cell host according to the invention comprises a polynucleotide containing a biallelic marker selected from the group consisting of 20-828-311, 17-42-319, 17-41-250, 20-841-149, 20-842-115, and 20-853-415, and the complements thereof.

An additional recombinant cell host according to the invention comprises any of the vectors described herein, more particularly any of the vectors described in the "Recombinant Vectors" section.

Preferred host cells used as recipients for the expression vectors of the invention are the following:

a) Prokaryotic host cells: *Escherichia coli* strains (I.E.DH5-α strain), *Bacillus subtilis, Salmonella typhimurium*, and strains from species like *Pseudomonas, Streptomyces* and *Staphylococcus*.

b) Eukaryotic host cells: HELA cells (ATCC No CCL2; No CCL2.1; No CCL2.2), Cv 1 cells (ATCC No CCL70), COS cells (ATCC No CRL1650; No CRL1651), Sf-9 cells (ATCC No CRL1711), C127 cells (ATCC No CRL-1804), 3T3 (ATCC No CRL-6361), CHO (ATCC No CCL-61), human kidney 293. (ATCC No 45504; No CRL-1573) and BHK (ECACC No 84100501; No 84111301).

c) Other Mammalian Host Cells.

The GSSP-2 gene expression in mammalian, and typically human, cells may be rendered defective, or alternatively it may be proceeded with the insertion of a GSSP-2 genomic or cDNA sequence with the replacement of the GSSP-2 gene counterpart in the genome of an animal cell by a GSSP-2 polynucleotide according to the invention. These genetic alterations may be generated by homologous recombination events using specific DNA constructs that have been previously described.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts-3 ng/μl—for P1 bacteriophage inserts—in 10 mM Tris-HCl, pH 7.4, 250 μM EDTA containing 100 mM NaCl, 30 μM spermine, and 70 μM spermidine. When the DNA to be microinjected has a large size, polyamines and high salt concentrations can be used in order to avoid mechanical breakage of this DNA, as described by Schedl et al (1993b).

Anyone of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC no CRL-1821), ES-D3 (ATCC no CRL1934 and no CRL-11632), YS001 (ATCC no CRL-11776), 36.5 (ATCC no CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan. The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the a polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct which alters the expression of a targeted gene in a cell type in which the gene is not normally expressed. This occurs when the a polynucleotide construct is inserted into the chromosomal DNA of the target cell, wherein the a polynucleotide construct comprises: a) a targeting sequence; b) a regulatory sequence and/or coding sequence; and c) an unpaired splice-donor site, if necessary. Further included are a polynucleotide constructs, as described above, wherein the construct further comprises a polynucleotide which encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles including 1994; Koller et al (1989) (the disclosures of each of which are incorporated by reference in their entireties).

XIII. Transgenic Animals

The terms "transgenic animals" or "host animals" are used herein designate animals that have their genome genetically and artificially manipulated so as to include one of the nucleic acid molecules according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid molecule according to the invention. In one embodiment, the invention encompasses non-human host mammals and animals comprising a recombinant vector of the invention or a GSSP-2 gene disrupted by homologous recombination with a knock out vector.

The transgenic animals of the invention all include within a plurality of their cells a cloned recombinant or synthetic DNA sequence, more specifically one of the purified or isolated nucleic acid molecules comprising a GSSP-2 coding sequence, a GSSP-2 regulatory polynucleotide, a polynucleotide construct, or a DNA sequence encoding an antisense polynucleotide such as described in the present specification.

Generally, a transgenic animal according the present invention comprises any one of the polynucleotides, the recombinant vectors and the cell hosts described in the present invention. More particularly, the transgenic animals of the present invention can comprise any of the polynucleotides described in the "Genomic Sequences of the GSSP-2 Gene" section, the "GSSP-2 cDNA Sequences" section, the "Coding Regions" section, the "Polynucleotide constructs" section, the "Oligonucleotide Probes and Primers" section, the "Recombinant Vectors" section and the "Cell Hosts" section.

A further transgenic animals according to the invention contains in their somatic cells and/or in their germ line cells a polynucleotide comprising a biallelic marker selected from the group consisting of 20-828-311, 17-42-319, 17-41-250, 20-841-149, 20-842-115, and 20-853-415, and the complements thereof.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native GSSP-2 protein, or alternatively a mutant GSSP-2 protein.

In a second preferred embodiment, these transgenic animals may express a desired polypeptide of interest under the control of the regulatory polynucleotides of the GSSP-2 gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to U.S. Pat. No. 4,873,191, issued Oct. 10, 1989; U.S. Pat. No. 5,464,764 issued Nov. 7, 1995; and U.S. Pat. No. 5,789,215, issued Aug. 4, 1998; these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a GSSP-2 coding sequence, a GSSP-2 regulatory polynucleotide or a DNA sequence encoding a GSSP-2 antisense polynucleotide such as described in the present specification.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8–16 cell stage (morulae) such as described by Wood et al. (1993) or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transgenic animal containing a nucleic acid molecule, a recombinant expression vector or a recombinant host cell according to the invention.

A. Recombinant Cell Lines Derived from the Transgenic Animals of the Invention

A further object of the invention comprises recombinant host cells obtained from a transgenic animal described herein. In one embodiment the invention encompasses cells derived from non-human host mammals and animals comprising a recombinant vector of the invention or a GSSP-2 gene disrupted by homologous recombination with a knock out or knock in vector.

Recombinant cell lines may be established in vitro from cells obtained from any tissue of a transgenic animal according to the invention, for example by transfection of primary cell cultures with vectors expressing one-genes such as SV40 large T antigen, as described by Chou (1989) and Shay et al. (1991).

B. Animal Models

A variety of well known animal models can be used to assay the molecules identified herein for biological activity, in the development and pathogenesis of tumors, and to test the efficacy of candidate therapeutic agents, including antibodies, and other agonists of the native polypeptides, including small molecule agonists. Animal models of tumors and cancers (e.g., liver, breast cancer, colon cancer, prostate cancer, lung cancer, etc.) include both non recombinant and recombinant (transgenic) animals. Non-recombinant animal models include, for example, rodent, e.g., murine models. Such models can be generated, for example, by introducing tumor cells into syngeneic mice, nude mice or scid mice using standard techniques, e.g., subcutaneous injection, tail vein injection, spleen implantation, intraperitoneal implantation, implantation under the renal capsule, or orthopin implantation, e.g., colon cancer cells implanted in colonic tissue. (See, e.g., PCT publication No. WO 97/33551, published Sep. 18, 1997).

Probably the most often used animal species in oncological studies are immunodeficient mice and, in particular, nude and scid mice. The observation that the nude mouse with hypo/aplasia could successfully act as a host for human tumor xenografts has lead to its widespread use for this purpose. The autosomal recessive nu gene has been introduced into a very large number of distinct congenic strains of nude mice, including, for example, ASW, A/He, AKR, BALB/c, BIO.LP, C17, C3H, C57BL, C57, CBA, DBA, DDD, I/st, NC, NFR, NFS, NFS/N, NZB, NZC, NZW, P, RIII and SJL. In addition, a wide variety of other animals with inherited immunological defects other than the nude mouse have been bred and used as recipients of tumor xenografts. For further details see, e.g., The Nude Mouse in Oncology Research, E. Boven and B. Winograd, eds., CRC Press, Inc., 1991.

The cells introduced into such animals can be derived from known tumor/cancer cell lines, such as, any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); a moderately well differentiated grade II human colon adenocarcinoma cell line, HT-29 (ATCC HTB-3 8), or from tumors and cancers. Samples of tumor or cancer cells can be obtained from patients undergoing surgery, using standard conditions, involving freezing and storing in liquid nitrogen (Karmali et al., Br. J. Cancer. 48:689–696 [1983]).

Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue. Boven and Winograd (1991), supra. Animal models of breast cancer can be generated, for example, by implanting rat neuroblastoma cells (from which the neu oncogen was initially isolated), or neutransformed NIH-3T3 cells into nude mice, essentially as described by Drebin et al., Proc. Natl. Acad. Sci. USA 83:9129–9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., Cancer Research 54:4726–4728 (1994) and Too et al., Cancer Research, 55:681–684 (1995). This model is based on the so-called "METAMOUSE" sold by AntiCancer, Inc., (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., J. Exp. Med., 146:720 [1977]), which provide a highly controllable model system for studying the anti-tumor activities of various agents (Palladino et al., J. Immunol., 138:4023–4032 [1987]). Briefly, tumor cells are propagated in vitro in cell culture. Prior to injection into the animals, the cell lines are washed and suspended in buffer, at a cell density of about 10×106 to 10×10' cells/ml. The animals are then infected subcutaneously with 10 to 100 kit of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., Br. J. Cancer, 41, suppl. 4:309 [1980]), and evidence indicates that tumors can be started from injection of even a single cell and that a very high proportion of infected tumor cells survive. For further information about this tumor model see, Zacharski, Haemostasis. 16:300–320 [1986]).

One way of evaluating the efficacy of a test compound in an animal model on an implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, Proc. 6th Int. Workshop on Immune- Deficient Animals Wu and Sheng eds., Basel, 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., Proc. Natl. Acad. Sci. USA, 82:6148–615 [1985]); gene targeting in embryonic stem cells (Thompson et al., Cell, 56:313–321 [1989]); electroporation of embryos (Lo, Mol. Cell. Biol_3:1803–1814 [1983]); sperm-mediated gene transfer (Lavitrano et al., Cell, 57:717–73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., Proc. Natl. Acad. Sci. USA 89:6232636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

The efficacy of the polypeptides identified herein and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinoma in dogs and cats is a preferred model as its appearance and behavior are very similar to those in humans. However, the use of this model is limited by the rare occurrence of this type of tumor in animals.

XIV. Methods for Screening Substances Interacting with a GSSP-2 Polypeptide

For the purpose of the present invention, a ligand means a molecule, such as a protein, a peptide, an antibody or any synthetic chemical compound capable of binding to the GSSP-2 protein or one of its fragments or variants or to modulate the expression of the polynucleotide coding for GSSP-2 or a fragment or variant thereof.

In the ligand screening method according to the present invention, a biological sample or a defined molecule to be tested as a putative ligand of the GSSP-2 protein is brought into contact with the corresponding purified GSSP-2 protein, for example the corresponding purified recombinant GSSP-2 protein produced by a recombinant cell host as described hereinbefore, in order to form a complex between this protein and the putative ligand molecule to be tested.

As an illustrative example, to study the interaction of the GSSP-2 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 3, with drugs or small molecules, such as molecules generated through combinatorial chemistry approaches, the microdialysis coupled to HPLC method described by Wang et al. (1997) or the affinity capillary electrophoresis method described by Bush et al. (1997), the disclosures of which are incorporated by reference, can be used.

In further methods, peptides, drugs, fatty acids, lipoproteins, or small molecules which interact with the GSSP-2 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 3, may be identified using assays such as the following. The molecule to be tested for binding is labeled with a detectable label, such as a fluorescent, radioactive, or enzymatic tag and placed in contact with immobilized GSSP-2 protein, or a fragment thereof under conditions which permit specific binding to occur. After removal of non-specifically bound molecules, bound molecules are detected using appropriate means.

Using in vivo (or in vitro) systems, it may be possible to identify compounds that exert a cell or tissue specific effect, for example, that increase GSSP-2 expression or activity only in hepatocytes. Screening procedures such as those described herein are useful for identifying agents for their potential use in pharmacological intervention strategies. Agents that enhance GSSP-2 expression or activity can be used to treat disorders caused by insufficient cell death such as cancer. If desired, treatment with a GSSP-2 protein, gene, or modulatory compound may also be combined with more traditional therapies used to treat insufficient cell death such as surgery, radiation therapy, and chemotherapy for cancer. Compounds that suppress GSSP-2 expression or inhibit its activity can be used to treat disorders associated with excessive cell death such as degenerative diseases. Likewise, treatment with a GSSP-2 protein, gene, or modulatory compound may be combined with more traditional therapies for diseases involving excessive cell death such as surgery, steroid therapy, or chemotherapy for autoimmune disease; antiviral therapy for AIDS; and tissue plasminogen activator (TPA) for ischemic injury.

Another object of the present invention comprises methods and kits for the screening of candidate substances that interact with GSSP-2 polypeptide.

The present invention pertains to methods for screening substances of interest that interact with a GSSP-2 protein or one fragment or variant thereof. By their capacity to bind covalently or non-covalently to a GSSP-2 protein or to a fragment or variant thereof, these substances or molecules may be advantageously used both in vitro and in vivo.

In vitro, said interacting molecules may be used as detection means in order to identify the presence of a GSSP-2 protein in a sample, preferably a biological sample.

A method for the screening of a candidate substance comprises the following steps:

a) providing a polypeptide comprising, consisting essentially of, or consisting of a GSSP-2 protein or a fragment comprising a contiguous span of at least 6 amino acids, preferably at least 8 to 10 amino acids, more preferably at least 12, 15, 20, 25, 30, 40, 50, or 100 amino acids of SEQ ID NO: 3:

b) obtaining a candidate substance;

c) bringing into contact said polypeptide with said candidate substance;

d) detecting the complexes formed between said polypeptide and said candidate substance.

The invention further concerns a kit for the screening of a candidate substance interacting with the GSSP-2 polypeptide, wherein said kit comprises:

a) a GSSP-2 protein having an amino acid sequence selected from the group consisting of the amino acid sequences of SEQ ID NO: 3 or a peptide fragment comprising a contiguous span of at least 6 amino acids, preferably at least 8 to 10 amino acids, more preferably at least 12, 15, 20, 25, 30, 40, 50, or 100 amino acids of SEQ ID NO: 3;

b) optionally means useful to detect the complex formed between the GSSP-2 protein or a peptide fragment or a variant thereof and the candidate substance.

In a preferred embodiment of the kit described above, the detection means comprises a monoclonal or polyclonal antibodies directed against the GSSP-2 protein or a peptide fragment or a variant thereof.

Various candidate substances or molecules can be assayed for interaction with a GSSP-2 polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

The invention also pertains to kits useful for performing the hereinbefore described screening method. Preferably, such kits comprise a GSSP-2 polypeptide or a fragment or a variant thereof, and optionally means useful to detect the complex formed between the GSSP-2 polypeptide or its fragment or variant and the candidate substance. In a preferred embodiment the detection means comprise a monoclonal or polyclonal antibodies directed against the corresponding GSSP-2 polypeptide or a fragment or a variant thereof.

A. Candidate Ligands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to 20 amino acids in length (Oldenburg K. R. et al., 1992; Valadon P., et al., 1996; Lucas A. H., 1994; Westerink M. A. J., 1995; Felici F. et al., 1991). According to this particular embodiment, the recombinant phages expressing a protein that binds to the immobilized GSSP-2 protein is retained and the complex formed between the GSSP-2 protein and the recombinant phage may be subsequently immunoprecipitated by a polyclonal or a monoclonal antibody directed against the GSSP-2 protein.

Once the ligand library in recombinant phages has been constructed, the phage population is brought into contact with the immobilized GSSP-2 protein. Then the preparation of complexes is washed in order to remove the non-specifically bound recombinant phages. The phages that bind specifically to the GSSP-2 protein are then eluted by a buffer (acid pH) or immunoprecipitated by the monoclonal antibody produced by the hybridoma anti-GSSP-2, and this phage population is subsequently amplified by an over-infection of bacteria (for example E. coli). The selection step may be repeated several times, preferably 2–4 times, in order to select the more specific recombinant phage clones. The last step comprises characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained by Competition Experiments

Alternatively, peptides, drugs or small molecules which bind to the GSSP-2 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 3, may be identified in competition experiments. In such assays, the GSSP-2 protein, or a fragment thereof, is immobilized to a surface, such as a plastic plate. Increasing amounts of the peptides, drugs or small molecules are placed in contact with the immobilized GSSP-2 protein, or a fragment thereof, in the presence of a detectable labeled known GSSP-2 protein ligand. For example, the GSSP-2 ligand may be detectably labeled with a fluorescent, radioactive, or enzymatic tag. The ability of the test molecule to bind the GSSP-2 protein, or a fragment thereof, is determined by measuring the amount of detectably labeled known ligand bound in the presence of the test molecule. A decrease in the amount of known ligand bound to the GSSP-2 protein, or a fragment thereof, when the test molecule is present indicated that the test molecule is able to bind to the GSSP-2 protein, or a fragment thereof.

C. Candidate Ligands Obtained by Affinity Chromatography

Proteins or other molecules interacting with the GSSP-2 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 3, can also be found using affinity columns which contain the GSSP-2 protein, or a fragment thereof. The GSSP-2 protein, or a fragment thereof, may be attached to the column using conventional techniques including chemical coupling to a suitable column matrix such as agarose, Affi Gel® or other matrices familiar to those of skill in art. In some embodiments of this method, the affinity column contains chimeric proteins in which the GSSP-2 protein, or a fragment thereof, is fused to glutathion S transferase (GST). A mixture of cellular proteins or pool of expressed proteins as described above is applied to the affinity column. Proteins or other molecules interacting with the GSSP-2 protein, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis based methods and sequenced. The same method can be used to isolate antibodies, to screen phage display products, or to screen phage display human antibodies.

D. Candidate Ligands Obtained by Optical Biosensor Methods

Proteins interacting with the GSSP-2 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 3, can also be screened by using an Optical Biosensor as described in Edwards and Leatherbarrow (1997) and also in Szabo et al. (1995), the disclosure of which is incorporated by reference. This technique permits the detection of interactions between molecules in real time, without the need of labeled molecules. This technique is based on the surface plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the GSSP-2 protein, or a fragment thereof, the GSSP-2 protein, or a fragment thereof, is immobilized onto a surface. This surface comprises one side of a cell through which flows the candidate molecule to be assayed. The binding of the candidate molecule on the GSSP-2 protein, or a fragment thereof, is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed GSSP-2 protein at their surface.

The main advantage of the method is that it allows the determination of the association rate between the GSSP-2 protein and molecules interacting with the GSSP-2 protein. It is thus possible to select specifically ligand molecules interacting with the GSSP-2 protein, or a fragment thereof, through strong or conversely weak association constants.

E. Candidate Ligands Obtained Through a Two-Hybrid Screening Assay

The yeast two-hybrid system is designed to study protein—protein interactions in vivo (Fields and Song, 1989), and relies upon the fusion of a bait protein to the DNA binding domain of the yeast Gal4 protein. This technique is also described in the U.S. Pat. No. 5,667,973 and the U.S. Pat. No. 5,283,173 (Fields et al.) the technical teachings of both patents being herein incorporated by reference.

The general procedure of library screening by the two-hybrid assay may be performed as described by Harper et al. (1993) or as described by Cho et al (1998) or also Fromont-Racine et al. (1997).

The bait protein or polypeptide comprises, consists essentially of, or consists of a GSSP-2 polypeptide or a fragment comprising a contiguous span of at least 6 amino acids, preferably at least 8 to 10 amino acids, more preferably at least 12, 15, 20, 25, 30, 40, 50, or 100 amino acids of SEQ ID NO: 3.

More precisely, the nucleotide sequence encoding the GSSP-2 polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non-limiting example the two different yeast strains may be selected from the following:

Y190, the phenotype of which is (MATa, Leu2-3, 112 ura3-12, trp1-901, his3-D200, ade2-101, gal4Dgal180D URA3 GAL-LacZ, LYS GAL-HIS3, cyh$^r$;

Y187, the phenotype of which is (MATa gal4 gal80 his3 trp1-901 ade2-101 ura3-52 leu2-3, -112 URA3 GAL-lac-Zmet$^-$), which is the opposite mating type of Y190.

Briefly, 20 µg of pAS2/GSSP-2 and 20 µg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His$^+$, beta-gal$^+$) are then grown on plates lacking histidine, leucine, but containing tryptophan and cycloheximide (10 mg/ml) to select for loss of pAS2/GSSP-2 plasmids bu retention of pACT-cDNA library plasmids. The resulting Y190 strains are mated with Y187 strains expressing GSSP-2 or non-related control proteins; such as cyclophilin B, lamin, or SNF1, as Gal4 fusions as described by Harper et al (1993) and by Bram et al. (Bram R J et al., 1993), and screened for beta galactosidase by filter lift assay. Yeast clones that are beta gal-after mating with the control Gal4 fusions are considered false positives.

In another embodiment of the two-hybrid method according to the invention, interaction between the GSSP-2 or a fragment or variant thereof with cellular proteins may be assessed using the Matchmaker Two Hybrid System 2 (Catalog No. K1604-1, Clontech). As described in the manual accompanying the Matchmaker Two Hybrid System 2 (Catalog No. K1604-1, Clontech), the disclosure of which is incorporated herein by reference, nucleic acid molecules encoding the GSSP-2 protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GALA dependent lacZ expression. Those cells which are positive in both the histidine selection and the lacZ assay contain interaction between GSSP-2 and the protein or peptide encoded by the initially selected cDNA insert.

F. Identification of Proteins Capable of Inhibiting Neoplastic Cell Growth

The proteins disclosed in the present application may be assayed in a panel of tumor cell lines currently used in the investigational, disease-oriented, in vitro drug-discovery screen of the National Cancer Institute (NCI). The purpose of this screen is to identify molecules that have cytotoxic and/or cytostatic activity against different types of tumors. NCI screens more than 10,000 new molecules per year (Monks et al., J. Natl. Cancer Inst., 83:757–766 (1991); Boyd, Cancer: Princ. Pract. Oncol. Update, 3 10 :1–12 ([1989]). The tumor cell lines employed in this study have been described in Monks et al., supra.

Other cell-based assays and animal models for tumors (e.g., cancers) can also be used to verify the findings of the NCI cancer screen, and to further understand the relationship between the protein identified herein and the development and pathogenesis of neoplastic cell growth. For example, cell cultures derived from tumors in transgenic animals (as described below) can be used in the cell-based assays herein, although stable cell lines are preferred. Techniques to derive continuous cell lines from transgenic animals are well known in the art (see, e.g., Small et al., Mol. Cell. Biol, 5:642–648 [1985]).

XV. Methods for Screening Substances Interacting with the Regulatory Sequences of the GSSP-2 Gene The present invention also concerns a method for screening substances or molecules that are able to interact with the regulatory sequences of the GSSP-2 gene, such as promoter or enhancer sequences.

Nucleic acid molecules encoding proteins which are able to interact with the regulatory sequences of the GSSP-2 gene, more particularly a nucleotide sequence selected from the group consisting of the polynucleotides of the 5' and 3' regulatory region or a fragment or variant thereof, and preferably a variant comprising one of the biallelic markers of the invention, may be identified by using a one-hybrid system, such as that described in the booklet enclosed in the Matchmaker One-Hybrid System kit from Clontech (Catalog Ref. no K1603-1), the technical teachings of which are herein incorporated by reference. Briefly, the target nucleotide sequence is cloned upstream of a selectable reporter sequence and the resulting DNA construct is integrated in the yeast genome (*Saccharomyces cerevisiae*). The yeast cells containing the reporter sequence in their genome are then transformed with a library comprising fusion molecules between cDNAs encoding candidate proteins for binding onto the regulatory sequences of the GSSP-2 gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the GSSP-2 gene. Then, the cDNAs encoding the fusion proteins are sequenced and may be cloned into expression or transcription vectors in vitro. The binding of the encoded polypeptides to the target regulatory sequences of the GSSP-2 gene may be confirmed by techniques familiar to the one skilled in the art, such as gel retardation assays or DNAse protection assays.

Gel retardation assays may also be performed independently in order to screen candidate molecules that are able to interact with the regulatory sequences of the GSSP-2 gene, such as described by Fried and Crothers (1981), Garner and Revzin (1981) and Dent and Latchman (1993), the teachings of these publications being herein incorporated by reference. These techniques are based on the principle according to which a DNA fragment which is bound to a protein migrates slower than the same unbound DNA fragment. Briefly, the target nucleotide sequence is labeled. Then the labeled target nucleotide sequence is brought into contact with either a total nuclear extract from cells containing transcription factors, or with different candidate molecules to be tested. The interaction between the target regulatory sequence of the GSSP-2 gene and the candidate molecule or the transcription factor is detected after gel or capillary electrophoresis through a retardation in the migration.

XVI. Method for Screening Ligands That Modulate the Expression of the GSSP-2 Gene Another subject of the present invention is a method for screening molecules that modulate the expression of the GSSP-2 protein. Such a screening method comprises the steps of:

a) cultivating a prokaryotic or an eukaryotic cell that has been transfected with a nucleotide sequence encoding the GSSP-2 protein or a variant or a fragment thereof, placed under the control of its own promoter;

b) bringing into contact the cultivated cell with a molecule to be tested; and c) quantifying the expression of the GSSP-2 protein or a variant or a fragment thereof.

In an embodiment, the nucleotide sequence encoding the GSSP-2 protein or a variant or a fragment thereof consists of an allele of at least one of the biallelic markers 20-828-311, 17-42-319, 17-41-250, 20-841-149, 20-842-115, and 20-853-415, and the complements thereof.

Using DNA recombination techniques well known by the one skill in the art, the GSSP-2 protein encoding DNA sequence is inserted into an expression vector, downstream from its promoter sequence. As an illustrative example, the promoter sequence of the GSSP-2 gene is contained in the nucleic acid of the 5' regulatory region.

The quantification of the expression of the GSSP-2 protein may be realized either at the mRNA level or at the protein level. In the latter case, polyclonal or monoclonal antibodies may be used to quantify the amounts of the GSSP-2 protein that have been produced, for example in an ELISA or a RIA assay.

In a preferred embodiment, the quantification of the GSSP-2 mRNA is realized by a quantitative PCR amplification of the cDNA obtained by a reverse transcription of the total mRNA of the cultivated GSSP-2-transfected host cell, using a pair of primers specific for GSSP-2.

The present invention also concerns a method for screening substances or molecules that are able to increase, or in contrast to decrease, the level of expression of the GSSP-2 gene. Such a method may allow the one skilled in the art to select substances exerting a regulating effect on the expression level of the GSSP-2 gene and which may be useful as active ingredients included in pharmaceutically and physiologically acceptable compositions for treating patients suffering from lipid metabolism related disorders.

Thus, also part of the present invention is a method for screening of a candidate substance or molecule that modulated the expression of the GSSP-2 gene, this method comprises the following steps:
  a) providing a recombinant cell host containing a nucleic acid molecule, wherein said nucleic acid molecule comprises a nucleotide sequence of the 5' regulatory region or a biologically active fragment or variant thereof located upstream a polynucleotide encoding a detectable protein;
  b) obtaining a candidate substance; and
  c) determining the ability of the candidate substance to modulate the expression levels of the polynucleotide encoding the detectable protein.

In a further embodiment, the nucleic acid molecule comprising the nucleotide sequence of the 5' regulatory region or a biologically active fragment or variant thereof also includes a 5' UTR region of the GSSP-2 cDNA of SEQ ID NO: 2, or one of its biologically active fragments or variants thereof.

Among the preferred polynucleotides encoding a detectable protein, there may be cited polynucleotides encoding beta galactosidase, green fluorescent protein (GFP) and chloramphenicol acetyl transferase (CAT).

The invention also pertains to kits useful for performing the herein described screening method. Preferably, such kits comprise a recombinant vector that allows the expression of a nucleotide sequence of the 5' regulatory region or a biologically active fragment or variant thereof located upstream and operably linked to a polynucleotide encoding a detectable protein or the GSSP-2 protein or a fragment or a variant thereof.

In another embodiment of a method for the screening of a candidate substance or molecule that modulates the expression of the GSSP-2 gene, wherein said method comprises the following steps:
  a) providing a recombinant host cell containing a nucleic acid molecule, wherein said nucleic acid molecule comprises a 5' UTR sequence of the GSSP-2 cDNA of SEQ ID NO: 2, or one of its biologically active fragments or variants, the 5' UTR sequence or its biologically active fragment or variant being operably linked to a polynucleotide encoding a detectable protein;
  b) obtaining a candidate substance; and
  c) determining the ability of the candidate substance to modulate the expression levels of the polynucleotide encoding the detectable protein.

In a specific embodiment of the above screening method, the nucleic acid molecule that comprises a nucleotide sequence selected from the group consisting of the 5' UTR sequence of the GSSP-2 cDNA of SEQ ID NO: 2 or one of its biologically active fragments or variants, includes a promoter sequence which is endogenous with respect to the GSSP-2 5' UTR sequence.

In another specific embodiment of the above screening method, the nucleic acid molecule that comprises a nucleotide sequence selected from the group consisting of the 5' UTR sequence of the GSSP-2 cDNA of SEQ ID NO: 2 or one of its biologically active fragments or variants, includes a promoter sequence which is exogenous with respect to the GSSP-2 5' UTR sequence defined therein.

In a further preferred embodiment, the nucleic acid molecule comprising the 5'-UTR sequence of the GSSP-2 cDNA or SEQ ID NO: 2 or the biologically active fragments thereof includes a biallelic marker selected from the group consisting of 20-828-311, 17-42-319, 17-41-250, 20-841-149, 20-842-115, and 20-853-415, and the complements thereof.

The invention further comprises with a kit for the screening of a candidate substance modulating the expression of the GSSP-2 gene, wherein said kit comprises a recombinant vector that comprises a nucleic acid molecule including a 5' UTR sequence of the GSSP-2 cDNA of SEQ ID NO: 2, or one of their biologically active fragments or variants, the 5' UTR sequence or its biologically active fragment or variant being operably linked to a polynucleotide encoding a detectable protein.

For the design of suitable recombinant vectors useful for performing the screening methods described above, it will be referred to the section of the present specification wherein the preferred recombinant vectors of the invention are detailed.

Expression levels and patterns of GSSP-2 may be analyzed by solution hybridization with long probes as described in International Patent Application No. WO 97/05277, the entire contents of which are incorporated herein by reference. Briefly, the GSSP-2 cDNA or the GSSP-2 genomic DNA described above, or fragments thereof, is inserted at a cloning site immediately downstream of a bacteriophage (T3, T7 or SP6) RNA polymerase promoter to produce antisense RNA. Preferably, the GSSP-2 insert comprises at least 100 or more consecutive nucleotides of the genomic DNA sequence or the cDNA sequences. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridization is performed under standard stringent conditions (40–50° C. for 16 hours in an 80% formamide, 0. 4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of GSSP-2 gene expression may also be performed using arrays. As used herein, the term array means a one dimensional, two dimensional, or multi-dimensional arrangement of a plurality of nucleic acid molecules of sufficient length to permit specific detection of expression of mRNAs capable of hybridizing thereto. For example, the arrays may contain a plurality of nucleic acid moleculues derived from genes whose expression levels are to be assessed. The arrays may include the GSSP-2 genomic DNA, the GSSP-2 cDNA sequences or the sequences complementary thereto or fragments thereof, particularly those comprising at least one of the biallelic markers according the present invention, preferably at least one of the biallelic markers 20-828-311, 17-42-319, 17-41-250, 20-841-149, 20-842-115, and 20-853-415. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of GSSP-2 gene expression may be performed with a complementary DNA microarray as described by Schena et al. (1995 and 1996). Full length GSSP-2 cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0. 2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of GSSP-2 gene expression may also be performed with full length GSSP-2 cDNAs or fragments thereof in complementary DNA arrays as described by Pietu et al. (1996). The full length GSSP-2 cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the GSSP-2 genomic DNA, the GSSP-2 cDNA, or fragments thereof can be done through high density nucleotide arrays as described by Lockhart et al. (1996) and Sosnowsky et al. (1997). Oligonucleotides of 15–50 nucleotides from the sequences of the GSSP-2 genomic DNA, the GSSP-2 cDNA sequences particularly those comprising at least one of biallelic markers according the present invention, preferably at least one biallelic marker selected from the group consisting of 20-828-311, 17-42-319, 17-41-250, 20-841-149, 20-842-115, and 20-853-415, or the sequences complementary thereto, are synthesized directly on the chip (Lockhart et al., supra) or synthesized and then addressed to the chip (Sosnowski et al., supra). Preferably, the oligonucleotides are about 20 nucleotides in length.

GSSP-2 cDNA probes labeled with an appropriate compound, such as biotin, digoxigenin or fluorescence dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., 1997), the dyes or labeling compounds are detected and quantified. Duplicate hybridizations are performed. Comparative analysis of the intensity of the signal originating from cDNA probes on the same target oligonucleotide in different cDNA samples indicates a differential expression of GSSP-2 mRNA.

XVII. Methods for Inhibiting the Expression of a GSSP-2 Gene

Other therapeutic compositions according to the present invention comprise advantageously an oligonucleotide fragment of the nucleic sequence of GSSP-2 as an antisense tool or a triple helix tool that inhibits the expression of the corresponding GSSP-2 gene. A preferred fragment of the nucleic sequence of GSSP-2 comprises an allele of at least one of the biallelic markers 20-828-311, 17-42-319, 17-41-250, 20-841-149, 20-842-115, and 20-853-415.

A. Antisense Approach

Preferred methods using antisense polynucleotide according to the present invention are the procedures described by Sczakiel et al. (1995).

Preferably, the antisense tools are chosen among the polynucleotides (15–200 bp long) that are complementary to the 5' end of the GSSP-2 mRNA. In another embodiment, a combination of different antisense polynucleotides complementary to different parts of the desired targeted gene are used.

Preferred antisense polynucleotides according to the present invention are complementary to a sequence of the mRNAs of GSSP-2 that contains either the translation initiation codon ATG or a splicing donor or acceptor site.

The antisense nucleic acids should have a length and melting temperature sufficient to permit formation of an intracellular duplex having sufficient stability to inhibit the expression of the GSSP-2 mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the GSSP-2 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of GSSP-2 antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0 572 287 A2

An alternative to the antisense technology that is used according to the present invention comprises using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme comprises (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995), the specific preparation procedures being referred to in said article being herein incorporated by reference.

B. Triple Helix Approach

The GSSP-2 genomic DNA may also be used to inhibit the expression of the GSSP-2 gene based on intracellular triple helix formation.

Triple helix oligonucleotides are used to inhibit transcription from a genome. They are particularly useful for studying alterations in cell activity when it is associated with a particular gene.

Similarly, a portion of the GSSP-2 genomic DNA can be used to study the effect of inhibiting GSSP-2 transcription within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the GSSP-2 genomic DNA are contemplated within the scope of this invention.

To carry out gene therapy strategies using the triple helix approach, the sequences of the GSSP-2 genomic DNA are first scanned to identify 10-mer to 20-mer homopyrimidine or homopurine stretches which could be used in triple-helix based strategies for inhibiting GSSP-2 expression. Following identification of candidate homopyrimidine or homopurine stretches, their efficiency in inhibiting GSSP-2 expression is assessed by introducing varying amounts of oligonucleotides containing the candidate sequences into tissue culture cells which express the GSSP-2 gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced GSSP-2 expression using techniques such as Northern blotting, RNase protection assays, or PCR based strategies to monitor the transcription levels of the GSSP-2 gene in cells which have been treated with the oligonucleotide.

The oligonucleotides which are effective in inhibiting gene expression in tissue culture cells may then be introduced in vivo using the techniques described above in the antisense approach at a dosage calculated based on the in vitro results, as described in antisense approach.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (1989), which is hereby incorporated by this reference.

XVIII. Pharmaceutical and Physiologically Acceptable Compositions

The present invention also relates to pharmaceutical or physiologically acceptable compositions comprising, as active agent, the polypeptides, nucleic acid molecules or antibodies of the invention. The invention also relates to compositions comprising, as active agent, compounds selected using the above-described screening protocols. Such compositions include the active agent in combination with a pharmaceutical or physiologically acceptable carrier. In the case of naked DNA, the "carrier" may be gold particles. The amount of active agent in the composition can vary with the agent, the patient and the effect sought. Likewise, the dosing regimen can vary depending on the composition and the disease/disorder to be treated.

Conventional pharmaceutical practice may be employed to provide suitable formulations or compositions to administer GSSP-2 polypeptide, polynucleotide and antibodies of the present invention to patients suffering from a disease (e.g., a degenerative disease) that is caused by excessive apoptosis. Administration may begin before the patient is symptomatic. Any appropriate route of administration may be employed, for example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, intrapulmonary (inhaled) or oral administration. Therapeutic formulations may be in the form of liquid solutions or suspensions; for oral administration, formulations may be in the form of tablets or capsules; and for intranasal formulations, in the form of powders, nasal drops, or aerosols.

If desired, treatment with a GSSP-2 protein, gene, or modulatory compound may be combined with more traditional therapies for neoplastic disease such as surgery, steroid therapy, or chemotherapy. Likewise, treatment with a GSSP-2 protein, gene, or modulatory compound may be combined with more traditional therapies for the disease involving insufficient apoptosis, such as surgery, radiation therapy, and chemotherapy for cancer.

The composition of the present invention, when administered as an anticancer composition, for instance, induces cytotoxicity of cancer cells, and thereby produces an anticancer effect. In this case, the composition of the invention, irrespective of dosage form and/or route of administration, can be used in combination with one or more of various anticancer agents known as cancer chemotherapeutic agents and/or radiation therapy. The active ingredient compound of the invention which can produce an excellent anticancer effect can thus markedly promote the effect of the other anticancer agent or agents used in combination, to produce a synergistic effect. Therefore, even when the partner anticancer agent or agents are used in doses much smaller than the usual doses, a satisfactory anticancer effect can be obtained, whereby the adverse effects of the partner anticancer agent or agents can be minimized. As such chemotherapeutic agents, included but not limited to, for example, 5-fluorouracil (5-FU; Kyowa Hakko Kogyo), mitomycin C (Kyowa Hakko Kogyo), futraful (FT-207; Taiho Pharmaceutical), endoxan (Shionogi & Co.) and toyomycin (Takeda Chemical Industries). In addition, the apoptosis regulating composition of the present invention may be administered with a vitamin D derivative to further enhance its cytotoxic characteristics (U.S. Pat. No. 6,087,350).

The pharmaceutically and physiologically acceptable compositions utilized in this invention may be administered by any number of routes including, but not limited to, parenteral, subcutaneous, intracranial, intraorbital, intracapsular, intraspinal, intracisternal, intrapulmonary (inhaled), oral, intravenous, intramuscular, intra-arterial, intramedullary, intrathecal, intraventricular, transdermal, subcutaneous, intraperitoneal, intranasal, enteral, topical, sublingual, or rectal means. In addition to the active ingredients, these pharmaceutically and physiologically acceptable compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co. Easton, Pa).

Pharmaceutically and physiologically acceptable compositions for oral administration can be formulated using pharmaceutically acceptable carriers well known in the art in dosages suitable for oral administration. Such carriers enable the pharmaceutically and physiologically acceptable compositions to be formulated as tablets, pills, dragees, capsules, liquids, gels, syrups, slurries, suspensions, and the like, for ingestion by the patient.

Pharmaceutical preparations for oral use can be obtained through a combination of active compounds with solid excipient, suiting mixture is optionally grinding, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titaniumdioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquidpolyethylene glycol with or without stabilizers.

Pharmaceutical formulations suitable for parenteral administration may be formulated in aqueous solutions, preferably in physiologically compatible buffers such as Hanks solution, Ringer's solution, or physiologically buffered saline. Aqueous injection suspensions may contain substances which increase the viscosity of the suspension, such as sodium carboxymethylcellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art. The pharmaceutically and physiologically acceptable compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutically and physiologically acceptable compositions have been prepared, they can be placed in an appropriate container and labeled for treatment of an indicated condition. For administration of GSSP-2, such labeling would include amount, frequency, and method of administration.

Pharmaceutically and physiologically acceptable compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans. Those of ordinary skill in the art are well able to extrapolate from one model (be it an in vitro or an in vivo model).

A therapeutically effective dose refers to that amount of active ingredient, for example GSSP-2 polypeptides or fragments thereof, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutically and physiologically acceptable compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutically and physiologically acceptable compositions maybe administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

XIX. Methods of Treatment

It is contemplated that the polypeptides of the present invention and their agonists, including antibodies, peptides, and small molecule agonists, may be used to treat various tumors, e.g., cancers. Exemplary conditions or disorders to be treated include benign or malignant neoplastic diseases (e.g., liver cancer, Ewing sarcoma and peripheral neuroepithelioma); leukemia (e.g. acute lymphoblastic leukemia, acute myeloid leukemia) and lymphoid malignancies (lymphoma); other disorders such as neuronal, glial, astrocytal, hypothalamic and other glandular, macrophagal, epithelial, stromal and blastocoelic disorders; and inflammatory, angiogenic and immunologic disorders. The anti-tumor agents of the present invention (including the polypeptides disclosed herein and agonists which mimic their activity, e.g., antibodies, peptides and small organic molecules), are administered to a mammal, preferably a human, in accord with known methods, such as intravenous administration as a bolus or by continuous infusion over a period of time, or by intramuscular, intraperitoneal, intracerobrospinal, traocular, intraarterial, intralesional, subcutaneous, intraarticular, intras ynovial, intrathecal, oral, topical, or inhalation routes.

Other therapeutic regimens may be combined with the administration of the anti-cancer agents of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service, ed., M. C. Perry, Williams & Wilkins, Baltimore, Md. (1992). The chemotherapeutic agent may precede, or follow administration of the anti-tumor agent of the present invention, or may be given simultaneously therewith. The anti-cancer agents of the present invention may be combined with an anti-oestrogen compound such as tamoxifen or an anti-progesterone such as onapristone (see, EP 616812) in dosages known for such molecules.

It may be desirable to also administer antibodies against tumor associated antigens, such as antibodies which bind to the ErbB2, EGFR, ErbB3, ErbB4, or vascular endothelial factor (VEGF). Alternatively, or in addition, two or more antibodies binding the same or two or more different cancer-associated antigens may be co-administered to the patient. Sometimes, it may be beneficial to also administer one or more cytokines to the patient.

In a preferred embodiment, the anti-cancer agents herein are co-administered with a growth inhibitory agent. For example, the growth inhibitory agent may be administered first, followed by the administration of an anti-cancer agent of the present invention. However, simultaneous administration or administration of the anti-cancer agent of the present invention first is also contemplated. Suitable dosages for the growth inhibitory agent are those presently used and may be lowered due to the combined action (synergy) of the growth inhibitory agent and the antibody herein.

For the prevention or treatment of disease, the appropriate dosage of an anti-tumor agent herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in Toxicokinetics and New Drug Development, Yacobi et al., eds., Pergamon Press, New York 1989, pp. 42–96.

For example, depending on the type and severity of the disease, about 1 µg/kg to 15 mg/kg (e.g., 0.1–20 mg/kg) of an antitumor agent is an initial candidate dosage for administration to the patient, whether, for example, by one or more separate administrations, or by continuous infusion. A typical daily dosage might range from about 1 µg/kg to 100 µg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

XX. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is a composition of the present invention, (e.g. polypeptide, polynucleotide, antibody or small molecule). The label on, or associated with, the container indicates that the composition is used for diagnosing or treating the condition of choice. The article of manufacture may further comprise a second container comprising a pharmaceutically or physiologically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

XXI. Therapies

Therapies may be designed to utilize GSSP-2 cytotoxic properties. In particular, therapies to enhance GSSP-2 gene expression or administration of GSSP-2 polypeptides are useful in promoting inhibition or death of cancerous cells. Cytotoxic GSSP-2 reagents may include, without limitation, full length or fragment GSSP-2 polypeptides, GSSP-2 mRNA, or any compound which increases GSSP-2 biological activity.

Another therapeutic approach within the invention involves administration of GSSP-2 therapeutic compositions (e.g., GSSP-2 polynucleodtide, antibody, small molecule agonist or recombinant GSSP-2 polypeptide), either directly to the site of a desired target cell or tissue (for example, by injection) or to a site where the composition will be further directed to the target cell or tissue, or systemically (for example, by any conventional recombinant protein administration technique). The dosage of GSSP-2 depends on a number of factors, including the size and health of the individual patient, but, generally, between 0.1 mg and 100 mg inclusive are administered per day to an adult in any pharmaceutically acceptable formulation.

A. Protein Therapy

Treatment or prevention of neoplastic disease can be accomplished by replacing mutant or surplus GSSP-2 protein with normal protein, by modulating the function of mutant protein, or by delivering normal GSSP-2 protein to the appropriate cells. It is also be possible to modify the pathophysiologic pathway (e.g., a signal transduction pathway) in which the protein participates in order to correct the physiological defect.

To replace a mutant protein with normal protein, or to introduce GSSP-2 polypeptides into cells it is not expressed in, it is necessary to obtain large amounts of pure GSSP-2 protein from cultured cell systems which can express the protein. Delivery of the protein to the affected tissues (e.g., cancerous tissues) can then be accomplished using appropriate packaging or administrating systems. Alternatively, small molecule analogs may be used and administered to act as GSSP-2 agonists and in this manner produce a desired physiological effect. Methods for finding such molecules are provided herein.

B. Gene Therapy

Gene therapy is another therapeutic approach in which normal copies of the GSSP-2 gene or polynucleotides encoding GSSP-2 polypeptides are introduced into selected cellular tissues to successfully produce normal and abundant GSSP-2 protein or GSSP-2 antisense RNA in cells which inappropriately either suppress cell death (e.g., cancerous liver cells) or enhance the rate of cell death (e.g., liver cell death leading to disease), respectively. The gene must be delivered to those cells in a form in which it can be taken up and encode for sufficient protein to provide effective function. Alternatively, in some mutants it may be possible to promote apoptosis/necrosis by introducing another copy of the homologous gene bearing a second mutation in that gene or to alter the mutation, or use another gene to block any negative effect.

Transducing retroviral vectors can be used for somatic cell gene therapy especially because of their high efficiency of infection and stable integration and expression. The targeted cells however must be able to divide and the expression levels of normal protein should be high. For example, the full length GSSP-2 gene, or portions thereof, can be cloned into a retroviral vector and driven from its endogenous promoter or from the retroviral long terminal repeat or from a promoter specific for the target cell type of interest (such as neurons). Other viral vectors which can be used include adenovirus, adeno-associated virus, vaccinia virus, bovine papilloma virus, or a herpes virus such as Epstein-Barr Virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Transplantation of normal genes into the affected patient can also be useful therapy. In this procedure, a normal GSSP-2 gene is transferred into a cultivatable cell type that is either exogenous or endogenous to the patient. These cells are then injected serotologically into the targeted tissue(s).

Retroviral vectors, adenoviral vectors, adenovirus-associated viral vectors, or other viral vectors with the appropriate tropism for cells likely to be the target of gene therapy (for example, epithelial cells) may be used as a gene transfer delivery system for a therapeutic GSSP-2 gene construct. Numerous vectors useful for this purpose are generally known (Miller, Human Gene Therapy 15–14, 1990; Friedman, Science 244:1275–1281, 1989; Eglitis and Anderson, BioTechniques 6: 608–614, 1988; Tolstoshev and Anderson, Curr. Opin. Biotech. 1: 55–61, 1990; Sharp, The Lancet 337: 1277–1278, 1991; Cornetta et al., Nucl. Acid Res. and Mol. Biol. 36: 311–322, 1987; Anderson, Science 226: 401–409, 1984; Moen, Blood Cells 17: 407416, 1991; Miller et al., Biotech. 7: 980–990, 1989; Le Gal La Salle et al., Science 259: 988–990, 1993; and Johnson, Chest 107: 77S–83S, 1995). Retroviral vectors are particularly well developed and have been used in clinical settings (Rosenberg et al., N. Engl. J. Med 323: 370, 1990; Anderson et al., U.S. Pat. No. 5,399,346). Non-viral approaches may also be employed for the introduction of therapeutic DNA into target cells. For example, GSSP-2 may be introduced into a cell by lipofection (Felgner et al., Proc. Natl. Acad. Sci. USA 84: 7413, 1987; Ono et al., Neurosci. Lett. 117: 259, 1990; Brigham et al., Am. J. Med. Sci. 298: 278, 1989; Staubinger et al., Meth. Enz. 101:512, 1983, asialorosonucoid-polylysine conjugation (Wu et al., J. Biol. Chem. 263: 14621, 1988; Wu et al., J. Biol. Chem. 264: 16985, 1989); or, less preferably, micro-injection under surgical conditions (Wolff et al., Science 247: 1465, 1990).

In another approach that may be utilized with all of the above methods, a therapeutic GSSP-2 DNA construct is preferably applied to the site of the desired therapeutic event (for example, by injection). However, it may also be applied to tissue in the vicinity of the desired therapeutic event or to a blood vessel supplying the target cells (e.g., cancerous cells) desired to undergo apoptosis/necrosis.

In the constructs described, GSSP-2 cDNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in liver cells, lymphocytes, neural or muscle cells may be used to direct GSSP-2 expression. The enhancers used could include, without limitation, those that are characterized as tissue- or cell-specific in their expression or those regulated by exogenous or endogenous factors. Alternatively, if a GSSP-2 genomic clone is used as a therapeutic construct (for example, following isolation by hybridization with the GSSP-2 cDNA described above), regulation may be mediated by the cognate regulatory sequences or, if desired, by regulatory sequences derived from a heterologous source, including any of the promoters or regulatory elements described above.

Antisense based strategies have employed to explore GSSP-2 gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target GSSP-2 mRNA. Antisense strategies may use a variety of approaches including the use of antisense oligonucleotides and injection of antisense RNA. For our analysis of GSSP-2 gene function, we employed the method of transfection of antisense RNA expression vectors into targeted cells. Antisense effects can be induced by control (sense) sequences, however, the extent of phenotypic changes are highly variable. Phenotypic effects induced by antisense effects are based on changes in criteria such as protein levels, protein activity measurement, and target mRNA levels.

For example, GSSP-2 gene therapy may also be accomplished by direct administration of antisense GSSP-2 mRNA to a cell target. The antisense GSSP-2 mRNA may be produced and isolated by any standard technique, but is most readily produced by in vitro transcription using an antisense GSSP-2 cDNA under the control of a high efficiency promoter (e.g., the T7 promoter). Administration of antisense GSSP-2 mRNA to cells can be carried out by any of the methods for direct nucleic acid molecule administration described above.

XXII. Detection of Conditions Involving Altered Apoptosis

GSSP-2 polypeptides and nucleic acid sequences find diagnostic use in the detection or monitoring of conditions involving aberrant levels of apoptosis. For example, decreased expression of GSSP-2 may be correlated with decreased apoptosis in humans. Accordingly, a decrease or increase in the level of GSSP-2 production may provide an indication of a deleterious condition. Levels of GSSP-2 expression may be assayed by any standard technique. For example, GSSP-2 expression in a biological sample (e.g., a biopsy) may be monitored by standard Northern blot analysis or may be aided by PCR (see, e.g., Ausubel et al., supra; PCR Technology: Principles and Applications for DNA Amplification, H. A. Ehrlich, Ed. Stockton Press, NY; Yap et al. Nucl. Acids. Res. 19: 4294, 1991), such as quantitative PCR.

Alternatively, a biological sample obtained from a patient may be analyzed for one or more mutations in GSSP-2 nucleic acid sequences using a mismatch detection approach. Generally, these techniques involve PCR amplification of nucleic acid molecules from the patient sample, followed by identification of the mutation (i.e., mismatch) by either altered hybridization, aberrant electrophoretic gel migration, binding or cleavage mediated by mismatch binding proteins, or direct nucleic acid sequencing.

Any of these techniques may be used to facilitate mutant GSSP-2 detection, and each is well known in the art; examples of particular techniques are described, without limitation, in Orita et al. (Proc. Natl. Acad. Sci. USA 86: 2766–2770, 1989) and Sheffield et al. (Proc. Natl. Acad. Sci. USA 86: 232–236, 1989).

In yet another approach, immunoassays are used to detect or monitor GSSP-2 protein expression in a biological sample. GSSP-2-specific polyclonal or monoclonal antibodies (produced as described above) may be used in any standard immunoassay format (e.g., ELISA, Western blot, or RIA) to measure GSSP-2 polypeptide levels. These levels would be compared to wild-type GSSP-2 levels. For example, a decrease in GSSP-2 production may indicate a condition involving insufficient apoptosis. Examples of immunoassays are described, e.g., in Ausubel et al, supra. Immunohistochemical techniques may also be utilized for GSSP-2 detection. For example, a tissue sample may be obtained from a patient, sectioned, and stained for the presence of GSSP-2 using an anti-GSSP-2 antibody and any standard detection system (e.g., one which includes a secondary antibody conjugated to horseradish peroxidase). General guidance regarding such techniques can be found in, e.g., Bancroft and Stevens (Theory and Practice of Histological Techniques, Churchill Livingstone, 1982) and Ausubel et al. (supra).

In one preferred example, a combined diagnostic method may be employed that begins with an evaluation of GSSP-2 protein production (for example, by immunological techniques or the protein truncation test (Hogerrorst et al., Nature Genetics 10: 208–212, 1995) and also includes a nucleic acid-based detection technique designed to identify more subtle GSSP-2 mutations (for example, point mutations). As described above, a number of mismatch detection assays are available to those skilled in the art, and any preferred technique may be used. Mutations in GSSP-2 may be detected that either result in loss of GSSP-2 expression or loss of normal GSSP-2 biological activity. In a variation of this combined diagnostic method, GSSP-2 biological activity is measured as apoptotic-inducing activity using any appropriate apoptosis assay system (for example, those described herein).

Mismatch detection assays also provide an opportunity to diagnose a GSSP-2-mediated predisposition to diseases caused by inappropriate apoptosis. For example, a patient heterozygous for a GSSP-2 mutation that induces a GSSP-2 over expression may show no clinical symptoms and yet possess a higher than normal probability of developing diseases or disorders, for example, a degenerative liver disorder. Given this diagnosis, a patient may take precautions to minimize their exposure to adverse environmental factors (for example, alcohol, UV exposure or chemical mutagens) and to carefully monitor their medical condition (for example, through frequent physical examinations). This type of GSSP-2 diagnostic approach may also be used to detect GSSP-2 mutations in prenatal screens. The GSSP-2 diagnostic assays described above may be carried out using any biological sample (for example, any biopsy sample or other tissue) in which GSSP-2 is normally expressed. Identification of a mutant GSSP-2 gene may also be assayed using these sources for test samples.

Alternatively, a GSSP-2 mutation, particularly as part of a diagnosis for predisposition to GSSP-2-associated degenerative disease, may be tested using a DNA sample from any cell, for example, by mismatch detection techniques. Preferably, the DNA sample is subjected to PCR amplification prior to analysis.

XXIII. Examples of Additional Apoptosis Assays

Specific examples of apoptosis assays are also provided in the following references. Assays for apoptosis in lymphocytes are disclosed by: Li et al., "Induction of apoptosis in uninfected lymphocytes by HIV-1 Tat protein", Science 268: 429–431, 1995; Gibellini et al., "Tat-expressing Jurkat cells show an increased resistance to different apoptotic stimuli, including acute human immunodeficiency virus-type 1 (HIV-1) infection", Br. J. Haematol. 89: 24–33, 1995; Martin et al., "HIV-1 infection of human CD4.sup.+ T cells in vitro. Differential induction of apoptosis in these cells." J. Immunol. 152:330–342, 1994; Terai et al, "Apoptosis as a mechanism of cell death in cultured T lymphoblasts acutely infected with HIV-1", J. Clin Invest. 87: 1710–1715, 199 1; Dhein et al., "Autocrine T-cell suicide mediated by APO-1/(Fas/CD95)", Nature 373: 438–441, 1995; Katsikis et al., "Fas antigen stimulation induces marked apoptosis of T lymphocytes in human immunodeficiency virus-infected individuals", J. Exp. Med. 1815:2029–2036, 1995; Westendorp et al., "Sensitization of T cells to CD95-mediated apoptosis by HIV-1 Tat and gp120", Nature 375:497, 1995; DeRossi et al., Virology 198:234–244, 1994.

Assays for apoptosis in fibroblasts are disclosed by: Vossbeck et al., "Direct transforming activity of TGF-beta on rat fibroblasts", Int. J. Cancer 61:92–97, 1995; Goruppi et al., "Dissection of c-myc domains involved in S phase induction of NIH3T3 fibroblasts", Oncogene 9:1537–44, 1994; Fernandez et al., "Differential sensitivity of normal and Ha-ras transformed C3H mouse embryo fibroblasts to tumor necrosis factor: induction of bcl-2, c-myc, and manganese superoxide dismutase in resistant cells", Oncogene 9:2009–2017, 1994; Harrington et al., "c-Myc-induced apoptosis in fibroblasts is inhibited by specific cytokines", EMBO J. 13:3286–3295, 1994; Itoh et al, "A novel protein domain required for apoptosis. Mutational analysis of human Fas antigen", J. Biol. Chem. 268:10932–10937, 1993.

Assays for apoptosis in neuronal cells are disclosed by: Melino et al, "Tissue transglutaminase and apoptosis: sense and antisense transfection studies with human neuroblastoma cells", Mol. Cell Biol. 14:6584–6596, 1994; Rosenbaum et al., "Evidence for hypoxia-induced, programmed cell death of cultured neurons", Ann. Neurol. 36:864–870, 1994; Sato et al., "Neuronal differentiation of PC12 cells as a result of prevention of cell death by bcl-2", J. Neurobiol 25:1227–1234, 1994; Ferrari et al., "N-acetylcysteine D- and L-stereoisomers prevents apoptotic death of neuronal cells", J. Neurosci. 1516:2857–2866, 1995; Talley et al., "Tumor necrosis factor alpha-induced apoptosis in human neuronal cells: protection by the antioxidant N-acetylcysteine and the genes bcl-2 and crmA", Mol. Cell. Biol. 1585:2359–2366, 1995; Talley et al., "Tumor Necrosis Factor Alpha-Induced Apoptosis in Human Neuronal Cells: Protection by the Antioxidant NAcetylcysteine and the Genes bcl-2 and crmA", Mol. Cell. Biol. 15:2359–2366, 1995; Walkinshaw et al., "Induction of apoptosis in catecholaminergic PC 12 cells by L-DOPA. Implications for the treatment of Parkinson's disease." J. Clin. Invest. 95:2458–2464, 1995.

Assays for apoptosis in insect cells are disclosed by: Clem et al., "Prevention of apoptosis by a baculovirus gene during infection of insect cells", Science 254:1388–1390, 1991; Crook et al., "An apoptosis-inhibiting baculovirus gene with a zinc finger-like motif", J. Virol. 67:2168–2174, 1993; Rabizadeh et al., "Expression of the baculovirus p35 gene inhibits mammalian neural cell death", J. Neurochem. 61:2318–2321, 1993; Birnbaum et al., "An apoptosis inhibiting gene from a nuclear polyhedrosis virus encoding a polypeptide with Cys/His sequence motifs", J. Virol. 68:2521–2528, 1994; Clem et al., Mol. Cell. Biol. 14:5212–5222, 1994.

The disclosures of all issued patents, published PCT applications, scientific references or other publications cited herein are incorporated herein by reference in their entireties.

Although this invention has been described in terms of certain preferred embodiments, other embodiments which will be apparent to those of ordinary skill in the art of view of the disclosure herein are also within the scope of this invention. Accordingly, the scope of the invention is intended to be defined only by reference to the appended claims.

EXAMPLES

Example 1

De Novo Identification of Biallelic Markers

The biallelic markers set forth in this application were isolated from human genomic sequences. To identify biallelic markers, genomic fragments were amplified, sequenced and compared in a plurality of individuals.

DNA samples

Donors were unrelated and healthy. They represented a sufficient diversity for being representative of a French heterogeneous population. The DNA from 100 individuals was extracted and tested for the de novo identification of biallelic markers.

DNA samples were prepared from peripheral venous blood as follows. Thirty ml of peripheral venous blood were taken from each donor in the presence of EDTA. Cells (pellet) were collected after centrifugation for 10 minutes at 2000 rpm. Red cells were lysed in a lysis solution (50 ml final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution. The pellet of white cells was lysed overnight at 42° C. with 3.7 ml of lysis solution composed of: (a) 3 ml TE 10-2 (Tris-HCl 10 mM, EDTA 2 mM)/NaCl 0.4 M; (b) 200 µl SDS 10%; and (c) 500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm. For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA). To determine the presence of proteins in the DNA solution, the OD 260/OD 280 ratio was determined. Only DNA preparations having a OD 260/OD 280 ratio between 1.8 and 2 were used in the subsequent examples described below. DNA pools were constituted by mixing equivalent quantities of DNA from each individual.

Amplification of genomic DNA by PCR

Amplification of specific genomic sequences was carried out on pooled DNA samples obtained as described above.

Amplification Primers

The primers used for the amplification of human genomic DNA fragments were defined with the OSP software (Hillier & Green, 1991). Preferably, primers included, upstream of the specific bases targeted for amplification, a common oligonucleotide tail useful for sequencing. Primers PU contain the following additional PU 5' sequence: TGTAAAACGACGGCCAGT; primers RP contain the following RP 5' sequence: CAGGAAACAGCTATGACC. Primers are listed in FIG. 5.

Amplification

PCR assays were performed using the following protocol:

| | |
|---|---|
| Final volume | 25 μl |
| DNA | 2 ng/μl |
| MgCl$_2$ | 2 mM |
| dNTP (each) | 200 μM |
| primer (each) | 2.9 ng/μl |
| Ampli Taq Gold DNA polymerase | 0.05 unit/μl |
| PCR buffer (10x = 0.1 M TrisHCl pH8.3 0.5 M KCl) | 1x |

DNA amplification was performed on a Genius II thermocycler. After heating at 94° C. for 10 min, 40 cycles were performed. Cycling times and temperatures were: 30 sec at 94° C., 55° C. for 1 min and 30 sec at 72° C. Holding for 7 min at 72° C. allowed final elongation. The quantities of the amplification products obtained were determined on 96-well microtiter plates, using a fluorometer and Picogreen as intercalant agent (Molecular Probes).

Sequencing of Amplified Genomic DNA and Identification of Biallelic Polymorphisms Sequencing of the amplified DNA was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software 2.1.2 version).

The sequence data were further evaluated to detect the presence of biallelic markers within the amplified fragments. The polymorphism search was based on the presence of superimposed peaks in the electrophoresis pattern resulting from different bases occurring at the same position. However, the presence of two peaks can be an artifact due to background noise. To exclude such an artifact, the two DNA strands were sequenced and a comparison between the two strands was carried out. In order to be registered as a polymorphic sequence, the polymorphism had to be detected on both strands. Further, biallelic single nucleotide polymorphisms were confirmed by microsequencing as described below.

Biallelic markers were identified in the analyzed fragments and are shown in FIG. 1.

Example 2

Genotyping of Biallelic Markers

The biallelic markers identified as described above were further confirmed and their respective frequencies were determined through microsequencing. Microsequencing was carried out on individual DNA samples obtained as described herein.

Microsequencing Primers

Amplification of genomic DNA fragments from individual DNA samples was performed as described in Example 1 using the same set of PCR primers. Microsequencing was carried out on the amplified fragments using specific primers. The preferred primers for use in microsequencing were between 19 and 21 nucleotides in length and hybridized just upstream of the considered polymorphic base. Preferred microsequencing primers are shown in FIG. 4.

The microsequencing reactions were performed as follows: 5 μl of PCR products were added to 5 μl purification mix [2U SAP (Shrimp alkaline phosphate) (Amersham E70092X)); 2U Exonuclease I (Amersham E70073Z); and 1 μl SAP buffer (200 mM Tris-HCl pH8, 100 mM MgCl$_2$) in a microtiter plate. The reaction mixture was incubated 30 minutes at 37° C., and denatured 10 minutes at 94° C. afterwards. Twenty μl of microsequencing reaction mixture was added to each well. The microsequencing reaction mixture contained 10 pmol microsequencing oligonucleotide (19mers, GENSET, crude synthesis, 5 OD), 1 U Thermosequenase (Amersham E79000G), 1.25 μl Thermosequenase buffer (260 mM Tris HCl pH 9.5, 65 mM MgCl$_2$), and the two appropriate fluorescent ddNTPs complementary to the nucleotides at the polymorphic site corresponding to both polymorphic bases (11.25 nM TAMRA-ddTTP; 16.25 nM ROX-ddCTP; 1.675 nM REG-ddATP; 1.25 nM RHO-ddGTP; Perkin Elmer, Dye Terminator Set 401095). After 4 minutes at 94° C., 20 PCR cycles of 15 sec at 55° C., 5 sec at 72° C., and 10 sec at 94° C. were carried out in a Tetrad PTC-225 thermocycler (MJ Research). The microtiter plate was centrifuged 10 sec at 1500 rpm. The unincorporated dye terminators were removed by precipitation with 19 μl MgCl$_2$ 2 mM and 55 μl 100% ethanol. After 15 minute incubation at room temperature, the microtiter plate was centrifuged at 3300 rpm 15 minutes at 4° C. After discarding the supernatants, the microplate was evaporated to dryness under reduced pressure (Speed Vac). Samples were resuspended in 2.5 μl formamide EDTA loading buffer and heated for 2 min at 95° C. 0.8 μl microsequencing reaction were loaded on a 10% (19:1) polyacrylamide sequencing gel. The data were collected by an ABI PRISM 377 DNA sequencer and processed using the GENESCAN software (Perkin Elmer).

Example 3

Analysis of GSSP2 mRNA Expression by Northern Blotting

Analysis of GSSP2 expression in different human tissues (adult and fetal) and cell lines, as well as mouse embryos in different stages of development, was accomplished by using poly A$^+$ RNA blots purchased from Clontech (e.g. #7780-1, 7757-1, 7756-1, 7768-1 and 7763-1). Labeling of RNA probes was performed using the RNA Strip-EZ kit from Ambion as per manufacture's instructions. Hybridization of RNA probes to RNA blots was performed Ultrahyb hybridization solution (Ambion). Briefly, blots were prehybridized for 30 min at 58° C. (low-strigency) or 65° C. (high stringency). After adding the labeled probe (2×10$^6$ cpm/ml), blots were hybridized overnight (14–24 hrs), and washed 2×20 min at 50° C. with 2×SSC/0.1% SDS (low stringency), 2×20 min at 58° C. with 1×SSC/0.1% SDS (medium stringency) and 2×20 min at 65° C. with 1×SSC/0.1% SDS (high stringency). After washings were completed blots were exposed on the phosphoimager (Molecular Dynamics) for 1–3 days.

Results from the Northern blot revealed GSSP-2 is only expressed in the liver and fetal liver and not in any of the cell lines tested. While GSSP-2 is expressed in the liver and fetal liver, it does not kill normal cells. In addition, the inventors found GSSP-2 is differentially expressed in obese mouse models: up regulated in mice fed a high fat diet (cafeteria diet) and in naturally obese mice (NZO), while it was not differentially expressed in either mice lacking the gene for leptin (ob/ob) or in mice lacking the gene for the leptin receptor (db/db), suggesting GSSP-2 is regulated by diet.

Example 4

Purification of His-Tagged GSSP2 Protein Expressed in E. coli (Soluble Fraction Only)

The protein of the invention was expressed in E. coli in a poly-His tagged form, using the following procedure. The DNA encoding GSSP 2 was initially amplified using selected PCR primers. The primers contain restriction enzyme sites that correspond to the restriction enzyme sites on the selected expression vector pET-30A+ (Novagen), and other useful sequences providing for efficient and reliable translation initiation, and proteolytic removal by enterokinase. The PCR-amplified sequences were then ligated into pET-30A+, which contains the poly-His sequence, and used to transform the E. coli strain BL-21. Bacteria were grown in LB media (Sambrook et al., Molecular Cloning, Cold Spring Harbor, N.Y., 1989) containing 34 µg/ml kanamycin. 50 ml of this initial culture were added to 1 L LB media/34 µg/ml kanamycin and incubated at 37° C. in an orbital shaker. Once an OD=0.4–0.6 at λ=600 nm was reached (~3 hours) isopropyl β-D-ThioGalactoPyranoside, IPTG (Sigma) was added to a final concentration of 1 mM. The bacteria culture was incubated at 37° C. for 3 hours with shaking and followed by centrifugation at 3,000 rpm for 30 min at 4° C. Cell pellets were frozen at −80° C. until purification.

Pellets from 1L cultures were resuspended in 50 ml of non-denaturing binding buffer (0.5 M NaCl, 20 mM Tris-HCl pH 8.0, 10% glycerol) containing 2 ml of 10 mg/ml lysozyme and incubated at RT for 20–30 min, or until lysed. After lysis 1 ml of IGEPAL (Sigma) was added, and the cells were sonicated as necessary. The solution was centrifuged for 30 min at 18,000 rpm in a SS34 rotor. The supernatant was collected and added to 4 ml of a Ni2+-NTA resin (Qiagen) 50/50 slurry (in non-denaturing buffer). The sample was rotated for 1 hr at 4° C., followed by centrifugation for 1 min at 1000 rpm. The resin was then resuspended in 5 ml of non-denaturing buffer, poured into a column and allowed to drain. After washing the column with 3 column volumes of non-denaturing buffer containing 10 mM imidazole, step-wise elution of the protein was carried out by adding, and collecting the eluates of 10 ml of non-denaturing buffer +0.1.0.2, 0.3, 0.5, and 1 M imidazole. Fractions containing the desired protein were pooled and stored at −20° C. Samples were removed to verify expression by SDS-PAGE analysis. Protein concentration was calculated by the BCA method (BioRad).

Endotoxin removal from the protein sample was carried out using the Acticlean Etox resin (Sterogene) as per manufacturer's instructions. Each protein sample was passed 3 times over the column.

Generation of GSSP-2 may also be performed by a number of methods well known in the art.

PCR Cloning

The GSSP-2 polypeptides of the present invention can be made using techniques well known in the art. One approach is to PCR the region of interest from the cDNA clone given the ECACC and given the accession No. 99061735. A preferred method uses primers with restriction sites on the end so that PCR products can be directly cloned into vectors of interest. Alternatively, GSSP-2 can also be generated using RT-PCR to isolate it from tissues such as liver and fetal liver which express GSSP-2.

E. coli Vector

For example, the coding sequence of the GSSP-2 DNA can be cloned into pTrcHisB, by putting a Bam HI site on the sense oligo and a Xho I site on the antisense oligo. This allows isolation of the PCR product, digestion of that product, and ligation into the pTrcHisB vector that has also been digested with Bam HI and Xho I. The vector, pTrcHisB, has an N-terminal 6-Histidine tag, that allows purification of the over expressed protein from the lysate using a Nickel resin column. The pTrcHisB vector is used for over-expression of proteins in E. coli.

BAC Vector

The coding sequence of the GSSP-2 DNA can also be over expressed in a Baculovirus system using the 6×His Baculovirus kit (Pharmingen), for example. The coding sequence of the GSSP-2 DNA is cloned into the appropriate vector using enzymes available in the multiple cloning site. This allows over-expression of the protein in a eukaryotic system which has some advantages over the E. coli system, including: Multiple gene expression, Signal peptide cleavage, Intron splicing, Nuclear transport, Functional protein, Phosphorylation, Glycosylation, and Acylation.

The coding sequence of the GSSP-2 DNA is amplified by PCR using oligos containing restriction sites for EcoRI or PstI. The resulting DNA product is digested with EcoRI and PstI and subcloned into the baculovirus expression vector pAcHLT (which carries a 6×His tag sequence). The expression vector containing the GSSP-2 DNA is transfected into Sf9 insect cells by standard procedures (Pharmingen). Recombinant virus is collected, amplified, and used to infect Sf9 cells at a MOI<1. Recombinant protein is recovered and purified over a Ni resin using standard procedures (Pharmingen).

Mammalian Vector

The coding sequence of the GSSP-2 DNA can also be cloned into a mammalian expression vector and expressed in and purified from mammalian cells. GSSP-2 is then generated in an environment very close to its endogenous environment. However, this is not necessarily the most efficient way to make protein.

Example 5

In vitro Tests of GSSP-2 Activity

The activity of various preparations and various sequence variants of GSSP-2 are assessed using various in vitro assays including those provided below. These assays are also exemplary of those that can be used to develop GSSP-2 antagonists and agonists. To do that, the effect of GSSP-2 on cell growth/viability in the presence of the candidate molecules would be compared with the effect of GSSP-2 on cell growth/viability in the absence of the candidate molecules. Specifically, inhibitors of gene expression and antagonists of GSSP-2 activity that decrease the concentration of GSSP-2 should serve as important therapeutic compounds in the treatment of liver degenerative disorders, while up-regulators of the gene and polypeptide agonists could serve as a means of treating neoplastic diseases.

Example 6

Cellular Proliferation Assay

Jurkat, HepG2, K562, N1 Fibroblast, HELA, C2C12, PLC (Human P01243 Lactogen Precursor), Hep3B and Primary hepatocyte cells were treated with GSSP-2 to determine the protein's effect on cellular proliferation.

Jurkat cells were grown in RPMI media 1640 (Gibco-BRL) supplemented with glutamine, penicillin, streptomycin, and 10% fetal bovine serum (FBS). Cells were treated with either venom like protein (VLP), which served as a control protein; GSSP-2 (at concentrations ranging from 5.0 to 50.0 µg); or buffer in which GSSP-2 proteins is dialyzed. Cells were maintained at 37° C. in humidified atmosphere containing 5% $CO_2$. The percent decrease in cellular proliferation was measured at 24, 48 and 72 hours after treatment.

The above procedure was repeated for HepG2, K562, N1 Fibroblast, HELA, PBMC (peripheral blood; mononuclear cells) and C2C12 cells. The above cells were treated with venom like proten (VLP), GSSP-2 (at concentrations ranging from 0.5 to 50.0 µg) and buffer in which GSSP-2 proteins is dialyzed. Cellular proliferation was measured at 48 and 72 hours.

In addition, PLC, Hep3B and Primary hepatocyte cells were treated with GSSP-2 to determine the protein's effect on cellular proliferation of various liver cells. The cells lines were treated with venom like proten (VLP), GSSP-2 (at concentrations ranging from 1.0 to 10.0 µg) and buffer in which GSSP-2 proteins is dialyzed and cellular proliferation was measured at 72 hours.

Results

This assay revealed GSSP-2 is toxic in some cells, while not exhibiting a toxic effect in others as measured by percent decrease in cellular proliferation and the number of cells over time. In addition to Jurkat cells (a T lymphoma cell line), GSSP-2 also inhibited cellular proliferation and induced cytotoxicity in K562 cells (ATCC No. CCL-243) and HTB-173 cells (a lung carcinoma). GSSP-2 also induced inhibition of cellular proliferation and cytotoxic activity in three hepatocarcinoma cell lines: Hep G2, Hep 3B and PLC. HELA cells, a human uterine cervical cancer carcinoma cell line, appear to exhibit a toxic effect when treated with GSSP-2. EL4 cells, a mouse lymphoma cell, appear to be the only transformed cells to be resistant to the GSSP-2-mediated effect. In contrast, GSSP-2 did not have an effect in any of the primary and untransformed cells tested thus far. These include primary rat hepatocytes, human fibroblasts, human peripheral blood mononuclear cells, and both mouse and human untransformed muscle cell lines. It was also observed that GSSP-2 seemed to have a greater cytotoxic effect in cells undergoing proliferation; thus suggesting GSSP-2 may play a role in cell cycle regulation. In conclusion, in vitro GSSP-2 has the potential for arresting or at least inhibiting cell proliferation and triggering cell death by way of apoptosis and necrosis in hepatocarcinoma and lymphoma cells without affecting normal hepatocytes and lymphocytes.

Example 7

Cellular Apoptosis/Necrosis Assay

Apoptosis analysis was performed using the Vybrant Apoptosis Assay Kit #3 (Cat # V-13242) from Molecular Probes. Briefly, cells were seeded in a 24-well culture plate at a density of $0.5 \times 10^6$ cells/ml in appropriate media supplemented with penicillin, streptomycin, and 10% fetal bovine serum (FBS). Cells were treated with test protein at concentrations ranging from 0.5 to 25.0 µg/ml. Buffer in which the test proteins were dialyzed was also tested in the assay. A negative control cell population incubated in the absence of any test reagent was also performed. Cells were treated in the presence or absence of test protein/buffer between 1–7 days prior to analysis in the apoptosis assay. Cells were maintained at 37° C. in humidified atmosphere containing 5% $CO_2$. Following the incubation period, cells were harvested and centrifuged at 1000 rpm for 5 minutes at 4° C. and washed 2× with cold phosphate buffer saline (PBS). After washing cells were stained with FITC-labeled Annexin V and propidium iodide as per manufacture's instructions, and analyzed by FACS.

The above procedure was done for Jurkat, HepG2, HELA, K562, N1 Fibroblasts, C2C12 and PLC cells. The cells were treated with either venom like protein (VLP), GSSP-2 (at concentrations ranging from 0.5 to 50.0 µg) or buffer in which GSSP-2 proteins is dialyzed. Jurkat cells were also treated with ACRP30. Apoptosis and necrosis were measured at 24, 48 and 72 hours.

Example 8

GSSP-2 Toxicity Protocol

This experiment was designed to assess the safeness of injecting GSSP2 in vivo and to examine whether any acute side effects could potentially arise from its administration.

Protein

GSSP2 protein was isolated and purified as described herein. First, it was expressed in *E. coli* and with 6-His tag, then the protein was passed through an affinity column for removal of endotoxin. Protein concentration was determined by the BCA test and protein concentration was adjusted to 25 µg/100 µl in physiological saline Mice There were a total of 24 mice:

8 mice (C57BL/6, mature>25 g) fed normal diet—injected with GSSP2;

8 mice (C57BL/6, mature>25 g) fed normal diet—control;

4 mice (C57BL/6, mature>40 g) fed cafeteria (high fat) diet—injected with GSSP2; and 4 mice (C57BL/6, mature>40 g) fed cafeteria diet—control.

Injection Protocol

Mice were injected twice a day for 7 days. Mice were injected at the same time every day, once early in the morning and once in the afternoon, with 25 µg of protein (100 µl), subcutaneously, in the back. Control mice were injected in the same manner with 100 µl of saline.

Data Collection

Animals were always starved for 3 hr before collecting blood. Blood samples were collected 2 days before first injection and right before first injection (baseline measurements), 1 hour after the first injection, at day 4 and day 8. A total of 100 µl of blood was collected each time except for the samples collected before and after the first injection (50 µl). Animals were sacrificed on day 8 and bled out. Blood was centrifuged for 5 min at 10,000 rpm, after which plasma was collected and frozen.

The levels of transaminases (AST and ALT, γ-glutamyl transpeptidase, Sigma Diagnostics kit), triglycerides (kit from Sigma Diagnostics), glucose (Trinder assay, kit from Sigma Diagnostics), and free fatty acids (use kit from Wako Chemicals USA) were measured for all plasma samples collected.

Free Fatty Acids (FFA)

Tests were carried out to determine the plasma concentration of free fatty acids (FFA), (FIG. 7). C57BL/6 male mice 12–14 weeks old, fed normal (N) or cafeteria (C, high fat) diet, were injected twice-daily for seven days with 25 mg GSSP2 in 100 ml volume, or with the same volume of saline (sal) alone (control). FFA measurements were preformed on 3 ml of serum using the Wako Chemicals FFA assay kit as per manufactures instructions. Baseline FFA values were measured two days before (day −1) the first injection. Test concentrations were determined four and eight days after the first injection.

Glucose

Figure 8:
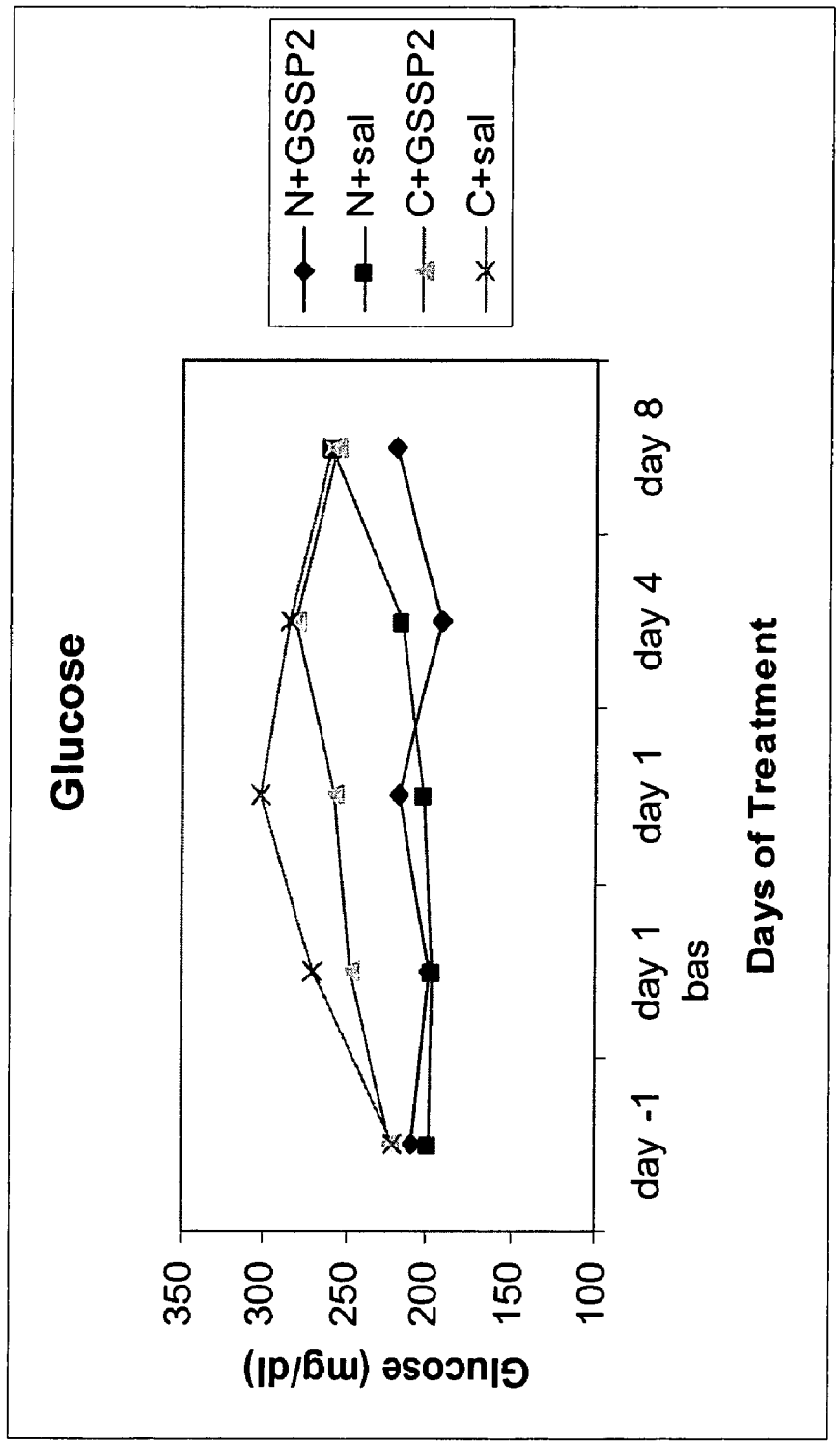

Tests were carried out to determine the plasma concentration of glucose (FIG. 8). C57BL/6 male mice 12–14 weeks old, fed normal (N) or cafeteria (C, high fat) diet, were injected twice-daily for seven days with 25 mg GSSP2 in 100 ml volume, or with the same volume of saline (sal) alone (control). Glucose measurements were preformed on 3 ml of serum using the Sigma Diagnostics glucose (Trinder) assay kit as per manufactures instructions. Baseline glucose values were measured two days before (day −1) and just prior (day 1 bas) the first injection. Test concentrations were determined 1 hour (day 1), four and eight days after the first injection.

Total Triglycerides

Figure 9:
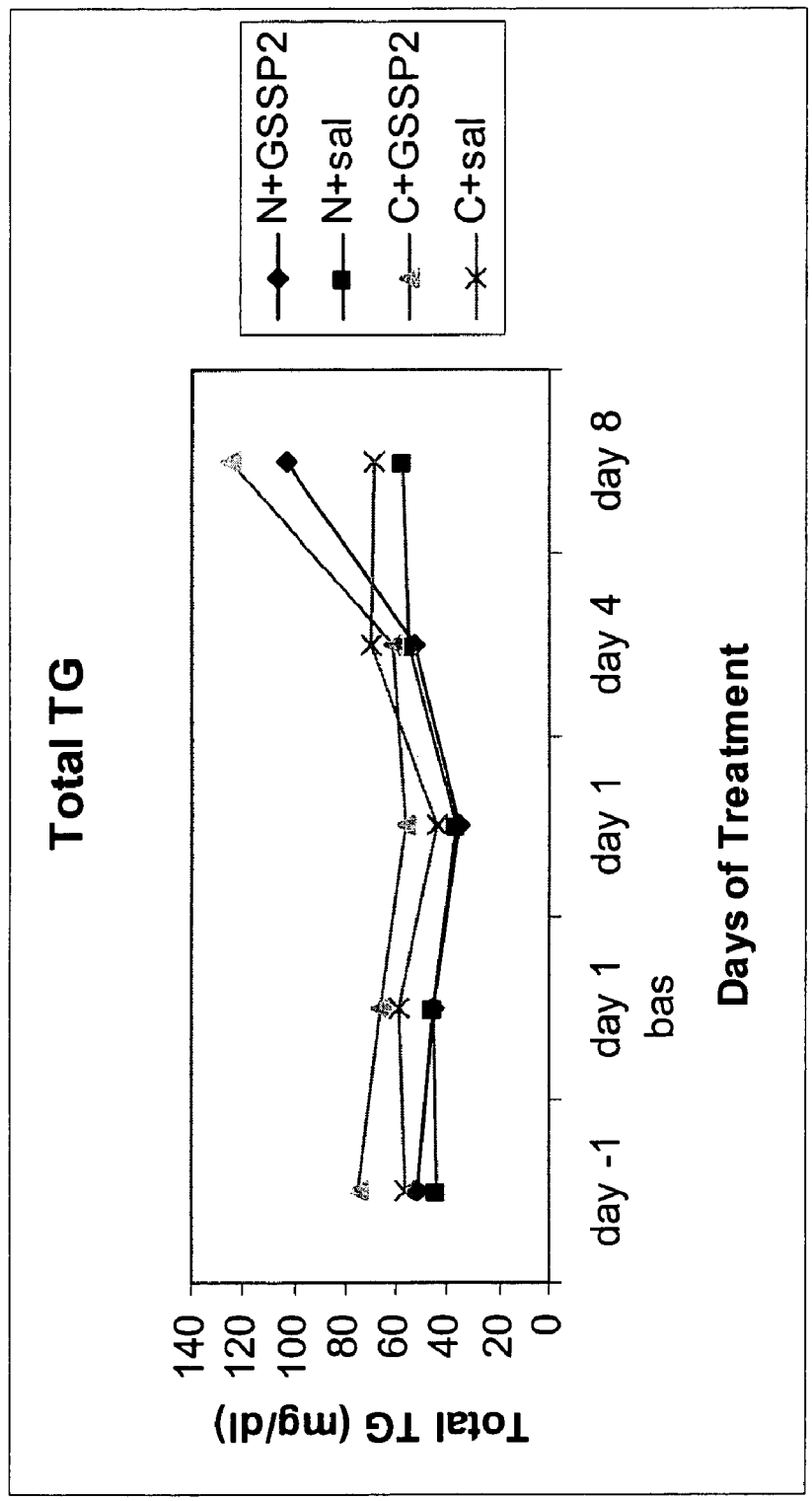

Tests were carried out to determine the plasma concentration of total triglycerides (TG, FIG. 9). C57BL/6 male mice 12–14 weeks old, fed normal (N) or cafeteria (C, high fat) diet, were injected twice-daily for seven days with 25 mg GSSP2 in 100 ml volume, or with the same volume of saline (sal) alone (control). Total TG measurements were preformed on 5 ml of serum using the Sigma Diagnostics TG (GPO-Trinder) assay kit as per manufactures instructions. Baseline TG values were measured two days before (day −1) and just prior (day 1 bas) the first injection. Test concentrations were determined 1 hour (day 1), four and eight days after the first injection.

Food Intake

Figure 10:
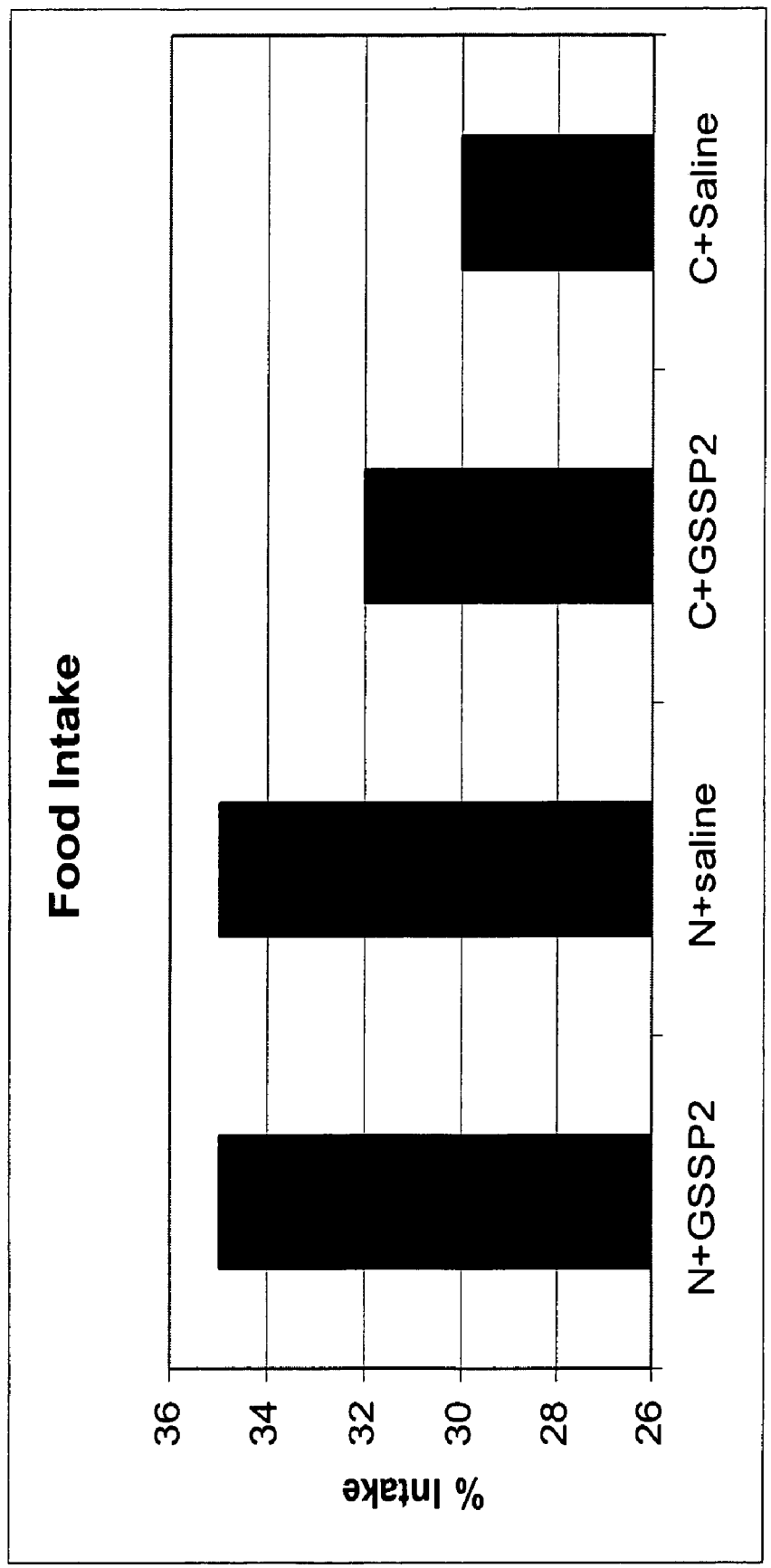
FIGS. 10 and 11 are graphs indicating food intake and body weight of test animals after injecting GSSP2 in vivo.

Tests were carried out to determine food intake (FIG. 10). C57BL/6 male mice 12–14 weeks old, fed normal (N) or cafeteria (C, high fat) diet, were injected twice-daily for seven days with 25 mg GSSP2 in 100 ml volume, or with the same volume of saline alone (control). Food intake was measured by weighing the food left in the cage at the end of the study (day 8).

Body Weight

Figure 11:
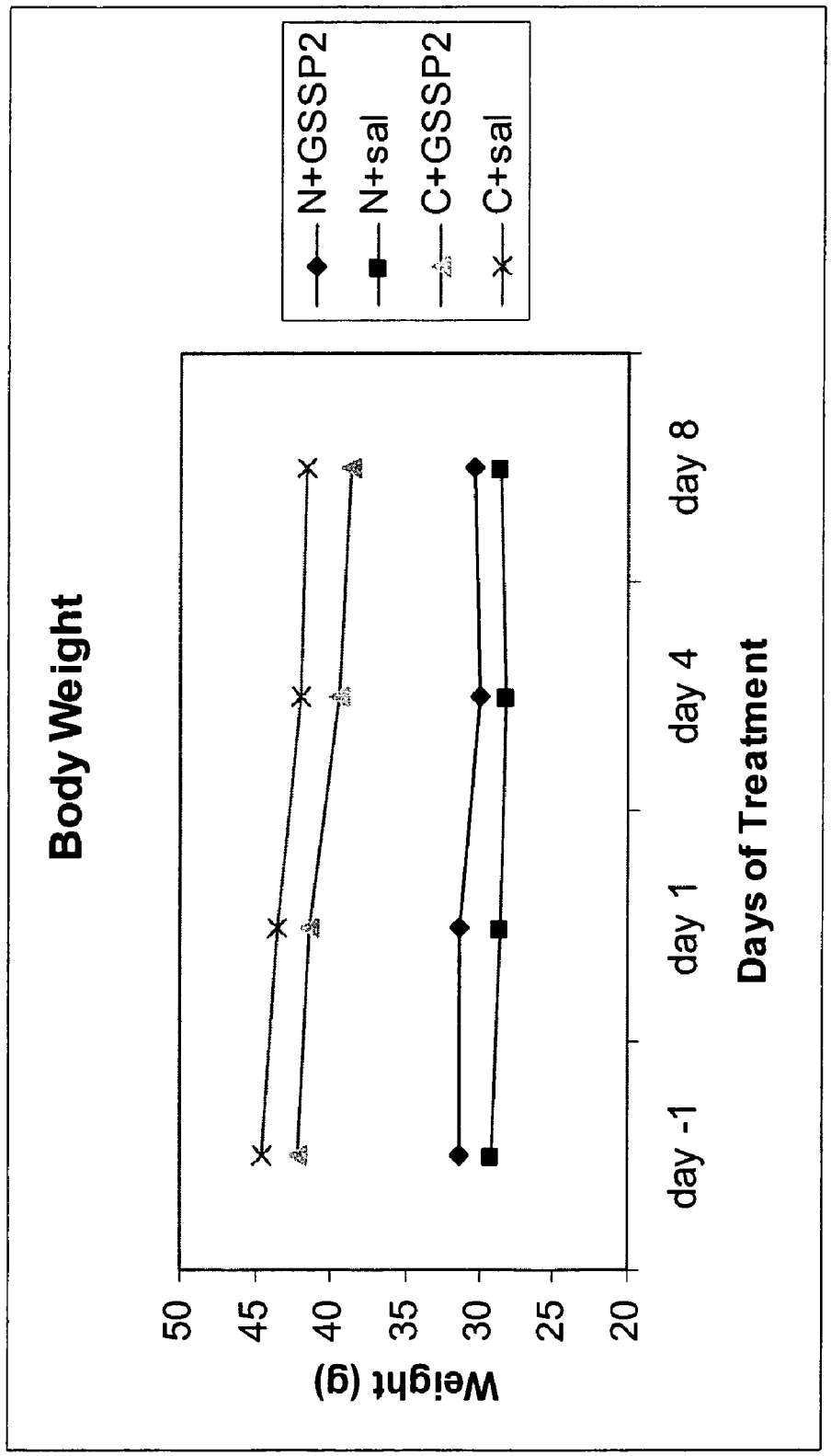

Tests were carried out to determine body weight (FIG. 11). C57BL/6 male mice 12–14 weeks old, fed normal (N) or cafeteria (C, high fat) diet, were injected twice-daily for seven days with 25 mg GSSP2 in 100 ml volume, or with the same volume of saline (sal) alone (control). Animals were weighted two days prior to the first injection (day −1), on the day of the first injection (day 1), and four and eight days after the first injection. Blood collection and body weight measurements were performed at the same time every day (i.e., early morning).

Liver Function

Evaluation of liver function was performed by determining the concentration of the serum transaminases GOT and GPT.

Results

Results of this study indicate that the in vivo administration of GSSP2 has no significant effect on any of the parameters examined, at least for the period of the duration of the study. Levels of glucose, TG, FFA, and liver enzymes were not affected by the injection of GSSP2. Furthermore, food intake and body weights did not change during the period of the study, a clear indication that the protein has no major toxic side effects. The increase on plasma TG observed at day 8 in the animals injected with GSSP2 is harmless and minimal when compared with the effect of other cytotoxic proteins (e.g. tumor necrosis factor α, TNFα). Further, test animals did not show any phenotypic or behavioral differences when compared with the controls. In conclusion, administration of GSSP2 in vivo seems to have no apparent acute or short-term deleterious effects.

Example 9

Preparation of Antibody Compositions to the GSSP-2 Protein

Substantially pure protein or polypeptide is isolated from transfected or transformed cells containing an expression vector encoding the GSSP-2 protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

Monoclonal Antibody Production by Hybridoma Fusion

Monoclonal antibody to epitopes in the GSSP-2 protein or a portion thereof can be prepared, for example, from murine hybridomas according to the classical method of Kohler, G. and Milstein, C., (1975) or derivative methods thereof. Also see Harlow, E., and D. Lane. 1988.

Briefly, a mouse is repetitively inoculated with a few micrograms of the GSSP-2 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21–2.

Polyclonal Antibody Production by Immunization

Polyclonal antiserum containing antibodies to heterogeneous epitopes in the GSSP-2 protein or a portion thereof can be prepared, for example, by immunizing suitable non-human animal with the GSSP-2 protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for GSSP-2 concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (1973). Plateau concentration of antibody is usually in the range of 0.1 to 0.2 mg/ml of serum (about 12 A. Affinity of the antisera for the antigen is determined by preparing competitive binding curves, as described, for example, by Fisher, D., (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Example 10

Drug Screening

This invention is particularly useful for screening compounds by using GSSP-2 polypeptides or a binding fragment thereof in any of a variety of drug screening techniques.

The GSSP-2 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acid molecules expressing the GSSP-2 polypeptide or fragment on the cell surface, e.g. as a fusion protein with a receptor. Drugs are screened against such transformed cells in competitive binding assays. Such cells, either in viable or fixed form, can be used for standard binding assays. One may measure, for example, the formation of complexes between a GSSP-2 polypeptide or a fragment and the agent being tested. Alternatively, one can examine the diminution in complex formation between the GSSP-2 polypeptide and its target cell, e.g. liver cell, or target receptors caused by the agent being tested.

Thus, the present invention provides for methods of screening for drugs or any other agents which can be used in the treatment of neoplastic diseases. These methods comprise contacting such an agent with a GSSP-2 polypeptide or fragment thereof and assaying (i) for the presence of a complex between the agent and the GSSP-2 polypeptide or fragment, or (ii) for the presence of a complex between the GSSP-2 polypeptide or fragment and the cell, or (iii) for the presence of a complex between the agent and the GSSP-2 receptor (which displaces the GSSP-2 from a GSSP-2/receptor complex), by methods well known in the art. In such competitive binding assays, the GSSP-2 polypeptide or fragment is typically labeled. After suitable incubation, the free GSSP-2 polypeptide or fragment is separated from that present in bound form, and the amount of free or uncomplexed label is a measure of the ability of the particular agent to bind to the GSSP-2 polypeptide or to modulate the cell proliferation inhibiting/arresting and/or apoptotic/necrotic inducing activity of the GSSP-2 polypeptide.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a GSSP-2 polypeptide, the peptide test compounds are reacted with the GSSP-2 polypeptide and washed. Bound GSSP-2 polypeptide is detected by methods well known in the art. Purified GSSP-2 polypeptide can also be coated directly onto plates for use in the aforementioned drug screening techniques. In addition, non-neutralizing antibodies can be used to capture the peptide and immobilize it on the solid-support.

This invention also contemplates the use of competitive drug screening assays in which neutralizing antibodies capable of binding a GSSP-2 polypeptide specifically compete with a test compound for binding to the GSSP-2 polypeptide or fragments thereof. In this manner, the antibodies can be used to detect the presence of any peptide which shares one or more antigenic determinants with a GSSP-2 polypeptide.

Example 11

Rational Drug Design

The goal of rational drug design is to produce structural analogs of a biologically active polypeptide of interest (i.e., a GSSP-2 polypeptide) or of small molecules with which they interact, e.g., agonists, antagonists, or inhibitors. Any of these examples can be used to fashion drugs which are more active or stable forms of the GSSP-2 polypeptide or which enhance or interfere with the function of the GSSP-2 polypeptide in vivo (Hodgson, *Bio/Technology,* 9: 19–21 (1991)).

In one approach, the three-dimensional structure of the GSSP-2 polypeptide, or of a GSSP-2 polypeptide-inhibitor complex, is determined by x-ray crystallography, by computer modeling or, most typically, by a combination of the two approaches. Both the shape and charges of the GSSP-2 polypeptide must be ascertained to elucidate the structure and to determine active site(s) of the molecule. Less often, useful information regarding the structure of the GSSP-2 polypeptide may be gained by modeling based on the structure of homologous proteins. In both cases, relevant structural information is used to design analogous GSSP-2 polypeptide-like molecules or to identify efficient inhibitors. Useful examples of rational drug design may include molecules which have improved activity or stability as shown by Braxton and Wells, Biochemistry, 31:7796–7801 (1992) or which act as inhibitors, agonists, or antagonists of native peptides as shown by Athauda et al., J. Biochem., 1 13:742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the GSSP-2 polypeptide may be made available to perform such analytical studies as X-ray crystallography. In addition, knowledge of the GSSP-2 polypeptide amino acid sequence provided herein will provide guidance to those employing computer modeling techniques in place of or in addition to x-ray crystallography.

Example 12

In vitro Antitumor Assay

The purpose of this screen is to evaluate the cytotoxic and proliferation inhibiting activity, and other biological activities described herein, of the test compounds against different types of neoplastic cells (Monks et al., supra; Boyd, Cancer: Princ. Pract. Oncol. Update, 3(10):1–12 [1989]). The antiproliferative activity of the GSSP-2 polypeptides is determined in the investigational, disease-oriented in vitro anticancer drug discovery assay of the National Cancer Institute (NCI), using a sulforhodamine B (SRB) dye binding assay essentially as described by Skehan et al., J. Natl. Cancer Inst., 82:1107–1112 (1990). The tumor cell lines that can be employed in this study ("the NCI panel"), as well as conditions for their maintenance and culture in vitro are described by Monks et al., J. Natl. Cancer Inst. 83:757–766 (1991). The tumor cell lines include, but are not limited to, cells derived from liver, blood (B, T, monocyte, neutrophiles, etc.), colon, pancreas, lung and breast carcinomas.

Cells from human cell lines are harvested with trypsin/EDTA (Gibco), if necessary, washed once, resuspended in IMEM and their viability is determined. The cell suspensions are added by pipet (100 µl volume) into separate 96-well microtiter plates. The cell density for the 6-day incubation is less than for the 2-day incubation to prevent overgrowth. Inoculates are allowed a preincubation period of 24 hours at 37° C. for stabilization. Dilutions at twice the intended test concentration are added at time zero in 100 µl aliquots to the microtiter plate wells (1:2 dilution). Test compounds are evaluated at five half-log dilutions (1000 to 100,000 fold). Incubations take place for two days and six days in a 5% $CO_2$ atmosphere and 100% humidity.

After incubation, the medium is removed and the cells are fixed in 0.1 ml of 10% trichloroacetic acid at 40° C. The plates are rinsed five times with deionized water, dried, stained for 30 minutes with 0.1 ml of 0.4% sulforhodamine B dye (Sigma), dissolved in 1% acetic acid, rinsed four times with 1% acetic acid to remove unbound dye, dried, and the stain is extracted for five minutes with 0.1 ml of 10 mM Tris base [tris(hydroxymethyl)aminomethane], pH 10.5. The absorbance (OD) of sulforhodamine B at 492 nm is measured using a computer-interfaced, 96-well microtiter plate reader.

A test sample is considered positive if it shows at least 20% growth inhibitory effect or a 1.25 reduction in cell growth at one or more concentrations. Preferably a test is considered positive if it shows at least 40% growth inhibiting effect or a 1.67 fold reduction in cell growth.

While the preferred embodiment of the invention has been illustrated and described, it will be appreciated that various changes can be made therein by the one skilled in the art without departing from the spirit and scope of the invention.

Example 13

Animal Models

A variety of well known animal models can be used to further understand the role of GSSP-2 in the development and pathogenesis of tumors, and to test the efficacy of candidate therapeutic agents, including antibodies, and other agonists of the native polypeptides, including small molecule agonists. The in vivo nature of such models makes them particularly predictive of responses in human patients. Animal models of tumors and cancers (e.g., breast cancer, lymphoma, colon cancer, prostate cancer, lung cancer, etc.) include both non-recombinant and recombinant (transgenic) animals, preferably hepatocarcinoma and lymphoma murine models. Non-recombinant animal models include, for example, rodent, e.g murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g. colon cancer cells implanted in colonic tissue.

Probably the most often used animal species in oncological studies are immunodeficient mice and, in particular, nude mice. The autosomal recessive nu gene has been introduced into a very large number of distinct congenic strains of nude mouse, including, for example, ASW, A/He, AKR, BALB/c, BIO.LP, C17, C3H, C57BL, C57, CBA, DBA, DDD, I/st, NC, NFR, NFS, NFS/N, NZB, NZC, NZW, P, RIII and SJL. In addition, a wide variety of other animals with inherited immunological defects other than the nude mouse have been bred and used as recipients of tumor xenografts. For further details see, e.g., The Nude Mouse in Oncology Research, E. Boven and B. Winograd, eds., CRC Press, Inc., 1991. The cells introduced into such animals can be derived from known tumor/cancer cell lines, such as, any of the tumorogenic lines listed in the NCI cancer screen (Monks et al., J. Natl. Cancer Inst., 83:757–766, 1991), and others such the ras-transfected NIH-3T3 cells; Caco-2 (ATCC HTB-37); a moderately well-differentiated grade I human colon adenocarcinoma cell line, HT-29 (ATCC HTB-3 8), or from tumors and cancers. Samples of tumor or cancer cells can be obtained from patients undergoing surgery, using standard conditions, involving freezing and storing in liquid nitrogen (Karmali et al., Br. J. Cancer. 48:689–696, 1983).

Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue (Boven and Winograd 1991, supra). Animal models of breast cancer can be generated, for example, by implanting rat neuroblastoma cells (from which the neu oncogen was initially isolated), or neutransformed NIH-3T3 cells into nude mice, essentially as described by Drebin et al., Proc. Natl. Acad. Sci. USA 83:9129–9133, 1986; or by injecting the human breast carcinoma cell line MCF-7 (ATCC HTB-22) as described by Lopez et al., Proc. Natl. Acad. Sci. USA 96:13023–13028, 1999. Similarly, animal models of colon cancer can be generated by passaging colon cancer cells in animals, e.g., nude mice, leading to the appearance of tumors in these animals. Injection of hepatocellular carcinoma-derived cell lines, such as PLC, HepG2 and Hep3B (ATCC CRL 8024, HB-8065 and HB-8064, respectively), into nude mice can be used as relevant experimental models of human solid liver cancer and metastases (Ain et al., J Surgical Res. 57:366–372, 1994; Zhai et al., Gastroenterology 98:470477). Among the many tumor models available one on the most commonly used can be obtained by injecting the lymphoma cell line EL4 (ATCC TIB-39) in C57BL/6 mice (Vallera et al., Cancer Res. 53: 4273–4280, 1993; Ehrke, et al., Int. J. Cancer, 63; 463471, 1995; Kutubudin et al., Blood 93:643–654, 1999).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines. For example, Meth A, CMS4, CMS5, CMS21, and WEHI-164 are chemically induced fibrosarcomas of BALB/c female mice (DeLeo et al., J. Exp. Med., 146:720 1977), which provide a highly controllable model system for studying the anti-tumor activities of various agents (Palladino et al., J. Immunol., 138:4023–4032, 1987). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 μl of the cell suspension, allowing one to three weeks for a tumor to appear. In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., Br. J. Cancer, 41, suppl. 4:309 1980), and evidence indicates that tumors can be started from injection of even a single cell and that a very high proportion of infected tumor cells survive. For further information about this tumor model see, Zacharski, Haemostasis. 16:300–320 1986.

One way of evaluating the efficacy of a test compound in an animal model on an implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, Proc. 6th Int. Workshop on Immune-Deficient Animals Wu and Sheng eds., Basel, 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g. Van der Putten et al., Proc. Natl. Acad. Sci. USA, 82:6148–615, 1985); gene targeting in embryonic stem cells (Thompson et al., Cell, 56:313–321, 1989); electroporation of embryos (Lo, Mol. Cell. Biol 3:1803–1814, 1983); sperm-mediated gene transfer (Lavitrano et al., Cell, 57:717–73 [1989]). For review, see, for example, U.S. Pat. No. 4,736,866. For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., Proc. Natl. Acad. Sci. USA 89:6232636, 1992. The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

What is claimed is:

1. A composition comprising an isolated, purified and recombinant polynucleotide comprising SEQ ID NO:2.

2. A composition comprising an isolated, purified and recombinant polynucleotide comprising the nucleotide sequence of clone 117-005-2-0-E10-FLC (ECACC Accession No. 99061735) encoding a human GSSP-2 polypeptide produced by liver cells.

3. A recombinant vector comprising a polynucleotide of claim 1 or 2.

4. A host cell recombinant for the polynucleotide of claim 1 or 2.

* * * * *

UNITED STATES PATENT AND TRADEMARK OFFICE
CERTIFICATE OF CORRECTION

PATENT NO. : 7,122,644 B2
APPLICATION NO. : 10/121034
DATED : October 17, 2006
INVENTOR(S) : Frances Yen et al.

It is certified that error appears in the above-identified patent and that said Letters Patent is hereby corrected as shown below:

Title Page, (60) Related U.S. Application Data,
Line 13, "filed on Dec. 28, 2000, now abandoned, said application No. 09/750,580 is a continuation-in-part of" should read --filed on Dec. 28, 2000, now abandoned, which is a divisional of application No. 09/750,580, filed Dec. 28, 2000, now Pat. No. 6,455,280, which is a continuation-in-part of--.

Column 1,
Line 16, "Dec. 21, 1999. This" should read --Dec. 21, 1999 (now abandoned). This--.
Line 24, "Jun. 21, 2000 (which" should read --Jun. 21, 2000 (now abandoned) and PCT International Pat. Appl. No. PCT/IB00/01011, filed Jun 21, 2000 (which--.

Column 19,
Line 8, "2-methylthio-N-6-isopentenyladenine" should read --2-methylthio-N6-isopentenyladenine--.

Column 32, Table 2,
Line 65, "          14271  15968 "

should read
          -- 4       14271  15968 --.

Column 45,
Line 20, "U.S. patents Numbered U.S. Pat. Nos." should read --U.S. Patents Numbered--.

Column 63,
Line 47, "and thereby" should read --and thereby--.

Column 97,
Line 2, "allele $a_j$ at" should read --allele $a_j$ at $M_j$--.
Line 14, "phenotype $(a_1/a_i,$" should read --phenotype $(a_i/a_i,$--.
Line 16, "$(a_1/b_1,$" should read --$(a_i/b_i,$--.
Line 23, "$M_1$ $(a_1/b_1)$" should read --$M_i$ $(a_i/b_i)$--.
Line 31, "Where $pr(a_1)$" should read --Where $pr(a_i)$--.
Line 31, "and $pr(a_i)$" should read --and $pr(a_j)$--.
Line 32, "$pr(haplotype$ $(a_1,$" should read --$pr(haplotype$ $(a_i,$--.
Line 36, "between $M_1$" should read --between $M_i$--.

UNITED STATES PATENT AND TRADEMARK OFFICE
CERTIFICATE OF CORRECTION

PATENT NO. : 7,122,644 B2
APPLICATION NO. : 10/121034
DATED : October 17, 2006
INVENTOR(S) : Frances Yen et al.

It is certified that error appears in the above-identified patent and that said Letters Patent is hereby corrected as shown below:

Column 99,
Line 14, "and F is" should read --and F$^-$ is--.

Column 121,
Line 12, "GALA" should read --GAL4--.

Column 129,
Line 13, "suiting mixture" should read --sulting mixture--.

Column 134,
Line 20, "Cornetta" should read --Cometta--.
Line 22, "407416" should read -- 407-416--.

Column 144,
Line 62, "y-glutamyl" should read --γ-glutamyl--.

Column 147,
Line 26, "(about 12A." should read --(about 12 μM).--.

Column 151,
Line 29, "470477" should read -- 470-477--.
Line 34, "463471" should read -- 463-471--.

Signed and Sealed this

Twenty-seventh Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,122,644 B2  Page 1 of 1
APPLICATION NO. : 10/121034
DATED : October 17, 2006
INVENTOR(S) : Yen et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 739 days Delete the phrase "by 739 days" and insert -- by 859 days --

Signed and Sealed this

Nineteenth Day of August, 2008

JON W. DUDAS
*Director of the United States Patent and Trademark Office*

SEQUENCE LISTING

<160> NUMBER OF SEQ ID NOS: 6

<210> SEQ ID NO 1
<211> LENGTH: 81001
<212> TYPE: DNA
<213> ORGANISM: Homo sapiens
<220> FEATURE:
<221> NAME/KEY: misc_feature
<222> LOCATION: 10946..12946
<223> OTHER INFORMATION: 5'regulatory region
<220> FEATURE:
<221> NAME/KEY: exon
<222> LOCATION: 12947..12958
<223> OTHER INFORMATION: exon 1
<220> FEATURE:
<221> NAME/KEY: exon
<222> LOCATION: 13470..13526
<223> OTHER INFORMATION: exon 2
<220> FEATURE:
<221> NAME/KEY: exon
<222> LOCATION: 13641..13752
<223> OTHER INFORMATION: exon 3
<220> FEATURE:
<221> NAME/KEY: exon
<222> LOCATION: 14271..15968
<223> OTHER INFORMATION: exon 4
<220> FEATURE:
<221> NAME/KEY: misc_feature
<222> LOCATION: 15969..17969
<223> OTHER INFORMATION: 3'regulatory region
<220> FEATURE:
<221> NAME/KEY: allele
<222> LOCATION: 1239
<223> OTHER INFORMATION: 20-828-311  : polymorphic base C or T
<220> FEATURE:
<221> NAME/KEY: allele
<222> LOCATION: 12347
<223> OTHER INFORMATION: 17-42-319   : polymorphic base C or T
<220> FEATURE:
<221> NAME/KEY: allele
<222> LOCATION: 15241
<223> OTHER INFORMATION: 17-41-250   : polymorphic base C or T
<220> FEATURE:
<221> NAME/KEY: allele
<222> LOCATION: 42218
<223> OTHER INFORMATION: 20-841-149  : polymorphic base A or G
<220> FEATURE:
<221> NAME/KEY: allele
<222> LOCATION: 45442
<223> OTHER INFORMATION: 20-842-115  : polymorphic base A or G
<220> FEATURE:
<221> NAME/KEY: allele
<222> LOCATION: 77058
<223> OTHER INFORMATION: 20-853-415  : polymorphic base C or T
<220> FEATURE:
<221> NAME/KEY: primer_bind
<222> LOCATION: 929..949
<223> OTHER INFORMATION: 20-828.pu
<220> FEATURE:
<221> NAME/KEY: primer_bind
<222> LOCATION: 1357..1377
<223> OTHER INFORMATION: 20-828.rp   complement
<220> FEATURE:
<221> NAME/KEY: primer_bind
<222> LOCATION: 12029..12050
<223> OTHER INFORMATION: 17-42.pu
<220> FEATURE:
<221> NAME/KEY: primer_bind
<222> LOCATION: 12581..12603
<223> OTHER INFORMATION: 17-42.rp complement
<220> FEATURE:
<221> NAME/KEY: primer_bind
<222> LOCATION: 14992..15012
<223> OTHER INFORMATION: 17-41.pu
<220> FEATURE:
<221> NAME/KEY: primer_bind

```
<222> LOCATION: 15460..15482
<223> OTHER INFORMATION: 17-41.rp complement
<220> FEATURE:
<221> NAME/KEY: primer_bind
<222> LOCATION: 42070..42090
<223> OTHER INFORMATION: 20-841.pu
<220> FEATURE:
<221> NAME/KEY: primer_bind
<222> LOCATION: 42572..42591
<223> OTHER INFORMATION: 20-841.rp   complement
<220> FEATURE:
<221> NAME/KEY: primer_bind
<222> LOCATION: 45328..45347
<223> OTHER INFORMATION: 20-842.pu
<220> FEATURE:
<221> NAME/KEY: primer_bind
<222> LOCATION: 45863..45883
<223> OTHER INFORMATION: 20-842.rp   complement
<220> FEATURE:
<221> NAME/KEY: primer_bind
<222> LOCATION: 76644..76664
<223> OTHER INFORMATION: 20-853.pu
<220> FEATURE:
<221> NAME/KEY: primer_bind
<222> LOCATION: 77166..77185
<223> OTHER INFORMATION: 20-853.rp   complement
<220> FEATURE:
<221> NAME/KEY: primer_bind
<222> LOCATION: 1220..1238
<223> OTHER INFORMATION: 20-828-311.mis
<220> FEATURE:
<221> NAME/KEY: primer_bind
<222> LOCATION: 1240..1258
<223> OTHER INFORMATION: 20-828-311.mis complement
<220> FEATURE:
<221> NAME/KEY: primer_bind
<222> LOCATION: 12328..12346
<223> OTHER INFORMATION: 17-42-319.mis
<220> FEATURE:
<221> NAME/KEY: primer_bind
<222> LOCATION: 12348..12366
<223> OTHER INFORMATION: 17-42-319.mis complement
<220> FEATURE:
<221> NAME/KEY: primer_bind
<222> LOCATION: 15222..15240
<223> OTHER INFORMATION: 17-41-250.mis
<220> FEATURE:
<221> NAME/KEY: primer_bind
<222> LOCATION: 15242..15260
<223> OTHER INFORMATION: 17-41-250.mis complement
<220> FEATURE:
<221> NAME/KEY: primer_bind
<222> LOCATION: 42199..42217
<223> OTHER INFORMATION: 20-841-149.mis
<220> FEATURE:
<221> NAME/KEY: primer_bind
<222> LOCATION: 42219..42237
<223> OTHER INFORMATION: 20-841-149.mis complement
<220> FEATURE:
<221> NAME/KEY: primer_bind
<222> LOCATION: 45423..45441
<223> OTHER INFORMATION: 20-842-115.mis
<220> FEATURE:
<221> NAME/KEY: primer_bind
<222> LOCATION: 45443..45461
<223> OTHER INFORMATION: 20-842-115.mis complement
<220> FEATURE:
<221> NAME/KEY: primer_bind
<222> LOCATION: 77039..77057
<223> OTHER INFORMATION: 20-853-415.mis
<220> FEATURE:
<221> NAME/KEY: primer_bind
<222> LOCATION: 77059..77077
<223> OTHER INFORMATION: 20-853-415.mis complement
<220> FEATURE:
<221> NAME/KEY: misc_binding
<222> LOCATION: 1227..1251
<223> OTHER INFORMATION: 20-828-311.probe
<220> FEATURE:
```

```
<221> NAME/KEY: misc_binding
<222> LOCATION: 12335..12359
<223> OTHER INFORMATION: 17-42-319.probe
<220> FEATURE:
<221> NAME/KEY: misc_binding
<222> LOCATION: 15229..15253
<223> OTHER INFORMATION: 17-41-250.probe
<220> FEATURE:
<221> NAME/KEY: misc_binding
<222> LOCATION: 42206..42230
<223> OTHER INFORMATION: 20-841-149.probe
<220> FEATURE:
<221> NAME/KEY: misc_binding
<222> LOCATION: 45430..45454
<223> OTHER INFORMATION: 20-842-115.probe
<220> FEATURE:
<221> NAME/KEY: misc_binding
<222> LOCATION: 77046..77070
<223> OTHER INFORMATION: 20-853-415.probe

<400> SEQUENCE: 1
cctcctgata tgacatcatg tgaacttctc acttcacctt taagtattct tagccaggca      60
cagtggcaca tgcttgaaat cccagcactt tgggaggctg aggcagggg atcgcttgag      120
gccaggattt caagaccagc ctgagcaaca tgtcaagacc cccacctcta caaaaaatta     180
aaaagttagc caggtgtggt ggtcatgcct gtagcccag ctacttagga ggctgaggtg      240
ggaggatcac ttgagcccag gagtttgagg ctgcagtgag ctatgatcac accactgcac    300
tccagctgga tgacagagca agaccctgtc tcaaaaaaca aaacaaaaca aaaacaccg     360
aaaaaccccc acagtaaatt agaagaaagc tgcataaatt agaagaagct gatgtgaaat    420
cctgagtcca tggttcaatt taggagggac catctggaga gcagggaacc cccaaaagtc    480
agtttcttta ggcttatttc cttgggccag ccaaatttct cagggagaat gttgttccat   540
tttcaatatg gggaaagatg gtgaactgag gagtctttta aaaaaattta ttttttgagat 600
ggggtctcat tctgtcgccc aggctagaga gcagtagcat gatcatggct cactgcggtc  660
tctaactcgt gggctcaagt aatccttctg cctcagcctc ctgagtagct aggaccacag   720
gtgccaccat acctggctaa ttttttgtatt ctttgcagag acagggtctc gctacattgc  780
ccaggctggt atcgaactcc tgggctcaag cgatcctcct gccttgcctt ctcaaagtgt   840
tgggattaca ggcatgagcc actgtgccca gcctcaaaat ttaatgtata agttttcct    900
taatttttct tagcacaaaa accctggccc ccaacaatac ctagttttct ccaggccgga   960
gtcccactct tttacccttt tcagagagaa taagcatctg gttttctgct gctttggggg  1020
tacccagcca agtagagttg aagagaacag ctgcttctca aacagactct cgaccaactg  1080
ccatatttct agtcccactg ccacccactc ttccagaaga atgttgacac taatgtcaga  1140
gcatttggag agtttagtag tgaaaatcag gggccttctt ggctttctcc actgctgctt   1200
caaaattcat gtcaggtgtg cctgtcacca ccgtttgayc atttggaagc tttccagctt  1260
cccaaatgtt gttattttg tctccttttc tattttccct ttgggtttat gcattttgta    1320
aaaagtgcac ttcaatgcca cgttattgag atttcagaga acagcagagg ctaatgcatg   1380
caattaatcc accgtccgtt actagaagtc aatcggatgc tctttagtct ctcttcccca  1440
tatactagtt taaagttat ccattctttc tattcgtttt atgggttatc cttaaaattt    1500
taatattctt gtctgaccta acaaagtcta tagataatca atatccctat ctttctcccg  1560
aataatgcaa aggctgctga atgctttcac tttgatctct cctttcccat ttccaggttg  1620
cttcggtctg atattttagt tcctcattac ttttaacacc tcctccaaag tagtcccttc  1680
atcaatagat gttttgagc cctccctacc atgtgataag cactggtcta ggcactggga  1740
```

```
gtacagtagg aaatgagata aacttggcca ggtgtagggt ggcttacacc tgtaatccca   1800
acacttttga ggccgaggcg ggcagctcgc ttgagcccat gagttcgaga ccagcctggg   1860
aaacatagcg agaccccgt ccctacaaaa aaatataaaa attagctggg catggtggtg    1920
tatgcctgtg gtcctagcta ctcagaagac tgaggtggga ggatcatctg agcccagggt   1980
ggtcgaggct gcagtgatta caccactgca ctccatcctg ggcaacggtg agaccctgtc   2040
tcaaaaaaca aacaaacaaa caagcaaaca aaaccccac aaactaaact atgtgtaaat    2100 acattttgt taggtagaac tatatgaaat tgccactatt tgaccaattt ttagtgaaaa    2160
ctagtctcat aagtgtgtgt gtgtgtattt tcactaatgt tttttggatt tacctaaacg   2220
tttactaatt tcattgctcc ccatgtctcc ttctatccta ttccttttt ctgggttctg    2280 tttcctttc agatttttag tagttctttt cagtgaggat ctgtgagtgg taaactctct    2340
ttctctgaaa ttaacttctt cctctcaaat aatagttcac ctgagtataa gtcttggttg   2400
gccattaatt tcctttcagt ctttagaagg tacattgatg ataaatcagt tgccggttta   2460
atcatgcttc gtgtgtagat cattagtctt tctctttggt tgattttaag atatccattg   2520
ccttcagtgt tctgcagatt cctgtgatgt gtcctcattt ggttgtgtgt taatttttcc   2580
taccaagact caggatgctt cctgtacctg aggattccgg tcacatcttg cttcaatgtt   2640
tgaaatttct cagccatcat cttttgaata ttgcctcttc cacagtccct gtgttctctt   2700
cgtggaaatc ctacaggcat atattggacc tcccattctg tcctccatgt ctcttaccgt   2760
ctattcatac cctccttttt atatttaatt tttttgagac agagttttgc tctgtggccc   2820
aggacggagt gcaattgcat gatcttggct cacggcaaac tctgcctccc aggttcaagc   2880
tattctcctg cctcagtctc ccaagtagct gggattacag gcatgcacca ccacgcccgg   2940 ctaattttg tatttttagt agagacgggg tttcaccata ttggccaggc tggtctgaaa    3000
ctcctgacct caggtgatcc acccacctcg gcctcccaaa gtgctgggat tataggcatg   3060
agccaccatg cctggccaat atcacccgcc tcggcctccc aaagtgctgg gattacaggc   3120
atgagccacc gtgcctggtc aatatcctcc ttttatttc tgtgattctt tctgtgtgat    3180
tttctcagat ctaccttcta gcttactaat tctctctcca actgtagcta aatgtgtttt   3240
atattataat gactatattt ttttcactta tagatgttct atttaattct ctttcttttt   3300
gacaaataga acttatttca aaacaaacaa aaggccaggc atggtggttc atgcctgtaa   3360
tcccagtgct ttgggaggct gaggcaggag gattgcttga gcccaggagt tcaaggccag   3420 cctggcaac atagtgagat cctttctcta ccaaaaaaat aaaaaatcag ctgggtgttg    3480
tgggacactc ctgtagtccc agaaactaca gattcttggg aggcagaggc tggaggattg   3540
cttgaggcag aggctggagg attgcttgag cctgggaggt tgaggctgca gtgaactgtg   3600
atcatgccac tgcactctag cctgggtgac aaagtgagat cctgtctcaa aaacaaataa   3660
acaaacaagc aaagaaacaa aaaaatgctt acacaggtta ctactttctt gctgggatag   3720
ttttaacact gcgttaagca taaacacctt tctttctgaa atgtatttga gatgtatatt   3780 gattttaaa aaacccacac ctccattaag gtctggtgat agcagtagaa acaatgtaga   3840
gtggctccac aatcatatag atgttttggg tgcgttctga gatggagtcc aggaacacca   3900
agtaaagact gctacctcac agtttacatc tgagttctta gaagacaaga ctgaaggaga   3960
acaatttgta acaagattta cttggcccgg gtgtggtggc tcacacctgt aatcccagta   4020
ctttgggagc tttgggagtc cgaggtgggt ggatcacctg aggtcaggag ttcaagacca   4080
```

```
gcctggccaa catggaataa ccccatctc tactaaaaat acaaaaatta gccaggcacg      4140
gtggcacacg cctgtaatcc cagctactca ggaggctgag gcaggagaat cgcttgaacc      4200
caagtgactg ggttgccgag agccgagatc acgccactgt actccagcca ccctgggtga      4260
cagagtgaga ctctgccaaa aaaaaaaaa aaaaaaaaa aatacttact gttcagaagg        4320
agaagtcata atgttgcttt aagaacagg tcacaaaaga aagactctag aagatcttct       4380
cacttggtgc atatcaagtg tctatttgag acccatacac ttgcttaatc catgtgttta     4440
aggcaaaagt gctgctgctg agcagtaagg aataaggtac ctgctaacct ttaccaatct      4500 acatttttaaa atccttctta ctacacatcc agaatgagtc agcaattctt gtgtattaaa    4560
aaacaaaaac acaaaacaaa gtagagggc aactctctta aaaatgcagc tatccgcaaa      4620
cactgtgata caaaacgaca gtcaaggaaa gggcagcaca acaagttca cctgaagga       4680 atctgttcaa agtctctgga tttaagaaca agttccctaa aagctcttac ttacagaaga    4740
aatcggataa taaatgtagc tggaatgatg gaattcttta agttttcatt ttgttttggg     4800
caactctgtg gcccaggctg gagtgcagtg gcttgatcac ggctcactgc agcctcaacc     4860
tcccaggctc tggtgatcct cccacctcag cctcctgagt ggctgggact acaagcatgt     4920
gtgccaccat gctaggctaa tttttgtatt ttatttttag tttttttttt tttttttttt    4980
tttttgtaga gacaggtttt gccatgttgc caaggctggt ctcaaattcc tgggttcaag    5040
tgatcctccc atctcagcct ccaaagagc tgggattaca ggcatgagct actgcacctg     5100
gcctagaatt ttttaaaaat cactatctgg caactctcag gataatattc gattcaggca    5160
aggatcatca atgaatgcta aaaccattgg gtgaaaaatt gttgcagaat gggatgctca    5220
catggcttca aagtattgct ccacaaatta cttatcaata acgtaaaaaa ccaaacttta    5280
ctagccatgg agaaatctgg ttgttatcac tttaatggag tgatcaaact taacatcact    5340
aaatagagtg caacctccag ctaggataca gtaagaaggg ccagatatca cctagtatt    5400 ttgccaaaaa tgttttaacct taatctaatc atgagaaagt aatcactcaa atccagaatg    5460
tgggacattt tacaagatgt cctccttgca ctcttccaaa aaaaaatcaa tgtcatgaaa     5520
acaaacaaat ggtgggttg gggagaacgg ttctaaattt aaaaactaaa gtgggataac     5580
aaccagatga gatgtgttag agcttgaatt tacagagaga gaaaaacaac tatgaaagca    5640
ttttggggaa aatctgaata tgtaggatat gttagatgat attaaggaat tgtgttaatt    5700 ttcaaggta tgataatgtt ttttctttt gtaaaagagt ccttatttt cacaatgtat       5760 gttgaagtat tcagagtgaa gtgtcatgtt ggctataatt atttcaaatg gttccacaca    5820
caaagcacat accacataca catatacata tacctccaac caactcaaaa catgttcaac    5880
actgaaacta aagatgcca ccaaacaggg aagcatgagt gtgtgttgca tctacccatt     5940
gtatcaatcc aggttcagtc agaaaaacaa aagccattcc acgtatttca agcatgaaag    6000
gctttaaaac aaaaaattaa aggtttatcc aactcttgga agggctggag gagtgaccac    6060
cttggtttgc agttcagaag gagtgactct caaacgctca ttagtaagtg gctacaaatg    6120
ggaagctcgc cttattatgc ctgcaatatc aatgcatgtg attcctggga aggtcaccca    6180
gaagctgctt taaactccaa gcctgtccat gcttctgtct gcaaccggca ttgaaacata    6240
atggcctctc ctcttccgtc tcacgctggc tgactctaac ctaggctcat atagagaagg    6300
gattctagaa aatgtattaa tagttccaag tgtcccctct gcatctcata aaagacctta    6360
gaaagggcac tgataatgct atttgcaaaa agacaatcca gcgcagttgt attttacagc    6420
acaggctctt taagtttggg ttatcagcaa aaaaccatta gagtatgaga aattcctttt    6480
```

```
taaattgtgg caaaatatac ataacataaa aattaccatt gtagctattg tacattgtag    6540
ctaagtatat agcccagtag cactaaatac atttacactg ttgtgcacca ctatctagct    6600
ccagaaactt ttaatcttcc caaacagaaa cttgtaccta ttaaccaata ccttctcctt    6660
cctcacttct cctagaaacc agaattatac tttctgtctc tacaaatctg actattctgg    6720
atacctcaga atcacagtat gtgtcgttct acgactggct tgtttcactt agcatcatgt    6780
cttcaagggt catccacgtt atagcatgtg tcagatttcc ttttcttttc ttttcttttt    6840
tttttttttt gagacacagt ctcgctctgt cacccaggct ggagggcagt agcacaatct    6900
cagttcactg cagcctctgc cttccaggtt caagcaattc tcgtgcctca gcctcccaag    6960
tagctggaat gacaggcatg caccaccaca cctggctaat ttttgtattt ttagtagaga    7020
cggggtttta ccatattggc caggctggtc ttgcacttcc ggcctcaagt gatctgcccg    7080
tctcggcctc ccaaagtgct gggattacag gcgtgagcca ctatgcctgg cccccgattg    7140 tcattatttta aggctaagtg atattttgtt gtctgtatat accacaattt gtttattcat    7200
tcatctgtca atggacattt ggggttgtttc cacccctgg ttattgtgga taatactact    7260
aggaacacga gcatacaaat atctgctcca gtccctgctt ttatcttttg gatatatgcc    7320
cagaggtgga attgctgggt cataaggtaa ttctagatta aatttttga gggactgccg    7380 tattgttctc caccatagct gcaccatttt acctttccag cagcagcgta caagcggtcc    7440
agcttctcca catcttcacc cacacttgct attttttggct tttatttat tttttaaaat    7500 aacattctaa tgggtgttaa gtggtcagaa atggttcttt taggagtaga gatagaggcc    7560 aggggggatgg ctcacacctg taatcccagc actttgggag gcctaggtgg gcggatcact    7620
tggggtcagg agtttgagat cagcctggcc aacatggtga aactccatct ctattaaaaa    7680
tacaaaaatt cgctgggtgt ggtggtgtgc actcccagct acttgggagg ctgagggaag    7740
agaatcgctt gaacccggga ggcggtagtt gcagtgagcc gagatcacac cactgtatgg    7800
cctggtgaca gagcaaggct ctgtctcaaa aaaaaaaaa aaaaaaaaag agtagagata    7860
gaaaagcatt gaaaacacag cctcagctca gctcagtctg ccatggtggg aagccattaa    7920
ttcttcactc ttgaaacctt ttcgtccttg gtgtggcaga ggctgcaagt ctcctctgca    7980
actttattct tcccttcttt ctcagttata aaatccctga ttttagaaat atctttattg    8040
agatataatt cacataccat aacattcact acaattgaat ggttttagt atattcacag    8100 atttgtacaa ctatcaccac aaactaagtt tagaactttt ttcatcatcc cacaaagaaa    8160
ccccacaccc attagcagtt attcactatt tctccccaat caacctcccc tcccctcaat    8220
agccctaggc agccaccagt ctactttctg tctctaccta tttgtctttt ctggacattt    8280
tatacaaatg agatttttaca acatgtagtc ttttgtgact ggcttttttc ccctagcata    8340 atgtttttcca ggttcatctg tggtgtagca ggtatcagta cttcaacccct ttttattgcc    8400 aaataatatt ccactatatg gataggtaac attttgttta tccattcatc aattgatgga    8460
catttgggtt gtttccattt tcttgactgt tatgaataat gttgccatga acattaatgc    8520
acaagttttt gtgcagatgt gtattttcat gtgtcttggt tttataccta ggaatagaat    8580
tgctgagtca taggagaact cctccatgtt taaccattaa tgaactgccg aactgttttc    8640
caaagaaatt gcaccattgt acaatcccac cagcaatgta tgagggtaga atccctgatt    8700
tttaactgat cattgaactc aggcccattc aaaacaaaga tgacatttcc taaccttcct    8760
tacaagtagt tctgaccagt gagatgggag aagaagttag gttttgtcct taaaagaaag    8820
```

```
gagagtggct gggtgcagtg gctcacgcct gtaatcccag cactttggga ggccgaggtg   8880
ggcggatcac ctgaggccgg gagttcaaga ctagcctgac caacatggag aaacctcgtc   8940
tctactaaaa atacaaaatt agctgggcgt cgtggcgcat gcctgtaatc ccagctactc   9000
aggaggctga ggcaggagaa tcgcttgaac ctggaggtg gaggttgtga tgagccgaga    9060
ttgtgccatc gcactctagc ctgggcaaga agagcgaaac tccatctcaa aaaaaaaag    9120 aaagaaagga gagtacattc tacactctcc tctcctccac cctgcccct ttccagtggc    9180 tggatgtgga catggtggta agctatctta gatcatgtgg acaagggaaa cataggga     9240 tattagaacc tccagacaga aggaacttag gaccctggac agctttgtgg agcagtgctc   9300
ccataccagc gtgaagtttt gtatgggaga aaacatacat ttccagcttt tgtaagccac   9360
tgttattttg ggtctctctc agagcagcca aatatataat ttaactaata tattttcttt   9420
ctgtgattct tctttatttt gattatactt ctacttctct gcccctcttt taggtgggag   9480
gtgctgctcc aagcactaac tcagaatata gaccctctcc ctcttgtaat agtgccagct   9540
tggagttctt tgcttccact gtaggggaag gaaggaaaaa atatggagaa ctcacatcca   9600
ctcttcattg tcctcaaaca gaagtaaccc attttgttct gctcacagcc cattggccag   9660
aactaactgt atggccccaa tctaattgca aaggagtctg ggaagtacag cacagcacat   9720
ggatctttgg aaagcgttaa ttttctctgc caaaggcttc ttttgttgtt gttgttgttt   9780
gaaatggagt cccgctccgt cacccgggct ggagtgcagt ggcccctatct cagctcactg   9840 caacctccac ctcccaggtt caagcactcc tccagccttg gcctcccaag tagctaggat   9900
tacaggcgtg tgccatcata cctggctatt tttttttgtat ttttagtaga gacagggttt   9960
taccgtgttg gccaggctgg tctcaaactc ttggcttcaa gtgatccgcc tgcttcggtc   10020
tcccaaagtg ttgggattac aggcgtgagc cactgtaccc ggccaatact ggtgttttct   10080
gacctcagcg tttttctttt ctcctgccat gtactctccc tagagatttc atctactccc   10140
aagtcttcca ctgctcctat ctgctgatga ctcccaaaac tcagtctcca gccgagactt   10200
ctctcctggg cttgagacat atgtatccaa ctgccagaac atctccagtg acagcctt    10260 gggcacaagg ccacactagc ttgtgggtac aagtaatcac ccaaagtcaa tttcagtggc   10320
tctccactcc cacatttttt caaccctgg aaatgttccc ttcccaaata ctctgagtct    10380
ctcttctctt ttgatgactg tggttttgtg actggatggt agctcctgtt gcttttttc    10440 ctttcaaatg aattttctct taggaggctt cttagccatt aagcaaatag acctcaactg   10500
ggcttgccct atgcctatct gaaacccagc ttaggttcga gttaggactc ctgttaatct   10560
gagctctcac ttcctgtccc aacctgctta tttttttgg tgaaagaaaa tatcatcccc    10620
ctagttgctc agaaacctgg gaatcattgg gattttttcc tctccttcac cttcctcatc   10680
caatcagtca ccaagtgcta tcaactctgc tgccttagta gccctcaata tatacttacc   10740
tatcaaccat cactgctatg ccatacttca ggccttcatt tctcacttgg attattaaaa   10800
tatccctaaa tagttcctct gccttctctc tggccaccct cctgagtgat ctctccatca   10860
tgtacctttc agtgactgct tgcacaagcc cctttgtgac ttggtcatag tctgctctct   10920
tgaaccacca gagccaagca cctgggttct gattctggtt gcaactctta ctgcgtgatg   10980
atggacaggc cacttgatct cctcaaacct cagttcctaa atcaaatgaa tgattgaatt   11040
cagtcactta actttgtatg tagtaggtag gcactgtgca aaacatacta gtggatatag   11100
agatgaataa gaaaaagccc ctgcactcaa agagctctcg gattcatcaa caaattattg   11160
tgcagttaga tagtaagtgc tataatccag gaatatacag tgttgtgtga ataatgtgga   11220
```

```
atcagtttat ctccagagca gaaaaaggtg aaggccgaag aaggcattca gagtgatact   11280
ggagctgtgt agcaggggct actactgttc cctcaaatcc tttcttctct tcttcctgag   11340
taatagagtc cttttttcagc taggcataca gccatccaaa ataaaaacta tatttcccag  11400
cctccttttc agctaagtgt agccatgtga ctaagttgtg gccaatggga tgtcagtaca   11460
agtggtaatg gcaatatctg ggatgtgtct ttaaaaggaa ggaacatgtc cttctccttt   11520
tcctccttcc tgttccctgg gaggtgaact tggtagctgg aggtgaagca gctggaactt   11580
ggatatgagc gtcttgttga tgataatagt gcaacaagat aaaagcagcc cgagctggcc   11640
tacatttaca tgagaaggaa ataagactcc attttgttta agctattctc ttgcatatat   11700
atatacacat atatatcagc taagtgtagc catgtgacta acttgtggcc aatgggatgt   11760
cagtatgagt ggtaagagca gtatcttgta tatatatatg tgtatatata cacacacaca   11820
tatatataca tatatgtatg caagaatata aatatacat gtgtgtgtgt atatatatac    11880
acacatatat atgtcccttg cagccaagtc taattctaac taatacaaac taactctaaa   11940
aaatgaatat atattcacca ggggatagc tatttcaagc agaggaagc ctgtataaag     12000 gctcagggaa tgctgtggtt ttatgtggca gcagatgaga ctggaaatga gtcaggatga   12060
gccacagtgg aggatgaatt aaatgggcag gagtgtggta gaaagacctg ttggaggcta   12120
tgaatgcaat caaggtgaca gacaactggt gcaatgatgg tagtggaaat ggaggagagg   12180
ggattgattc aagatgcatt taggaccaag aatcgggagc ttgtgaacgt gtgtatgagt   12240
actgtagacg gagtgggtgt gtcatcagag aagatctgag catttgggct tgctctcctc   12300
agaggccctg cgagtggagt tcagcttttc ctcatgggc aaatctyact ttcgctccag    12360
ttcctggggc tcagagtccc tggcccagat gcctcttgcc atctcatctt caccctgcct   12420
ggcttccctt gcttgttcca ggattgtttc ataagaggg atgtggttgg tctttaaccc   12480
tatgaatgct ggctgaggat gcctgcggaa cctgtagtga agctttcagg ggctgctcgg   12540
gttctggctg gtaggtgaac actgtccatc ttgccggctg ggacacagtg actctgggta   12600
gttgtgtaag agaggggccc ttggcagaca aacaggttct tctctgttgg tgggccagcc   12660
agcaggtcag tgggaaggtt aaaggtcatg gggtttggga gaaactgggt gaggagttca   12720
gccccatccc ccgtaaagct cctgggaagc acttctctac tggggcagcc cctgatacca   12780
gggcactcat taaccctctg ggtgccaggg aaagggcagg aggtgagtgc tgggaggcag   12840
ctgaggtcaa cttcttttga acttccacgt ggtatttact cagagcaatt ggtgccagag   12900
gctcagggcc ctggagtata aagcagaatg tctgctctct gtgcccagac gtgagcaggt   12960
gagcagctgg ggcagaggga tgggggtcac agtcctaagg gagggcattg caggtggcct   13020 cagggagag cctggggtgg cccctaagac gtcctcttgg aacattttgg cagagttgcc    13080
tcttcgccct cattatggct cagttttttcc accatgaaat gggagggagg gagacaggtg   13140
ggcaggggag aggtggtaga agtggcctag agaactgttc ctggggtctg ggacctttgc   13200
gaagggttta gagcaccacg ctccctgcta tgtgactgag gtagcaagag cacgccctct   13260
tcccatgttt gaggaagaca ccctagcctc cttgactcac ctaggtcagt cctcttgagc   13320
cccaacagct ctgtgctccc cagcccaagg aagggtaac aggatttcgg gcagttgccc    13380
ctgcagaggc cccctgggca agtccctgc gccatgtccc ttcgtctcct tcttccccta   13440
accaggcctc cctccacctg tcttctcaga gcaggtaatg gcaagcatgg ctgccgtgct   13500
cacctgggct ctggctcttc tttcaggtgg gtctccgacc ctgacttcaa cgtgggggtg   13560
```

```
tgggtggagg ctggccagag ggccctgtcc accctggggg aggagagccc aggccctgat    13620
tacctagtcc ctctccacag cgttttcggc cacccaggca cggaaaggct tctgggacta    13680
cttcagccag accagcgggg acaaaggcag ggtggagcag atccatcagc agaagatggc    13740
tcgcgagccc gcgtgagtgc ccaggggaag gggtgtaggc gaagggagga gacagctggg    13800
ccatgccatg atgacctgcc tctgctgcct caacctctgt ggccgctgct gggacagagg    13860
aaaggagcgg tgctagctct gtctgcagat cccggccatc ctgggctctt tagcgccctc    13920
tgcctgcagc ccccgccttg acaactccgt agctgttgcc cccttgctca ctgaggcgcg    13980
ggacctggga tcaatcggga ggacgcccgc tgcagtcccc agaatcaaag gatgatgtgg    14040
cgcatctatg tttctttgga gagtgttgta ggtctggatt tgtatgggca atgtgtttgt    14100
gcttcgtgcg tgagttgtta ctggccaggg ctaggacaag agccctcgac cctggggcca    14160
acgccctgcg tccttggttc ccccagagga tcagtgcgcg atgacttggg gacaaaggag    14220
atgatggggc ctagcagtct gacggcctgg atatctgtcc ccttctccag gaccctgaaa    14280
gacagccttg agcaagacct caacaatatg aacaagttcc tggaaaagct gaggcctctg    14340
agtgggagcg aggctcctcg gctcccacag gacccggtgg gcatgcggcg gcagctgcag    14400
gaggagttgg aggaggtgaa ggctcgcctc cagccctaca tggcagaggc gcacgagctg    14460
gtgggctgga atttggaggg cttgcggcag caactgaagc cctacacgat ggatctgatg    14520
gagcaggtgg ccctgcgcgt gcaggagctg caggagcagt tgcgcgtggt gggggaagac    14580
accaaggccc agttgctggg gggcgtggac gaggcttggg ctttgctgca gggactgcag    14640
agccgcgtgg tgcaccacac cggccgcttc aaagagctct ccacccata cgccgagagc    14700 ctggtgagcg gcatcgggcg ccacgtgcag gagctgcacc gcagtgtggc tccgcacgcc    14760
cccgccagcc ccgcgcgcct cagtcgctgc gtgcaggtgc tctcccggaa gctcacgctc    14820
aaggccaagg ccctgcacgc acgcatccag cagaacctgg accagctgcg cgaagagctc    14880
agcagagcct ttgcaggcac tgggactgag gaaggggccg gcccggaccc ccagatgctc    14940
tccgaggagg tgcgccagcg acttcaggct ttccgccagg acacctacct gcagatagct    15000
gccttcactc gcgccatcga ccaggagact gaggaggtcc agcagcagct ggcgccacct    15060
ccaccaggcc acagtgcctt cgccccagag tttcaacaaa cagacagtgg caaggttctg    15120
agcaagctgc aggcccgtct ggatgacctg tgggaagaca tcactcacag ccttcatgac    15180
cagggccaca gccatctggg ggaccccctga ggatctacct gcccaggccc attcccagct    15240
ycttgtctgg ggagccttgg ctctgagcct ctagcatggt tcagtccttg aaagtggcct    15300
gttgggtgga gggtggaagg tcctgtgcag gacaggagg ccaccaaagg gctgctgtc     15360 tcctgcatat ccagcctcct gcgactcccc aatctggatg cattacattc accaggcttt    15420
gcaaacccag cctcccagtg ctcatttggg aatgctcatg agttactcca ttcaagggtg    15480
agggagtagg gagggagagg caccatgcat gtgggtgatt atctgcaagc ctgtttgccg    15540
tgatgctgga agcctgtgcc actacatcct ggagtttggc tctagtcact tctggctgcc    15600
tggtggccac tgctacagct ggtccacaga gaggagcact tgtctcccca gggctgccat    15660
ggcagctatc aggggaatag aaggagaaa gagaatatca tggggagaac atgtgatggt    15720
gtgtgaatat ccctgctggc tctgatgctg gtgggtacga aggtgtggg ctgtgatagg     15780 agagggcaga gccatgtttc cctgacatag ctctacacct aaataaggga ctgaaccctc    15840
ccaactgtgg gagctcctta aaccctctgg ggagcatact gtgtgctctc ccatctccca    15900
gcccctccct ctgggttccc aagttgaagc ctagacttct ggctcaaatg aaatagatgt    15960
```

```
ttatgataga agtttgcctg gcgtgactct catttggacc atgtctgaaa gcagtggcct    16020
caccactatc cccaaagcac acccatcacc cactccattc ccttgctgct ctttctcatc    16080
cacccactcc cagtccaggt ctgtcaaagg gggtctggct gggctctgct tcagggatcc    16140
tggctagaca acggctgtct gtcacacctg gcaggagggc ctgggttacg ggcccttcct    16200
ctgcacctgc actgttcact agcctgctcc ccacaggac actgtgcatg gaatgcaggc     16260
tgtgtctgga agagctgtgg ccctggtgga cctaagattc ctgaggtggg ctgcctcctt    16320
tgttcctgct gttctagagt ttgaatggcc tcttttatg ccggactctc ttctggggac     16380
tcccctcact caggggcacc aatgctccct atagatcccc tgggaactga aactgggtg     16440 tggtggagga cgtggaaagg gtaaacacag ctccttgtct ttggacttcc ctgtccggcc    16500 cccttcctc ccagctcagc ctactgtccc cgggttctca gcacctgcct gctccccaac     16560
cccatagcac agaccccaca catatgtagg ctcatcatgc ctgcaggctg gtcttccctg    16620
acaccgtgga ttttgacaat gttggcaaca gaactgggtt gtggacccag cacctggaga    16680
gaggaagtgc tagaaaggta gaaataataa aaggtgtttt tgttgttgtt aggaaactgg    16740
aaaagcatag gtcaagggct atgatgggga tgaggagta ggagtgaaaa tgagggctgt     16800
gtacttgagg ctgggattgg ggaaggtagt gatgaggaca gaatagggag tgggaagaac    16860
agaaagggac agagggattc agggattgtg agagagggga agaggctgag ccacccggag    16920
gggcgaccta gcacgcaagc agtatgtggc ccaacactgg aaccaagcag cccggctccg    16980
ggcgcacctt ctcagggatt cctcaggac aagtccagcc ccttgtcgtc aaggctcttg     17040
tagaccgacg tagggaccaa tagaaccccg tgcggtggag ctattgtgaa ggagcaaaaa    17100
agtgccctgg ttctaagagg acgtcttagg ggaagtgacg gctgagttga ggtggatccg    17160
gctggcgatg taaggttcga gccatataaa cccgggaacc gggagcccctt gacgacattg    17220 ttccccgagt gcccggagtc tgcggctttt ttggggtgg tggcagctgg cggaagtgac     17280
gggagagggg tggggccgcg agagcggcgg aagtaggaag ccgaggtctg aattgcgcgt    17340
ggtggccatg gcgccagcg gggctgtgga accaggccc ccggggctg ccgtcgcccc       17400 gtcgcccgcc ccggccccgc cgcctgcccc tgatcacctg ttccggccca tcagcgccga    17460
ggacgaggag cagcagccca ccgagatcga gtcgctatgc atgaactgtt actgcaatgt    17520
gaggcggggg cgcggccgcg agcggcgggt gggtagggct tgtgccggga cgagccgggg    17580
gtcagaccca gccaggtggg cccggccggg gaccccgagg agcgcccgga gatagtaggg    17640
cggggaaagg gagtttcatt gattttttc cttagctact ttctacttca ccagggcatg     17700
acgcgcctcc tgctcaccaa gattcccttc ttcagagaaa taatagtgag ctccttttcc    17760
tgcgagcact gtggctggaa caacacggag atccagtcgg caggcaggat ccaggaccag    17820
ggagtgcgct acactttgtc tgtcagggct ctggaggtga gaggacctca gagcaggtac    17880
ctcagtattc tagagagaga ttcggtactg gggtcagagc tctggtccag gcggtcggat    17940
cttaaataaa tcccctatg tctcctagcc ttagttctt ttgtaaaatg gtactggtgt       18000
tgtcatcagc tcaagtgaga taagatttgt gaaaatgctt tgtaaatgtt gtctgagggt    18060
atgaaatgag cagtagttgt tatgaatagt attctcacca tttggacagc ctggctcaca    18120
ccacctgtac tattcgaaag gagcagtctg gaccctgtgg agtggcgaga gggagagaca    18180
gctgggctgc ggtctgatgg aaggggacgg tctggttatt acttgaggag aagctgttct    18240
gcagtctctt tgtactgaac gtattctttt cttcccagga catgaacaga gaagtggtga    18300
```

```
agactgactc tgctgccaca aggattcctg agctagattt tgaaattcct gcctttagcc    18360
agaaaggagg taagtttaag atcagagtat ttgggctgtt cgcatgtagc tagaatctta    18420
ccctctttct tgcaaaaccc cctggtgcca ggtctagtgg tttgtgtatg ggttctacca    18480
tgtaatcatt gtaatcttca ttagttaatc atgagtggaa agcttaggta aaacagctcg    18540
agatggtaga aagtaatggt aataccatag tgtgtttatt gtagaatttt agcatcacta    18600
ttatcagaca tgaatggaac cttgcacctg gccttctcat tttacagatg aggaaattaa    18660
gacccagaga gttcaagtga attgcccagg gtcatacagg gacttgatag cagagctgag    18720
gctaagtcac acttgtcttt tgttcttgtt cacaagctct gaccactgtt gaaggattga    18780
tcacccgtgc tatctctggc ctggagcagg accagcctgc acgaagggta agctggggtt    18840
ttctgattgt agcagctcaa ggaataattg cttatataga gtgtcccatg tgtctgaaga    18900
gtctctgact aagtgttgga aacttgctgg gtaagcatat ggtggtgctg gagctgctag    18960
aatgttgcat atgttataat tattgtcttt tccacttccc tccctcagta tatattcagg    19020
cctcatcaga caatataaca ttacctctga agagcctttc ctaatcccct tgggttatct    19080
gtgtttcctg agtattccac tgcatcttat atttattatg acagaagtaa tatattatag    19140
ctgcatcttt agttatttgt ctccttaatt ggttggggag tcccatgaga ggactgatat    19200
atatactatt atatctctaa cgtggcatga gtgcctgggc taaatggttg aatgagtgag    19260
aaaaatgagg ctcacctgtc accacccgtc aacttcaggc ttgtttgcta catctcattg    19320
tgaagcctga gtcactctgt ttccactcac actgagatag gtggtgactt cctaatggaa    19380
gtaacatggg catgacaagg ggcagggcat aaggtacacc accagggctg atgctttact    19440
ctctgttcat ggcaggcaaa caaagatgct acagctgaaa gaattgatga gttcattgtc    19500
aaactgaagg agctaaagca agtagcctcc cctttcactc tggtgagtat tgagaggctg    19560
gagttgccct tgattagggg aggagggacc attaagactg ctgggatttt ccactgtgat    19620
gcctgcgtgg tctgatagta ggtgatgtag gattgtttat gattttcttt tgcagtgact    19680
ctctcttctc ccatttgtta gatcattgat gatccctcag ggaacagttt tgtggaaaac    19740
ccacatgctc ctcagaaaga tgatgccctg gtgatcacac actacaaccg gacccgacag    19800
caggaagaga tgctgggggct tcaagtaagt ggactgaagg atccagaaga atgctctgga    19860
attatcgcgc actctggatt gcttggagtc agtggaactt attttgctgc tgctgctctg    19920
tgtgccctat ctcagcttgt ttgtgcttct catcttgctt atgtccagga cttgggtaaa    19980
cttcacagaa aggatggcag tggctgtgat cctatcttaa gtcctgttct tcctttggtt    20040
ggggctttac tttgtggttt ctctaactga tgaggtggca cctgacataa ctgatgaggt    20100
ggcacctgag catttctccc actccagggc agggtgttgg ggacactgag gtatacctgc    20160
caacttgcga cctgcatctt tgctatttta ggaagaagca ccagcagaga agccagaaga    20220
ggaagatctc agaaatgaag tgagtcacat tggctactgg tgaggaagga gcagagttgt    20280
gggctgagac tgatgctgtt cagcatctgt cttccttgtc accaacatag atgaccacta    20340
gcataccaac tgagtgtctt tagcctgaac atcccatctg ggagggctca cccttttgtcc   20400 tcatgttgtg ttccaggtgc tccagttcag cacaaactgc ccagaatgca atgcccccgc    20460
tcagaccaac atgaagctag tacgtatctt ttgccaagca gttgggttgc tcttcatctg    20520
actcaggcat gaagattata atcaggctgg gagcatccct ttcaaggaaa acacatgctt    20580 tatcccagt gataaggaag atattatctt tgattagact gtgtaccttg ggttttgtgt     20640
tcaaagagaa aattaggcca tggtcactag gctgtgtgtg tgtgacctga gccatgcctt    20700
```

```
caaatgtgtg aacagggatt gccatgggtt gggaacttgc cctcttctgg aggactctgt   20760
gggctgcctc ttgtgaatat ttcctgcagt tctgggacca gcatatgttt gtgtggggtt   20820
tggctttgtt ttttccccaga tggtggtctt gttcgcctgg aagtagattt ccttaactcc   20880
gttttccaga aatccctcac tttaaggagg ttatcatcat ggctaccaac tgcgagaact   20940
gtgggcatcg gaccaatgag gtgggtgggc gccattattt gggaagaaga ctagcttaag   21000 ggtaacccccc ttttaactat cattcttcct aagtacttca gtactcgggg gcagggggtg   21060
tagagtagct tgggtctttt tcttaggtct agtgcagggt gatgagccct tgaaggaatg   21120
ggaattagcc tagagaagaa aagttagaga ttctataact tgtttaagac atattaaagg   21180
ttgatgatat ggaagagaga agtcttttga cccactcctc agaggtgtgg aagttcaggg   21240
aggcagactt tgacttcaca atgaagaact caatagagct gtctgaaaat agaatgagct   21300
gccttagaga attataaatt cccttccccct gagtgtatct gagtataagc taattaaatt   21360
ctttaaccag aatattataa aggagaccca cacattggat gcagtggatg aaaggactgc   21420
aataaatgct taaagtctc tttcaacccc aaaagtcttt ttttttttttt tttttttttaa   21480 gggaaattca gagtttattg gcaatttggg ataagttttg gcacgttacc agggttgggc   21540
actgttcctg gccagctctt ggtgtttttg gtttgggcga ctgctgttta gaaggctctt   21600
tctttggtag ctattaatga ccctaactga ttggatgtcc aagcctacac tccaggtctc   21660
ctgggtacca agtgaggctc aggtcttctc tctgttgctc ctgactgtta tcgatgcagg   21720
tgaaatctgg aggagcagta gaacccttgg gcaccaggat caccctccac atcacagatg   21780
cctcagatat gaccagagac ctcctcaagg taacagtctg cttgggaaag tcactgttgt   21840
cctcataagt tagataaact gtctctatct agggggaagtt gtcttttaga aataatgttc   21900
agggacatga ggtatctcct acttccctgg ctttgaggac ccctgagcag agggagttaa   21960
tctaagattg gaattgcagg tttagaaggt gaccctgtta gctctttctg atgacctggt   22020
agctttttgg cctccagtgt ctatctgggt cctcttctct gtctgtcccc tagtgacagg   22080 ataccctgaca gctcgaagct atgactgagt ttcccttttat taagttggat ctattcccgt   22140
ggttcagatg gacaggagtg agtctcaagc tttaacaagg gagtcagaga aaactgagac   22200
agctgccctt gtccgcagtc tatcactgct ggtattaatt gggcaggagg cctctggttg   22260
gctttctttg cttctgactt aaagcttaaa ctgacctctc atttcacagt ctgagacttg   22320
cagtgtggaa atcccagagc tagaatttga actgggaatg gcagtcctcg ggggcaagtt   22380
caccacactg gaagggctgc tgaaagacat ccgggaactg gtgagtcact tgagtagtgt   22440
gtaaaccacc tttgagcaat ttggctgtgt gaagagggac tggaagactt cagacatcct   22500
aattttcggt gctggtaact gtgggtttct ttgccttaaa gctggtttaa gagacttaaa   22560
tattactttg gatggtgaag acaagtttat gggaaatgtt gaatgaaaat tccaggccta   22620
actttgggac tttatagtta ttttgtggtc ttggacaagt catttatttt actgtaaagt   22680
taggggatga gggtccttct agcacctaaa acttcccaac ataaaaaaca tacatgtatg   22740
ggttgactta gcccaaatat ttatctcctt gatgaattat ttcacttgat tctctgttgg   22800 gcatttgta tttgtaaatt gtacttttttc tttgcatttc ttctccaaat tagtatcaga   22860
gatcatattc taagaacatg tttcgatttt gttttacatt gccagttttg ttatcttggc   22920
acattatccc atagactcct aggagtgact gccttggtca gaaaggtggt gtgggctaaa   22980
tggaaaccaa gtttccctga cagggcaccc actgtcaccc cctgcctagt ttatggtcag   23040
```

```
gcctaacaaa tataaagcca gtattcacat agtttggatt atcatttatt gcaggtgacc   23100
aaaaatcctt tcacactggg cgacagttcc aatcctggac agacggagag actacaggag   23160
tttagccaga agatggacca ggtaagaggt cactggccag tcagtactta gaatcctggg   23220
gctccagtga acaggaggct gcatgctcat gtcttgccac ttttttgaaca tctaaccatc   23280 atgttgggga ttcttcttct ggttttcttt tcttttttt tttttggag acagagtctc      23340 gttctgttgc ccaggctgga gtgcagtggc gtgatctcgg ctcactgcaa cctctgcctc   23400
ccgggttcat gcgattctgc tgcctcagcc tcccgagtag ctgggattac aggcgcacac   23460
caccacgcct ggctaatttt ttgtatttt agtagagaca gggtttcact atgttggcca    23520
gactggtctc gaactcctga cctcgtgatc tgcctgcctg gcctcccaa agtgctggga    23580 ttacaggcgt gagccaccgc acctggccct cttctggttt tctatattcc atgtcttctt   23640
tcttgttttt ctcccttatt ttgttagagc atcttctcca gtagcttcct gggaaaaagt   23700
gcatgggaaa taaatttct gggaccttcc acatctgaac atgtctttat tctgttatca    23760
cactagagtg attattggct gggaatacga ttctaggata gaaataattt tttatcagaa   23820
tttcgaagac tgcactatgg tcttccagtt tggtaaagac attgtactat agtcttccac   23880
tttggctatt gagaagtctg aagccatttg attcctggtc ttttatatgt gacctagtct   23940
tgtgatctct tcgtttcctt tgatgtgaaa tttcagggtg tgccttggtg tgggtcagtt   24000
ttcatccact gggctaagca cttggtagat gtatttttc agtctggaaa actcatgtgg    24060
ttcagttcta ggaagctttc atgaattatt ctattgaaga ttatctttt tctgattttt    24120 tttttctgtt ctttctgaaa actcctgggt tttagatatt agacttactt gtctggtctt   24180
ctataattta ctcttttttt ggtcctattt ttggtttctt ggtttttttg ttcttctttg   24240
ggagattccc tcaactttat tttccaaccc ttcaattgag gttttcattt ccactaaaac   24300
ttttattttc caaggagctt tttaaaaaat agcatcctgt cttaaggatg tagtattttt   24360
tcttcttgag gattattatt tttaaattt tttcagcatg cagtttatat agcacttatt    24420
gatactgatg ttggatcttt tttgacattt tattctcctt gcatcctttt tttccccatt   24480
tgatttccca tctttcagtg ttaagggctt tgctcagatg tctgataatc attgattgtc   24540
ttcttacaag tagcgggcta aagacctgag tagggggtga gccttgttga catgggctt    24600 attacagggg aatttaactt agctgttttg ctgaggtggc ctccaatgcc agaattgtta   24660
ggtctttcct cttgggctag tcagacaaag aggctatgcc tgccagacaa gaaccaaccc   24720
aatttatatt acagaatcct ccaaagtttt aagaattggt gaaattaggt agctctgaaa   24780 gtagaggga aaggatctaa ataaggact gttagaaaag ccaacatcag caagctgtgg     24840 accaggggt gctggcccag ttgaaggtag agggaaagga ctcaagaaca aggaggttaa    24900
atgactgtgg ctgctccatt tcctggcctg agggtaaaga cttggctggc agtgttctga   24960
gagctgtggg aagggggctg gggtgtgtat gtattctgtt tcccataagc ttacattcat   25020
ttaacctact tgttcttgat tccttccct ctaccttcaa ctgggccagc acccctagt     25080 ccacagcttg ctgatgttgg ctttttctaac agtccttatt ttagaaccctt tcccctctac  25140 tttcagagct acctaatttc accaattctt aaaacttttg gggattctgt aatataaatt   25200
gggttggttc ttgtctggca ggcatagcct cttttttta aaattttttc tttactttca    25260
tttatttcat ttcttttttt atttatatat atatttatta tacttaagtt ctagggtaca   25320
tgtgcacaac gtgcaggttt gttacatatg tatacatgtg ccatgttggt gtgctgtacc   25380
cattaactag tcatttacat taggtatatc tcctaatgct atccctcccc cctccccga    25440
```

-continued

```
catagcctct ttttaccagg ggttatgtaa aatttacttg ctgtgttctc tctctccttt    25500
agatcatcga aggtaacatg aaggcccact ttattatgga tgatccagca ggaaacagtt    25560
acttgcaggt atagtagacc ttccctgatg tttcatagag atacattttc tgatcttcct    25620
tgaatatgta tcatttccct agaaactgaa agacttgatt ctaaatggac tgcttttttac   25680 caaggaggca gaagttagaa gatacataag ggagaaaaga ggggggtgtg ggaggggatt    25740
ttttttttaa gtgtatgtaa agaaggaaaa aaaaggata ctctgaggcc ccttttttttt    25800 ctgtagtcaa gctcttgtcc cagttctgga gttttcattt tgcaaatctg attatggatt    25860
gaggagaaat ggtaccttgt ccggaggcca agataggaaa ctgataggct ttaagttgac    25920
tgaggagaga gtctggtgat tgatgtacct ttaccattta ttggatactt accatgggtc    25980
aggcaaaact cttctaagtt ctttccaaga ttaagaccat ttgtcatact tttcataaga    26040
aggtgcagat ataacaaaat aggtggattg ttccctgatt ctgggctgg ggtcttctac     26100 ccctggccca tgtgggctct gttgctaccc actagttcag tctagccatg ggaaattgga    26160
ggccaataaa aagaaaaaaa cccaaaactc attctgttct tgggaaggtg ggaattggaa    26220
gctgcctgca gagaggggga gtggcacagc ggcactgatt gtctctcctt gaccttgcag    26280
aatgtgtatg cgcctgaaga tgatcctgag atgaaggtgg agcgttacaa gcgcaccttt    26340
gaccaaaatg aggagctagg gctcaatgac atgaagacag agggctatga ggcaggcctg    26400
gctccgcaac ggtagcagtg ggtggctcaa gggccagcct ccagcgctgc tctttctgta    26460
ggttatttat tagtattgga tgaaggcgaa ggctgggagt gtctttccca ccagcccttg    26520
cccatggtgg ggaggacatc tggtctgagt cagagatctg tgcacacttt ctaaacagct    26580
tgtgatgcaa gtgtgagcct attgtgttac ttgaccttat tttggaagtt ttgaattggc    26640
ctaggaggaa acccagaaat gaaccagggg tatgtcatca ctttttttcat atcaagtcct    26700 caccctcctt ccacataatg ctctatcctc taaggttgga actctgaagt tggagaaggt    26760
ggaataaagt tacacctgga gtttgttgtt ggttttgagt atataaaata ctgactttga    26820
acaggaaagg agtctcctga ggggagaccg agtccagcac aagtgaagga gttaccattg    26880
aaatgatgac tttcaaacag cactggcctc tgtattgacc ctatccttgt ttgatatcat    26940
gctgttagaa ttcagcctcc taaagaaaat ttcccgtgt atctactgta atttggggat     27000
tgcagctggc atttaattca ttccttcagc agatgcttgc ttatctactt tatgccaagc    27060
acaccacaga acagaggaca aaataaatct ctttcatgga acttgaagtc tagtggggaa    27120
aaatgacaat aaacagatga ggaaaacagt acatcggatg gtgattagtg tcatggagga    27180
atgtaaagca gggaatgggg ctgggttgtg caaggaaatg gggagtaggg aagatcttct    27240
gaacaagaag gtgataattt gacatttggg caaagctgag gaggaggtca gggagtgagc    27300
tgtgtgggta tctgggggaa gagatttcct ggcagaggga actgcaaatg ctagagctgt    27360
gaggttagag ccagtggggg tacctgatca gttagcccta ctctcagtta gaaatgttga    27420
aacacattca tccagagaga aaggaggctc tctgcagttc ttctgaaagt taaggaccag    27480
tgaacactct gctgcttggg ccctggactt cccagccagt gttctttgca ctgtagtctc    27540
ctgcctctca taaacaaaag gtgactcctg tggtgcagac tgcagggtat ttgttcaata    27600
aagaccagtt cattgattaa gatgttatca caaacccttat tgctttgtgt tgcaaacttt    27660
tttttttttt ttttttggtag agacagagtc tcgcgctgtt gcccaggctg gagtgcagtg    27720
gtgtgatctt ggcttattgc aacctttgcc tcccgggttt aagcaattct gcctcagcct    27780
```

-continued

```
cccgagtagc ggggactaca ggcgcacgcc gccacaccca gctaatttct tttgtatttt    27840
agtagagacg gggtttcacc gtgttgccca ggctggtctc gaactcctga gctcaggcaa    27900
tccgccagcc ttggcctccc aaagtgctag gattacaggc gtgagctacc gcgtccggct    27960
gtgttgcaaa cttaactctg aagaatgagt tagagatgat ttagcaatca gacatctact    28020
ctcgttgctc tgttaaacta ctctcaaagg tcacaagtga ttttccactt ggaaagtgtt    28080
atctatttct gtcacatttg atagtggacc atctcttctt aacccttctt ttggctctcg    28140
agatactgta cccttggttt tcccttcact ttgaatattt cttatttgga cactttgcct    28200
cctcccctct tactaaattt gtttctgaga gttctgcttt cagacatctc tccatatcag    28260
attctttggc atcttactat catgtgggac taacttccat acctgtatct ctaatttctg    28320
taagtgaggg cgagagtaag gtgtttggag actcaggtta gcaaatgact cattcaaact    28380
ataaagcttc agtactttgg gcaaacttct cacaggcaac tattctaccc taagagatta    28440
tctctagata tgtttccagc tgacttggga atctaagttt accagacaac cctctgatct    28500
atcatttggt ctcttaagta gacttcccca tagtgtaggt gtgctctgtt aagataaact    28560
gcagtatcag gttcattttc cattgtgaag gaaaaaaaat ggcactctgg cttattactg    28620
aatctcttgt gagtttggtt ggtgtgaggc aatctcccag aatccaccca gttcctagga    28680
aatgatgacc tgagtttctg aacttgaaga ctgaggacca ggtgccagac tgggataacc    28740
cagctaaggt acttcctgcc ctttgatgac aaggcattct tcagtttcat acccttctct    28800
tgaattatct ttcagctcct ttctcatttc ataaagtgtg tcaggatggg agcttacata    28860
tagttaactg agtcttgctc cacagcaccc agcatatgac acatggttaa taaaatctgt    28920
taaaatcctc catcatagat taaaccctat taggacacta gggataacat ctataggtaa    28980
aaagataggg aaagggtctc gctttaaggc cagggtaggt gagtcaaagt gccaggaaca    29040
tgtggattca gtttcacagc catgagtaac atttaagtgg aaaaggtttg tgattgtgtt    29100
aaaaaaggaa agtggttcat gcatgagggc acgcctccta ctttcatggg tcaagtatgt    29160
gaaatgcagc catgttcggt cattagacgt gtggacgaac atacaggtag gtactgaatg    29220
tacatctgtg tcatgatgag tggaggaggg gaggtgagtg ttgggagcaa gtatgaaggg    29280
cagttgactt ggccaactga aaactttaat gatggcaaca ctttcattct aacatcagta    29340
tatttccttc tttgtacacc tgtggtatgt gcctgatgca cactgcagaa aatggtgtct    29400
ctgcttacat ttagggcagt ggtggctaag actacttggc tttattccta ttaaaaaatg    29460
ttttttacac acttcttttt aaggcaaatg gcagtgtttc caactgtgga gagaaaaagc    29520
tgcttatttt gtgcgttcac ctcagtttag tattggcact tccaatgctt gttttcctag    29580
tctgtaaaat ggggataatt aggataaaca aaattatccc cattttacag gtgacaaaac    29640
agcctcagag aggttacttc cagaaggaag cagagctttt ttttttttt ttttttttt    29700
ttttttttg agacggagtc tcactctgtt gcccagactg gagtgcagtg gcgtgatctt    29760
ggctcaccac aacctctgcc tcccaggttc aagcgattct cttgcctcag ccttctgagt    29820
agctgggact acaggtgcac gccaccatgc ctggctaatt ttttttttt ttttttttt    29880
ggagacagtc ttgctctgtc acccaggatg gagtgcagtg gtgcgatctt ggctcactgc    29940
agccttgcct cctgggttca gcaattctc ctgcctcagc ctcctgagta gctgggatta    30000
cagacgccca ccactgcacc cagctaattt ttgtattttt agtagagatg gggtttcacc    30060
atgttggtca ggctggtctc aaaccccgta cctcgtgatc cacctgcctt ggcctcccaa    30120
agtgcaggga ttacaggcgt gagccaccgt gcctggccag aagtagagct tctaagaggc    30180
```

-continued

```
aggtgtcaaa cccatgccag tcagactctg aaacctgagg tctgaatatt ttaagctcag   30240
ctccacaatt actgtatttg ttctattaga tacaactgca gagagaggcc aaagctcaga   30300
gcaggccatt ggcacggcat ctgatcctgc ttaactgccc tgcagcacag ggtggagaca   30360
cttgggcctt gtcaggctaa gggactgggg taggatgggt agcagtggaa ttgaagacaa   30420
agaaaacaaa tgggcagaag atgggtgggt ggaagttcag agggctatcc tggcagtgtt   30480
cactggagca gaagtgtgag gctttctgaa tgcctgctga caccagggtg gggcagggct   30540
gtgtagtgtg agatgcacca aattggacga gaagccaagg caggcttgtg tatggggtac   30600
cctggggccc tccgcctagt gaagccctat cttctcagcc cagcgtcctc gtctcacaag   30660
ccctcagagc cccagcctgc tttccttcct gggcctgtgc tgcaaccccc tcaacatggc   30720
ccactgggta aaaattcatg cttcaagact gatccccaag cctgttttgt attatataag   30780
taaagaattt tttaaacact tatccccaga taatgtgtat ttatttataa agtatagccc   30840
tgtctgcttg actaatatat taaaaaagtg acctttttga ctcttggtcc aagaaactat   30900
tgtttgcact tttgtgtagt tgtgtatagc atcctgcaaa ttctgtcaga agtctgtgat   30960
ttcagtaaca ctaaaacttc tctctcaaat ggtacaagtt ttcagtttta agacaagttc   31020
tgggaatcta atgtacaaca tgttgactat agctaataat tctgtattgt ttacttgaag   31080
tttgctaaga caaatttgct taagtgcccc ccccccgaac tactacataa attagtgaag   31140
gatgttttac ttaatttgat tttggtaatc attacacaat gtataattat atccagtcat   31200
cacattgtac accttgaata tatataattt tttgtcaaat aataaagctg ggaagaaaac   31260
gataaaactg acaatctaac atatatgatg aggtaaaaag atctggtatt tcaagaaatt   31320
tggatgacct cttgcacccc acttcgctag cctctactcc ctagagtcat gttctgacta   31380
tgtgaagttg agcaacttcc ttaatcttgc cacgcttcag ttcttatctg taaaatatga   31440
taatgaaacg atttgagaat tgtgagggtt aaatgagata attcaggtaa agctctaaac   31500
cccctgcaaa gaataaagtc ttttctttcc ccccaaaact tgagtgttag aattcattct   31560
ctctggtttc tctcttttac tatgctaaaa aatgatccag gtccgtcctt ctcattggca   31620
agattgtttt acagtttcct tcaagagata actgggggct acttgtaata gaacactaga   31680
agagttacac aggtcttaga aactacgttt tcatagtaa ttatgttggt ttgcacttcc   31740
tggcttcctt tcttggacgg taggtacctg gaagcctagt ggagcagatt ccccccactt   31800
aaagatactt ataaaaataa cgaacatagt tccgatgacc atgtgcccaa caccgctctg   31860
cgcacttcac acagtaatat catctcagcc tgtgaccgtt ccgagttagg tgccgggatt   31920
ctccctgttt tgtgataact tgcccgaggt cgtacagcta gccagctatg gaaccagtat   31980
tcaaactcgg ctacgctgca gcccgtggcc ctccactttc ttgctcgtgc tctggagttt   32040
aagcggccga tggggcggg gtcctttggg tcaggttgtg gcctcataga acagcgcttg   32100
ctgcggttgg atggatgggt gggtgggtgg gtgagtgaat gaagagaaga aacctggtgg   32160
cgtcgtccca gggctgtgga gcgccccgaa ggtgcgcacg tccctggcta gcctgcgagc   32220
gcgtcccggt ggccgcacct gccagccgcg cgattcttag cactctccgc cacttccggc   32280
cgtggccccg ccctgtcggg tggctggcgt ccgttacgcg ttgaggcatt ttgtccccag   32340
cgccgacccg tctctctgcc cccgccgctg ccatggcggc agctccgccg ctttccaagg   32400
ccgagtatct gaagcgttac ttgtccgggg cagatgccgg cgtcgaccgg ggatctgagt   32460
ccggtcgcaa gcgtcgcaaa aagcggccga agcctggcgg ggccggcggc aagggggtgag   32520
```

-continued

```
ttggtaccgg ccggggcggg gcctgcgacg tctagccacc ccttcccaac tccgccctcg   32580
gccgcccggc agttccttcc ctcttggcgg gtctctaggc ttctccgccg accctgctc    32640 atgctcaggg ccccactcac atcgcttgag gccccccgcc ttgcctctgc cgccccgctt   32700
acatctcgag cctctgagca gtagcgtcag tgcgttaaag ccggggtgta actttgatta   32760
ctcttttccc gccttggtag acttccgtcc tctcccatag agaatgaata ttgtgcctcg   32820
agaataatgg agcggattca aagcctctgt gcttggatct ttagggcccg gtacctgcct   32880 gtgggattc  ccagatccca aggacttggt tctgaatcag agacctttga tcacctcctg   32940
ttactcttag taatagtcct aacgtgagaa gctaacattt atatagttat acttttcttg   33000
ccaggcacca ttataagaaa tttaaacata tataagttta tttaagcctc accacactac   33060
catgaagtgg gtattatttt catatgggac aactttgtgg cccagtgtag tgggccctac   33120
caaatcgttt tccacccaga accacagaat gtgacattta gaaatagggt ctttggagat   33180
gtaatcagtt aagatgaggt catacttgat taaggtgggt gccaaatcca agatgactgt   33240
ttgcctttta aaagaggga agtatggata cagacacagc aacaaaggaa aaacgaccat    33300
gtctagatga aggctgagat tggattggat ttatgttgcc aaaagccaag gtatgcttgg   33360
ggctaccaga agctgggaga ggcaaggaaa gattctctgc tagagacttt ccagggagga   33420
tggccttgca gacacctgga tttcagattg ctagcttcca gaactgcgag agagtttctg   33480
ttgttttatg ccacgcaatt tgtggtactt tgttacagta accctaaggc actgagatac   33540
ccagtgaagt cacattgttc taaagaacta gtccaagttc ttttctggtt tggtgcttgc   33600
cttattattg tcttcgtctt tctgcctcgc tgacttgtgt ggatcctttg gaggcagtgc   33660
catgtgatga aagtagcttg agtgttggag cagcactggt cagagttcga atcctagctg   33720
tgccacttta taggctgtgt acccttgggc aaggtgtttc atctcactga gctgcagttt   33780
ccttatcttt aaaatgagaa taataataat aatggtttta ttaagtggtg gttgtgatta   33840
gagggattgc attaagtgac cctggctttt tgaataactt cacatcatgg cagtcattgt   33900
tattatttgg gctcaactat atagtttatc cacgtaacaa acatttattg aatatttcgt   33960
attccagtta ctgtagggtg ttgaggatgc ctctgtgaac aaaaaaaaca tagtccctgt   34020
tcttgtggag cttatagatt aatgggaata caggctttaa gcaactaatt acacaactaa   34080
tcgatatatt ttctttatga taaatgcaat gaaagtattc caagagtttt taacaagggt   34140
tcttagtctt gagtgagtgt gggatggtga gggaattggg tgaagcagtc aagaaaagtt   34200
tgccaaagga agttaaattt gtgttaggac ctgaagaatg aggaagagtt tcctggaatg   34260
agaaagagtt tcctagcact ttgggaggcc aaggcgggtg gattgcttgc atctaggagt   34320
ttgagaccag tctgggcaac atggtgaaac cctgtttcta caaaaaatac aaaaaagtag   34380
tcaggcacag tggcacatgc ctgtagtccc agctacttgg gagactgagt agggagaata   34440
acttaacccc gggaagtcaa ggctgcaggg agccatgatg gtgtccctgc actccagcct   34500
gggcagcagt gtgagaccct gtctcaaaaa agaaaagac tagggccggg cgcggtggct    34560
cacgcctata atcccagcac tttgggaggc caaggcgggc ggatcacgag gtcaggagat   34620
cgagaccatc ctgactaaca cggtgaaacc ccgtctctac taaaaataca aaaattagc    34680 caggcgtggc agtggtcgcc tgtagtccca gctactcagg aggctgaggc aggagaatgg   34740
tgtgaacccg ggaggcagag cttgcagtga gctgagatcg tgccactgca ctccagcctg   34800
ggcaacagag cgagactccg tctcaaaaaa aaaaaaaag aaaagattg aaaagagtag     34860 atcaggcaga gggaaggaac tgcatatgtg aaaactgatg tgataggaac ttggctcctt   34920
```

```
tctaagcacc aaaggatgac cagggaggtg ttcaaccaag gaagtagcag taggagatga    34980
agttgacctt gtagacaaag actggaccat gcaggatcct gtagaatttt gaactttatt    35040
ttaaaaccaa tagataaatg ttttttatgct ggtatcctag aatgactctt tttgatcttc    35100
ttattctcat ttagaatgcg gattgtggat gatgatgtga gctggacagc tatctccaca    35160
accaaactag aaaaggagga agaggaagat gatggagatt tgcctgtggt atgtatcttt    35220
ggggctgtca ggattttgaa atgaagcaag cttctcaatt tccttttttt tttttttttt    35280
gagatggagt ctcgctctgt cacccaagct ggagtgcaat ggcatgatct tggctcactg    35340
caacctccgc ctcccgggtt cagatgattc tcctgcctca gcctcctgag tagctgggat    35400
tacaggcacc cgccatcatg cctggctaat ttttttttt taatttttgt agaaatgggg    35460
tttcaccatg ttggccaggc tggtcttgaa ctcatgacct caggtgatcc acccaccttg    35520
gcctcccaaa gtgctgggat tacaggcgtg agccattgtg ccaggccaag cttctcaaat    35580 ttattttttcc agcttagggt agatttgtag gggggttagt tgagaacaga aaagaggtga    35640
cagtttccaa agagctgttt aaaatagttt tctttgctga tgcctataca ccaacttgtc    35700
tctttatgga gggtccatca gcctagaaat gagatggatc acagagagag gacttctcga    35760
catcagtgtt agagtaatga tgagacttag ctgtggttca ttttgttgga atcttcctta    35820
aaaacaatgc tgaggttcag ttatagggaa cttttttattt gctccttttt tcagtgcttt    35880
aactaagctt tcaaattgta tattcttgcc taagtactgg agatatgtag attaatagaa    35940
catagctgta ttttagagat tataccctag aatgaaaaac tgaatttcag ataaatttca    36000
acagtatggt aaatgttggg gatgtttcac atacgtacca agtaccatta gagcccgggg    36060
aggtagcata ctttgtattc tgttgggaga tatcctgaaa gatgtaaata ctgagttttg    36120
aagggtaagt aagagccagg tggacaaaat cataggcaaa tgacctccca gtggttcatg    36180
aaaccattgc tgagaatttc tgagaaacaa agtggaaagg agagctgtag ataggctgaa    36240
ttccactaaa gttggtaaag atggattcca gtgagtattt aatattaatt cccagcaaaa    36300
ttcttttttt tttttttttt ttgagacgga gtctcaccgt gttgcccagg cttgagtgta    36360
gtggtatgat ctcggctcac tgcaagctct gcctcctggg ttcacaccat tctcctgcct    36420
cagcctcctg agtagctggg actacagggg cccaccaaca cgcccggcta attttttgtg    36480
tttttttttg tatttttagt agagacaggg tttcatcatg ttagccaggt tggtcttgat    36540
ctcctgacct cgtgatccgc ccacctcggc ctcctgaagg gctgggatta catgtgtgag    36600
ccactgcacc tggccaattc ccagcaaaat tctaaaatag attatttaaa agagggcttg    36660
ctagtaatta gaagggaaat agtgatctta gggagccaat ttagttttgg tcagaagaag    36720
taaatattaa caatgtttgt tgtttttttt taattttata aaagcaatgc atatttatta    36780
cagaatattt gggaattaaa aaagtttaa agttttttaaa agaataaaca cttgcatgtt    36840
accatccaaa gataactgct aatacttgga tgcatatctc ttcaggtttt tctctttaga    36900
gattatacac gcttgtattt tatttttttg aacataattg ggatcatact gtacatagg    36960 ttttggagtc tactcctctg ctaaataata tgttgtggat actctggtaa gaccttaaaa    37020
tattctttga gtgtatgatt tttaacggtt atgtagtagt tcaatatata tattttatct    37080
gttctgttac tggatacatg gattgtttcc acttataaaa tatcatacat cgttgtacat    37140
aaatcatttg tagaaatcag tttatttctt tattcccata aaatgaaatg agtggatcaa    37200
agggtatggt tcgctttagt tatattccca tgttgctttc caaaaggtgc taccaattta    37260
```

```
cactcccact agaggtgatg agaatgccag tttgcctacg tcgtcaatat tagagcacta   37320
ttattattat tattattatt attattatta tttttgagac agggtcttgc tctgttgccc   37380
aggctgaaat acagtggtgt gatcatgccc cattgtagcc tctaccttcc aggtgcaagc   37440
aatcctccta ccttagtcct gcacgtagct ggtaccacag gtgcgcacct ccatgcctgg   37500
ctaattttgg gtattttttg tagagatgag gtctctgtgt tgcccagtct ggtcttgacc   37560
tcctgggctc aagtgatcct cctgcctagg cctcctaaag tgttgggatt acaggtgtta   37620
gccacatgcc ccaccaatat tgaaggatta ttaacaaaac aaaaccaata gcaaacctat   37680
gctgatttag caagtgagta atggtatcca gtttcttttt tttttttttt ttttttggtg   37740
gagtctcact ctgttgccca ggctggagtg cagtggcgtg atctcggatc actgcaagct   37800
ccgcctcccg ggttcacgcc attctcctgc ctcagcctcc cgagtagctg ggactacagg   37860
cacctgccac catgcctggc taattttttg tattttttagt agagatgaag tttcactgtg   37920
ttagccagga tgatcttgat ctcctaactt catgatctgc ctgcctcggc ctcccaaagt   37980
gctgggatta cagacgtgag ccaccgtgcc tgcccagtt tctttgaaca ctagtgaaat   38040
gaatcatttt ttatatggtc attaggctta tgttgtgggt gtattttatc atttgccttt   38100
tcacttagtt cataattgtt tttattattt tttttttttg agacatattc tcacactgtc   38160
accaacgctg gagtgcagtg gctcaatctt ggctcactgc agcctctgcc tcccaggttc   38220
aagtgaacct cctgcctcag cctcccaaat agctgggatt acaggcgcct gccaccatgc   38280
ccagctaatt tttgtgtttt tggtagagac ggggtttcac cgtgttgcct aggctggtca   38340
tgaactcctg ggctcaagca atccacccgc ctcagcctcc caaagtgcta ggattacagg   38400
aatgagccac cgcacctggc cattttcttt tataatattg tcttgctttt atgatggccc   38460
aaaaacctaa acaaggagg ctttagtgcc actgctctct gcattggtta aaacagatct   38520
tgattactga attcattttt gtaactgcaa gatcaccacc accaccagta ataatggtaa   38580
aacgattatg atgattacga tagcagtggc agcacaggaa taattaatag gtgtcattta   38640
ttgggcattt atcatgtacc aagcatggct aagcttacgt gaattatctc attcaatcct   38700
tatagcaatc ctttgaatcc cacttttaca aatgaggaaa ttgaggctta gaataattta   38760
ccaaaggtta cacaaatgct aagtggccga gctgggttt agatcttaat tcatcttgcc   38820
cgaaacctgt gcttttaacg ctcagtgaga gatctcaaaa ctgggttata tgaagaatga   38880
tggtaggatt ttgggagaag tagagggcta ttatgacctg gatttaaatt ccagttctgc   38940
cacttgttag cttgtgacat tgagaaagtt actgaacttc tccgaatcag tttgctattc   39000
agtagtgtgg agcctttctt tacaggatta ttgtgagaat cgagttagat tatatgagta   39060
aaccacaaaa cacagtacct tgcacatagt tgctactctg taactaggat ttattatgcc   39120
agcaatcttg aaagtttgtc atgtggactt acatcacagg tcagaactag aatgaattca   39180
aagaagttat aggaaggcag atacggtact agtaaaacta agaactttct aacatttttg   39240
aaaaatgcag tggactgtgt tgtaagataa tgagttcctt gtcaggaagg gattgggcga   39300
gtgaccactt attaggaata ctatagaaa gattctgatt tgttcagaag tttagaagat   39360
atgaaatgtg gttttagctc ttaaagatta atgattctgt gtacatctca gtggctcttt   39420
ttggtttgtat tcaagaaaac ctatcactgt gactacctac aacaagaaag gattcataga   39480
aacccaaagt ccttgattag tgctaggcat gatgggggga gccacctatg tttccactgt   39540
taatgtagaa gtaaagtgt aaaggaatt tagttgttag tttacaagtg gctgttgtgt   39600
acctagcagg ttaataaaaa ggtttgtaat gaaaaaaatt aacctttgca gggtaattga   39660
```

-continued

```
ttaattagag aaggatctac aattaaacca atacagtgac aatcagatgt ttatggagca    39720
aacataactg aagacccta cttacttctt catgaccatt ttggatatat gtacgccctt    39780
gtgttaggaa tcggaatggt tgtaacttca ggttcttgag acagtgcttc ttggctggat    39840
cctgtggatt tcctaagata ggaaatcttt actctcacag gtggcagagt tgtggatga    39900
gcggccagaa gaggtaaagc agatggaggc ctttcgttcc agtgccaaat ggaagcttct    39960
gggaggtgag ttccaacaat agataaatct aaatttccat tagtagggga gatctttttt    40020
cctttttctat acttttcttt agaggaatgc atagtttgtt ttagcatgtc attgatcctg    40080
aaaaataaag caggaaaaag gaagttggac ttcttcagag gtagtaagac ataggaactt    40140
atagaccaga tattcctctt tctcttatat tttggcatta ggattactga ggttggtgac    40200
taatttggag gcctttgagc acccattcct ctttgactca gaataggaga gcacttggtg    40260
tataggcaag actttgggag gagtttacaa gaaacaggag cagaatttgg ggactttagc    40320
taccactatc ctcttccaca atgaagcaac tcatttctgg ggggtcaagg accagtgtat    40380
tttgttctgt ttgtgttagt aaatttctct cttcttccct taagtattgg tgttttatag    40440
tgcattaccc tccacttgcc cactttggac tcttcctaag ctaataatct taatttaact    40500
ctctttaaaa aaatttgagt ccttgagaat tggataaaaa gcatttgttt gtcacatctg    40560
tttgagcata gactagtctt atttgccatg atattcccct atctagcaca aggagctacc    40620
tttaataaat atttgtagaa ttgtttaatt gctagtaggt atttgatttt tgtagcctaa    40680
tcagaattct ttttccaaaga gaatcttttg gtctccatgt ctgtttgtct aggaagacac    40740
acagacacac acatacacac ggtgccttttt cttgtgtatc tgaatgttta aaggtcagt    40800
cacacacaca cacagtcaca ctcacactca ctcactcctt ttcttctgcc ttgctttcac    40860
tcccccatcc caatttgtta ttggaagtac gcttaccaat ctctgaccct tgcttccttc    40920
agatttactg ttaggccccc cacagacatc atacttttct ctgtggagtg gattccaatc    40980
agatagggct gttccccaaa gtaaaggagt tgacttggtt taattcatcc atttaacaag    41040
tattcatcag ttcctaccca gcttttattt gtatttgggc tgtggagctc aatgacaaga    41100
aatagaggta gaggaagaac tggattttga aactgttcca gttgctatag atatttcatt    41160
ctgtggtgcc tttgaatatg gaaggtctca aactatgtat tttaacttta aagctttaca    41220
tattttaaag attgcacatg gactctggag tcaaatagag ctggatttaa atattcctct    41280
accacttatt agcaatatga cttttggcaag ttaatctttc tgagtatcaa cttcctcatc    41340
tataaatgaa atgacagtat ttatgtccta ggcttgttgt gagaattgaa tcaggtaatc    41400
tctatgaaac actggcacac agtaggtgat tggtaattac ttgctccttt ctttttttgtg    41460
gtgattttc ccctctctaa gaaagagcac agtgaaatgg attaaatagt taacagcatt    41520
ttatttgat attcaccgtt ttagtcaatt tacctattga agaagagtg agtacaaact    41580
ataaagtatc taggcaaaat atcagtagga gccactagct gggaactctg cacaaatgag    41640
gttttagaaa gaacattgga ctgggagtta gaagacttgg attctagcct gtgtcttcat    41700
tttaggagct gtgaccttag gtaagaaatc actcagctcc tcagctgaaa acagaggctg    41760
tggcctctgt tttcatgctg taatacaagg gtacctgccc tgcttacctt aaagggtata    41820
atatgaaaaa tgtgctgaaa atgctttgca aatttatgac ttggtaggcg gaggggttat    41880
tcttaagata ttcatgagtg gtggtttgct gcccctaagc aagaaaactg tgcaggcctt    41940
ttgggctttc tgagcagttc tgaggtatgt gctactggag catcttttga aactgggtgt    42000
```

-continued

```
gggggtggac agagggacag agcatttgtg ggaatctgac tctttgttat ttgtgtttag    42060
gccacaacga agacctaccc tcaaacagac attttcgtca cgatacccg gattcatctc    42120
ctaggagggt ccgtcatggt accccagatc catctcctag aaggaccgt catgacaccc    42180
cggatccatc tcctaggagg gcccgtcatg acaccccrga tccttctccc ctcagagggg    42240
ctcgtcatga ctcagacaca tctcctccca ggaggatccg tcatgactcc tcagacactt    42300
cacccccaag gagggcccgt catgattctc cagatccttc tcccccaagg aggcctcagc    42360
ataattcttc aggtgcatct cctaggagag tccgtcatga ttcaccagat ccctctcctc    42420
ctaggcgagc ccgtcatggt tcctcagata tctcttcccc cagaagggtc cataacaact    42480
cccctgacac atctaggagg actcttggct cttcagacac acagcaactc agaagggccc    42540
gtcatgactc ccctgatttg gctcctaatg tcacttattc cctgcccaga accaaaagtg    42600
gtaaagcccc agaaagagcc tctagcaaga cttctccaca ttggaaggag tcaggagcct    42660
cccatttgtc attcccaaag aacagcaaat atgagtatga ccctgacatc tctcctccac    42720
gaaaaaagca agcaaaatcc cattttggag acaagaagca gcttgattcc aaaggtgagc    42780
atatgactgt ccatgagagg gatgtatgta tccctgggag cttctttttg gccgtttagt    42840
tgatttatta ggtataagaa tggaatttct ttgggaaagt tttgaaaagt gagaggctgg    42900
gtttgggaga gttgaacaat tatggtggca gggaggaagg ttttcatatg tcttttttatg   42960
tgctcgctcc accccatata aaagtacaat ttatttgttg cagaagcttt ggaatgtaca    43020
gaagtatata aagataaaat gtgacacaaa attctgtcat tcagaggtaa ttattgttag    43080
tgttgtggcc agggtcatct tagtctttt tggtttgcat tttttatata gttgagctct    43140
ggctgtgtag aacatttgta ttgcatgtgc aatcttgcct gctgtccttt cttaacgtag    43200
tcttcctcag gccataaaac atctttatgt tagtataatt tttaatagtg tttaactaca    43260
aatttaacca ttttcctaat aatgaatgtt tttggttatt tctaagtttt ttcttctgta    43320
attctataat gaacatcctt gtacataaac tgttgtcccc attttggatt atttccttat    43380
ctacttctag atagatttcc tcgaaattca actacttcta tataagtttc ctagaaagct    43440
gagaagttga tgtactgggt cagaagatgt gggcgtttta aagactgtcg atacatattg    43500
cagaatgccc tttgggaggt gacttgtgat gcttatacag tcgctagaac ttaggcctgt    43560
gcagtgaaat ttttactcc ctcttttgtt cctaggaact attttaattt taaaattaaa    43620
gtactttgtt atcctttagt ccaaggatat cagactatat tccaggtatt tctgacttt    43680
gccacactat ggagagctga ctacaagtta ttttgtcttt ccatggggtgg ggttactgac   43740
atagaggagt gtgtggagat tttacacacc agttacagtc agtggtcact tgggaataga    43800
atgccatatt ctacctgttg gtcttaaaag ttgtttctga ctttgctctt ctcctgtgcc    43860
atccatactt atgtttaggt taatgataat tcttcatagg aaaactaaat aaatatgtac    43920
attagcttgg taagttatct ttttagattc ttccaagggg attaaagaac tctttggcca    43980
ggcatggtgg ctcaagccta taatcccagc actttggagg ccgaggtggg cagatcacct    44040
caggtcagga gttcaagacc agcctggcca acatagcgaa accccatctc tactaaaaac    44100
acaaaaatta gctgggcgtg gtggcacaca cctgtaattc cagctacttg ggaggctgag    44160
gcacaataat tgcttgaacc caggaggcgg aggttgcagt gagctgagat catgccactg    44220
cactccagcc tgagactgtc tcaaaaaaaa aaaataata ataatgtaag gaattcttta    44280
atttctaggt tcttctccca gccataggag atttcatgta agttcttcac ctaggggaca    44340
tcagagtcac acagattctt tgctcctatc caggtgactg ccagaaagca actgattcag    44400
```

```
accttctcttc tccacggcat aaacaaagtc cagggcacca ggattctgat tcagatctgt   44460
cacctccacg gaatagacct agacaccgga gctctgattc tgacctctct ccaccaagga   44520
ggagacagag gaccaaatct tctgattctg acctgtcccc gcctcgaagg agtcagcctc   44580
ctggaaagaa ggtcaggatt ttcaggagcc atgtccttct tttcgtgtga ctcttctctc   44640
tcagctttat atatgtccca gagaatcaag ccaagaagaa ggatgtagct ctgagaagtg   44700
tagtaaatct tagttaaaag gacctttgga ggtctttcct tctgaaggca aactggctat   44760
aacccatccc agatggactt acagatacca gatttcccaa gtagcttctg cgtttatagc   44820
ctcttaattc tacaatctca ttttaacagg tctagaaaaa cttcctattt tcttaggaat   44880
aaaccgagga ctgtaatttg cagagtgaag tttggagcac aagcattgtg tcaaacggat   44940
cacatacaga aattctcctt ctgccactta ctgtctgtga gatttgggca agatgcttaa   45000
tatctctaaa cctcagtttc tttatctgta aattgtggat aatagtagta cctactgtgt   45060
aaggttgtta tgataattaa gccagtgtaa gtaaaactct tagcacagtg tctgggacaa   45120
agtaagcatc tagtgttagt gatttactag tataaattgg actataggtc tctgtatcca   45180
gagcttaagg agaggcactt aaaatatgaa accacttta gaaatcatgt tgtctgagaa   45240
gtcaatggtt tgttttaaat tcatgataag gcttgatgaa ttagccaaaa aaccccaaaa   45300
tccatatgaa ccttgagtaa ttatattgta aagaacattg gtagtagtaa aggaatctta   45360
tttgtaagtg gttaagaaac agaatgatag agcctgtgat gtgcattttt ctccccagtg   45420
cagacttatc aggtaaatct trtctgtaga agactctgag aagactggtc ctggcagggt   45480
agaccagcct gttctttacc caggaagtga gattcttctt ttttagggaa aaaagaggtc   45540
tctgtttcag ctggacctct tggcatttta tatatccatt tagttcatgg acaacttaat   45600
attattccaa tttcgttgct gaaggatatc aagatatact gtgtgcttca ttcgtgggct   45660
gatttgctat cttgatgcta agtggaaatt agcaaaaagt tttcatttgt tagatcttct   45720
gttattacca tgaaatatat ccacaattta aggatcttag gtttgcttga gtttgtactg   45780
taaatggaat atttttatcag tatgggtctc taatggaagg cttagtgctt tatactggtt   45840
tctgatcaga tgacctgaga tagtcttcat gtgtgcagtt tatatactga aaagtcagaa   45900
atacaaatgc gtagccctcc atttaatata ttgttagtgt ttctgcttat tcttaaactt   45960
gatggttttg atgatggttt tcttttatag ttttttgaatc ctatggtaat tattgagaat   46020
ataaagctag agttttaggt ttaattattg ctggtcatta gacacaaatg caactaactg   46080
tgtacccatg gaacctactg tcacatcatc tcattaatgt tggatgctcc cttttccgtt   46140
gcataggctg cacacatgta ttctgggggct aaaactgggt tggtgttaac tgacatacag   46200
cgagaacagc aggagctcaa ggaacaggat caagaaacca tggcatttga aggtaaaaat   46260
atgaaagtgc agagaccaat ttaggctcat actgttttt tttttaatt tagcttattg   46320 tacctgatat tttgaacttt taattgctat caaatttcag ctctggtttt atgcattgtt   46380
gtaatttctc agtgaatccc agtgcttctt tccttcttga aaaatgccat ttcgcccagg   46440
cgcggtggct catgcttgta atcccagcac tttggtaggc cgaggcgggt ggatcagctg   46500
aggtctgtag ttcaagacca gcctggctaa catgatgaaa ccctgtctct accaaaaata   46560
caaaaaaaaa ctagccaggc atggtgttgc atgcctgtaa tcccagctac tcaggaggct   46620
gagacaggag aatcgcttga acctgggagg tggaggttgc agtgagccaa gatcgcgcca   46680
ctgcactcca acctgggcaa cagagtgaga ctccatctca aaaaaaaaaa aaaaaaaaa   46740
```

```
aggaaaatgc catttcttgg gcccagtgcc aatatgcacc aagatgttgg taggaactac    46800
tttggtctgg ctgcagaagt tcttatctag cattagaatc ccaagcggtt gatttgatct    46860
cttagaatgt tatttctgat tttgatcctg atatttgagt ataattttcc tttgcagctg    46920
aatttcaata tgctgaaacc gtatttcgag ataagtctgg tcgtaagagg aatttgaaac    46980
tcgaacgttt agagcaaagg aggaaagcag aaaaggactc agagagagat gagctgtatg    47040
cccagtgggg aaaagggtaa gggaaccact gaaagggtaa acaagatggc agtgactgga    47100
acaagtcatt tctctgctct tctgatcact cactttctta ttatgccttc agagctgtta    47160
tcagtaatgg gaaatttggt gtgctgaatc ttcttcctag gatattgata tattccacgc    47220
ttctagtggg tattctggga attttaccct gctcagtatt tgccctaggg tactagaaag    47280
aggagattgt ccaaacttag cagtatggtc catctcgtgt agaagtggaa atgtcataca    47340
ggatagcaaa cactcttggt tcctttttgc ccaggcttgc ccagagccgg caacagcaac    47400
aaaatgtgga ggatgcaatg aaagagatgc aaaagcctct ggcccgctat attgatgacg    47460
aagatctgga taggatgcta agagaacagg aaagagaggg ggaccctatg ccaacttca     47520 tcaagaagaa taaggccaag gagaacaaga ataaaaaagg tgggacttct gggaatcatc    47580
agctggaggt gacttgtgaa gagagaatca ttaggatgct gatacatagc tatatgcaaa    47640
gaaggatttc ccaaataatt taaattcatt gtatttgtga gtttagattc aactcaattg    47700
gtctttctat ataaaaattt ttccaggcca ggcgcagtgg ctcatgtttg taatcctagc    47760
acttcgggag gccgaggtgg gtggatcacc ttagagttcg agaccagcct ggccaacatg    47820
gtgaaacccc atctctacta aaaatacaaa aaaaaaaaaa aatagccggg tcatggtggt    47880
gcacgcctgt aatcccggct agttgggagg ctaaggcacg agaattgctt gaacccagga    47940
ggcagaggtt gcagtgagct gagatcgtgc cactgtactc cagcctgggc aacagagtga    48000
gactctacta aaaaaaaagg aaaattccac attgccatcc agctctgaat taaactatgt    48060
cattaactga atacttttt cttactcctc tcattagtga gacctcgcta cagtggtcca    48120
gcacctcctc ccaacagatt taatatctgg cctggatatc gctgggacgg agtggacagg    48180
taagcctggg tatttcttac attttctacc tgactgtaac cttccctaac cactcgtaag    48240
ttgctccaca cttatttca ttctctgctt taatcacaag gtgaaaaata tgcactttgc    48300
ttgcttcttt ttctgaggtc cacaaatcct atttctcatg cttggaacac tcctccttct    48360
gtttcctttt cataatactt tttaaagctc tggacaaaca cctcaggtgg ttcagataag    48420 acacccttg ttttggacat tggttacttt taatgatatt ttgtaaggtt tagagggtt     48480 gagtgatgag ttgtagtctg gagccttcta cctgatatat cttaaaatg tagcctctga    48540 atctttattc acttatggt tttaggaggc agtcactttt aatgtcttcc agtcctctac    48600
cccacctcat ctgtctacct accaacatct gtacccacgt actctaactt cctgttatga    48660
tggatgaata tttgcttcca tccaaagtca gtttgtatac tcacatatta gatcccatct    48720
cctcttgcct actaaaggac attgttttag tatctagcac aataattctt aaactttta    48780 atctcaggac ccttttacag tcttttttt tttgagatgg agcctcgccc tgtcgcccag    48840
gctggagtgc agtggcgcag tctcggctca ctgcaacctc tgcctcctgg gttcaagcga    48900
ttctcctgcc ctagcctccc gagtagctgg gattaccggc gcccgctgcc acacccagct    48960 aatttttgt atctttaata gagacggagt ttcaccatgt tgccaggctg gtctcaaact    49020
cctgacctca ggtgacccgc ccacttcagc ctcccaaagt gctggtatta caggcttaca    49080
ggattacagg attacaggtg agccaccatg cccaaccact cttatttttt tttgaggcag    49140
```

```
agtcttgctc tgttgctcag gctggagtgc agtggtgcaa tctccacttc ccgggttcaa    49200
gcaattctca tgcttcagtg gcctgagtag ctgggattac aggcatgtgt caccatatcc    49260
agctaatttt tgcatttttta gtagagacga ggttttgcca cattggccag gctggtcttg    49320
aattcttggg ctcatatgat tgtctgcctc gatttcccaa agtgctggga ttacacgctt    49380
gagccaccgt gcctggccta cgctcttaaa aattactgat gacctcaaaa agcttttgtt    49440
gatgtggatt atatatattg atatttacca cattataaat taaaactcag acatttaaaa    49500
agtatttatt cattcaaaaa aaaataaact aattatgtta acataattac tgtatattta    49560
aatgaaaaat aattacattt tccaagtgaa aaaacagaag gatggcattg atttacattt    49620
ttgcaaatct cattaatgtc tgacttaata ataggtaact tgactctgta tttgtctgtt    49680
gtgatttgtt cagttgaagt atagaaagaa aatttagcct cacacatagg tagttagaaa    49740
gagaaggcat attatatttc ttaatgttac acaaaaactc aacaagtgct ggtttcttaa    49800
aggtgagcta tgtggaacct gaaaccagat caaagaactt tccttactgt tatattaatt    49860
ttttttaatac tttgagtgga tcttttaccc atgcatgatt ttataacatc atgcattggt    49920
catttgtaaa atattggttt gctgagttgt tcagaccttc caaatgttga catatttcca    49980
ctatacaata tcagaaaatc acttttgtta acatcacttc cggtcttatc acaaaactct    50040
ttaaataatg ggaagttaaa gagttcacag tttttcagaa ttctaattta cacttgaaag    50100
tttaaatgtt atcactggca tttccattgc ttgagctatt tccatttaat agcttaatt    50160
ctctgctgag atttcccatc tgttcattat gagatatttt cctcttcttg aaaatatttg    50220
tgatatgtaa ttggtgcttt gaagtccttc ctgtctgtta attgcaacat tggattcacc    50280
acaggattgg tttctatatt ggcagctttt tcttcagtgt gtattacatt ttcctgttta    50340
tttacctgtc tggtcacttt tttaaattgt tactggacat catgaatgat atactgtaga    50400
gactttgagt tctgttacac tgtattgtca gttgttttcc ttcaggtaaa gctcactttg    50460
tacaatagct ttttatagat tccatcagat tttgtaccta gagggtcttc catctttgca    50520
tacagtttaa tttcttactt tacaatctag atgcttttttg ttttcttttcc ttgccctgtt    50580
gcattagcta gcacttcagt gcagatgttg aatagaagta gtgagagcag acatctttgc    50640
tttgttccta atctcaggaa gaaaacattt agtttttaca acacatttat taaatgtgtt    50700
gtagctgtgt aggttttttg tagatatcct ttatggagtt aaagttgcct tctattcctg    50760
ttttgctgag agttttgttt tcaggaatgt atgttggatt ttgttcaaaa tattttctaa    50820
ttatcctttt ggtttattct ttgctccatg ggttatttag gagtgcatta attccaaata    50880
tttggacttt tctagatatc ttactgctat ttacttataa tttaattcca tttttggtcag    50940
ataatatact gtaatatttt gatcttttga aatttgttgg ccaggcacag tggctcatgc    51000
ctgtaatccc aacattttgg gagcccaagg cagacggatt gcttgagcct aggagtttga    51060
gaccagcctg ggcaacatgg caaaaccctg tctctacaaa aaaatacaaa aattagtcgg    51120
gcatggtggc acacgcctat agtcccagct actgtggagg ctgaggtggg aggatcactg    51180
agcccaggga ggtcgaggct gcaatgtgct gtgattgcac cactgcactc cagcctggat    51240
gacagagtga gaccatgtat caaaaaacaa taataaaaat gaaatttgtt aaggtgtgtt    51300
ttatggccca gtgcatagtc tatcttctga atgtttcctt tgcacttgaa gagaacgtat    51360
attctgtagc tatataaggt agtgttttat aaaagtcagt gaggtcaagg tgtttagatc    51420
ttagatcgcc tgtattctgg gttttttgtg tttgtatttt tctatcagtt actatcaatt    51480
```

```
gtggatttttt tgttttagct ggtttatttt gttttttcaac tctaaaattt ccatttaata   51540
gcttacattt ctctgctgag atttcccatc tgttcattat gagacatttt cctcttcttg   51600
aaaatattta tgatatgtaa ttagtgcttt gaagtcctgt ctgctaattg caacattgga   51660
ttcaccacag gattggtttc tattgacagc ttttcttca gtgtgtatta cattttcctg   51720
tttatttacc tgtctggtca cttttttaaaa ttgttactac gcatcatgaa tgatacactg   51780
tagagacttt gagttctgtt acactgtatt cctcttaagt gtgttagttt ttattctagc   51840
aggtagttaa catagctgaa ctccaaactg tctcctttgc agtggaccgc agctacaatc   51900
tttgctcagt tcttttagtt tctagctgcc attttttaa ttggcctgat ggtatttct   51960 ctgcacatgt gtcatttaac agttagccaa ggatttgact agggtttgta tgtagatttt   52020
gaggttcatc tcttttgtag ttccttctct tccaagatttt ccccctaat ttcctagctg   52080 ttctgcccac tttgcactaa ttcctcaagc cagtaagcct gtggctttct gccttcatga   52140
gccatgctgt ttgggaagtt gccctccagc aaatctcttt tcacatatag acttcatcca   52200
gttcatactt acttttggtc actcttccac accttcaaat acctattttt tttgttttgt   52260
ctaggtttta tagttgctaa ctgaggatag gttagtctgt tcgggttact ctgcaatgtc   52320
tagaatctgt ctccccacct tatatgggcc taaggcgttg tcttctgtcc ctcggggtgc   52380
cgtcaaaatc caacagccag gtgtggtggc gtgtgtctgt agtaccagct atttgggagg   52440
ctgaggcagg aagatcgctt gaacccagga gtttaagtcc aggctaggca acatagtgag   52500
accccaactc cagaataaaa aaatttaagg ctcttctttc tgatattggc agatatctat   52560
aagttgactg tagttcctca tcttggcaga tatctttagg gtagctgtgg ttacaggcta   52620
gcttactagt tccgtttgca gttcactgta tgtaggcttt ttggtagaag gaggattttt   52680
cagaacactc atttgccata catacagcca gaagtagatc ttttatagc acaaccctac   52740 agatgttccc tgctaccgag ttttttgtttt ttgtttttta attttggac ccaaaactta   52800 gaattctccc tgacctagtt tttttacta gtatttaatt tgtcttcatt tttctcagtt   52860 gctttttcc acttcttgtt ctgattttat cctagatttc ttctcttatt tcccttgtc   52920 accccttgctt tcttttgtt attcatcttt catcatcttt tctagttttg tctcttttcg   52980
gcctgctgca aggaatatt tccggaacag atacatagta tctgttggaa aaacccataa   53040
gataattacc cagcctctct taattgaaag agaaacgggg ccgggtgcgg tggctcatgc   53100
ctataatctc agcactttgg gaggccgagg cgggcagatc acgaggtcag gagattgaga   53160
ccatcctggc taacatggtg aaaccctgtc tctactaaaa aaaatacaaa aaattagctg   53220
ggcgtggtgg cgggcgcctg tagtcccagc tgctcggaag gctgaggcag gagaatggtg   53280
tgaacccggg aagcggagct tgcagtgagc cgagatcgtg ccactgcact ccagcctggg   53340
caacagagca agactccgtc tcaaaaaaaa gagaaactga ggcccaataa ataagcagtt   53400
tgcctagagt catgcaattt ccctgagaaa gctggaatta gaactctgcg ttcctgattc   53460
tctggtccaa agctctttcc actgtgagtt ctcctgcaat tgttttctg attctgctta   53520 ggatttggtg tttgttattc atatgtcctt tgtattatca tattagtgta actctcttaa   53580
gaccttattt ccaaggtaaa aaacagtggt ttccttggtg ctttggaata ccatccatgc   53640
ttctaaggtt ggagaggatg ccatttataa taagcttccc ttctttttt tttgagacgg   53700 aatttcgctc ttgttgctca ggctggagtg caaaatggca cgatcttggc tcactggaac   53760
ctccgcctcc taggttcaag caattctctt gcctcagcct cccgagtagc tgggattaca   53820
ggcgtgagca ccacgcccag ctaatttttg tattttagt agagacaggg tttcaccatg   53880
```

```
ttggccaggc tggtctcgaa cttctcatct caggtgattc acctgcctcg gcctcccaaa    53940
gtgctgggat tacaggcgtg agccaccatg tccggccaag cttcccttct taaagccctc    54000
tgttactcac tccactcatc ccttaaggga aagtcttagc atacatgtta taagtgtaag    54060
cagctaggta gtaggtacta gggattccat gattaaagag atatagcccc tgagcccagg    54120
agctcacttt caatctagaa tagaagacag acagtttcaa cgctgtttgg ttagtgttac    54180
tatagaagat tttcaagatg ttttgggagc acaaaggaag agtaagttga gccttaggag    54240
gatgtgagtg atcaggaagt gcttcctaac ggatgaaatg tgggagctga gttttaaggg    54300
atgttggtaa ccagccaaga taagaaggaa aggaaggata ttaaaggaag agggtcctat    54360
atgtgcagag tcataaggct atgagacacc atggtgttac caggtggtgg gggtccctaa    54420
gtaatttgct gttgttggat agcataaagc gtgagatgga tgagagaggt tggcagaccg    54480
tgatcacaga aggccctgga agcctatctg aggagcttgg tcttcaccct agaggtaaag    54540
gggagacacg gaaggattaa aaacagctct gcatttttaga tagacaaatc cattatagca    54600
gtaatatgaa ggatttgaaa ggtacaagat tggaagtaga acagatacaa ggcttttgca    54660
gtagctcagg ctgaaagtaa tgagtgtctg aactacgact tgcaggcagt ggtagtaagg    54720
atggttagta agagaatagg aagtgggggat gtggtcaggg gtgagctggt gggacctgtt    54780
tgctgatttg gggaagagga aggaggagtc attggatttg gcaacaagga atgtcagtga    54840
tgacctgaaa gggctagttc cgttgtgtag tgaaacaatg gccaggttct aatgtattaa    54900
ggagtgaatg aaaagtgagg aaacaaatag tgaatacagg cttttttaaga agtttagata    54960
agaagaccaa gagaatgcat ggtaattaaa gggatttgag gtccactcac tacctccttg    55020
aaattcaccc ctgtattgtt ttccatgaca ccctactcct ggttcttttc tctgatcatt    55080
cttggccacc tttgcaaact cctcttcctc tgtgcacctc ttaagtcttt cccagggctc    55140
catccataat ttttagctgt tctcactcta tgtgctccct ctggctgatt cttacctagt    55200
catgttttca actatgacct atatgtacat gatttccaaa tcagtatttg catcttggtc    55260
tggtgtattt agctgtttgt tggatttctc tattgattta gacttgagag atttcaaatg    55320
cattgtattc aaagctgaac tcatcagctt ctactgtaag cctgctccta ctcttgtgct    55380
ctctaacttg cctcctcctt cttttgtcctt gtgtacctaa tcaattagtg ctgctaatta    55440
gtcttactaa ttttgcctcc tgtgtcttct ctcttccgtc cctctttatc attgccttca    55500
tcatctgttg cctggaccat tgcagtgatt ttcctgcccc agatcccctc cagagtgatc    55560
tctttgaaat gcagtttaag ttcttgcttt aaacccatcg tttctggatg aaatctaagc    55620
tttttaccat ggcctacgca gctcattatg cattggcctc tgcgcctttc caactttgac    55680
tcatggctgt tcccttttgtc atacttcagg ttccagccat accagtttgc ctttggtttg    55740
ctgcacatac caggccactt cttatttccg tgcctttgtt cttgttgctc attctgttct    55800
gaaatgacct ccagacccctt tctggcccctt ccatcccag tgctgtagtt aacacagagc    55860
ctttactgat cattccttgcc caaccctcat gtcacctttt tatcataccct ccccccaagct    55920
gattaagata cccattctgt ttccatgaca ccccatgcgt atttctacca gagtttatgc    55980
tgttcttttta atttattttgt ttaaatgtct ctctcttcca ctagtctggg agttcatcag    56040
gacaggtgct gtgtcatact cattttcatg tagtgtctac catggtaccct agtatataat    56100
gaaaattcaa taaatgtttg tgtaatgaat ggataaaata taagatgtgg acatcagctg    56160
agagagaacc aggcttttag agtggcaaac gtttgaaata gctgtcagag tgggggaagg    56220
```

```
gtgtgaacaa ggactaagaa aaggatgaat gatatatttt gtcccttcga ttctattgca   56280
tatgccttaa atattttctt ttcttttttg tttctttctt tctttttttt tttttttttt   56340
ttgagacaga gtctctgtca cccaggctgg agtgcagtgg cacgatctcc gctcactgca   56400
acctctgctg tccaggttca gcgattctc  ctgcgtcagc ctcccgaata gctggattac   56460
aggcacctgc cactgcacct ggctaatttt tgtattgtta gtagagacag ggtttcacca   56520
tattaggcag gctggtcttg aatgcctgac ctcgtgatct acccgccttg gcctcccaaa   56580
gtgctgggat tacaggcgtg agccgccgtg cccggccatg cctaaaatat tttcatatga   56640
ctccttactt tccccccttt tcattatatt gtgaactctt cccttctttt tgaaacaaat   56700 gccccttca gggttctagc tgaatagtat gtctcttttg attgcagatc caatggattt   56760
gaacagaagc gctttgccag gcttgccagc aagaaggcag tggaggaact tgcctacaaa   56820
tggagtgttg aggatatgta acttcctga  ggctgtgggg gtggctgggc tgtggtagtg   56880
ggcataggca gcgagatatc cagtggtaac agttgtctgt gctaataatt ggagcccaca   56940
cagaccagca acttgttgaa tgccagtttt gaccacagaa gaatattcga gacctgatgt   57000
ttggactgag gtacctgtac ttcttgggtg tgacagcacc ggctgttgct ggctttcaga   57060
ggaagcattg atttctcatt gaccagggtt tgttcttggt agggttttc  tttttctttt   57120 ttaaataaac atgtatttat tttttaaaa  ttatcttctt aactgggtat tctgttttgg   57180
gaagaataca ggctaatatt gaacctgtgg ggatttgggg ggtggtggtt gaattttcta   57240
ctaatctaga aagcagtgtg agtaaaaact ttcttagtga tagatccttc ctctgagaaa   57300
acaggaatta gtactaaact agactcagga atagacacac agatatttgg agacatggtg   57360
tatgataaag atagtgtcac aagttagtag ggaagagatg gataatagtg ctcagaaaat   57420
tggcttatta tatggacaaa aataaagttg aaccctcata ccatataaaa caaaaatccc   57480
aaagtgatta aagacctaaa tgaaagataa cgtgatatac agctagtagg aacaaatggc   57540
aaatgttttt gtgccttggg gtaaagataa atttcttaaa taagatccca aagcacaatg   57600
cataagattt gatagctttg attactttgt aattaaaggt ttctatttag caaagcatcc   57660
catagtcaaa gctaaagatg gatacggatt aggagaaaat atttgcagtg tctaaaactg   57720
acaaggattg catatacaag ggatagaata tagaaagagc ttctgcaaat catgaagaaa   57780
aagacagatg aaataaaaat atgcaaaaat atgaataggt aaaatctaaa gagaaaacca   57840
gagtggctca taagtatatt acctcactag taattacaga tacgctaatt aaaacactga   57900
gtttctacct tacatcttag tttggcaaaa ataagcaaga gactgatctg atggggaatc   57960
agaactcatg gaatatttc  tcttcttttc ttttctcttt tcctttcttt ctttttttt   58020 ttttttttaa aaagacagag tcttactctg tcatccaggc tggagtgcag tggtgcctct   58080
gcctcccagg ttcaagcaat cctcccacct cagcctcctg agtagccagg actgtaggca   58140
tgcgctacac aattttttgtt tttttagtag agatgggggtt tcaccatgtt ggccaggctg   58200
atctcgtact cctgacctca ggtgatccgc ccgccttgtc ctcccaaagt gctgggatta   58260
caggcatgaa ccactgtgcc cggctacatg gaatatttca gctggtgtat tcattttgga   58320
gaacaaatga atgaaactta ctgaaatcaa gtaataccta gggagcgata ttgcagtttt   58380
taatagtgtg gctctggagc tatactgcct gaatttgaat cccagctatg tcgtttgcta   58440
gctgtgtaac ctttggtaag ccagttaact tctctatgcc ttagtttttt cgtctgtgaa   58500
atagacataa tagtacctac ctcataggtt tattgtaagc ttagaacaat gcctggcaca   58560
cagtagtgtc acagaattat tagctgttat tattatcatt gtcatcatta tcatcaagta   58620
```

```
gggcagccag cttccacgat ggcccctaat gatctctgcc ctctggtata taaaccttg    58680 tatagtcccc tcccacaata ataaggttg acctgtgtaa ccaataggat gtactagaaa    58740
tgtgtgactt acgaaggtag gtcataaaag gtattaaaat atctgccttg tgctatcttg    58800
gatccttgct ctggaggatg ccagcttcca tatcatgagg acactcaagc agccctctgg    58860
agaggcccag gtagagaagc tctgaggcct ctcaccaaca gccagcacca aattgccttc    58920
tgtaggagtg aatcaccttg gaagtgcatc cgccagctct actcaagccc tccctcaggc    58980
ttgcagccct gatcgacctc gtgagagatc ctgacccaga acatccagct ccagattctt    59040
gaaccaaaga aactctgaga taataaatgt ttagtattta tttatttatt tgaggtggag    59100
tcttactctg tttcccaggc tggagtgcag tggtgtgatc ttggctcacc acaacctctg    59160
cctcccgggt tcaagcaatt ctcctgcctc agccacccga gtagctggga ctacaggtgc    59220
ccatgcccag ctaattttg tatttttagt agaggtgggg tttcactatg ttggccaggc    59280
tggtcttgaa ctcctgacct cgtgatctgc ccacctcggc ctcccaaagt gctgggatta    59340
caggcatgag ccactgcgcc tggccatgtt tagtatttt taaaaactgc tttattgaga    59400
tataatttac atactacaca attcacccac ttaaggtgta tgattcagtg gcttgtaata    59460
tatcacagag ttatgcaacc atcaccacat ttaattttaa aacatttta tcatcttgtg    59520 ggtacaagaa accttgtacc cattagcagt cactccccac tttcccctaa cttctccagc    59580
cttaggcaaa cactaatcta ctttctgcct gtatagttg cccgttctgg actttcatat    59640
attaataaga tatgagtgag actgtcatat aatatttggc cttttgtgtc tggctttttg    59700
tgcttagcat aatgtttca aggttcatcc atgttgtaat atgtatcagc cctacattcc    59760
tttttaaggc tgaataatat tcccttgtgc ggatatacca catttatttt atgcatcatt    59820
tgatgggcat tcgagttgtt tccactgttt gggtattatg aataatgctg ctgtgaacaa    59880
ttcatgtata agttttgta tggatgtata ttttcttttt tatattccta ggggtggata    59940
tattcctagg agtgaaattg ctgggtcata tgtaactcca tgtttaactt tttgaggaac    60000
tgccaaactt attccaaaga aatgtatgcg cgttccaatt tctccacatg cttgccaaca    60060
cttattattt gtcttttga ttatagccat cctgatgggt gggaggtggt atatcattat    60120
ggttttgatt tgcatttttcc tggtggctag tgatgttgag catctttata tatcttttgg    60180
agaaatcttt attcaaatcc tttgcccatt tttcatttgg gttattggtt atatatacac    60240
atacacaggc actctcttac gtaaagggt ctttatatat atcttggtta taagtccttt    60300
actagataca tgatttgcaa atacttttct cattctatgg gttgttattg ttttaagctg    60360
ctcaagcatt tagggaagga agtttgcatt tagggtaggg aagcaacagc agttacagtt    60420
ataaccataa caattgttat acagcaacag ataactaata ctttatgtac atacttcaaa    60480
gtagttccac tcctggctat atccttcgga gaaatttgca taaatccttg aggagtagat    60540
acaaggatgt ttttctatgt atagtttggg tggcaagaat ttggaaaaaa cttagatgtc    60600
catcactaag gaaattgata agtaaaatgt ggtatatgca tataatggag ttttttttt    60660 aagtcaaatg caagctgtta ggaatttcgt gaaatggtag acttcaagtg aaaaaataag    60720
gaacagtgaa atttaaagca aaaatcagct atataaacac atgaagtgat attattttat    60780
aaggaggata tacaccttaa tcagtagaat aggtttgtgg gagggaacag aatgagacta    60840
gaatggagaa tgaagcgggg aaagggaagc aaagagggct ttgcatggat gaaagtgatc    60900
gtgtatcatg aactcaggcc tgtgataact cagttctgtg cacctgaagc cctaagtgca    60960
```

```
gctccagaag caaggtctgg tttcatggaa ttgacattta gtacccatat tagttagggt   61020
agactaaact gctaaagcag actccaaata gacatgtgtt tccccctgc tcactcgtgt    61080
aacatgcagg tcgtttcagg ttgagaaagt aggagtgaga tactctatga agttgtttag   61140
ggatcaggct gatgccagct tcactatggc ttccaaggtt gtgttgggca ttaccatttt   61200
agtgagttga gcagaacgtg aaggattgct tggcagatgt taccggctag ctctagaagc   61260
ggcacacact tctactcata ttctgttggt aagaacctag tcacaaggct ccctcttaat   61320
gcaaaggagc ccgaggcata taatatgcat caggaagaag ggataaatgg atgttgttgg   61380
acacataaca tattatcttt gccacattat atacttctca gacttgtaaa gaaaggctgt   61440
ccatccccca gccatttgag acatacatag attttttaaat agttttgaga cctgaaaatc   61500
ccgaagggag tatcagttgg ggtcactacc aagttaggga tgtctcttcc ctaactctgg   61560
ccagtgattg tcagagaagg gcttaggtag ggagataaaa tgtaaactgg aattgtgtcg   61620
agaatcagca tttatgagat ggaagtactt tatttatttt tacagctcag atcttgctgt   61680
gttgcccagg ctggagtgct atggcatgct tgaaacttgt gggctgtgat cctactgtct   61740
cgccttccca aggtggcaga ggaggcattc aactcctagc tcattgtcac accccttctg   61800
cacagctagg ttttgtttct gtatgggttc gggttttaac ttcattttttg tgggaccctc   61860
acgctgtttc ttaggaacac ctcactctta agaggctcag aggctttaga aatctgaaat   61920
cactttttt cccttaacaa aggaatgtat tatttattta tttattcatt ttttatttt    61980
ttgagaccga gtctcgctct gtcgcttagg ctggagtgca gtggcacgat ctcggctcac   62040
tgcgacctcc acctcctggg ttcaagcaat tctgcctcag tcttccgagt agctgagatt   62100
acaggcatgc gcaggaatgt attatttatt tttaagcaga gattaaggtg tagggaaagc   62160
agttagattc tgtttcaggt gagctctatg tttagtaggc attagtgaac atttaaaaac   62220
tccacccct ccaatttctc tgcctgtaag tgtgagaaca cagcacatct tgtagggcag    62280
agatcgcaag cctgtccagt ccctagctga ctgtcatttc ctaggctgtc tactagaggg   62340
cagtgtgata tgccttttct agactggcga aagcggagcc ctgggtctat acacacttaa   62400
taatagtagg ccttagatct agaacataat cctgtttcca atatggaaaa gattttcaag   62460
agagagacct agtatttagg ttttgaccag aatctcccett acttgggctt tggaaacctt   62520
tctctacgtg gaagattttt ttttttcctt taatcaaatc tcctttcttg cgcctcctcc   62580
actttcaagt ttagacttaa gaagccatga gcaatgtgaa aaacctctga attgtacatt   62640
ttaaaagggt gaactttatg gtatgataat tatatctgaa tttaaaaata ttaaaacagg   62700
ccgggaatgg tagtgcattc ctgtaattcc agctactcaa gaggtcaagt gggaggatca   62760
cttaagcaca ggagttcagg accagcctgg acaatgagac cccatctcaa tgaaataaat   62820
aaaatttaaa aaatgtaaaa acaacaaaaa agaagaatca ctgagcagac actctggctc   62880
agatagaata taatagtagt aatagacgta gtaatagact ggaatgactc agtctctcct   62940
ttatctctcc tgaatgattc aaacttgatg gtgttgatct tggccttata cagcttcacc   63000
cttttcagaaa acaagggtac gtgggcgatc ttggtggtga gttgatactc aggcagtacc   63060
tgtgaaccca ccccttggg agggacaga gagcagtctg ctgaaaaagg agtcagtctt     63120
tccctccgca tatcacatcc agcgccctct gtcagctaag gaattacaaa gtgtgtgact   63180
ttatcctgtc acacgtaaaa atgcaatctc tagtgcttag taaacagggc ctgttttctt   63240
tattttcctt ttagtaggag aggaagcaat tgtgcagaga ggttaacttg ctcaaaatcg   63300
ctctgagttg ggaaagagtc agaatttaaa caacagattc ctctccctgc agttgtcacc   63360
```

```
cccacctatc ttcactccag tagcaaggta agaggtgagg gggcagtcca agggactgtt    63420
tcctgtccag agcagttctt accaggggtt ctcatagcct ctgcaaggag gtcctagtgt    63480
acttgaagct gagttcccca gtcctggaag aactgcttgc tggtagtttc agtttggaac    63540
tcggctttga agatcctaac caagtgtgtt agaggggcac gtgcccttga ctcgtgtgtg    63600
tgtgtgtgtg tgtgtgtgtg tgtgtgtgtt ttgagacagt ttcattctgt cacccaggct    63660
ggagtacagt ggcgcgatct cagctcactg taacctctgc ctcctgggtt caggcaattc    63720
ttgtgcctca gcctccccag tagctgggat tacagatgtg cgccaccaca cccagctgat    63780 tttttgtattt tcagtagaga ccgggtttca ccatgttggt caggctggtc tcaaactcct    63840
gatctcaggt gatccgccca ccttgcctcc caaagtgttg ggattatagg cgtgagccac    63900
tgcgcctggc cccttgtctc tttttgccag gggcttggga ggtggtagac aagacctctg    63960
ggaagagagg aatgcctgtc tgggaaaaaa attattgttt taattgctct ctttcattaa    64020
gtacttactg tgtgtcaaat gtgtatgttc agtgcgtact tacattacct ctgttgtcag    64080
ggagagatca gtctgtgaat ggttgtagat tagggagagc cacatttctg ggtctcccaa    64140
gaaaaggggg gttgggatat cccagcagga taaactcttc cttgttttcc cccatacatc    64200
ctgaagttat aggaccttca tgctgattac ttgttgacag agagcttggg cactttaccc    64260
tggtcactgt gtccccatca aatttgacag tgctgttgcc acccaggatg gccgtctcct    64320
gctttggcca gctcagctct tcatgcagat taagtagtgg gctgccagcc ggggcagtt    64380 tccttctgca catgctggat atgtttgctg cccggggtaa aaataatgct gcaggatgga    64440
gccatgccaa ggggcttcag gtggtattta acatctcctg gggctatttc ctcctgggct    64500
tccaactgct gaaaagcagc tcccttctgc tgctcccccc agtgggaagt tcagtttgtg    64560
gggggttgag gggggcgag ggggggtcct tctgaccttc ccttcattaa ttgggcttag    64620
taggggaagt cagtggtggt cagtctccta gagtgagagg tcatcaaaaa gtagtccatg    64680
ttacctccta tcaagttact taacttctct gagccacagt ttccttattt atttattttt    64740
tgtttttttt tttgatacag agtctcgctc ttgtccctca ggctggagtg cagtggcgca    64800
atctcagctc actgcaacct ccgcctcccg ggttcaagtg attctcctgc ctcagcctcc    64860
tgagtagctg ggattacagg ctcctgccac catgcccggc taattttgt attttaata    64920 gagacggggt ttcaccatgt tggccaggct ggtctcgaac tcctgacctc aggtgatcca    64980
cccaccttgg cctcccaaag tgctgggatt acaggcgtga ccactgcac ctggccacac    65040 aatttcctta tttgtaaaat cagggtaata cctcccttc tggttattga gaggatctga    65100
aataaagtta tctagcatag tgtctggcat gtagtaggtg cttaataaat agtttcttaa    65160
aatagatact taaagagcat gtctgctgcc tcagtggcac atgtcccagt ctctgttgat    65220
ccttctcttg tcttattcct ggctttacct gaacaccagg gtcacagttc tctggctgtg    65280
tttggagagc cagtgtctct tgctgggtgg gattgaggga tgtactattt gaagaagagt    65340
agtcaaacag gtggggatct tctgtcccct ggagaggggg tgtctagagg cgggggagaa    65400
gtgattggct tgttccagtg attcttgcct gtctcatggt agccttctat tacccattgc    65460
cccttgtcag gggagaggtg ggtgctggtg gtgtgtccca gacaggacccc agtttgaatt    65520 tatttgaagc tggggacata agaactagtg gtggggggtgg ggaggggtga ggagttctct    65580
gcatttaaca tttaagggca tgtggaattt caaaagcagt tttcaccagc atttcatgtt    65640
tgtttggttg tttcttttgc ctttgagcat agtgctggtt gggggcaggg tggcttatga    65700
```

```
tgaagatagt cagtggtgga ctcctgcata ggtgggtgga actccatata ggaaaacaca    65760
ttaccgctgg gcttagtgcg gttgctacgg tgtctgtgtc tcctaagggg caggaaaaag    65820
aacagtctct aggagcaaaa gaggaagaga attgagtcag gggttttgtt ctctctctgc    65880
ttccaaagct gcaaggctgt gtccatgaga ccttgaggaa gcccctccag ttcctcagtg    65940
ggagggaaga aggttggccc tctgcactgg ctgtgttttg acagaagtaa aactcttgac    66000
tcagccttca aagttcaagg gtgggatatt gggagaggat gagcagcttt ttggcttgtt    66060
aagaaagtca cgttttttggc cagtataaag tggaggaggc agagtggggt gaggtgtgtg    66120
ggagtcctgt gggatggaga aagcagtctg ccaagggcca tgttacctgt gggtgatgca    66180
gagaggctgt ggtcataatg gggagcaggt agtgagaact ctgtggggag ggctgtgttt    66240
gaaccactga ggtctgagca gggcccaggg caggaagcgt cctgtgttct ctgcctatcc    66300
accctgcatt aaaggagggg aagcagagag caggagctct ggggacaggg agggagtga    66360 gaggggatg ccaggtagtg ggtgactaga ggactcttat ccacagtctc agagcacaca    66420
gagatggctg aaggatgcca ctttaagtga taccttctgg tcatgctggc agtagcttct    66480
gtgctcagca ccatcttctg tcccccagct tttgaggggg cacctatgct ttggcaaatg    66540
gactttggtt ctgaggtttg gtgtcttagg ttgcctcaag cctgcactgg ttttgggaga    66600
ggaggtagag gcagctgtgt ccccaacaat agatgactgt ggccagcagc taagggaagg    66660
gtccaactct ggatctccac cgtgtgtgtg tgtgtgtgtg tgtgtgtgtg tgtgtgtgtg    66720
tgtgtgccca agctctggcc ctgcagatgt ctatcttttc ctgccctcat ctctgcttcc    66780
cacacccacc ccccacccac gtgcacacac caggtgttgt cctgagacct gagacagagg    66840
ggtgagctgc atcttgtcag ctgtgtagat ctgccagtag ctctacagtg gctccctttc    66900
agaatctgga atcacaaaat aagaatctca gagttggaag atacctaaaa gggcttctag    66960
ttattccacc ttccccatac caattagtgt gtaagtattt ccatcagttc actagctcaa    67020
ctgctgttcc cctctagtac catggaaatg cagtgttaat tcgattaatc ctagaatcaa    67080
agttggaaag agccttcgac aagagctaat cctcacactc accccagtgc caggatcccc    67140
tggcaaaaca catttatgtg atgtgccgtt ccactcacat ttgaacatat gtattccatt    67200
cctgagcaac tctagctttt ttccagttgt ctttcccat ggcttcacca tttgtctgaa     67260
ttatccaact tggggcttat ataaaaaaaa gactaactcc tttctatctg acacaatttt    67320
agatgtgttg ggataaattt ttctcccctgt gccctacctg tttcccttcc tgggcccaca    67380
gcattaagct aataggagga gagtcttgca ttaaaactta tacaggaaag gaagcagaca    67440 atctttaca taataaggta gtaggaaatt aatcttcata cacggagttt tatttttgaa     67500
attattatat tcttatttgt ataaatgtat ggaatagagg tgcaatttg ttccatgcac     67560 agcttgtgta gtggtgaatt cagggctttt aggatatcca tcacttgcat aatgtacata    67620
aggcccatga agtaatttct catcattcac cccctccca ccctctcacc cttccaagtc     67680
tccattgtct atcattccat gctcttatgt ccatgtgtac acattattat tatttttga     67740 gacagagtcc cacttagtca cccaggctgg agtgcagtgg cgcgatctca gctcactgca    67800
ccctccacct cctgggttca agcgattctc ttgcctcagc ctcccgagta gctgggatta    67860
caagcaaaca ccaccatgcc tggctaattt tttttttttt taatactttt attagagaca    67920
gggttttgcg ttgttggcct ggctggtctt gaactcctga cctcaggtga cctacctgcc    67980
tcagcctccc aaagtgttgg gattacaggt atgagccacc gtgcccaggg tgtacgcatt    68040
atttagcccc cacttacaag agaggacatg caatatatgt cttcctgtgt ctgatttggt    68100
```

```
ttcacttaag ataatggctt ccagttccat ccatgttgct gcaaaagacc atgatttcat   68160
tctttttta  tggccgaata gtattccatt gtgtatatat actacagttt ctttatccaa   68220
tcatccattg atggccactt agattgaggt tgattctata tttttgctat tgtgaacagt   68280
gctgtgatag acatatgagc acacacagaa ggtttaatgg tgttcatgga cacctcccct   68340
agagggcctc atccttctcc tctaccctca gttcaacagc agaaccaagc gtgacaacct   68400
gtgccagagg ctgacaccag agggagaggc aggaggaaaa ggatgcagga ccctagaaga   68460
gccataatgt tgccattaga agaaagctgc tgggcccatc tgactttttt tttcccccag   68520
tttcttcaac catccttttt aatgcatgat ttcgagtctc acactgactt ctctgaactc   68580
attccagttg gagtgagctg ggccataatg ttcaaagtgt gctgatcaga gtacaatggg   68640
tatcacttcc ctcagtgtag acattatgcg tgtgtgtatg tgtgtgttta tatgtatagt   68700
gtaacctcaa actcctgggc tcaagagatc cttcttgcct cagcctcctg agcagctgag   68760
actataggtg tgcaccacca tgcctggcta aattttaaat attttgtaga gatggggtc    68820
acgctatgtt gcccaggctg gtctcgaact cctgggctcc ctctcacctc agcctgccaa   68880
aatgttggga ttacaggcat gagccaccac actcagctag atattctatt taattaacta   68940
attaattaat ttttttagtg ggttaaggag tggaacgttt aatagacaga agaaagcaga   69000
gaggagagca gttccttgtg aaggagagag agatgtctga aaaaaggcct agatagatat   69060
tctattttaa tcagtgtatt taagattgga ttagctttct tttttttttt tttttttttt   69120
tttttttttt tttttgaga tggagtctca ctcttgttgc ccaggctgga gtgcaatggc   69180
acaatctcag ctcactgcaa cctctgcctc ccaggttcaa gccattatct tggctcagcc   69240
ccctgtgtag ctgggattac aggcacctac caccacgcct ggctaattt tatatttttt    69300
agtagagatg gggtttcacc atgttggcca ggctggtttc aaactcctga cctcaggtga   69360
tccacccgcc tcggcttccc aaagtgctgg gattacaggt gtgagctacc atggctggcc   69420
tggattagct ttcatggtga ccacatcaca ccacggattc ccactgcact atcgtcagaa   69480
gctcccgtgt ctcctttaca catatcgtga gaaaggagag ggagccatgt tgcatccatc   69540
tctttatttg tgcagttggt gttttggact cagtatagtt accttaaacc tctagaaatc   69600
ctactttctt gttcttctat gctttctcag catgaaagtg gtaggatgct aagctttgtt   69660
ctggttttc  ttggtgcagg agaggaggag gccggaatgg gggttacaac ttgggcccgg   69720
ttatactcct gaggctcaga tgagcccggc caacatggcc tcatgctgga gaggacttag   69780
cttctgagtc aatttgaaaa gtcttttaat atgaattaaa gagaaagtgt gggctgggg    69840
cagtggctca tgcatgtgat cctagtgctt tgggaggctg aggtgggtag gttgcttgag   69900
cccaggagtt tgagaccagc ctgggcaaca tagtgagacc ttgtctctac aataagttaa   69960
aaaattagct gggcatggtg gcacccacct gtagccccag ctacttgaga ggctgaggtg   70020
gaaggatcac ttgagtctgg gaggttgagg ctgcagtgag ctgtgattga gccactgcac   70080
tccagccagg gtgacagagt aagactctgt ctcaaaaaaa aaaagttgt  tggcaaagac   70140
aaaactacta ttcaagcact catctgaggt gctaggagac ccccgggctt tgtggcaggg   70200
gctagaaggg ccctgtctgc ccagttatac ttaggaactg agaatttgaa ctcttgctac   70260
tgctcccagg acaggatctg cttaccaatt cagccatttt ctgagttttc atggcacttt   70320
gaggacagca tttatcatac tattttgtgc gttgggagtt cctatggcca gaaactattt   70380
cttattcatt ttcaaatccc tagctccaaa gccaaggtat tacaccccag aactaatagc   70440
```

-continued

| | |
|---|---|
| tatcatttat taagtactaa cttaggcact aaaattaggt actctccata tattaatctc | 70500 |
| acaacaaccc aacaaggtta atgctaatat ttccatgttg taggtgaaga aactgaggct | 70560 |
| aaagaccaca gctctaccaa agcctctgct ctttcttcaa atgaatgagt gagtcggggg | 70620 |
| cggttgctct gagtgagagt gggccagagt gggttcaggg cattcaggag ccaccacagc | 70680 |
| tcattcgtgg aggtgtctaa tcagctatgc taattgattg tcgtgtctgc aatatcagat | 70740 |
| gcatgcttaa ttagcacatg aactctcctg tcagatattc ctggaggggc tctgccagcc | 70800 |
| aacctaggcc cagccacagg agcctgctgc tttcttggaa acagggtggg gaagcatgat | 70860 |
| gatcccagta ttgacaagga tcccctgaga acaggaaggt ccactgcttt gtcgtgtggg | 70920 |
| aagcagattc aggatgaagc cctgtctaca agatgtgtcc agtctcctcc gcctcgaggc | 70980 |
| ccttggttca tcgacctctt ccctacagcc tttggacttt gcaccactct ttgaggcctc | 71040 |
| tgtgcttttt tccaagctcc tgcttctgcg ctggtcttcc tctccctagc aaatccttat | 71100 |
| tcacccttaa gggtccagct caaatgtcac ttcctttgtg gagttccccc tggcccccgt | 71160 |
| gctacccgca gagtggcaga atcaaatgct tcctcttcag acttgctcct attgtacttg | 71220 |
| tacctacctg actctaatgt gagtctcttc aaattacagt gtttttgacg tgttttttctc | 71280 |
| ccccggccag acttagggct tattcaaggc agagaccaca gtcttcagca tccggcacaa | 71340 |
| agcccggcct gtacaagaca ctcagtacat ttaatttgtt gaattaaact gaatgctagg | 71400 |
| ttgaggttcc actgcaggta agaactgggc aagtgtaaac ttccagaact cagcagctat | 71460 |
| ttattagtga tatgcagatg taggtagggc atctttgaaa tcttcccaag gattctgtga | 71520 |
| tccttatttt tccttttcac aataatcctc tcctacttgg gaaaaggggg gataaaatcg | 71580 |
| cactttggcc ccagcctggg gagaatcttg gcattaggct gggggggccat ggtgggagga | 71640 |
| agcatgggac tggggcctaa aggccatcaa ccagactgca agctgcctga gtgcaggatg | 71700 |
| tgacttcccc tccctcccac acatatggcc attgcttcac ctggagtgac ttgggactgg | 71760 |
| ggaatcaggg gtgggcagca gtgcaggaaa acccatccgc accagcctgg ggctccctct | 71820 |
| tctcactacc tcatgaggcc ctgtggagtg tggactgttg ctgctgtcct gatcccccaa | 71880 |
| atgccataac tgctgacttc tgatgtaaat agtgtacatt tgttttttac tttgcagcta | 71940 |
| atttgcatta acttctctga atgacagaca tataggaatt ccctgatttc tatgacctca | 72000 |
| cttccacacc acaaaaaacc acagtggtcc ctatacctct gtactcaggg actcccaacc | 72060 |
| caggtgggca gataccaggg ggtttctgag gagccctgca tcaagcaggc accagcccag | 72120 |
| gaggaagcga tccaggaatc ccactacccc ggagcccact gctctggcgt ctctttcttg | 72180 |
| tctctcgggg ttgtgcgggg tgagggcatg ggggtttgtg aaatgtcttc gtgattttgt | 72240 |
| aattcaggct agggagtcat tcggagaaaa gcgaatgaaa agtagggtaa agggaaaga | 72300 |
| ggggctttgt gacttaggtg ggctttgcag aaggacagga agccacaccc cgagccttac | 72360 |
| aaggcaagct ggatggggct gcccggctgc aatgggatg gaccgataca gaccgctcag | 72420 |
| tgtagccacc tgctggacac atggagtcat agcgttctgc ttccttcatg cttcctaccc | 72480 |
| tccagctgcg cctgctcttc tttcttcctt ctttctcctc cttccgccta gttccgcccc | 72540 |
| ggcccgcata cctgctttcc ctcttccctc aggtgtgact acccagatgc atctgtcttg | 72600 |
| gcccagggct ggggactctg aatttcctcc tttggtgatg actgaaaggg agcagctatc | 72660 |
| cctggttgag gccagagaga aggcttttca tctccatgtt cagtctctcc accttctcgc | 72720 |
| ttggcttgct gggatcctgc gcttggctgc gattagaggc cactgaattt attgtccaaa | 72780 |
| ctgggatgct tctgagagtg aagggtgtgt gtgcttgcta ttagtaatta tgcagagaca | 72840 |

```
acagctgtag accagaattg tcccgggcca gcggggactc atggtaagca tagttccgag    72900
ggtccgccgg ccttttcggc cgtgcgtcag gtgtggaagg ctaaggcggc cagcagaggc    72960
tgctgcggca cttgttatgt gcctcactat ctaaaaagct cctttttgcca tgctgggact   73020
gtggtgggtg aagttggttg tcgtacaggg ctaaggtccc ctgagtagtg attgtaccag    73080
atttgctcac ctgggcctgg cgcacaatgg gataagaaag ccgcctgctt cctctagtct    73140
gggtgggaga cacagcccaa agtcccaggg cctaccttct cagaaactcc ccatcatcct    73200
ggattggact gtgcctttcc tgaattctga cacttcttgt tcctgcccct tcaggcaaag    73260
actgggcaag cagtttccta gcactgccag ctctgaggct ggtgcctttc tgggtggatt    73320
attggccttc ctggatacat tggcaggagg actcatgggt cggccccagg atgcctggc     73380
cagagggac ccaaggaatg cctgacagtt tctctgcctg acttgcaggg gggaattcag     73440
accagccttg gagtcctgtg aaggggaagg gctcctggaa tcttctagcc ctccttcctc    73500
tcacccagtt ctaactctgg cagaaagacc tcatttcctc ttccccatgt gggagacttt    73560
ccctcccttg accctcttg cagttgggag accttgatcc ttgtgggagg aaggggttgc     73620
tgtaccagga tggggtccct ccgctcccct ggccagggga agcatgacct gctgagctgg    73680
agtctggccc cgcaagctgt tgtggcctga cctgtagttg cttgcccagt accagcccct    73740
ctctcccatc ttctctccct gctcacctga agggagaggc cagtatcagg cttccaggc    73800
tacgtgctgg tgatcatacc atggcaaagg gcggtgtctc acacaggctg cgggagagct    73860
gccctgctta agcagagaat tctggagcag cagtgggtat cccaggcagc cacagggatt    73920
gccatggcaa cacgcgaggc agcagcagcg ggagacggga tggagcaggg cgttttctag    73980
gctagagctg aattcctggg gtggtcagga gagggctgga gggcaagaga tccataaacc    74040
cacagctgcc ccgacagagg gcagtctgcc tttgctcctg gccccttgtc agtggaaatc    74100
cgacaccccc tggtacatgt ctgttaggtg tccagcctgg gcagagggcc ttgttggtgt    74160
gtggagaggg ggaaggggaa tcaaacttaa ctgcagagat ttgttttctc agtacatctg    74220
aagaatagaa atgggtttta ggctgcgcca gcctgcgttt ttctacctgg gggactctga    74280
gccatcaaag ttaacctaga ctagtaaccg gggatcaatt acagacctgt aatatgcttt    74340
ccaacttccc cattgtaaaa gcagcctatt tggaaaaaaa ataaatgaaa gtgcttttct    74400
tggtctctgg tgccactgag ccagtgtgat tccctccctc cccagttgcc tttgcccact    74460
tctcactcat tacctctact caattagcca aggctgggtt aacccctcaa gagccaggat    74520
ttgggtgaga ggggattgct gtcaccttct acaggcacgc cctcctccta gcacagttct    74580
cgggagcgca gagcgggcca agtccagagc ctgccaacct cctccccacc ctctctctcg    74640
ctgccaaatc tgactttgat tagcgtgtgg agggggaaga aagcaggaaa atagaatatt    74700
aaaatcttaa ttcaatttaa aacactgtca ttcacaggca tgccaaacag tgagatgact    74760
aattattatg caaatgaggc agatagaaaa gtgattaata attgcacaaa ttaaaaatta    74820
ttgtaaacat cctgtgacga gtgataagtc cgatggagag gcgagagcgg tgggccgggg    74880
aggccatggc ggagctggct cctgcatcct tatttcctca ttaggggat ttaattagcg     74940
cctgatgatg gggctccgtg ctgccagggg tggaggagtt ggtggccagg gcctgggcgg    75000
tctgtgctgg atcctcggtt tttctccagt tcctccttat tgctctgtgg ctgggctgg    75060
agctggctgc acaggaggag gggtgggttg gggttgggga aaggctggac accatagagg    75120
agcaggtgct gtgcaaagct tctctgccgc cttccactgg ccttttgccc gctgctacct    75180
```

```
ctgtcattta agtcctcagg tgtgggtcag gggtgttggt gaggaggccc ctgggtgagg    75240
aactgtgggc acatcctgat tcagccaggc atattcctca gggtttagtg aagcgacaca    75300
cagggcacgt ccccaatgct gaaaggtccc agggaggata gacaggtata tgatgctgcc    75360
tggggcctca gggttgcctt gggtccaagt ttccctgact ctgctgggca catagaaact    75420
aagtcagtgt cctgagccaa gtgacttgcc cttagccatg ttcaacctgc atccaagcgc    75480
cccgcagcag ggaatgctta ggagtcactt tggcttgggt gggcatggct gctgcaaggc    75540
agggacagag ggaggccgag ttctttgggc ccagcagcac caggtgcttt ccagggcatg    75600
cagccctcct ggattcctcc tgcccaaata gggaagcagc tgatatgttc ttgacaaaac    75660
ataccagcca gccacagtac agcttccccc tgccagtccc cgagccctga actctgagca    75720 ggagggatg ggactgggtc taggctcaag gaaaggtggc tgatgatggg aaatccatct    75780
ccctgctcca cccccagtca ccatggacct tagggagatg gtcttccttg tccagagaag    75840
accacagaat aagctgggag gtgaagagcc tggtgaagag cttttgctct tcagaggaac    75900
agtggatgct ggaaattctg gcagttggga aggcttctgg acagggccaa ggtgggaatc    75960
tggcctttga aagatgtaga ggactcagaa agagggttg gaggtgagaa atagagaaa    76020 tagcgttatc caagtctttta ccttctctct aagagcccag attttcctaa cggggctaag    76080
aagctgaggt tttcacaggc caaaggccca gcctgtgtgt ccctaaattt ctcttcctga    76140
gactgtggtg taaaattaat ttttttttcc tggtgagggt ttggaggtga gaaaggttta    76200
tttctgtttc aggactcaca cagttatccc agggttaata acctgcacac agccttgtca    76260
ccacagccac tagtacccct cttcccaccc cctctctgcc agcctcatgt cttcactctg    76320
gttcctgggt ttctctagtc cctttctgat tcctggagga ggaaagttct ttcctattgg    76380
gactgcaagt ccaccctct gacttctggc taaagcttcc tggactctga aggctctccc    76440
ttcactgtga actgtttagc catagctgcc aaccttcaac aaactccctt ctccatctcc    76500
tctctttgcc cactcctgac tcctgcccta tgctaccctg agccctcct gggttcttat    76560 tctgttttttc ttttgttttg gtttctctgg ggctctgctg aggcagcaaa gggtgatggg    76620
gtatggtact gattctgtgt ttaccttgga caaactatat cacctctctg tttcctcatt    76680
gttataactg ggaaaatgct acaatctcat ggaatctttc actttcccat cttcatcagt    76740
tcatttattc catcaagact tcacctctac gcgtcaagtc ctggggatgc aaagctgcag    76800
atggtctcaa ggaacgcgag ccctgttggg aggcagataa aggaacagca cgcgcagagg    76860 cccgaggag ggaggagaat agaagtgtgg agactggcaa gggatttggg atggcaggag    76920
gacaggttgc actggggagt ggtagagttg gaggcctttt gttccctgga atttcaatac    76980
gattttgtgg gctctgagca ggtaagaaag gactttgttg gggtggcagg caggactaac    77040
actgtgtttt agaaagaycg ttttggcagc agtgtggaga tgggcaaggc tggaggcagg    77100
gtccccaccc agaggcagct gctgctgtct gtatgaaaga cgatgaactg cagccatcag    77160
gtgtggctca agagtcacgg gaagaggaga gagctttgtc atgagtcaga aaaggcagga    77220
tgcagcatct cagtgactgt gagggtgacc gaggggcgt cttgggtgac acctgggttt    77280
ctggcatgga gcaatgctct tctttgagaa gagggatcta gggaagaagg agagatgatg    77340
atggtgttgc tttgggaatc ctgggaatga ccacccctggg tttagttgcc tgggacggag    77400
tgggaattga atatctgcta ttgaatattt gatattgaac atgctgaatt tggcgcttca    77460
tctgccttgc ctgttttatt tctcactctg accatacta gatctttga aaggaggctt    77520 gacccctatcc tgaagcttga ccctgacctt ctacctttca acattttggt tagcgggcgc    77580
```

```
ctgcttgcgg actttctgag atgcacttct cagttattca gctgtgtcta cattcattcc    77640
cacaggctct gggcaggttg aagaaccca catttgaccc tatggcattg gacttgggtt    77700
gttgctacct ctattctgtg ccatggggaa gaaggctctt ctctgctgag tcctaacagg    77760
cagatactgg ctgtaaatcc tttctagacc cctccccggt gcccacgctc tgaggctact    77820
cggagggcgt tgtgttgttg ctgagacccc tgaatcgcac tacttcaggc tgtcccctca    77880 cctcggggt ggagataagg cctggggtct gagtttgagg ggactgacgc caggcagggc    77940
tcctagcagt aaggtggaac tgcttccctc ctcagagcga ctttctaaac cagcttccca    78000
ttcctctgag gctgccgcca ccctgggaa gcacacattt gtggttgccg aacagttgaa    78060
gggcagtggc tctttcttcc agggcagtgt gggcctgcct ctggctcccc cgggagggct    78120
gcacccccac ccacctgtgc ccctcattaa gagtaagcag cccagagtgc agcacttggt    78180
gggacccatg aagaccccac caggagtccc tagtggtccc cagtgtctcc attatgccct    78240
ctgcagttct cacagtgccc taggaaagtc catgtgcttt tgctctccag agagctcctg    78300
gtcactttct aatatgtctc cagcaactca gcattatcag tattgcccca atatctcttt    78360
gatggaatcc ctatcaggct actggcattc atagctactt cccacagaat cccaggaaca    78420
ctccagtaat tcccagtgag ctcccagtag tgccaggttg ctcccatacc tcacagtggg    78480
cttctagtga tatcacattg tgtacccagg agcacctggt gttcccccaa gaacgttcca    78540
gcatgttccc aagaatgctc caacacatgg catcaacatt ccactattcc tgcaagattt    78600
ccagtagatg ccattacttc tcaagttatc tccaccaatg ccactgatgt gcttagagga    78660
gaatctgctg tcctgcccac caggaatgaa gagaggttct ttgcctactc ctcctgcaag    78720
acacctgggc tttcctgctt tgggaggctg gtagggaagg caaggagtg ggaataacat    78780 ttgttgagtg atagccgtgg cttaggcatt tatttgtgca ataaactgca aggtgggtgg    78840
tatccctatt ttatagactc agaaactgtt acccagagag tggagtaatt tttttccaaa    78900
ggcagtaagt ggcagggagt gatcagaagg gcagctctgt caggtctgac atccctgctt    78960
gtccggagcc tgcagagacc cagagaaggc aaatcccagg gccagagatg cacagggtag    79020
gggcggggga gggtgggcag cgggctctag gctccttcct tccctcccta ctttgttttc    79080
tcctttggat tgcaggcgta ttcattcctg agaaagaaag gaaagggtt aggactggtt    79140 gagctgtcct ggtttctttg gagagaagct gtggttcccg gaacgtcttg gctctctggg    79200
gactgcaggg gtcagatcca tcccctccag tttcacatgc ctactcagct tccacattcc    79260
acatccagtg gctcaccaga cccacccacc ggcccagatg acccagttcc agggccggcc    79320
tcagggttct gggctccctc ctgggcctgc cctcagccct gggcacaacc tcaaactcca    79380
ggtcctgggt tgtacatccg ccttctgcc cctttcccac actcgctgct gctctcccac    79440
tggctgcctt ccctggcatg ggtgaccttg ctagtgccag gggactctga acagcgctga    79500
ctcagcaggt ggggcgatgg agccactctg caggtgggga aacaggggag caaggctggt    79560
tctttccttt ccctgacccg gcggggtccc tttgcccttg ggagtgtgga cggaagggca    79620
gggagctgga cagggaggat gaggtccagc gccctgggtg agggccctgg tcggggagac    79680
ggtgcccggt ggcttggcct ccctagcaag gactctgccc cttgttcctc agcctgtcag    79740
ggagaagagg aagggctctc tctggtgctg tgtcgagcag cagcctccca cacggagtgg    79800 ggagggaaa gttgaaacgc accttgactc ctgaccatct cctcccccac ctcaccccca    79860
cccccaccac ggcagacatt gttggaaggc atattaatgg aggggttagg cagttttggag    79920
```

-continued

```
acagactgcc taggttcatg tccttctcta tctcattctt ggacatatca cttagggtct    79980
ctgaaccctg atttctccat ttataaaatg tggctaataa tgttacttac ctgtcacatg    80040
gtaaatgctc aattgaaaag gctaacatga gaatgccatt ttctgttatg tacatgatgc    80100
ttcatacaat cacactggcg cacatatgcg attatgtgtg ggctttctgt gcgctctgcc    80160
cttccccagc tttgctgtct gtccttgttg cttccagaag gttgagaggg aggtgagggg    80220
tctgctcctg acaatgctga ctactgaggg gctgagtgct gcccaggaaa gtaggtagca    80280
gaggagagaa gacttggcct aagcgaggga gccagggcct tacagaggaa aggaaaaggg    80340
ggcaggggga aggaggacag ggagggtggc tgggtatggc aggagtcagg gcatctcaga    80400
ggcatgaagg agctgggggt gctgccttcc tactcgggct cacccgtcca gcccccacac    80460
tgccctccac accagacacc cagcagtgct gctaaggcca ctggccaggg ggtgtgggcc    80520
acctgcacct actgcttgcc tttggggag attttttttg gggggattct tggctctctt     80580
gggttatgct cctccttctg gtgtacccta ggcaggaag agtttgggga gaatgggagg     80640
ctgctgtgag ggttataggt gggttacttc acggactccg tgagtctggg gctccttctg    80700
tgaagtctca gtgacaggac acgaacccaa gaactgttgg catgtggcat ccttgcctca    80760
ggagctcttc agcaagtgct ggagttcaca tggccagcct gagggagggg tcttctgtgt    80820
tctctctgca ccccttcccc tccctgcagc ccagtgtcct cagggcaggg gtgggtggca    80880
gtggggagga gggaggggag atggtctgtg atctctggtt gcagtgaatt tgggactaaa    80940
catcattaat gctgacagat gccagccata ctaacttgta gaataacagg acaatctagg    81000
g                                                                   81001
```

<210> SEQ ID NO 2
<211> LENGTH: 1879
<212> TYPE: DNA
<213> ORGANISM: Homo sapiens
<220> FEATURE:
<221> NAME/KEY: 5'UTR
<222> LOCATION: 1..29
<220> FEATURE:
<221> NAME/KEY: CDS
<222> LOCATION: 30..1121
<220> FEATURE:
<221> NAME/KEY: 3'UTR
<222> LOCATION: 1122..1879
<220> FEATURE:
<221> NAME/KEY: allele
<222> LOCATION: 1153
<223> OTHER INFORMATION: 17-41-250    : polymorphic base C or T

<400> SEQUENCE: 2

```
agacgtgagc agagcaggta atg gca agc atg gct gcc gtg ctc acc tgg gct        53
                      Met Ala Ser Met Ala Ala Val Leu Thr Trp Ala
                       1               5                  10 ctg gct ctt ctt tca gcg ttt tcg gcc acc cag gca cgg aaa ggc ttc         101
Leu Ala Leu Leu Ser Ala Phe Ser Ala Thr Gln Ala Arg Lys Gly Phe
             15                  20                  25 tgg gac tac ttc agc cag acc agc ggg gac aaa gcc agg gtg gag cag         149
Trp Asp Tyr Phe Ser Gln Thr Ser Gly Asp Lys Gly Arg Val Glu Gln
         30                  35                  40 atc cat cag cag aag atg gct cgc gag ccc gcg acc ctg aaa gac agc         197
Ile His Gln Gln Lys Met Ala Arg Glu Pro Ala Thr Leu Lys Asp Ser
     45                  50                  55 ctt gag caa gac ctc aac aat atg aac aag ttc ctg gaa aag ctg agg         245
Leu Glu Gln Asp Leu Asn Asn Met Asn Lys Phe Leu Glu Lys Leu Arg
60                  65                  70                  75
```

```
cct ctg agt ggg agc gag gct cct cgg ctc cca cag gac ccg gtg ggc      293
Pro Leu Ser Gly Ser Glu Ala Pro Arg Leu Pro Gln Asp Pro Val Gly
            80                  85                  90 atg cgg cgg cag ctg cag gag gag ttg gag gag gtg aag gct cgc ctc      341
Met Arg Arg Gln Leu Gln Glu Glu Leu Glu Glu Val Lys Ala Arg Leu
        95                 100                 105 cag ccc tac atg gca gag gcg cac gag ctg gtg ggc tgg aat ttg gag      389
Gln Pro Tyr Met Ala Glu Ala His Glu Leu Val Gly Trp Asn Leu Glu
    110                 115                 120 ggc ttg cgg cag caa ctg aag ccc tac acg atg gat ctg atg gag cag      437
Gly Leu Arg Gln Gln Leu Lys Pro Tyr Thr Met Asp Leu Met Glu Gln
125                 130                 135 gtg gcc ctg cgc gtg cag gag ctg cag gag cag ttg cgc gtg gtg ggg      485
Val Ala Leu Arg Val Gln Glu Leu Gln Glu Gln Leu Arg Val Val Gly
140                 145                 150                 155 gaa gac acc aag gcc cag ttg ctg ggg ggc gtg gac gag gct tgg gct      533
Glu Asp Thr Lys Ala Gln Leu Leu Gly Gly Val Asp Glu Ala Trp Ala
                160                 165                 170 ttg ctg cag gga ctg cag agc cgc gtg gtg cac cac acc ggc cgc ttc      581
Leu Leu Gln Gly Leu Gln Ser Arg Val Val His His Thr Gly Arg Phe
            175                 180                 185 aaa gag ctc ttc cac cca tac gcc gag agc ctg gtg agc ggc atc ggg      629
Lys Glu Leu Phe His Pro Tyr Ala Glu Ser Leu Val Ser Gly Ile Gly
        190                 195                 200 cgc cac gtg cag gag ctg cac cgc agt gtg gct ccg cac gcc ccc gcc      677
Arg His Val Gln Glu Leu His Arg Ser Val Ala Pro His Ala Pro Ala
    205                 210                 215 agc ccc gcg cgc ctc agt cgc tgc gtg cag gtg ctc tcc cgg aag ctc      725
Ser Pro Ala Arg Leu Ser Arg Cys Val Gln Val Leu Ser Arg Lys Leu
220                 225                 230                 235 acg ctc aag gcc aag gcc ctg cac gca cgc atc cag cag aac ctg gac      773
Thr Leu Lys Ala Lys Ala Leu His Ala Arg Ile Gln Gln Asn Leu Asp
                240                 245                 250 cag ctg cgc gaa gag ctc agc aga gcc ttt gca ggc act ggg act gag      821
Gln Leu Arg Glu Glu Leu Ser Arg Ala Phe Ala Gly Thr Gly Thr Glu
            255                 260                 265 gaa ggg gcc ggc ccg gac ccc cag atg ctc tcc gag gag gtg cgc cag      869
Glu Gly Ala Gly Pro Asp Pro Gln Met Leu Ser Glu Glu Val Arg Gln
        270                 275                 280 cga ctt cag gct ttc cgc cag gac acc tac ctg cag ata gct gcc ttc      917
Arg Leu Gln Ala Phe Arg Gln Asp Thr Tyr Leu Gln Ile Ala Ala Phe
    285                 290                 295 act cgc gcc atc gac cag gag act gag gag gtc cag cag cag ctg gcg      965
Thr Arg Ala Ile Asp Gln Glu Thr Glu Glu Val Gln Gln Gln Leu Ala
300                 305                 310                 315 cca cct cca cca ggc cac agt gcc ttc gcc cca gag ttt caa caa aca     1013
Pro Pro Pro Pro Gly His Ser Ala Phe Ala Pro Glu Phe Gln Gln Thr
                320                 325                 330 gac agt ggc aag gtt ctg agc aag ctg cag gcc cgt ctg gat gac ctg     1061
Asp Ser Gly Lys Val Leu Ser Lys Leu Gln Ala Arg Leu Asp Asp Leu
            335                 340                 345 tgg gaa gac atc act cac agc ctt cat gac cag ggc cac agc cat ctg     1109
Trp Glu Asp Ile Thr His Ser Leu His Asp Gln Gly His Ser His Leu
        350                 355                 360 ggg gac ccc tga ggatctacct gcccaggccc attcccagct cyttgtctgg        1161
Gly Asp Pro  *
    365 ggagccttgg ctctgagcct ctagcatggt tcagtccttg aaagtggcct gttgggtgga   1221 gggtggaagg tcctgtgcag gacagggagg ccaccaaagg ggctgctgtc tcctgcatat   1281
```

-continued

```
ccagcctcct gcgactcccc aatctggatg cattacattc accaggcttt gcaaacccag   1341
cctcccagtg ctcatttggg aatgctcatg agttactcca ttcaagggtg agggagtagg   1401
gagggagagg caccatgcat gtgggtgatt atctgcaagc ctgtttgccg tgatgctgga   1461
agcctgtgcc actacatcct ggagtttggc tctagtcact tctggctgcc tggtggccac   1521
tgctacagct ggtccacaga gaggagcact tgtctcccca gggctgccat ggcagctatc   1581 agggaatag aagggagaaa gagaatatca tggggagaac atgtgatggt gtgtgaatat   1641
ccctgctggc tctgatgctg gtgggtacga aggtgtggg ctgtgatagg agagggcaga   1701
gcccatgttt cctgacatag ctctacacct aaataaggga ctgaaccctc ccaactgtgg   1761
gagctcctta aaccctctgg ggagcatact gtgtgctctc cccatctcca gcccctccct   1821
ctgggttccc aagttgaagc ctagacttct ggctcaaatg aaatagatgt ttatgata    1879
```

<210> SEQ ID NO 3
<211> LENGTH: 366
<212> TYPE: PRT
<213> ORGANISM: Homo sapiens

<400> SEQUENCE: 3

```
Met Ala Ser Met Ala Ala Val Leu Thr Trp Ala Leu Ala Leu Leu Ser
1               5                   10                  15

Ala Phe Ser Ala Thr Gln Ala Arg Lys Gly Phe Trp Asp Tyr Phe Ser
            20                  25                  30

Gln Thr Ser Gly Asp Lys Gly Arg Val Glu Gln Ile His Gln Gln Lys
        35                  40                  45

Met Ala Arg Glu Pro Ala Thr Leu Lys Asp Ser Leu Glu Gln Asp Leu
    50                  55                  60

Asn Asn Met Asn Lys Phe Leu Glu Lys Leu Arg Pro Leu Ser Gly Ser
65                  70                  75                  80

Glu Ala Pro Arg Leu Pro Gln Asp Pro Val Gly Met Arg Arg Gln Leu
                85                  90                  95

Gln Glu Glu Leu Glu Glu Val Lys Ala Arg Leu Gln Pro Tyr Met Ala
            100                 105                 110

Glu Ala His Glu Leu Val Gly Trp Asn Leu Glu Gly Leu Arg Gln Gln
        115                 120                 125

Leu Lys Pro Tyr Thr Met Asp Leu Met Glu Gln Val Ala Leu Arg Val
    130                 135                 140

Gln Glu Leu Gln Glu Gln Leu Arg Val Val Gly Glu Asp Thr Lys Ala
145                 150                 155                 160

Gln Leu Leu Gly Gly Val Asp Glu Ala Trp Ala Leu Leu Gln Gly Leu
                165                 170                 175

Gln Ser Arg Val Val His His Thr Gly Arg Phe Lys Glu Leu Phe His
            180                 185                 190

Pro Tyr Ala Glu Ser Leu Val Ser Gly Ile Gly Arg His Val Gln Glu
        195                 200                 205

Leu His Arg Ser Val Ala Pro His Ala Pro Ala Ser Pro Ala Arg Leu
    210                 215                 220

Ser Arg Cys Val Gln Val Leu Ser Arg Lys Leu Thr Leu Lys Ala Lys
225                 230                 235                 240

Ala Leu His Ala Arg Ile Gln Gln Asn Leu Asp Gln Leu Arg Glu Glu
                245                 250                 255

Leu Ser Arg Ala Phe Ala Gly Thr Gly Thr Glu Glu Gly Ala Gly Pro
            260                 265                 270
```

```
Asp Pro Gln Met Leu Ser Glu Glu Val Arg Gln Arg Leu Gln Ala Phe
        275                 280                 285

Arg Gln Asp Thr Tyr Leu Gln Ile Ala Ala Phe Thr Arg Ala Ile Asp
    290                 295                 300

Gln Glu Thr Glu Glu Val Gln Gln Leu Ala Pro Pro Pro Gly
305                 310                 315                 320

His Ser Ala Phe Ala Pro Glu Phe Gln Gln Thr Asp Ser Gly Lys Val
            325                 330                 335

Leu Ser Lys Leu Gln Ala Arg Leu Asp Asp Leu Trp Glu Asp Ile Thr
        340                 345                 350

His Ser Leu His Asp Gln Gly His Ser His Leu Gly Asp Pro
        355                 360                 365
```

```
<210> SEQ ID NO 4
<211> LENGTH: 5381
<212> TYPE: DNA
<213> ORGANISM: Homo sapiens
<220> FEATURE:
<221> NAME/KEY: misc_feature
<222> LOCATION: 1..918
<223> OTHER INFORMATION: 5'regulatory region
<220> FEATURE:
<221> NAME/KEY: exon
<222> LOCATION: 919..930
<223> OTHER INFORMATION: exon 1
<220> FEATURE:
<221> NAME/KEY: exon
<222> LOCATION: 1442..1498
<223> OTHER INFORMATION: exon 2
<220> FEATURE:
<221> NAME/KEY: exon
<222> LOCATION: 1613..1724
<223> OTHER INFORMATION: exon 3
<220> FEATURE:
<221> NAME/KEY: exon
<222> LOCATION: 2243..3940
<223> OTHER INFORMATION: exon 4
<220> FEATURE:
<221> NAME/KEY: misc_feature
<222> LOCATION: 3941..5381
<223> OTHER INFORMATION: 3'regulatory region
<220> FEATURE:
<221> NAME/KEY: allele
<222> LOCATION: 319
<223> OTHER INFORMATION: 17-42-319 : polymorphic base C or T
<220> FEATURE:
<221> NAME/KEY: allele
<222> LOCATION: 3213
<223> OTHER INFORMATION: 17-41-250 : polymorphic base C or T
<220> FEATURE:
<221> NAME/KEY: conflict
<222> LOCATION: 1241
<223> OTHER INFORMATION: 17-39-343 : T in ref genbank AC007707
<220> FEATURE:
<221> NAME/KEY: conflict
<222> LOCATION: 1447
<223> OTHER INFORMATION: 17-40-202 : G in ref genbank AC007707
<220> FEATURE:
<221> NAME/KEY: primer_bind
<222> LOCATION: 1..11022
<223> OTHER INFORMATION: 17-42.pu
<220> FEATURE:
<221> NAME/KEY: primer_bind
<222> LOCATION: 553..11575
<223> OTHER INFORMATION: 17-42.rp complement
<220> FEATURE:
<221> NAME/KEY: primer_bind
<222> LOCATION: 899..11920
<223> OTHER INFORMATION: 17-39.pu
<220> FEATURE:
<221> NAME/KEY: primer_bind
<222> LOCATION: 1246..12267
```

```
<223> OTHER INFORMATION: 17-40.pu
<220> FEATURE:
<221> NAME/KEY: primer_bind
<222> LOCATION: 1441..12461
<223> OTHER INFORMATION: 17-39.rp complement
<220> FEATURE:
<221> NAME/KEY: primer_bind
<222> LOCATION: 1632..12651
<223> OTHER INFORMATION: 17-40.rp complement
<220> FEATURE:
<221> NAME/KEY: primer_bind
<222> LOCATION: 2964..13984
<223> OTHER INFORMATION: 17-41.pu
<220> FEATURE:
<221> NAME/KEY: primer_bind
<222> LOCATION: 3432..14454
<223> OTHER INFORMATION: 17-41.rp complement
<220> FEATURE:
<221> NAME/KEY: primer_bind
<222> LOCATION: 300..318
<223> OTHER INFORMATION: 17-42-319.mis
<220> FEATURE:
<221> NAME/KEY: primer_bind
<222> LOCATION: 320..338
<223> OTHER INFORMATION: 17-42-319.mis complement
<220> FEATURE:
<221> NAME/KEY: primer_bind
<222> LOCATION: 3194..3212
<223> OTHER INFORMATION: 17-41-250.mis
<220> FEATURE:
<221> NAME/KEY: primer_bind
<222> LOCATION: 3214..3232
<223> OTHER INFORMATION: 17-41-250.mis complement
<220> FEATURE:
<221> NAME/KEY: misc_binding
<222> LOCATION: 307..331
<223> OTHER INFORMATION: 17-42-319.probe
<220> FEATURE:
<221> NAME/KEY: misc_binding
<222> LOCATION: 3201..3225
<223> OTHER INFORMATION: 17-41-250.probe

<400> SEQUENCE: 4
cagcagatga gactggaaat gagtcaggat gagccacagt ggaggatgaa ttaaatgggc      60
aggagtgtgg tagaaagacc tgttggaggc tatgaatgca atcaaggtga cagacaactg     120
gtgcaatgat ggtagtggaa atggaggaga ggggattgat tcaagatgca tttaggacca     180
agaatcggga gcttgtgaac gtgtgtatga gtactgtaga cggagtgggt gtgtcatcag     240
agaagatctg agcatttggg cttgctctcc tcagaggccc tgcgagtgga gttcagcttt     300
tcctcatggg gcaaatctya cttttcgctcc agttcctggg gctcagagtc cctggcccag     360
atgcctcttg ccatctcatc ttcacccgtc ctggcttccc ttgcttgttc caggattgtt     420
tcataaagag ggatgtggtt ggtctttaac cctatgaatg ctggctgagg atgcctgcgg     480
aacctgtagt gaagctttca ggggctgctc gggttctggc tggtaggtga acactgtcca     540
tcttgccggc tgggacacag tgactctggg tagttgtgta agagagggc ccttggcaga     600 caaacaggtt cttctctgtt ggtgggccag ccagcaggtc agtgggaagg ttaaaggtca     660
tggggtttgg gagaaactgg gtgaggagtt cagccccatc ccccgtaaag ctcctgggaa     720
gcacttctct actggggcag ccctgatac caggcactc attaaccctc tgggtgccag     780
ggaaagggca ggaggtgagt gctgggaggc agctgaggtc aacttctttt gaacttccac     840
gtggtattta ctcagagcaa ttggtgccag aggctcaggg ccctggagta taaagcagaa     900
tgtctgctct ctgtgcccag acgtgagcag gtgagcagct ggggcagagg gatggggtc     960 acagtcctaa gggagggcat tgcaggtggc ctcaggggag agcctgggt ggcccctaag    1020 acgtcctctt ggaacatttt ggcagagttg cctcttcgcc ctcattatgg ctcagttttt    1080
```

```
                                 -continued ccaccatgaa atgggaggga gggagacagg tgggcagggg agaggtggta gaagtggcct    1140
agagaactgt tcctggggtc tgggaccttt gcgaaggggt tagagcacca cgctccctgc    1200
tatgtgactg aggtagcaag agcacgccct cttcccatgt ctgaggaaga caccctagcc    1260
tccttgactc acctaggtca gtcctcttga gccccaacag ctctgtgctc cccagcccaa    1320 ggaagggta acaggatttc gggcagttgc ccctgcagag gcccctggg caagtcccct    1380 gcgccatgtc ccttcgtctc cttcttcccc taaccaggcc tccctccacc tgtcttctca    1440
gagcagataa tggcaagcat ggctgccgtg ctcacctggg ctctggctct tctttcaggt    1500
gggtctccga ccctgacttc aacgtggggg tgtgggtgga ggctggccag agggccctgt    1560
ccaccctggg ggaggagagc ccaggccctg attacctagt ccctctccac agcgttttcg    1620
gccacccagg cacggaaagg cttctgggac tacttcagcc agaccagcgg ggacaaaggc    1680
agggtggagc agatccatca gcagaagatg gctcgcgagc ccgcgtgagt gcccagggga    1740
aggggtgtag gcgaagggag gagacagctg ggccatgcca tgatgacctg cctctgctgc    1800
ctcaacctct gtggccgctg ctgggacaga ggaaaggagc ggtgctagct ctgtctgcag    1860
atcccggcca tcctgggctc tttagcgccc tctgcctgca gcccccgcct tgacaactcc    1920
gtagctgttg ccccttgct cactgaggcg cgggacctgg gatcaatcgg gaggacgccc    1980
gctgcagtcc ccagaatcaa aggatgatgt ggcgcatcta tgtttctttg gagagtgttg    2040
taggtctgga tttgtatggg caatgtgttt gtgcttcgtg cgtgagttgt tactggccag    2100
ggctaggaca agagccctcg accctggggc caacgccctg cgtccttggt tcccccagag    2160
gatcagtgcg cgatgacttg gggacaaagg agatgatggg ggctagcagt ctgacggcct    2220
ggatatctgt ccccttctcc aggaccctga agacagcct tgagcaagac ctcaacaata    2280
tgaacaagtt cctggaaaag ctgaggcctc tgagtgggag cgaggctcct cggctcccac    2340
aggacccggt gggcatgcgg cggcagctgc aggaggagtt ggaggaggtg aaggctcgcc    2400
tccagcccta catggcagag gcgcacgagc tggtgggctg gaatttggag ggcttgcggc    2460
agcaactgaa gccctacacg atggatctga tggagcaggt ggccctgcgc gtgcaggagc    2520
tgcaggagca gttgcgcgtg gtgggggaag acaccaaggc ccagttgctg gggggcgtgg    2580
acgaggcttg ggctttgctg cagggactgc agagccgcgt ggtgcaccac accggccgct    2640
tcaaagagct cttccaccca tacgccgaga gcctggtgag cggcatcggg cgccacgtgc    2700
aggagctgca ccgcagtgtg gctccgcacg ccccccgccag ccccgcgcgc ctcagtcgct    2760
gcgtgcaggt gctctcccgg aagctcacgc tcaaggccaa ggccctgcac gcacgcatcc    2820
agcagaacct ggaccagctg cgcgaagagc tcagcagagc cttttgcaggc actgggactg    2880 aggaagggc cggcccggac ccccagatgc tctccgagga ggtgcgccag cgacttcagg    2940
ctttccgcca ggacacctac ctgcagatag ctgccttcac tcgcgccatc gaccaggaga    3000
ctgaggaggt ccagcagcag ctggcgccac ctccaccagg ccacagtgcc ttcgccccag    3060
agtttcaaca aacagacagt ggcaaggttc tgagcaagct gcaggcccgt ctggatgacc    3120
tgtgggaaga catcactcac agccttcatg accagggcca cagccatctg ggggacccct    3180
gaggatctac ctgcccaggc ccattcccag ctycttgtct ggggagcctt ggctctgagc    3240
ctctagcatg gttcagtcct tgaaagtggc ctgttgggtg gagggtggaa ggtcctgtgc    3300
aggacaggga ggccaccaaa gggctgctg tctcctgcat atccagcctc ctgcgactcc    3360
ccaatctgga tgcattacat tcaccaggct ttgcaaaccc agcctcccag tgctcatttg    3420
```

```
ggaatgctca tgagttactc cattcaaggg tgagggagta gggagggaga ggcaccatgc   3480
atgtgggtga ttatctgcaa gcctgtttgc cgtgatgctg aagcctgtg ccactacatc    3540 ctggagtttg ctctagtca cttctggctg cctggtggcc actgctacag ctggtccaca    3600
gagaggagca cttgtctccc cagggctgcc atggcagcta tcagggggaat agaagggaga  3660 aagagaatat catggggaga acatgtgatg gtgtgtgaat atccctgctg gctctgatgc   3720
tggtgggtac gaaaggtgtg ggctgtgata ggagagggca gagcccatgt ttcctgacat   3780
agctctacac ctaaataagg gactgaaccc tcccaactgt gggagctcct taaaccctct   3840
ggggagcata ctgtgtgctc tccccatctc cagcccctcc ctctgggttc caagttgaa    3900 gcctagactt ctggctcaaa tgaaatagat gtttatgata aagtttgcc tggcgtgact    3960 ctcatttgga ccatgtctga aagcagtggc ctcaccacta tccccaaagc acacccatca   4020
cccactccat tcccttgctg ctctttctca tccacccact cccagtccag gtctgtcaaa   4080
gggggtctgg ctgggctctg cttcaggat cctggctaga caacggctgt ctgtcacacc    4140
tggcaggagg gcctgggtta cgggccttc ctctgcacct gcactgttca ctagcctgct    4200
cccccacagg acactgtgca tggaatgcag gctgtgtctg aagagctgt ggccctggtg    4260 gacctaagat tcctgaggtg ggctgcctcc tttgttcctg ctgttctaga gtttgaatgg   4320
cctcttttta tgccggactc tcttctgggg actcccctca ctcaggggca ccaatgctcc   4380
ctatagatcc cctgggaact gaaactgggg tgtggtggag gacgtggaaa gggtaaacac   4440
agctccttgt ctttggactt ccctgtccgg cccccttttcc tcccagctca gcctactgtc  4500
cccgggttct cagcacctgc ctgctcccca accccatagc acagacccca cacatatgta   4560
ggctcatcat gcctgcaggc tggtcttccc tgacaccgtg gattttgaca atgttggcaa   4620
cagaactggg ttgtggaccc agcacctgga gagaggaagt gctagaaagg tagaaataat   4680
aaaaggtgtt tttgttgttg ttaggaaact ggaaaagcat aggtcaaggg ctatgatggg   4740
gatgaggagg taggagtgaa aatgagggct gtgtacttga ggctgggatt ggggaaggta   4800
gtgatgagga cagaataggg agtgggaaga acagaaaggg acagagggat tcagggattg   4860
tgagagaggg gaagaggctg agccacccgg aggggcgacc tagcacgcaa gcagtatgtg   4920
gcccaacact ggaaccaagc agcccggctc cgggcgcacc ttctcaggga ttcctcaggg   4980
acaagtccag ccccttgtcg tcaaggctct tgtagaccga cgtagggacc aatagaaccc   5040
cgtgcggtgg agctattgtg aaggagcaaa aaagtgccct ggttctaaga ggacgtctta   5100
ggggaagtga cggctgagtt gaggtggatc cggctggcga tgtaaggttc gagccatata   5160
aacccgggaa ccgggagccc ttgacgacat tgttccccga gtgcccggag tctgcggctt   5220
tttttggggt ggtggcagct ggcggaagtg acggagagg gtgggggccg cgagagcggc    5280
ggaagtagga agccgaggtc tgaattgcgc gtggtggcca tggcggccag cggggctgtg   5340
gaaccagggc ccccgggggc tgccgtcgcc ccgtcgcccg c                      5381
```

<210> SEQ ID NO 5
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 5
tgtaaaacga cggccagt                                                  18

-continued

```
<210> SEQ ID NO 6
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 6
caggaaacag ctatgacc                                                 18
```